United States Patent
Schiltz et al.

(10) Patent No.: US 12,042,543 B2
(45) Date of Patent: Jul. 23, 2024

(54) SUBSTITUTED 3-AMINO-5-PHENYLBENZAMIDE COMPOUNDS AS COVALENT INHIBITORS OF ENHANCER ZESTE HOMOLOG 2 (EZH2) AND PROTEOLYSIS-TARGETING CHIMERIC DERIVATIVES THEREOF (PROTACS) THAT INDUCE DEGRADATION OF EZH2

(71) Applicant: Northwestern University, Evanston, IL (US)

(72) Inventors: Gary E. Schiltz, Naperville, IL (US); Jindan Yu, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 17/735,003

(22) Filed: May 2, 2022

(65) Prior Publication Data

US 2023/0346953 A1    Nov. 2, 2023

Related U.S. Application Data

(60) Provisional application No. 63/201,459, filed on Apr. 30, 2021.

(51) Int. Cl.
*A61K 47/55* (2017.01)
*A61K 47/54* (2017.01)
*A61P 35/00* (2006.01)

(52) U.S. Cl.
CPC ............ *A61K 47/55* (2017.08); *A61K 47/545* (2017.08); *A61P 35/00* (2018.01)

(58) Field of Classification Search
CPC ........ A61K 47/55; A61K 47/545; A61P 35/00
USPC ...................................................... 514/375
See application file for complete search history.

(56) References Cited

U.S. PATENT DOCUMENTS

| | | |
|---|---|---|
| 2018/0085465 A1 | 3/2018 | Bradner et al. |
| 2018/0134684 A1 | 5/2018 | Bradner et al. |
| 2018/0186785 A1 | 7/2018 | Crews et al. |
| 2018/0327419 A1 | 11/2018 | Bradner et al. |
| 2019/0016703 A1 | 1/2019 | Gray et al. |
| 2019/0071415 A1 | 3/2019 | Bradner et al. |
| 2019/0076539 A1 | 3/2019 | Phillips et al. |
| 2019/0076540 A1 | 3/2019 | Phillips et al. |
| 2019/0076541 A1 | 3/2019 | Phillips et al. |
| 2019/0076542 A1 | 3/2019 | Phillips et al. |
| 2019/0106417 A1 | 4/2019 | Gray et al. |
| 2019/0151295 A1 | 5/2019 | Crew et al. |
| 2019/0151457 A1 | 5/2019 | Bradner et al. |
| 2019/0194190 A1 | 6/2019 | Yang et al. |
| 2019/0255041 A1* | 8/2019 | Jin ........................ A61K 31/444 |
| 2019/0262502 A1 | 8/2019 | Garcia-Gareta et al. |
| 2019/0263798 A1 | 8/2019 | Harling et al. |
| 2019/0275161 A1 | 9/2019 | Heightman et al. |
| 2020/0022966 A1 | 1/2020 | Tang et al. |
| 2020/0085817 A1 | 3/2020 | Jaenisch et al. |
| 2020/0102298 A1 | 4/2020 | Gray et al. |
| 2020/0140456 A1 | 5/2020 | Phillips et al. |

OTHER PUBLICATIONS

An et al., "Small-molecule PROTACs: an emerging and promising approach for the development of targeted therapy drugs," EBioMedicine. Oct. 2018; 36: 553-562.
Gu et al., "PROTACs: an Emerging Targeting Technique for Protein Degradation in Drug Discovery," Bioessays. Apr. 2018; 40(4):e1700247.
Kong, et al., "Astemizole Arrests the Proliferation of Cancer Cells by Disrupting the EZH2-EED Interaction of Polycomb Repressive Complex 2," J. Med. Chem. 2014, 57(22), 9512-9521.
Knutson, S. K, et al., "Selective Inhibition of EZH2 by EPZ-6438 Leads to Potent Antitumor Activity in EZH2-Mutant Non-Hodgkin Lymphoma," Mol. Cancer Ther. (2014) 13(4):842-54.
He, et al., "Design and synthesis of (E)-1,2-diphenylethene-based EZH2 inhibitors," Bioorganic & Medicinal Chemistry Letters, 30(5), 126957; 2020.
Qi, et al., "An allosteric PRC2 inhibitor targeting the H3K27me3 binding pocket of EED," Nat. Chem. Bio. 2017, 13, 381-388.
Lin, et al., "Discovery of Potent and Selective Covalent Protein Arginine Methyltransferase 5 (PRMT5) Inhibitors," ACS Med. Chem. Lett. 2019, 10, 334.
Ma, et al., "Discovery of a first-in-class EZH2 selective degrader," Nat Chem Biol. 2020, 16, 214.
Kuntz, et al., "The Importance of Being Me: Magic Methyls, Methyltransferase Inhibitors, and the Discovery of Tazemetostat," J. Med. Chem. 2016, 59, 1556.

* cited by examiner

*Primary Examiner* — Kristin A Vajda
(74) *Attorney, Agent, or Firm* — Quarles & Brady LLP

(57) ABSTRACT

Disclosed are covalent inhibitors of enhancer zeste homolog 2 (EZH2) which may be utilized as EZH2 targeting agents. The disclosed compounds may be characterized as substituted 3-amino-5-phenylbenzamide compounds. The disclosed compounds may be utilized as covalent inhibitors of EZH2 and further may be derivatized to form proteolysis-targeting chimeric molecules (PROTACs) that target EZH2 for degradation. The disclosed compounds and PROTACs may be used in pharmaceutical compositions and methods for treating cell proliferative disorders associated with EZH2 activity, such as cancer.

13 Claims, 41 Drawing Sheets

A. No additional treatment
B. Pre-treat cells with 5uM MG132 for 4 hours and then continuous with 5uM MG132
C. Treat with 10uM MG132 along with inhibitors

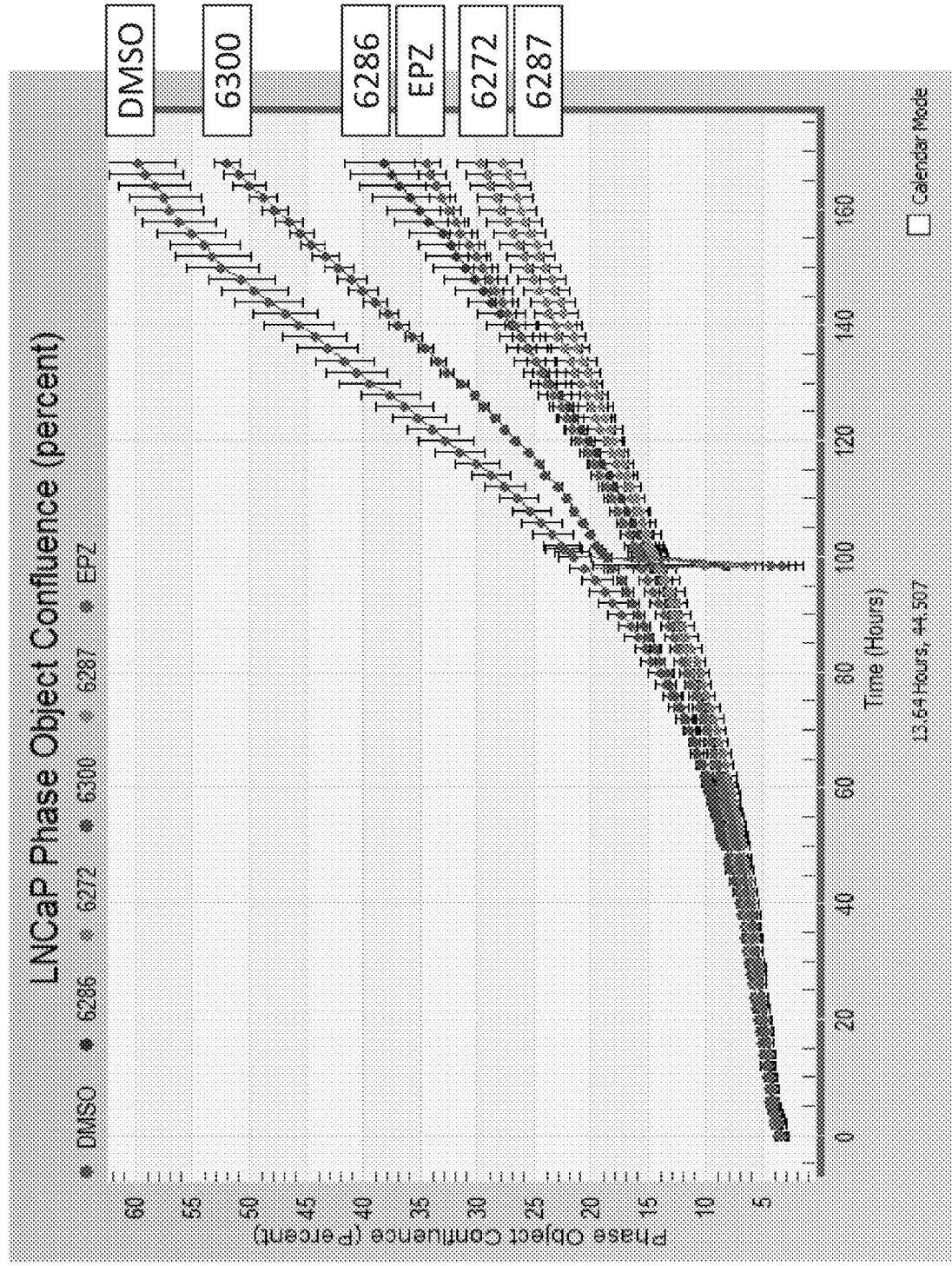

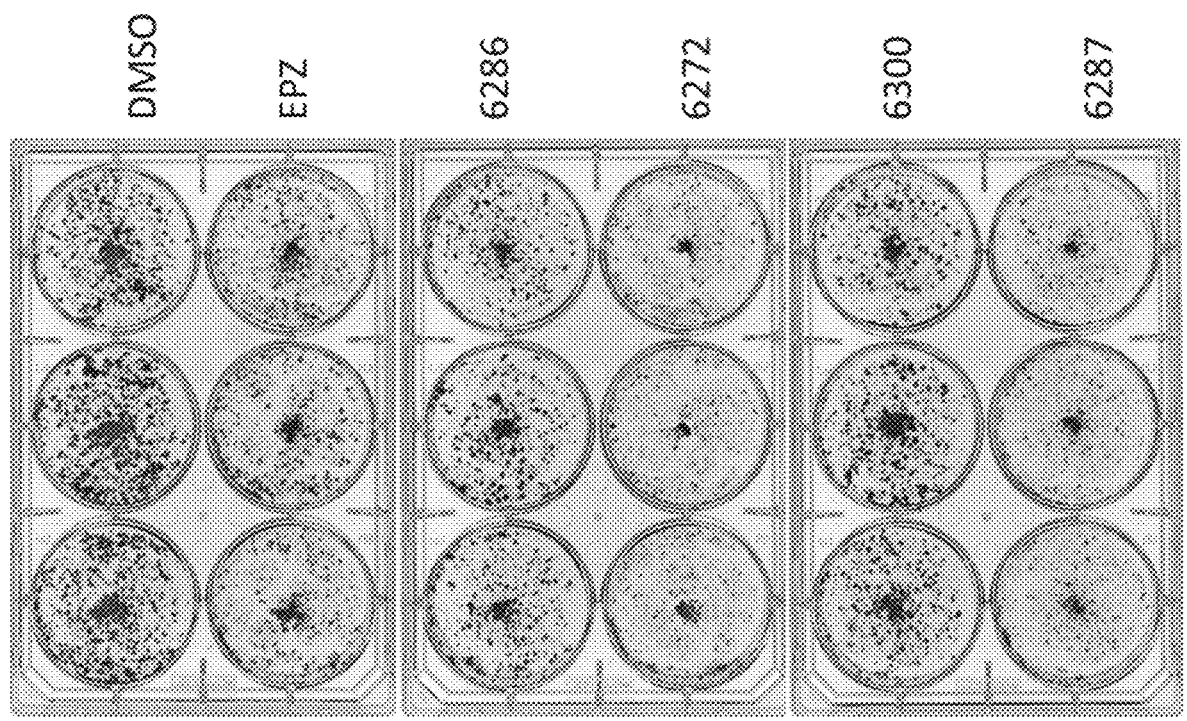

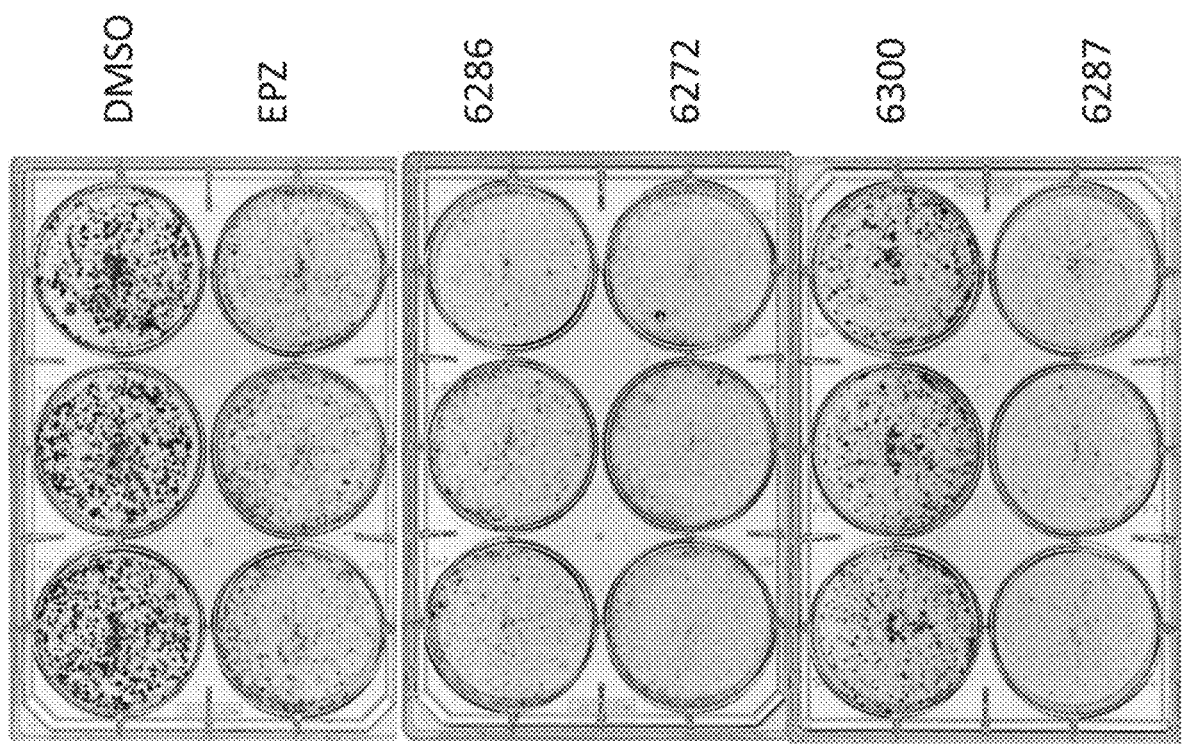

Figure 35
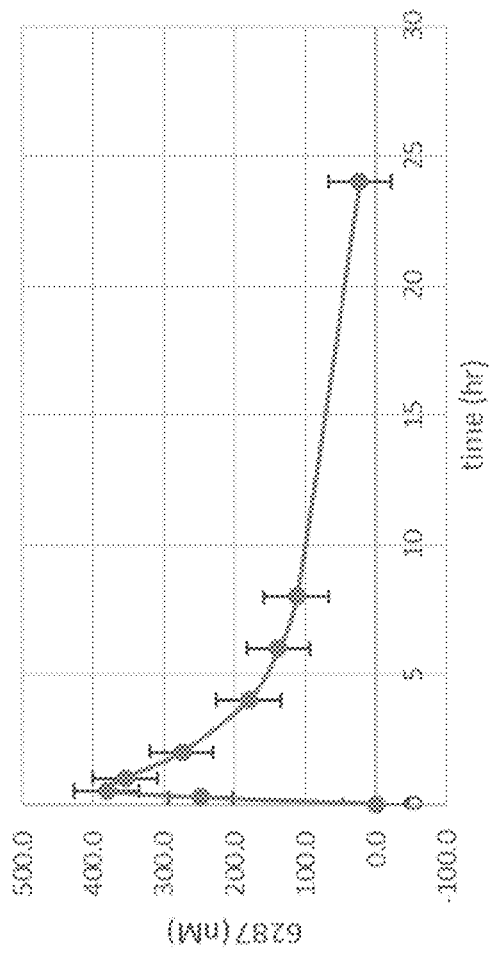
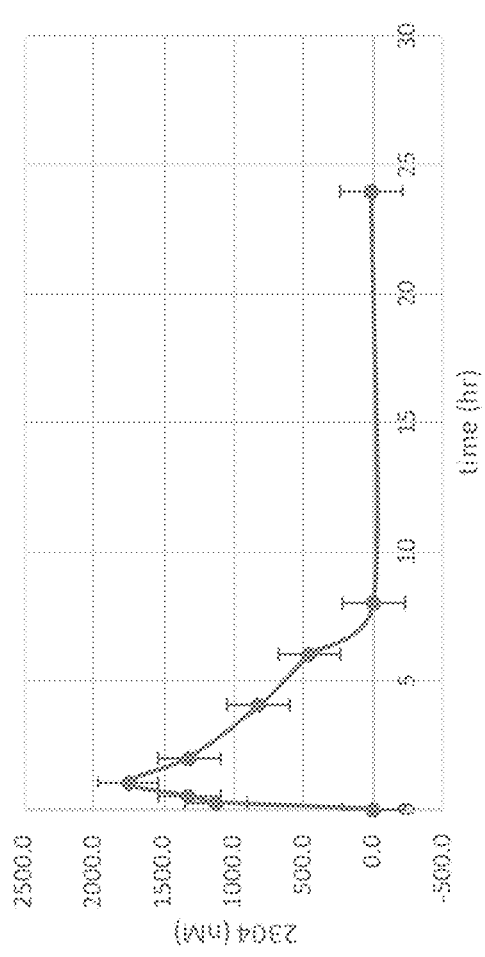

Figure 35 (Cont.)
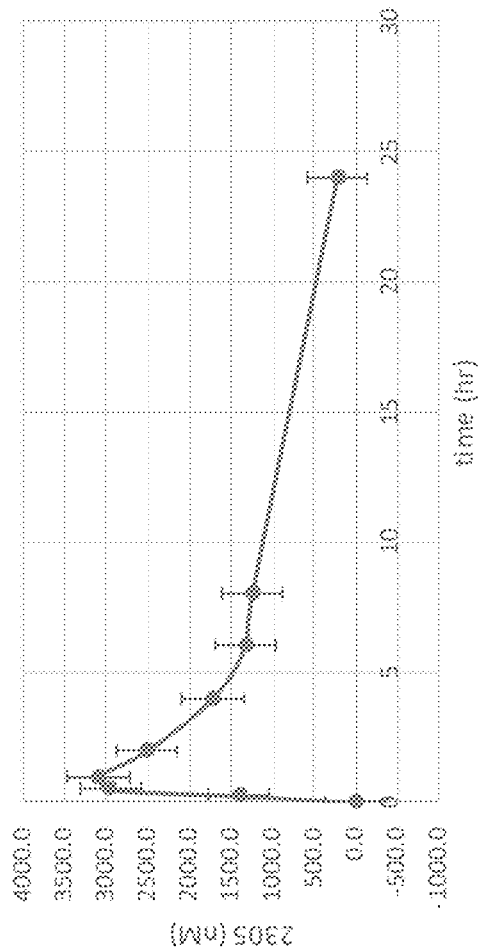
2305, IP, 4 mg/mL
| $T_{1/2}$ | hr | 6.0 |
| $T_{max}$ | hr | 0.75 |
| $C_{max}$ | ng/mL | 5305.00 |
| $C_{max}$ | µM | 4.23 |
| $AUC_{last}$ | min*ng/mL | 2183723 |
| $AUC_{last}$ | µM.hr | 29.1 |
| $AUC_{INF\_obs}$ | min*ng/mL | 2325827 |
| $AUC_{\%Extrap}$ | | 6.1 |
| $Cl\_obs$ | mL/min/kg | 1.7 |
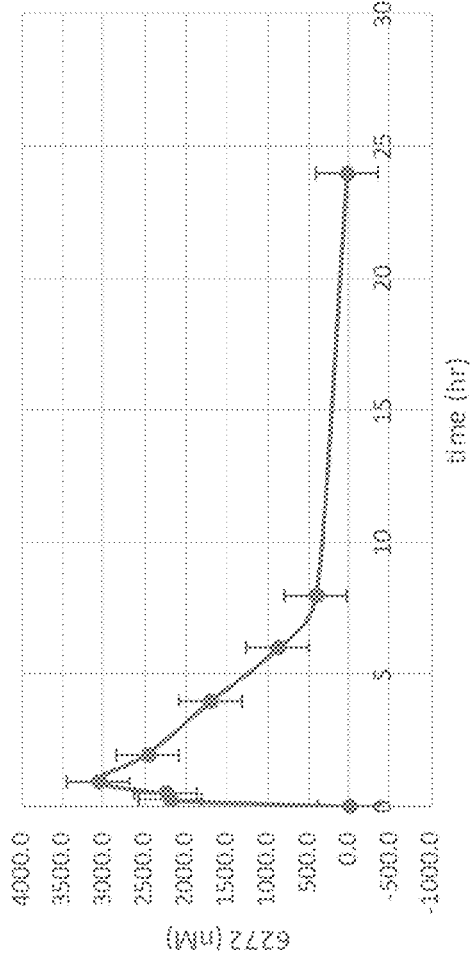
6272, IP, 4 mg/mL
| $T_{1/2}$ | hr | 3.46 |
| $T_{max}$ | hr | 0.83 |
| $C_{max}$ | ng/mL | 3650 |
| $C_{max}$ | µM | 3.09 |
| $AUC_{last}$ | min*ng/mL | 1277389 |
| $AUC_{last}$ | µM.hr | 18.00 |
| $AUC_{INF\_obs}$ | min*ng/mL | 1286951 |
| $AUC_{\%Extrap}$ | | 0.75 |
| $Cl\_obs$ | mL/min/kg | 3.11 |

SUBSTITUTED 3-AMINO-5-PHENYLBENZAMIDE COMPOUNDS AS COVALENT INHIBITORS OF ENHANCER ZESTE HOMOLOG 2 (EZH2) AND PROTEOLYSIS-TARGETING CHIMERIC DERIVATIVES THEREOF (PROTACS) THAT INDUCE DEGRADATION OF EZH2

CROSS-REFERENCE TO RELATED APPLICATIONS

The present application claims priority to U.S. Provisional Patent Application No. 63/201,459, filed Apr. 30, 2021, the entire contents of which are hereby incorporated by reference.

STATEMENT REGARDING FEDERALLY SPONSORED RESEARCH

This invention was made with government support under grant number W81XWH-17-1-0405 and W81XWH-17-1-0406 awarded by the U.S. Army Medical Research and Materiel Command. The government has certain rights in the invention.

BACKGROUND OF THE INVENTION

The field of the invention relates to covalent inhibitors of enhancer zeste homolog 2 (EZH2) and proteolysis-targeting chimeric derivatives thereof (PROTACs) that induce degradation EZH2. In particular, the field of the invention relates to substituted 3-amino-5-phenylbenzamide compounds and PROTAC derivatives thereof that target the EZH2 for degradation that may be utilized for the treatment of diseases and disorders associated with the activity of EZH2 such as cell proliferation diseases and disorders including cancer.

The protein EZH2 is an essential component of the PRC2 complex. EZH2 is a methyltransferase enzyme that produces H3K27me3. Aberrant EZH2 activity leads to tumor growth and is a well-validated target in a variety of cancers. Previously, Kong et al. have demonstrated that astemizole arrests the proliferation of cancer cells by disrupting the EZH2-EED interaction of polycomb repressive complex 2 (J. Med. Chem. 2014, 57(22), 9512-9521). However, existing EZH2 inhibitors require very high doses to sufficiently inhibit enzyme activity. As such, EZH2 inhibitors that are effective at lower doses are desirable.

In addition to its enzymatic function, EZH2 is also able to increase tumor cell proliferation in a non-enzymatic manner. Because of this, enzyme inhibitors may not fully abolish all of its oncogenic functions and therapeutic agents that induce degradation of EZH2 are desirable.

Proteolysis-targeting chimeric molecules (PROTACs) are an emerging technology that may be utilized to target previously "undruggable" targets, such as transcription factors and non-enzymatic proteins. (See, e.g., An et al., "Small-molecule PROTACs: An emerging and promising approach for the development of targeted therapy drugs," EBioMedicine. 2018 October; 36: 553-562; and Gu et al., "PROTACs: An Emerging Targeting Technique for Protein Degradation in Drug Discovery," Bioessays. 2018 April; 40(4):e1700247, the contents of which are incorporated herein by reference in their entireties). PROTACs are chimeric molecules that may be characterized as "hetero-bifunctional" in that PROTACs include a ligand for recruiting an E3 ubiquitin ligase, a linker, and another ligand to bind with the protein targeted for degradation. Designed as such, PROTACs "hijack" the E3 ubiquitin ligase to the protein which is targeted for protein degradation via ubiquitination, even if the targeted protein is not a physiological substrate for degradation via the ubiquitin-proteasome system.

Here, we disclose covalent inhibitors of EZH2. The disclosed EZH2 inhibitors may be derivatized to form PROTACs that induce degradation of EZH2.

BRIEF SUMMARY OF THE INVENTION

Disclosed are covalent inhibitors of enhancer zeste homolog 2 (EZH2) which may be utilized as EZH2 targeting agents. The disclosed compounds may be characterized as substituted 3-amino-5-phenylbenzamide compounds. The disclosed compounds may be utilized as covalent inhibitors of EZH2 and further may be derivatized to form proteolysis-targeting chimeric molecules (PROTACs) that target EZH2 for degradation. The disclosed compounds and PROTACs may be used in pharmaceutical compositions and methods for treating cell proliferative disorders associated with EZH2 activity, such as cancer.

The disclosed compounds may include substituted 3-amino-5-phenylbenzamide compounds having a Formula I:

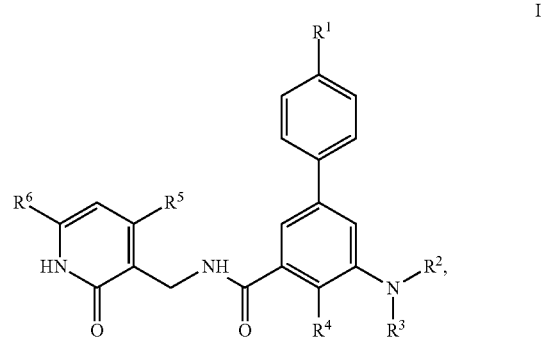

wherein
$R^1$ is hydrogen, alkyl, or —$CH_2$—X, wherein X is selected from hydrogen, alkyl, amino, piperazinyl (e.g. piperazin-1-yl or N-piperazinyl), morpholinyl (e.g., morpholin-4-yl or N-morpholinyl), piperidinyl (e.g., piperidin-4-yl or N-piperidinyl), and maleimidyl (e.g., N-maleimidyl), and X optionally is substituted with a substituent selected from alkyl, alkoxy, —C(O)—H, —C(O)—$(CH_2)_m$—$CH_3$ where m is 0-20, —C(O)—$(CH_2CH_2O)_n$—H or —C(O)—$(CH_2CH_2O)_n$—$CH_3$ where m is 1-16, —C(O)—$CH_2OCH_3$, —C(O)—$CH_2$—CH($CH_2CH_2CH_3$)$_2$, —C(O)—CH═CH-phenyl, —C(O)—$CH_3$, —C(O)—$CH_2Cl$, —C(O)—CH═C($CH_3$)$_2$, —C(O)—CH═$CH_2$, —C(O)-ethynyl, —C(O)-adamantyl, —S(O)(O)—H, —S(O)(O)—$CH_3$, —S(O)(O)-phenyl, —C(O)—$CH_2$—$CH_3$, —$CH_2$—S(O)(O)—H, —$CH_2$—$CH_2$—S(O)(O)—H, —CH2-CH2-S(O)(O)—$CH_3$, —$CH_2$—$CH_2$—S(O)(O)-phenyl, —CH═CH—S(O)(O)—H, —CH═CH—S(O)(O)—$CH_3$, and —CH═CH—S(O)(O)-phenyl;
$R^3$ is selected from hydrogen, alkyl, piperidinyl (e.g., piperidin-4-yl) and oxane (e.g., oxan-4-yl), wherein $R^3$ optionally is substituted with a substituent selected from alkyl, alkoxy, —C(O)—H, —C(O)—$(CH_2)_m$—

CH$_3$ where m is 0-20, —C(O)—(CH$_2$CH$_2$O)$_n$—H or —C(O)—(CH$_2$CH$_2$O)$_n$—CH$_3$ where m is 1-16, —C(O)—CH$_2$OCH$_3$, —C(O)—CH$_2$—CH(CH$_2$CH$_2$CH$_3$)$_2$, —C(O)—CH=CH-phenyl, —C(O)—CH$_3$, —C(O)—CH$_2$Cl, —C(O)—CH=C(CH$_3$)$_2$, —C(O)—CH=CH$_2$, —C(O)-ethynyl, —C(O)-adamantyl, —S(O)(O)—H, —S(O)(O)—CH$_3$, —S(O)(O)-phenyl, —C(O)—CH$_2$—CH$_3$, —CH$_2$—S(O)(O)—H, —CH$_2$—CH$_2$—S(O)(O)—H, —CH$_2$—CH$_2$—S(O)(O)—CH$_3$, —CH$_2$—CH$_2$—S(O)(O)-phenyl, —CH=CH—S(O)(O)—H, —CH=CH—S(O)(O)—CH$_3$, and —CH=CH—S(O)(O)-phenyl;

R$^3$ is hydrogen or alkyl;
R$^4$ is hydrogen or alkyl;
R$^5$ is hydrogen or alkyl; and
R$^6$ is hydrogen or alkyl.

The disclosed compounds may exhibit one or more biological activities. The disclosed compounds may inhibit one or more biological activities of EZH2 protein (e.g., the methyltransferase activity of EZH2). The disclosed compounds may inhibit the growth of cells that express EZH2 protein (preferably by at least about 10%, 20%, 30%, 40%, or 50%, at a concentration of less than about 100 µM, 50 µM, 10 µM, 1 µM, 0.1 µM, 0.05 µM, 0.01 µM, 0.005 µM, 0.001 µM, or less). The disclosed compounds may not inhibit the growth of cells that do not express EZH2 protein (preferably at a concentration of greater than about 0.001 µM, 0.005 µM, 0.01 µM, 0.5 µM, 0.1 µM, 1.0 µM, 10 µM, and 100 µM or higher).

The disclosed compounds may be derivatized to form PROTACS that induce degradation of EZH2. The disclosed PROTACs may comprise a moiety that binds to EZH2 (e.g., a moiety that bind to EZH2 covalent) and that are covalently attached to a moiety that binds to a ubiquitin ligase. The disclosed PROTACs typically include a first targeting moiety that binds to EZH2 (M$_{EZH2}$) which may be derived from a substituted 3-amino-5-phenylbenzamide compound. The first targeting moiety may be covalently attached via a bond or a linker (L) to a second targeting moiety that binds to a ubiquitin ligase such as an E3 ubiquitin ligase (M$_{E3}$). As such, the disclosed PROTACS may be described as having a formula M$_{EZH2}$-L-M$_{E3}$ or M$_{E3}$-L-M$_{EZH2}$.

The disclosed PROTACs preferably target the E3 ubiquitin ligase moiety to EZH2 which subsequently is ubiquitinated and targeted for degradation. The disclosed PROTACs may be utilized for the treatment of diseases and disorders associated with the biological activity of EZH2 such as cell proliferation diseases and disorders including cancer.

The EZH2 targeting moiety of the disclosed PROTACs (M$_{EZH2}$) typically is linked via a bond or a linker (L) to a second targeting moiety that binds to an E3 ubiquitin ligase (M$_{E3}$). The EZH2 targeting moiety may comprise a radicalized form of a compound of a Formula I, for example wherein the EZH2 moiety is attached to the linker via a radicalized form of substituent R$^1$ or R$^2$ of Formula I.

Suitable linkers for the disclosed PROTACs may include, but are not limited to linkers comprising an alkyl moiety and/or a polyethylene glycol moiety. Other suitable linkers for the disclose PROTACS may include an alkyl moiety, an alkylalkyne moiety, and/or an aminoalkyl alkyne moiety.

The E3 ubiquitin ligase targeting moiety of the disclosed PROTACs (M$_{E3}$) typically binds and/or targets the PROTACs to an E3 ubiquitin ligase. Suitable E3 ubiquitin ligases may include, but are not limited to, Von Hippel-Lindau (VHL) E3 ubiquitin ligase, cereblon (CRBN) E3 ubiquitin ligase, inhibitor of apoptosis protein (IAP) E3 ubiquitin ligase, and mouse double minute 2 homolog (MDM2) E3 ubiquitin ligase.

The E3 ubiquitin ligase targeting moiety of the disclosed PROTACs (M$_{E3}$) typically is derived from a compound that binds to an E3 ubiquitin ligase, for example, as a ligand for an E3 ubiquitin ligase. Suitable ligands may include, but are not limited to, ligands derived from thalidomide, pomalidomide, lenalidomide, VHL ligand 1 (VHL-1), VHL ligand 2 (VHL-2), VH032, VL-269, LCL161, hydroxyproline-based ligands, and HIF-1α-derived (R)-hydroxyproline, including radicalized forms.

The disclosed PROTACs may exhibit one or more biological activities. The disclosed PROTACs may inhibit the growth of cells that express EZH2 (preferably by at least about 10%, 20%, 30%, 40%, or 50%, at a concentration of less than about 100 µM, 50 µM, 10 µM, 1 µM, 0.1 µM, 0.05 µM, 0.01 µM, 0.005 µM, 0.001 µM, or less). The disclosed PROTACs may not inhibit the growth of cells that do not express EZH2 (preferably at a concentration of greater than about 0.001 µM, 0.005 µM, 0.01 µM, 0.5 µM, 0.1 µM, 1.0 µM, 10 µM, and 100 µM or higher).

Also disclosed are pharmaceutical compositions comprising the disclosed compounds and PROTAC derivatives thereof and a suitable pharmaceutical carrier, excipient, or diluent. The disclosed pharmaceutical compositions may comprise an effective amount of the compound or PROTAC derivative thereof for inhibiting the growth of cancer cells when administered to a subject in need thereof.

Also disclosed are methods for treating cell proliferation diseases and disorders such as cancer. The methods may include administering the disclosed compounds or PROTAC derivatives thereof or pharmaceutical compositions comprising the disclosed compounds or PROTAC derivatives thereof to a subject in need thereof, for example, to a subject having cancer. The disclosed compounds and PROTAC derivatives thereof or pharmaceutical compositions comprising the disclosed compounds and PROTAC derivatives thereof may be administered with additional therapeutic agents, optionally in combination, in order to treat cell proliferative diseases and disorders. Cell proliferative diseases and disorders treated by the disclosed methods may include, but are not limited to, cancers selected from the group consisting of multiple myeloma, leukemia, non-small cell lung cancer, colon cancer, cancer of the central nervous system, melanoma, ovarian cancer, renal cancer, prostate cancer, lymphoma, and breast cancer.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

References to the compounds and molecules of Tables 1 and 2 in the drawings is done by the last four digits of the name shown in the Tables.

μM over a time course. Cell lysates were collected and subjected to western blot (WB) analyses using indicated antibodies. GAPDH was used as a loading control.

Figure 1:
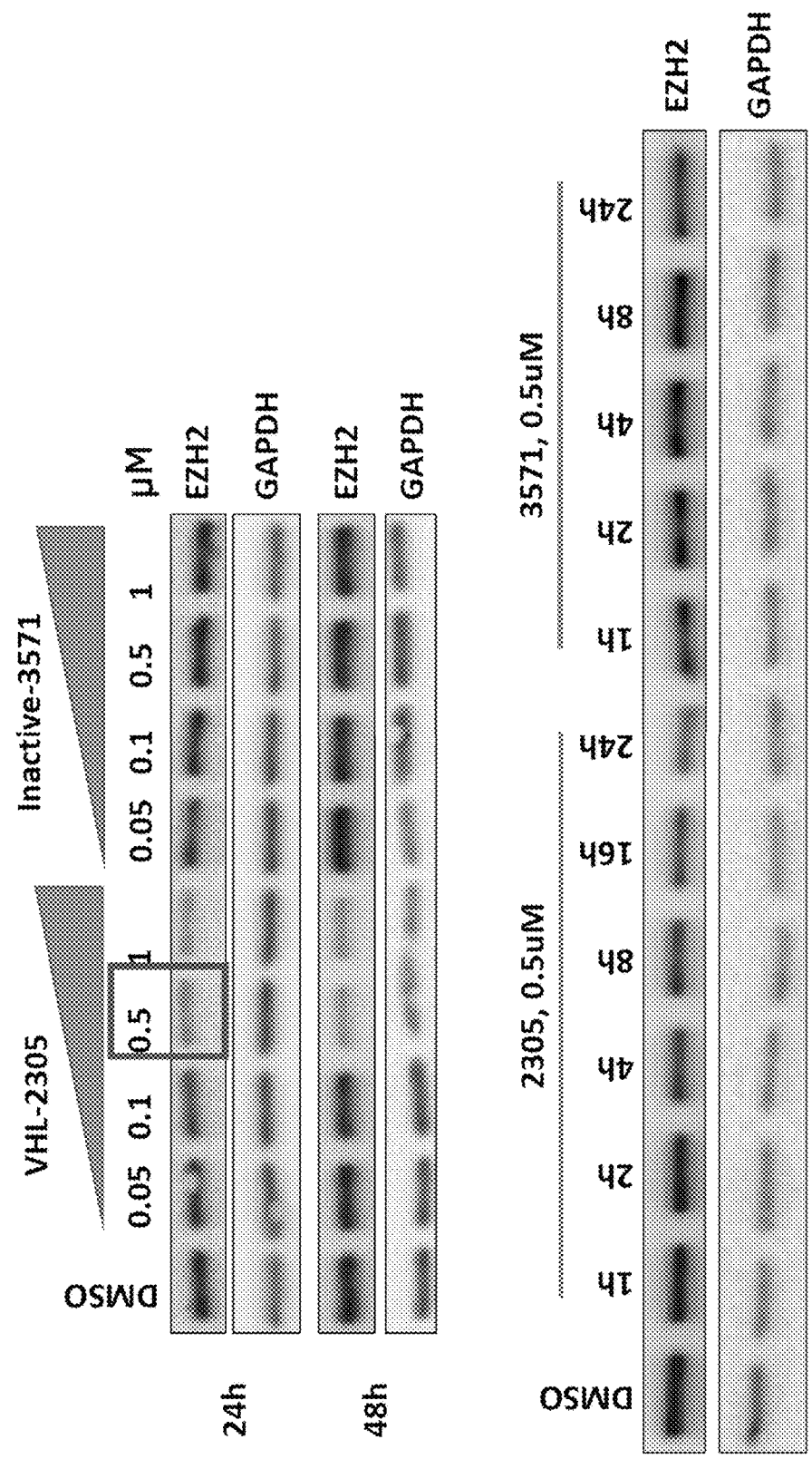
FIG. 1. VHL-2305 decreases EZH2 protein levels in prostate cancer (PCa) cells. PCa cell line C4-2B was treated with VHL-2305 or its inactive compound VHL-3571 (top) with increasing doses for 24 or 48 hours or (bottom) at 0.5
Figure 2:
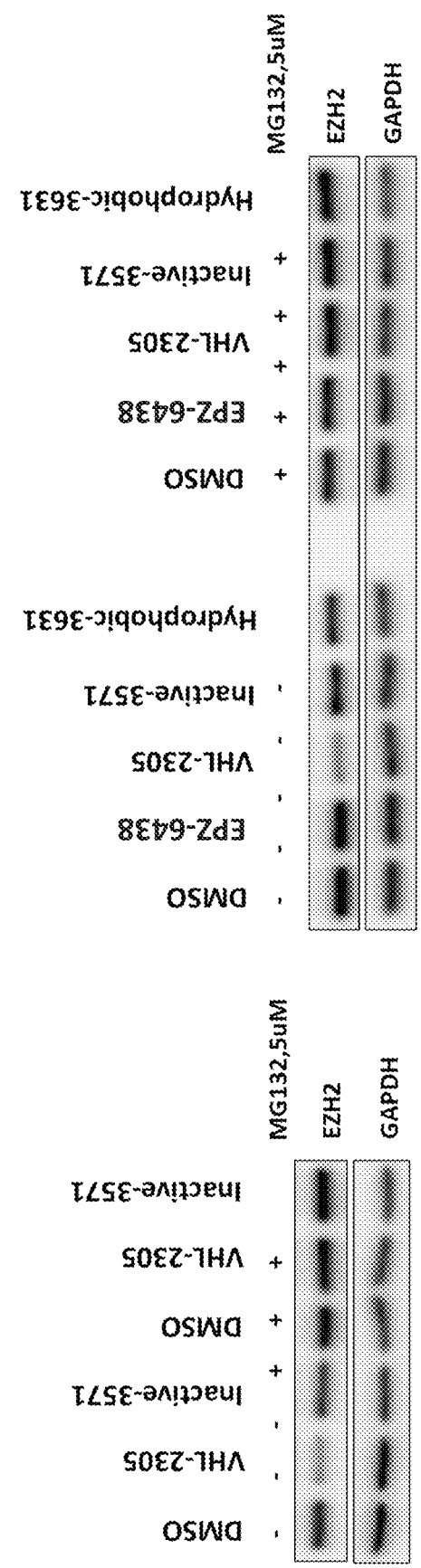

FIG. 2. VHL-2305-mediated EZH2 protein degradation can be rescued by proteasome inhibitor MG132, suggesting a mechanism involving ubiquitination and targeted degradation in the proteasome. (left) C4-2B cells were transfected with HA-ubiquitin (HA-Ub). (left) The cells are then treated with 5 μM VHL-2305, its inactive compound VHL-3571, and EPZ-6438 (Knutson, S. K, et al. Mol. Cancer Ther. (2014) 13(4):842-54), with or without MG132 blockade of proteasome function. (right) C4-2B cells were treated with indicated compounds with or without MG132. Cell lysates were collected and subjected to WB using anti-EZH2. GAPDH was used as a loading control.

Figure 3:
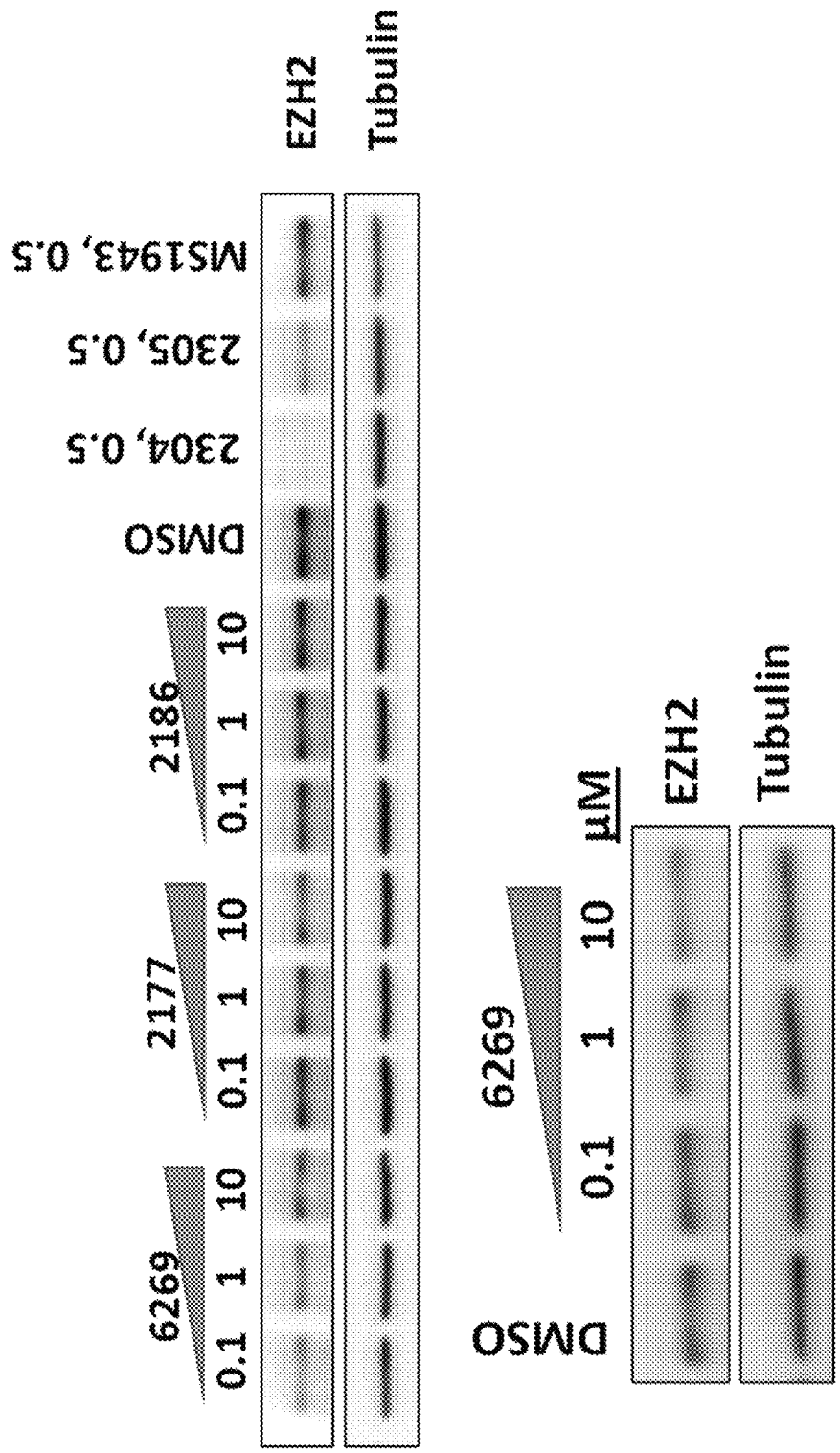

FIG. 3. Comparison of activity of compounds 6269, 2177, and 2186 to 2304 in degrading EZH2. C4-213 cells were treated with indicated compounds for 24 hours with indicated doses before WB analyses.

Figure 4:
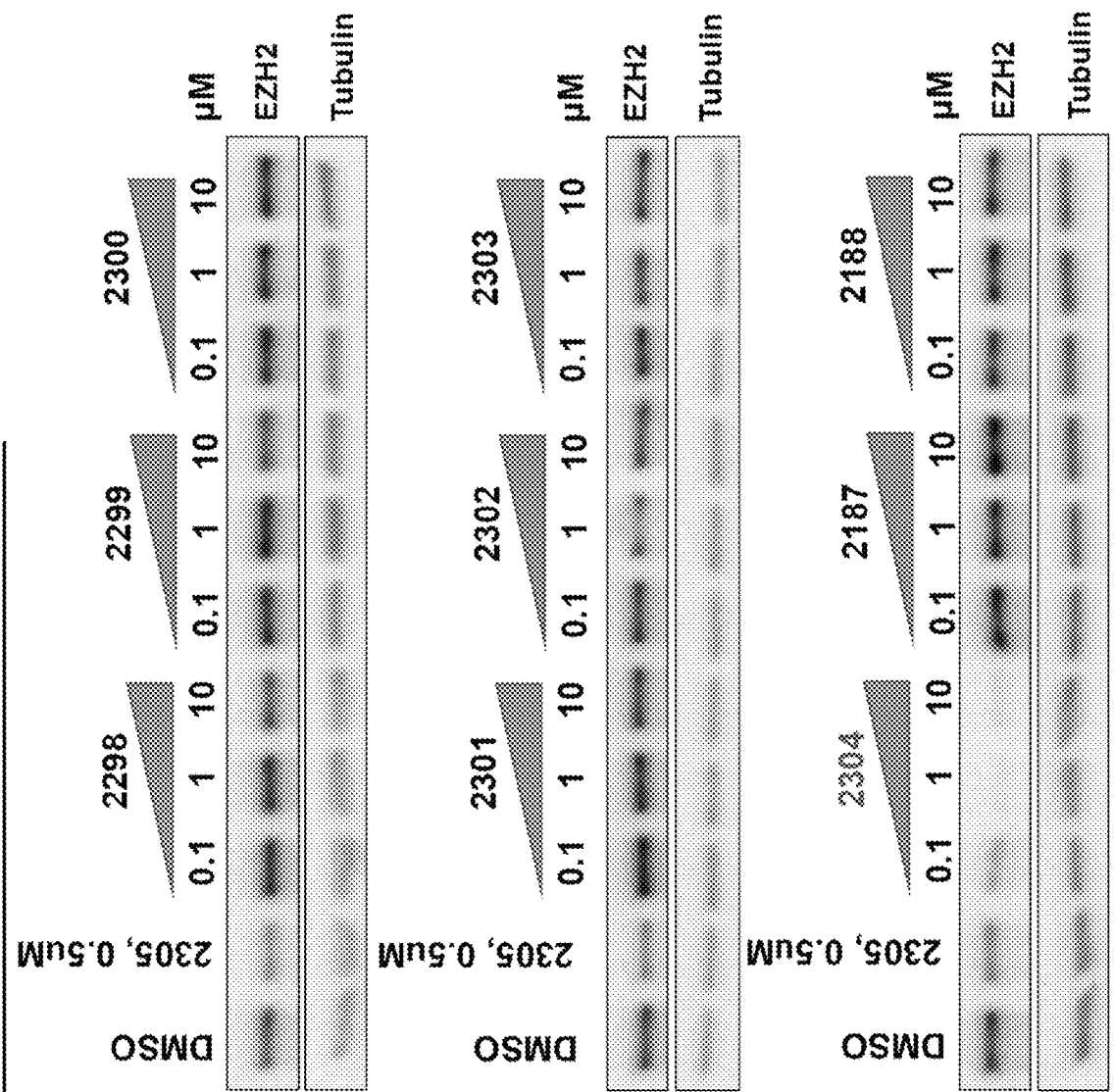

FIG. 4. Comparison of activity of 2298, 2299, 2300, 2301, 2302, 2303, 2304, 2187, and 2188. Compound 2304 is the most effective out of a list of VHL-PROTAC. C4-2B cells were treated with indicated compounds for 24 hours with indicated doses before WB analyses.

Figure 5:
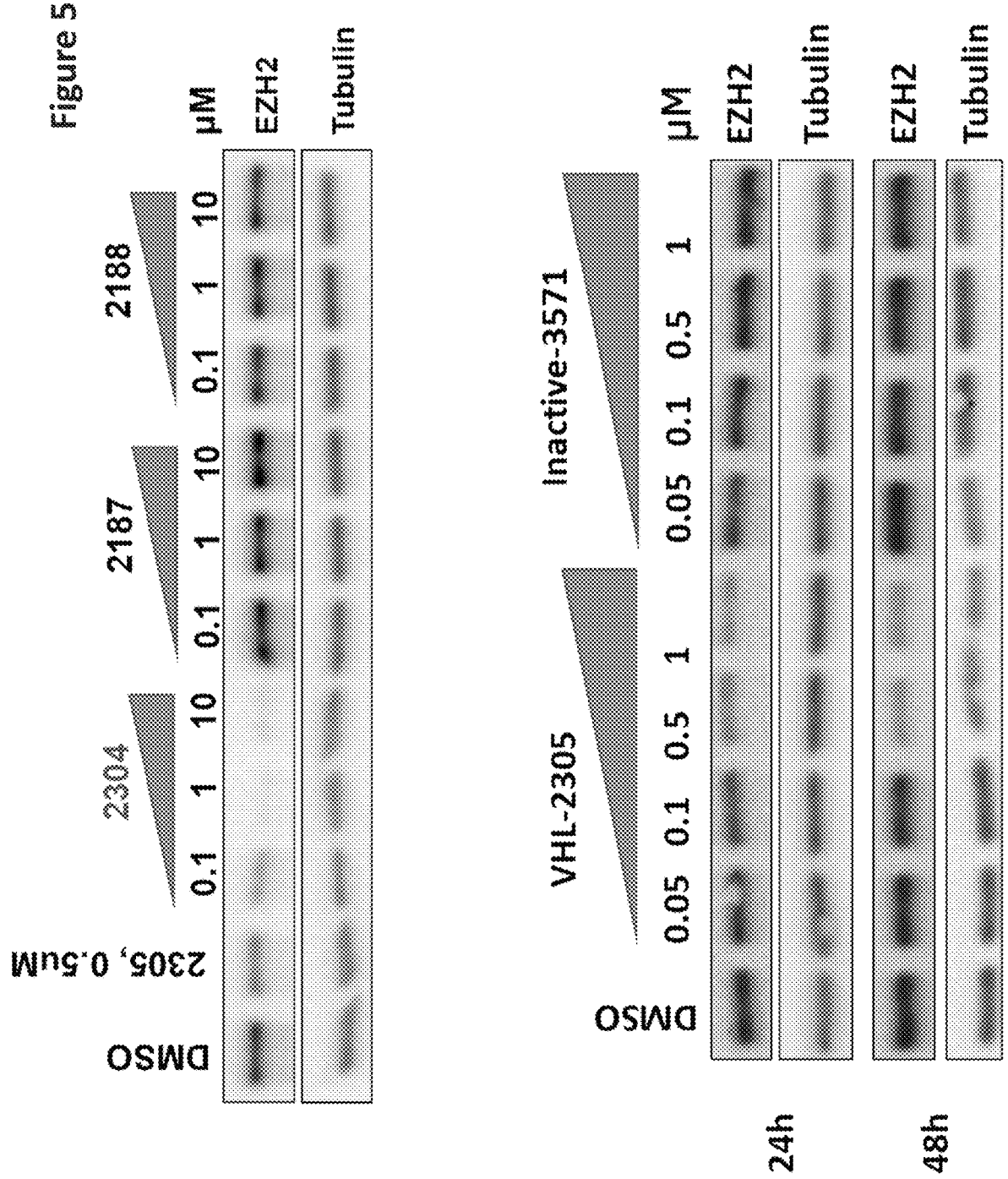

FIG. 5. Compound 2304 and 2305 are effective in degrading EZH2 protein. C4-2B cells were treated with indicated compounds for 24 or 48 hours with indicated doses before WB analyses.

Figure 6:
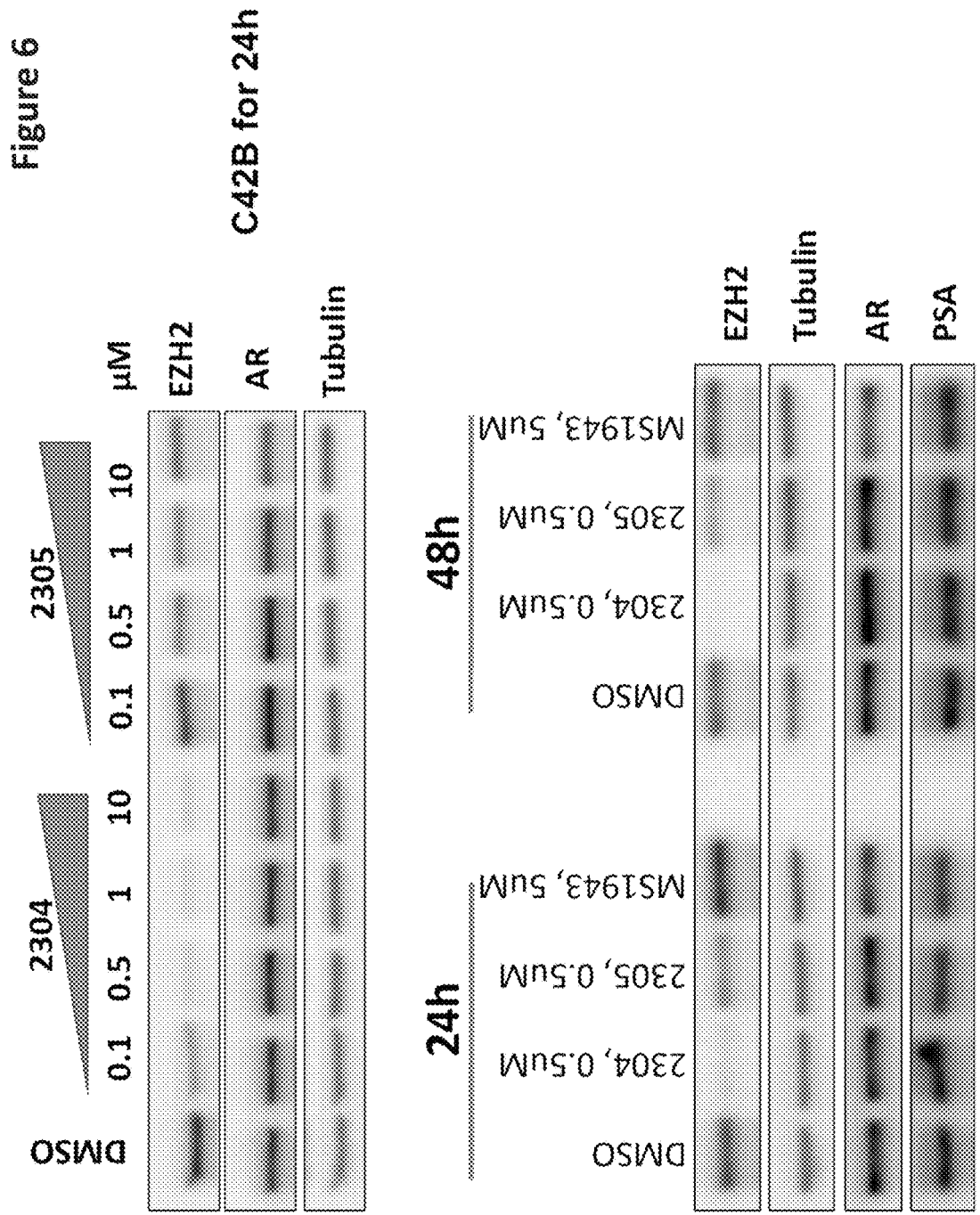

FIG. 6. Compound 2304 is more effective than 2305 in degrading EZH2 protein. C4-2B cells were treated with indicated compounds for 24 or 48 hours with indicated doses before WB analyses.

Figure 7:
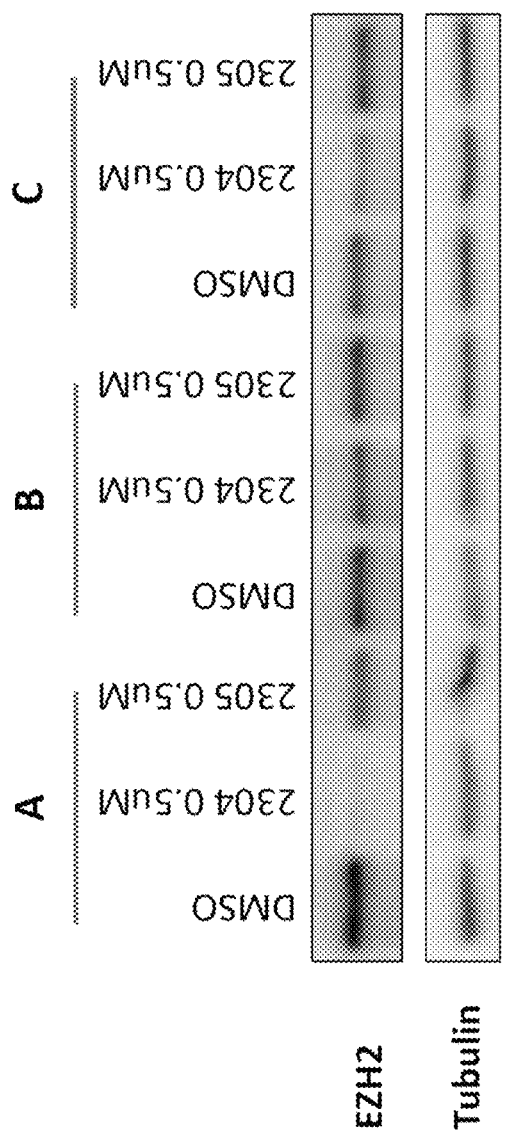

FIG. 7. Proteasome inhibitor MG132 restored EZH2 in cells treated with compound 2304 and 2305. C4-2B cells were treated with indicated compounds for 24 hours at indicated doses without (A) or with 5 μM or 10 μM MG132 (B-C) before WB analyses.

Figure 8:
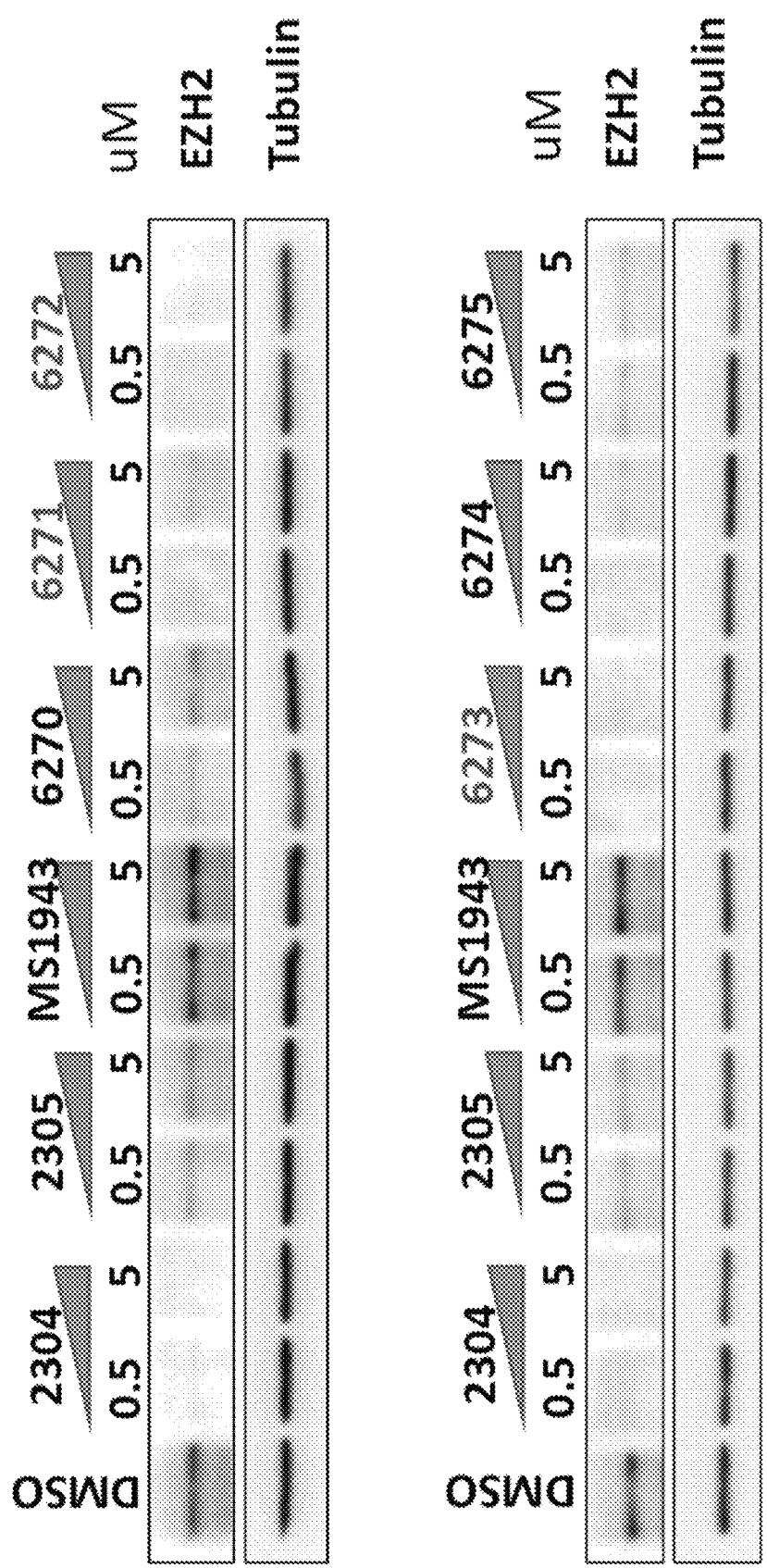

FIG. 8. Compounds 6270-6275 at μM doses are effective in degrading EZH2 protein. C4-2B cells were treated with indicated compounds for 24 hours with indicated doses before WB analyses.

Figure 9:
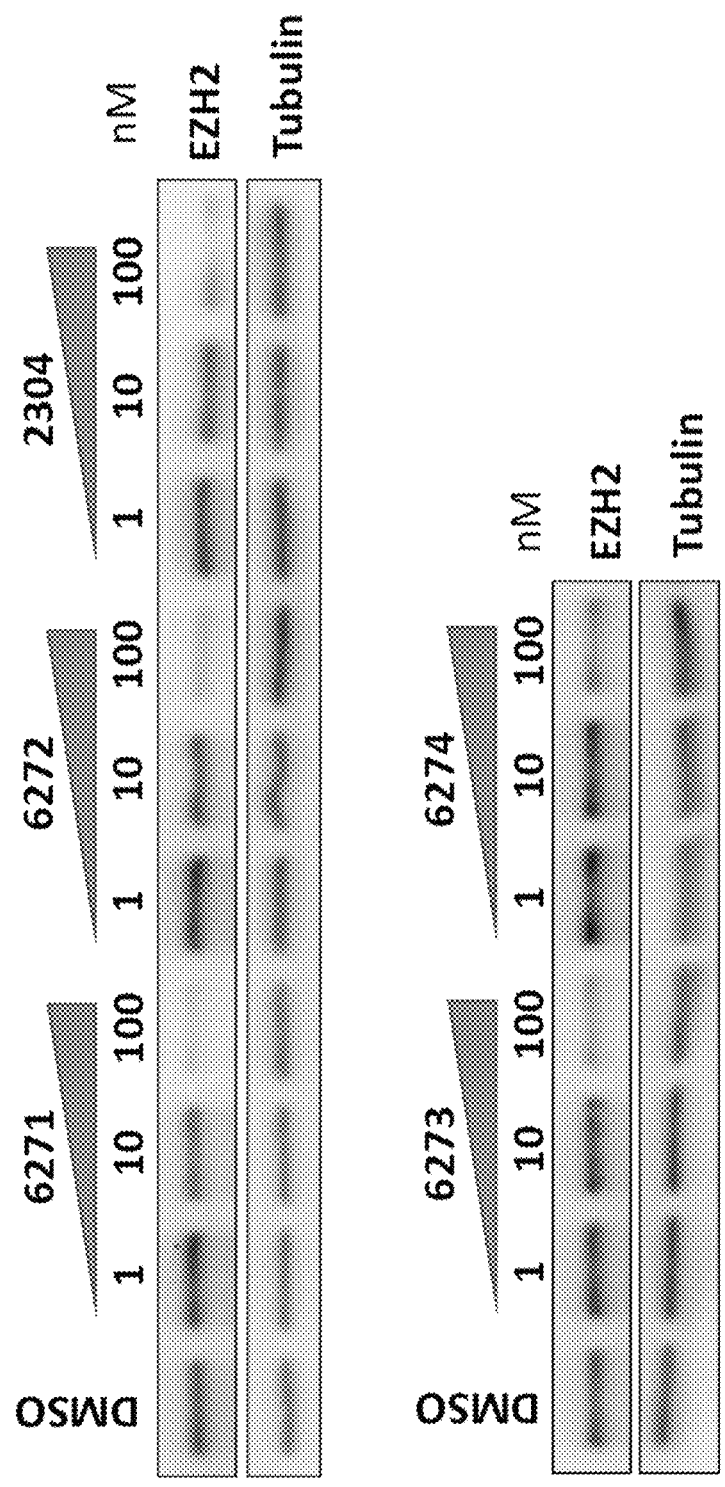

FIG. 9. Compounds 6270-6275 at nM doses are effective in degrading EZH2 protein. C4-2B cells were treated with indicated compounds for 24 hours with indicated doses before WB analyses.

Figure 10:
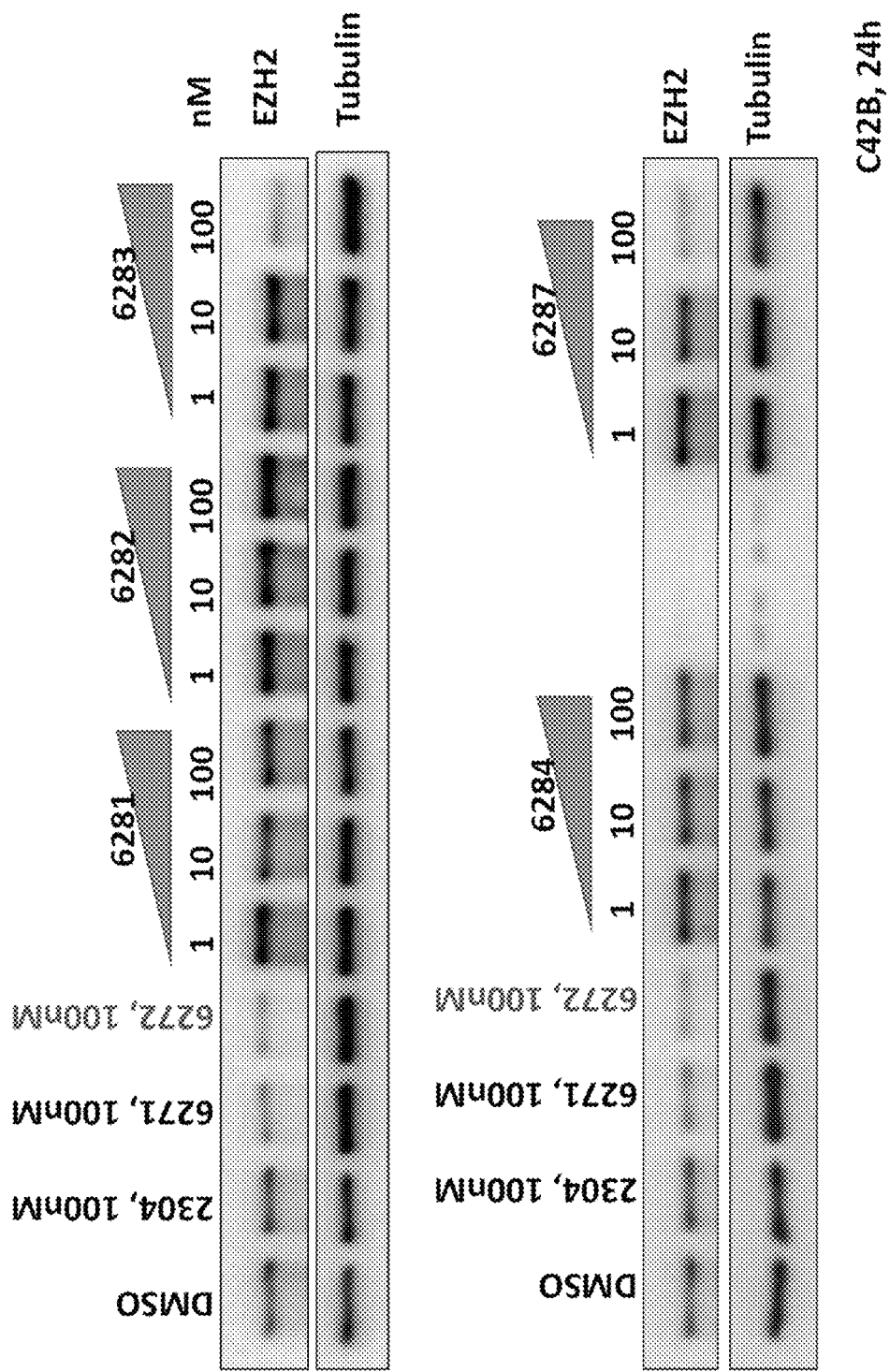

FIG. 10. Compound 6272 at nM doses is more effective than 2304 in degrading EZH2 protein. C4-2B cells were treated with indicated compounds for 24 hours with indicated doses before WB analyses.

Figure 11:
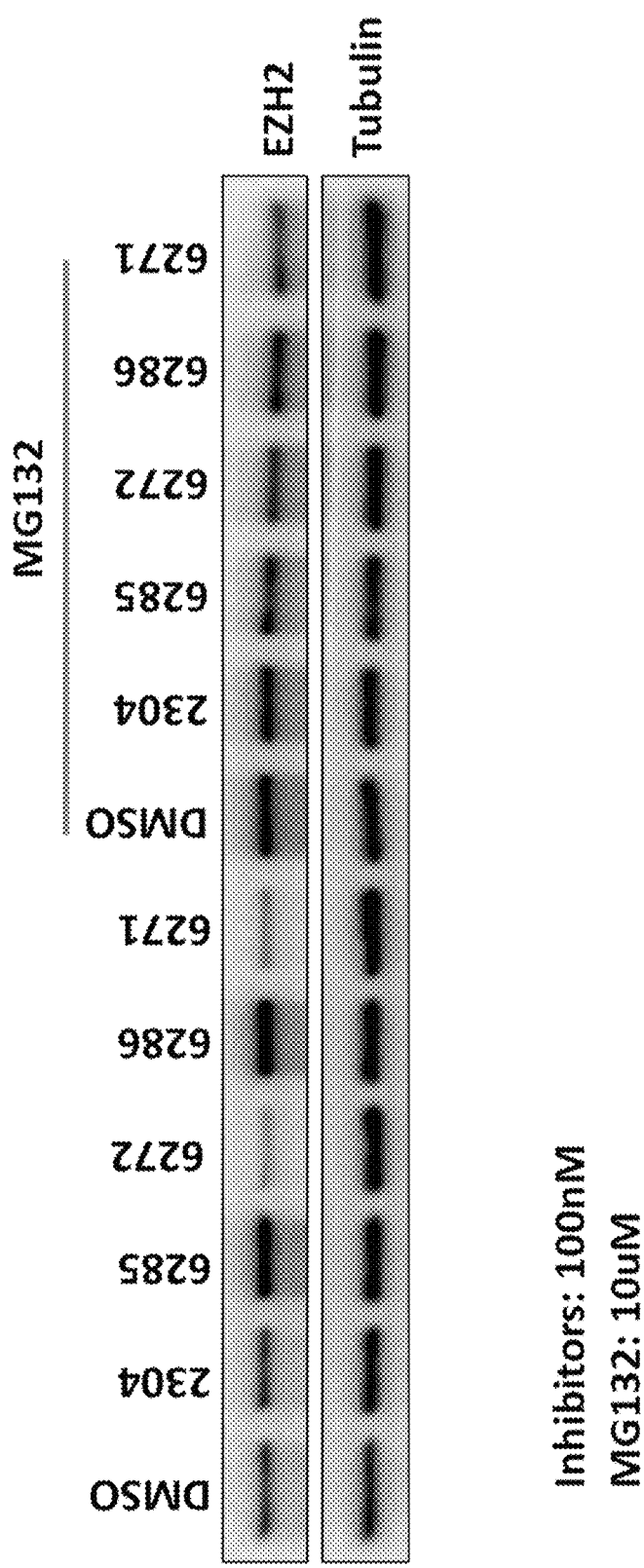

FIG. 11. Proteasome inhibitor MG132 restored EZH2 in cells treated with compound 6271 and 6273, similar as 2304. C4-2B cells were treated with indicated compounds for 24 hours at indicated doses without (left) or with 10 μM MG132 (right) treatment before WB analyses.

Figure 12:
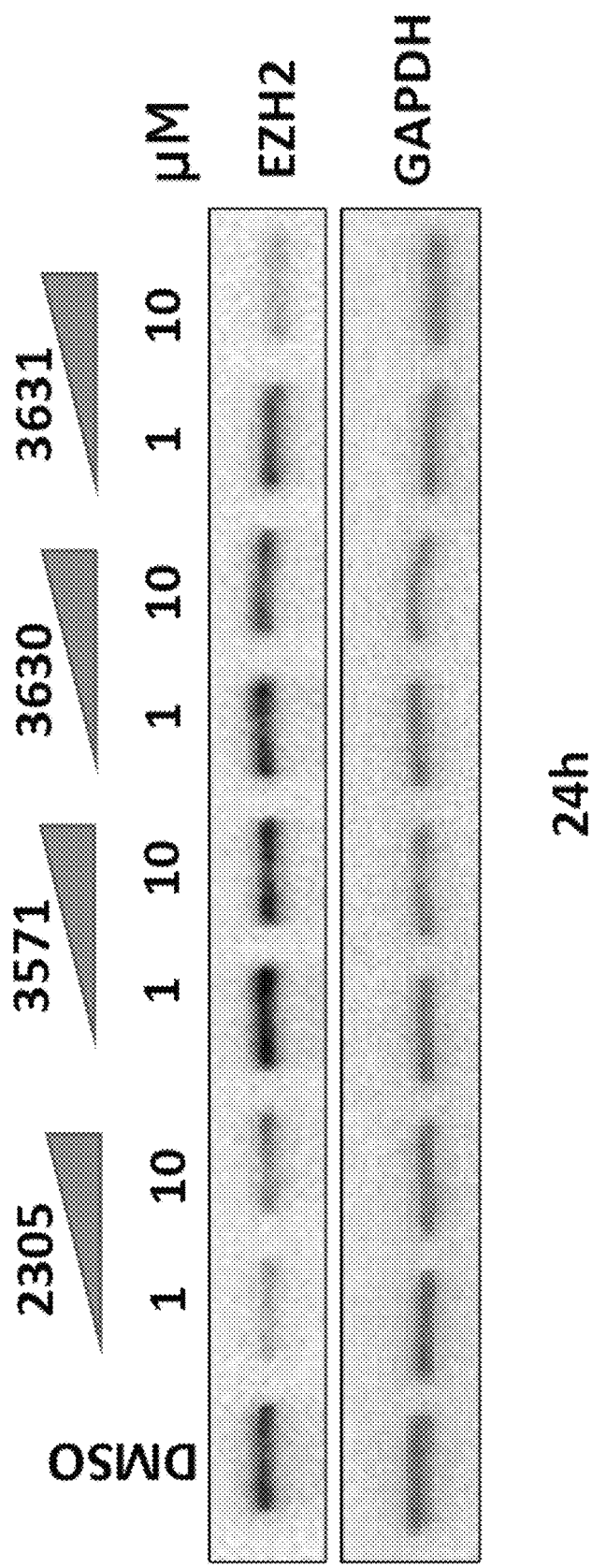

FIG. 12. Compounds 3571, 3630, 3631 are less effective than 2305 in degrading EZH2 protein. C4-2B cells were treated with indicated compounds for 24 hours with indicated doses before WB analyses.

Figure 13:
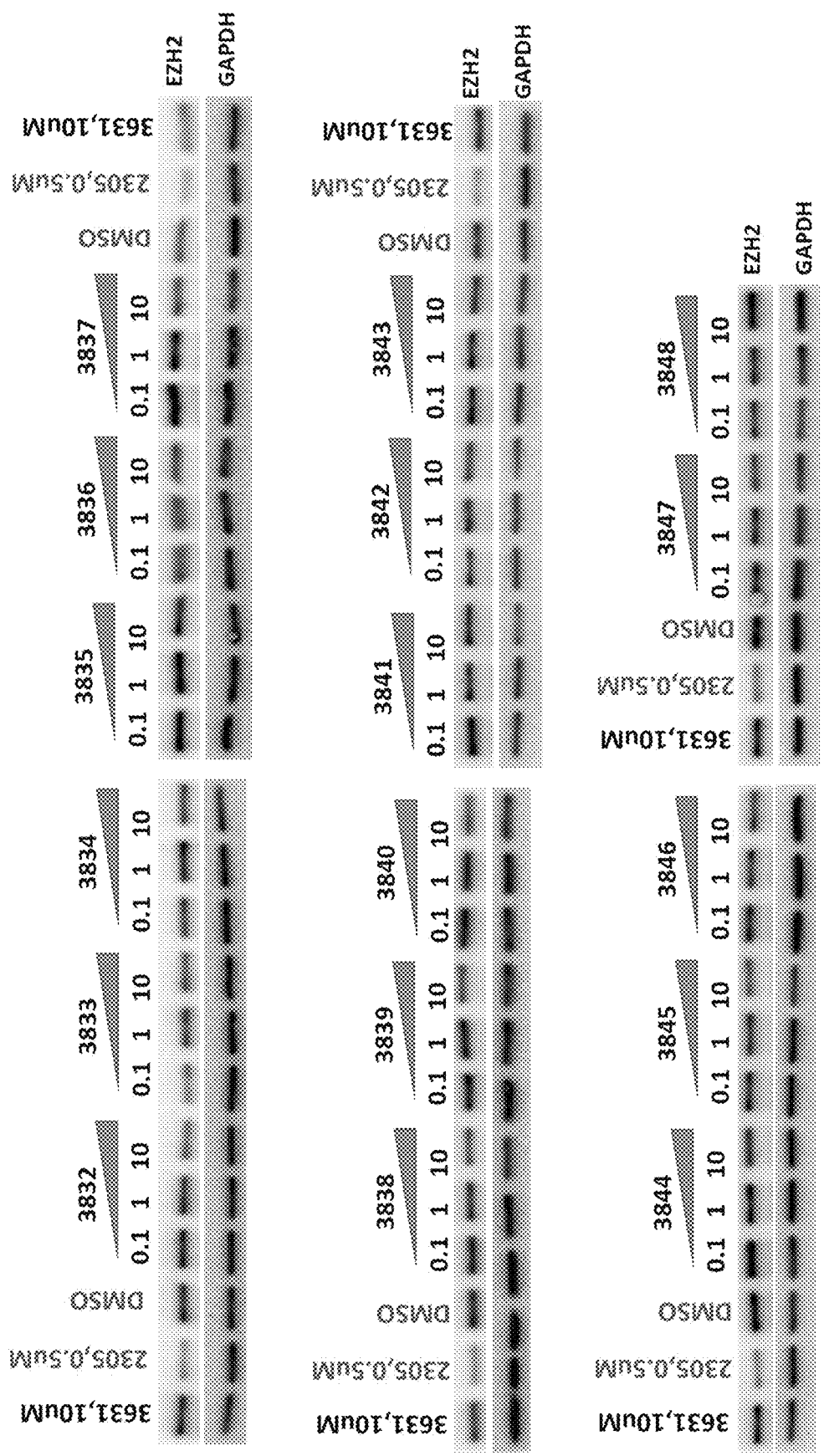

FIG. 13. Compounds 3832-3848 are mostly not effective in degrading EZH2 protein. C4-2B cells were treated with indicated compounds for 24 hours with indicated doses before WB analyses.

Figure 14:
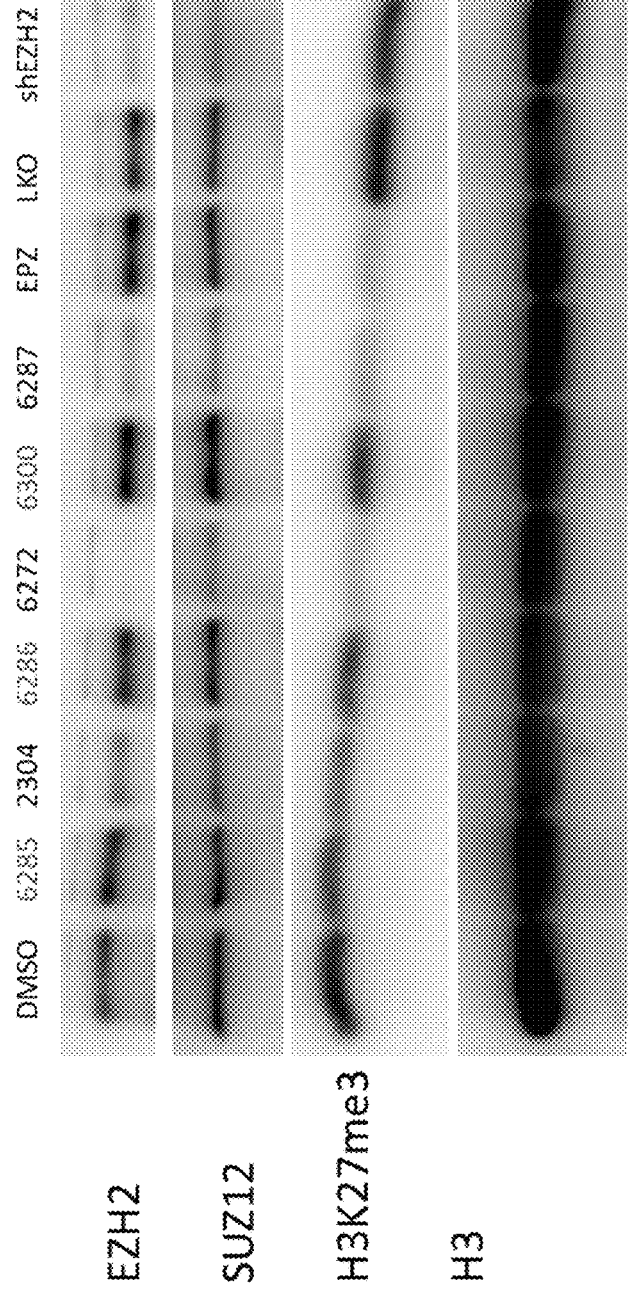

FIG. 14. Treatment of C4-2B cells with indicated compounds at 10 μM for 6 days. Active degraders 2304, 6272, and 6287 showed strong degradation of EZH2, as well as reduction of PRC2 component SUZ12, and reduced H3K27me3 levels. Compounds 6285, 6286, and 6300, which each have inverted stereochemistry at the hydroxyl stereocenter on the pyrrolidine and are therefore not expected to bind VHL, show no ability to degrade EZH2. Knockdown of EZH2 using shEZH2 is used as a control.

Figure 15A:
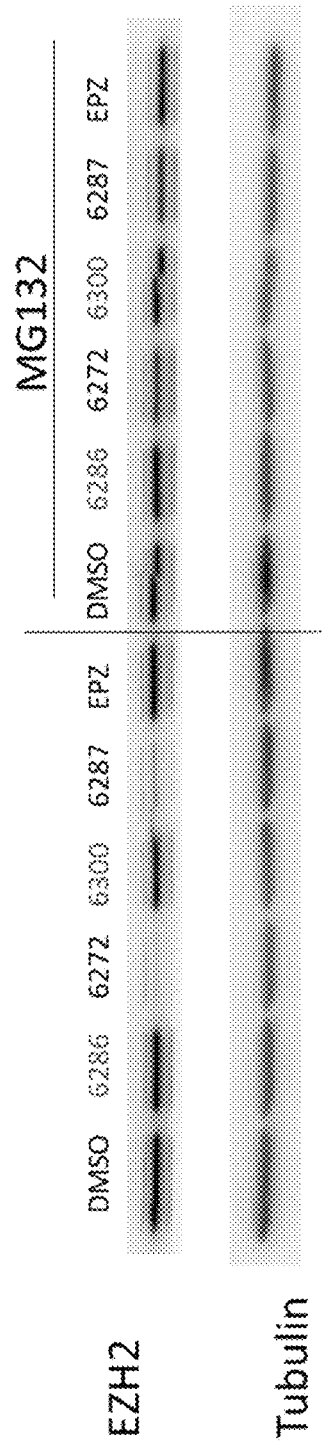
Figure 15B:
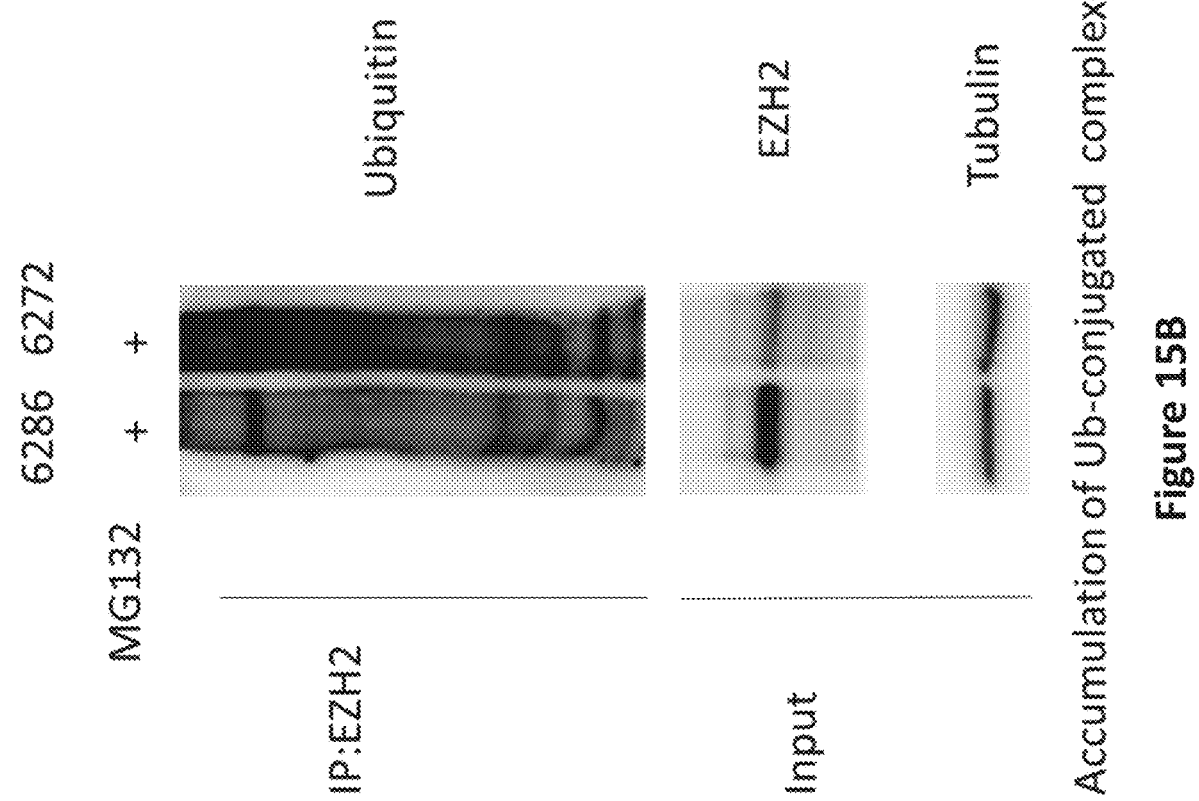

FIG. 15A-15B. (FIG. 15A) C4-2B cells were treated with indicated compounds at 10 μM for 24 hrs, with and without proteasome inhibitor MG132, and effects on EZH2 degradation were measured. (FIG. 15B) C4-2B cells were treated with indicated compounds plus proteasome inhibitor MG132 to block proteasome-mediated degradation of polyubiquitinated proteins. The active degrader 6272 shows a much greater degree of ubiquitination of EZH2 than the inactive compound 6286.

Figure 16:
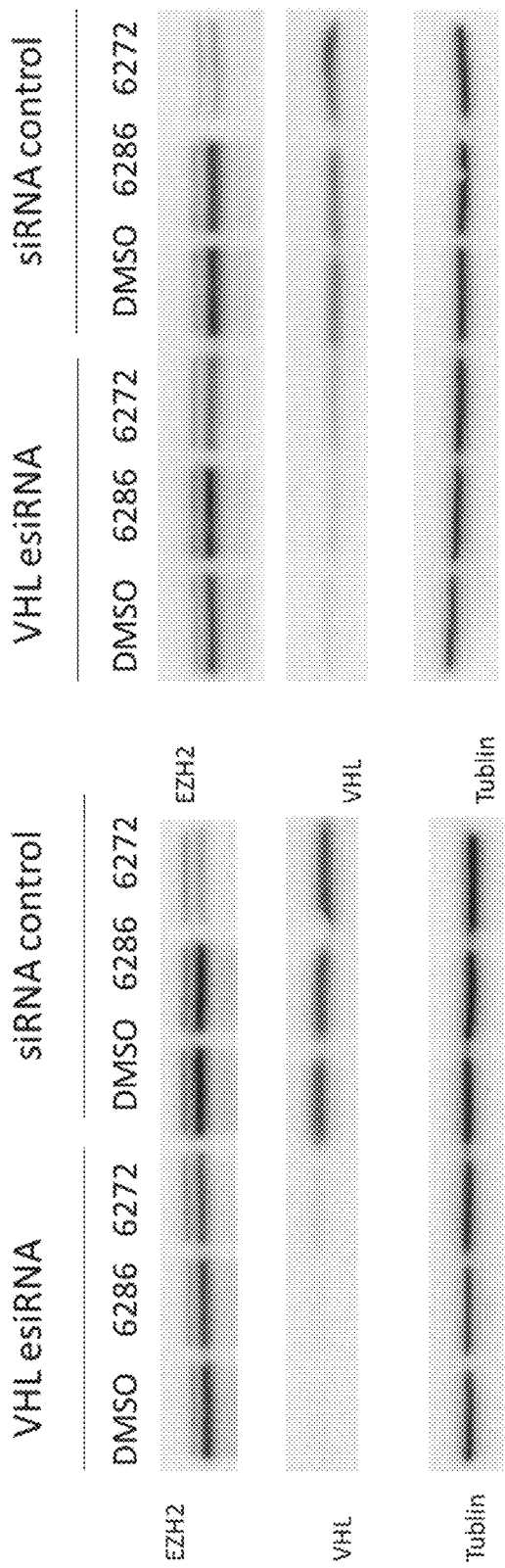

FIG. 16. Cells were treated with indicated compounds with either esiRNA knockdown of VHL or siRNA control (no EZH2 knockdown) and blotted for EZH2 and VHL. Knockdown of VHL results in the inhibition of the ability of active compounds 6272 to degrade EZH2. Compound 6286 is an inactive control. When VHL is present, as shown in the siRNA control lane, 6272 is able to strongly degrade EZH2. Experiment was run in duplicate with both replicates shown on the left and right sides.

FIG. 17A-17B. (FIG. 17A) Live imaging cell proliferation of LNCaP cells. Cells were treated with indicated compounds and monitored over 168 hours for proliferation by phase object confluence. DMSO is set as the negative control. Non-degradatory compounds 6300 and 6286 show limited ability to inhibit cell proliferation. EZH2 catalytic inhibitor EPZ-6438 ("EPZ") shows significant effects, while degrader compounds 6272 and 6287 show the greatest ability to decrease LnCaP proliferation. (FIG. 17B) Colony assays using LnCaP cells after treatment with the indicated compounds for 7 days. EPZ-6438 ("EPZ") shows a reduction in colonies versus DMSO negative control. Active degraders 6272 and 6287 show significant reduction in the colonies, while inactive derivatives of 6272 (6286) and 6287 (6300) show attenuated anti-proliferative effects.

Figure 18:
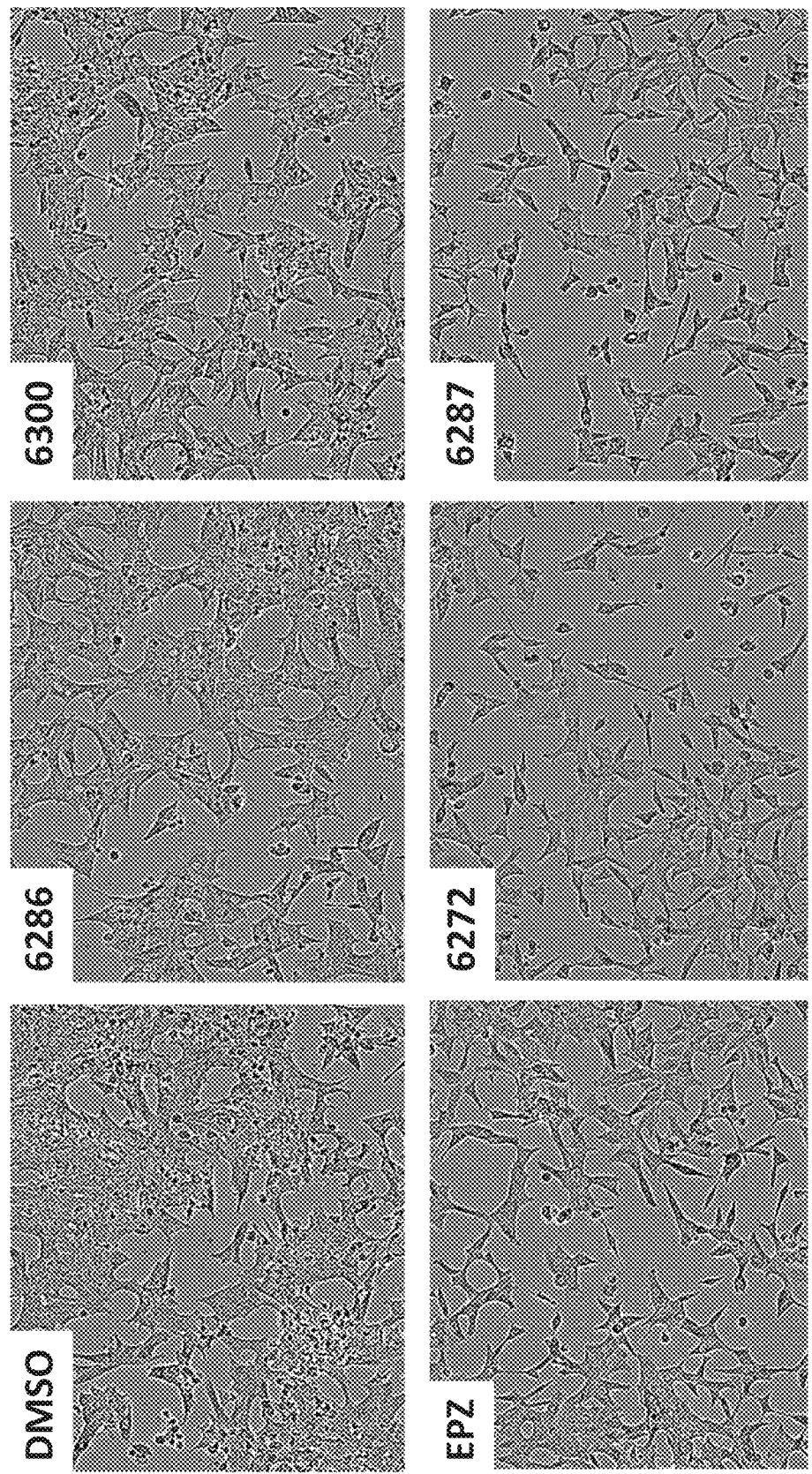

FIG. 18. Imaging of LnCaP cells after 12 days' treatment with the indicated compounds. Active degraders 6272 and 6287 show significant reduction in the cell density, while inactive derivatives of 6272 (6286) and 6287 (6300) show attenuated anti-proliferative effects.

Figure 19A:
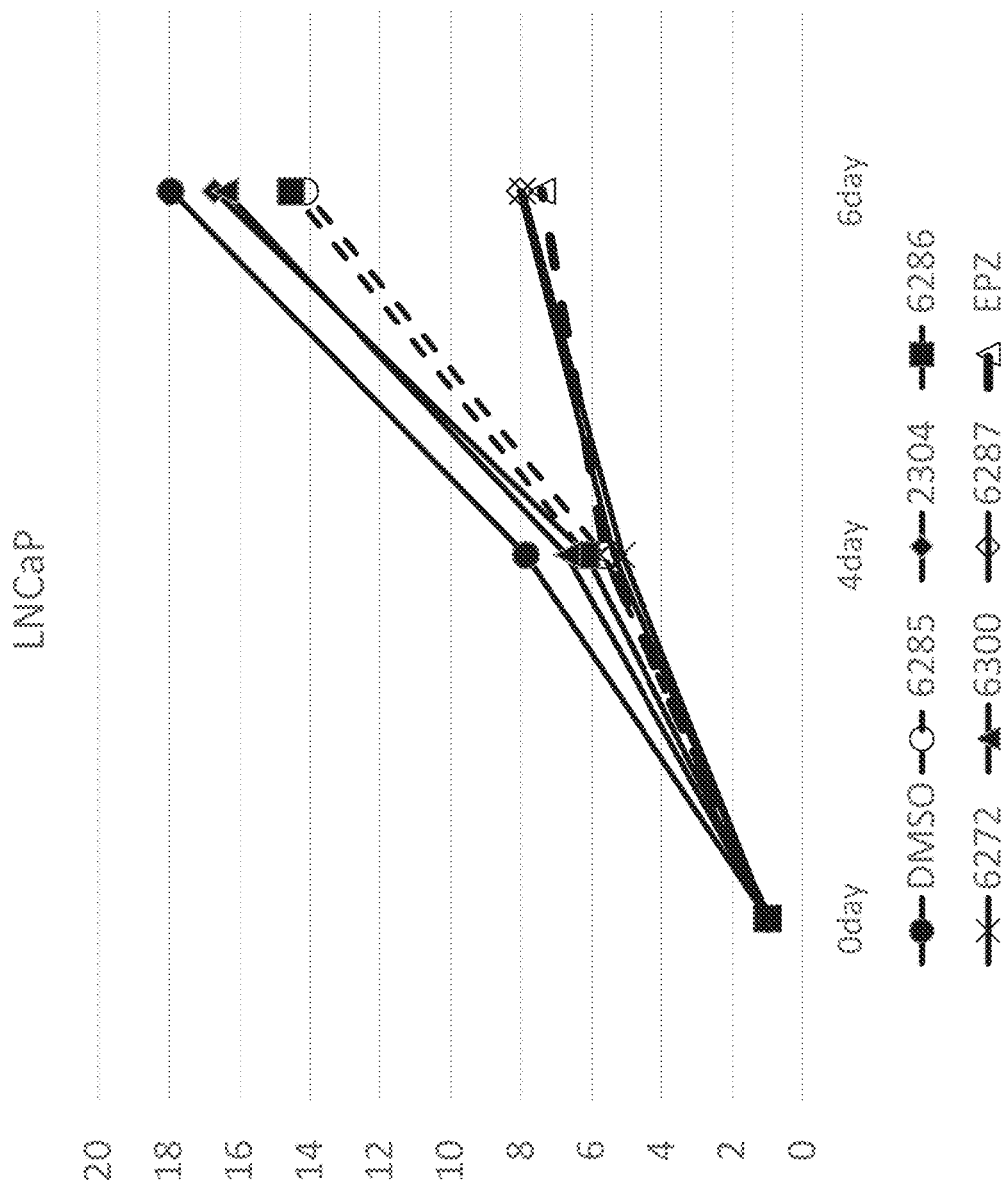
Figure 19B:
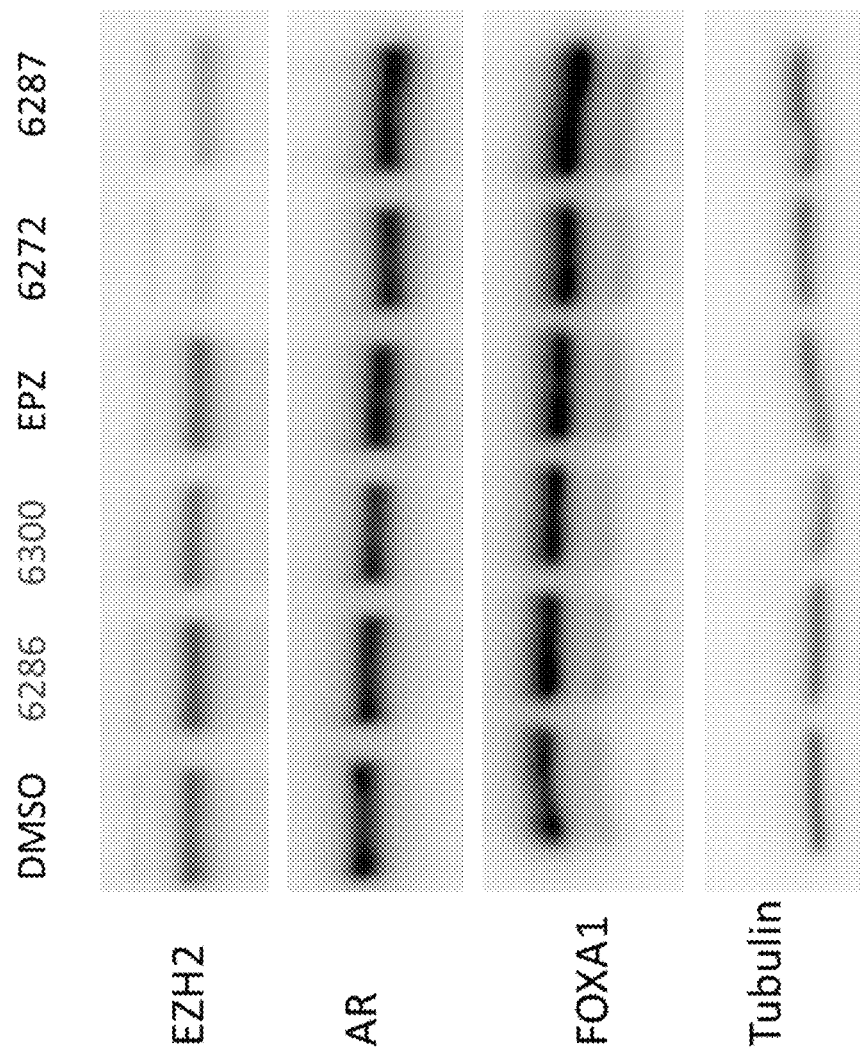

FIG. 19A-19B. (FIG. 19A) WST cell proliferation assay of indicated compounds in LNCaP cells. Cells were treated for 6 days. EPZ-6438, 6287, and 6272 all had similarly potent effects on inhibiting the proliferation of C4-2B cells at 6 days. Other, less potent EZH2 degraders, had a weaker ability to inhibit proliferation. (FIG. 19B) Effects of indicated compounds on EZH2, AR, and FOXA1 by western blot at 1 μM in LNCaP cells.

Figure 20A:
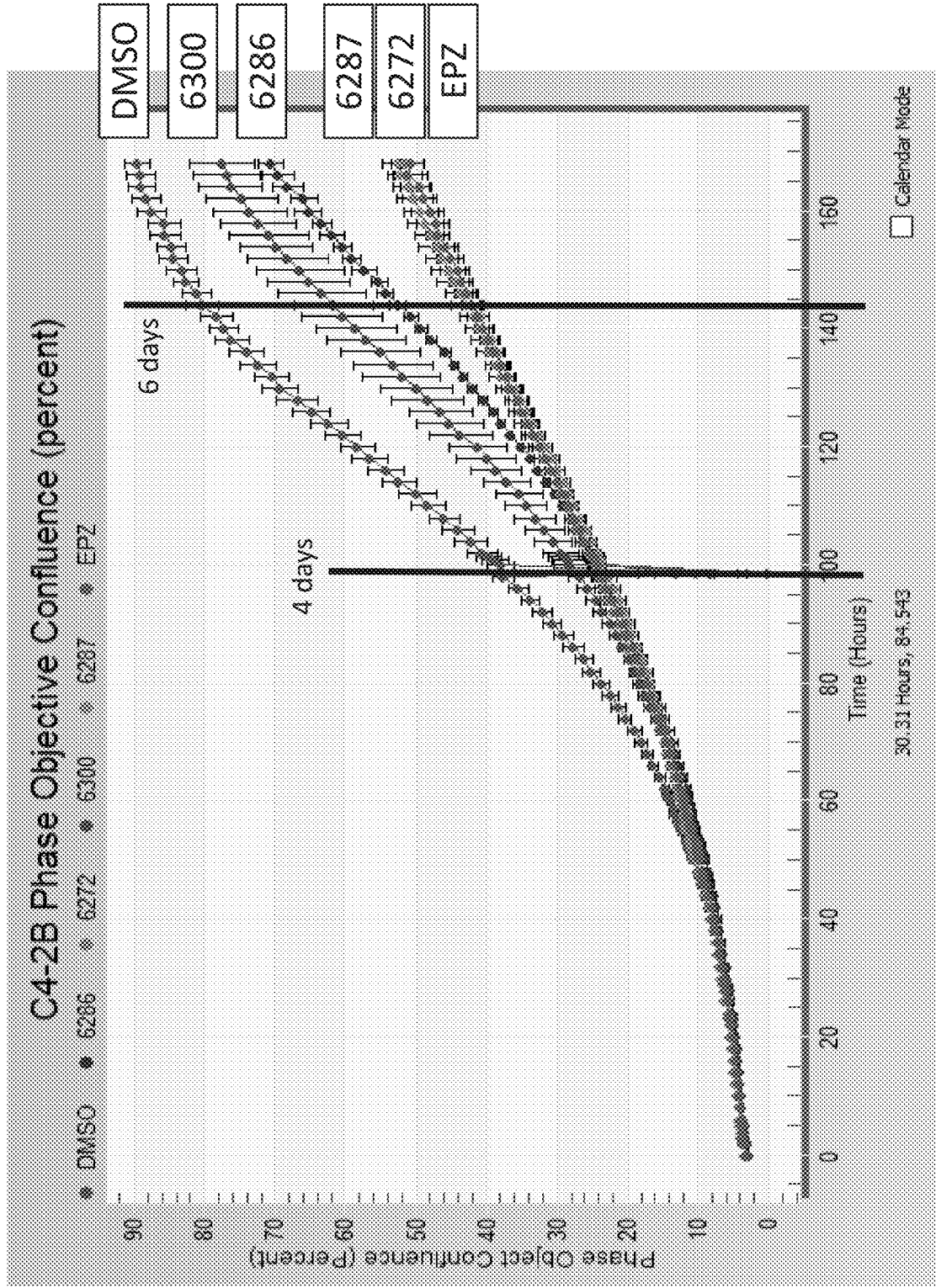

FIG. 20A-20B. (FIG. 20A) Live imaging cell proliferation of C4-2B cells. Cells were treated with indicated compounds and monitored over 168 hours for proliferation by phase object confluence. DMSO is set as the negative control. Non-degradatory compounds 6300 and 6286 show limited ability to inhibit cell proliferation. EZH2 catalytic inhibitor EPZ-6438 ("EPZ") shows significant effects that are similar to degrader compounds 6272 and 6287 in their ability to decrease C4-2B proliferation. (FIG. 20B) Colony assays using C4-2B cells after treatment with the indicated compounds for 7 days. EPZ-6438 ("EPZ") shows a reduction in colonies versus DMSO negative control. Active degraders 6272 and 6287 show significant reduction in the colonies, while inactive derivatives of 6272 (6286) and 6287 (6300) show attenuated anti-proliferative effects.

Figure 21:
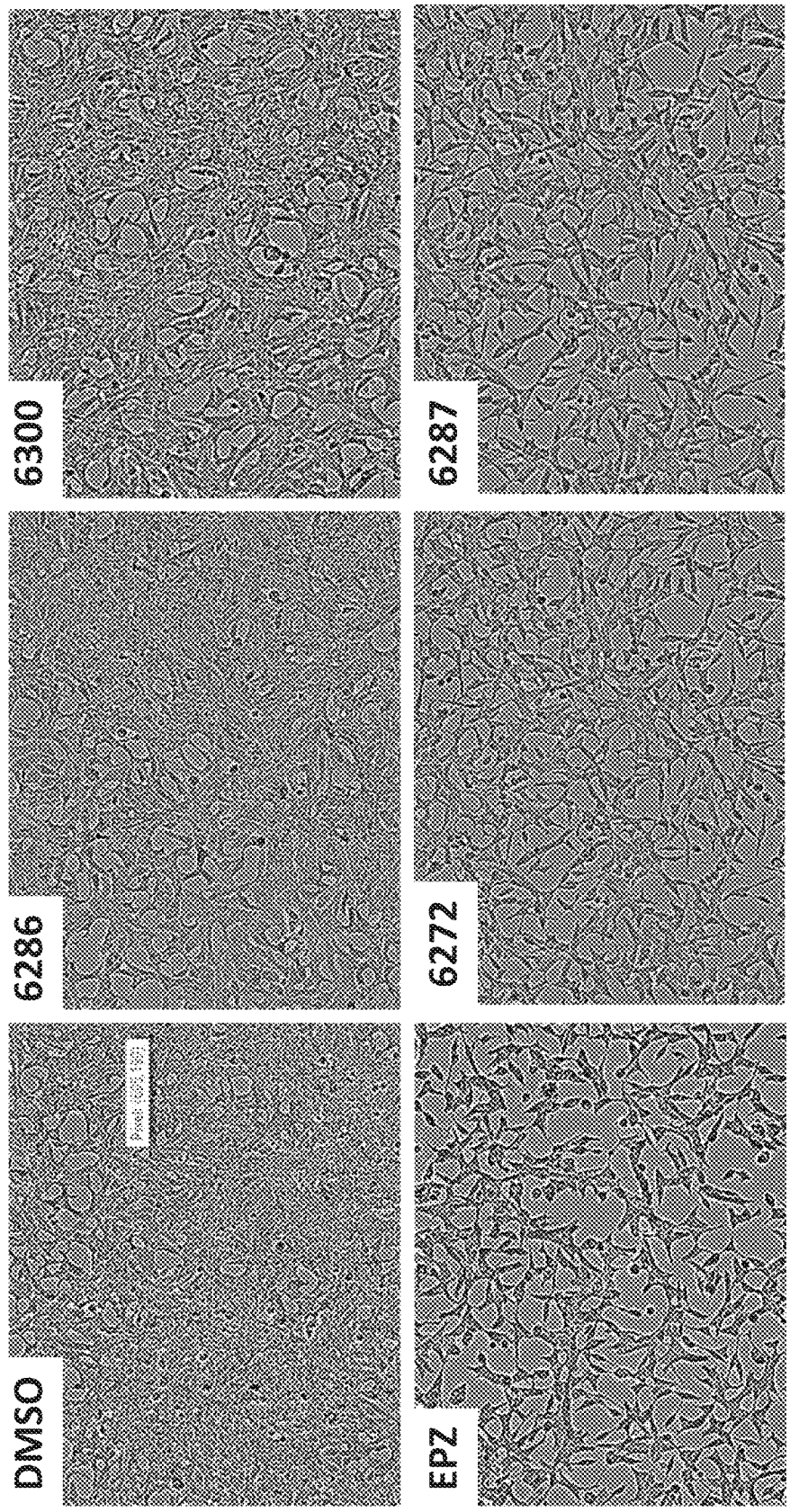

FIG. 21. Imaging of C4-2B cells after 12 days' treatment with the indicated compounds. Active degraders 6272 and 6287 show significant reduction in the cell density, while inactive derivatives of 6272 (6286) and 6287 (6300) show attenuated anti-proliferative effects.

Figure 22A:
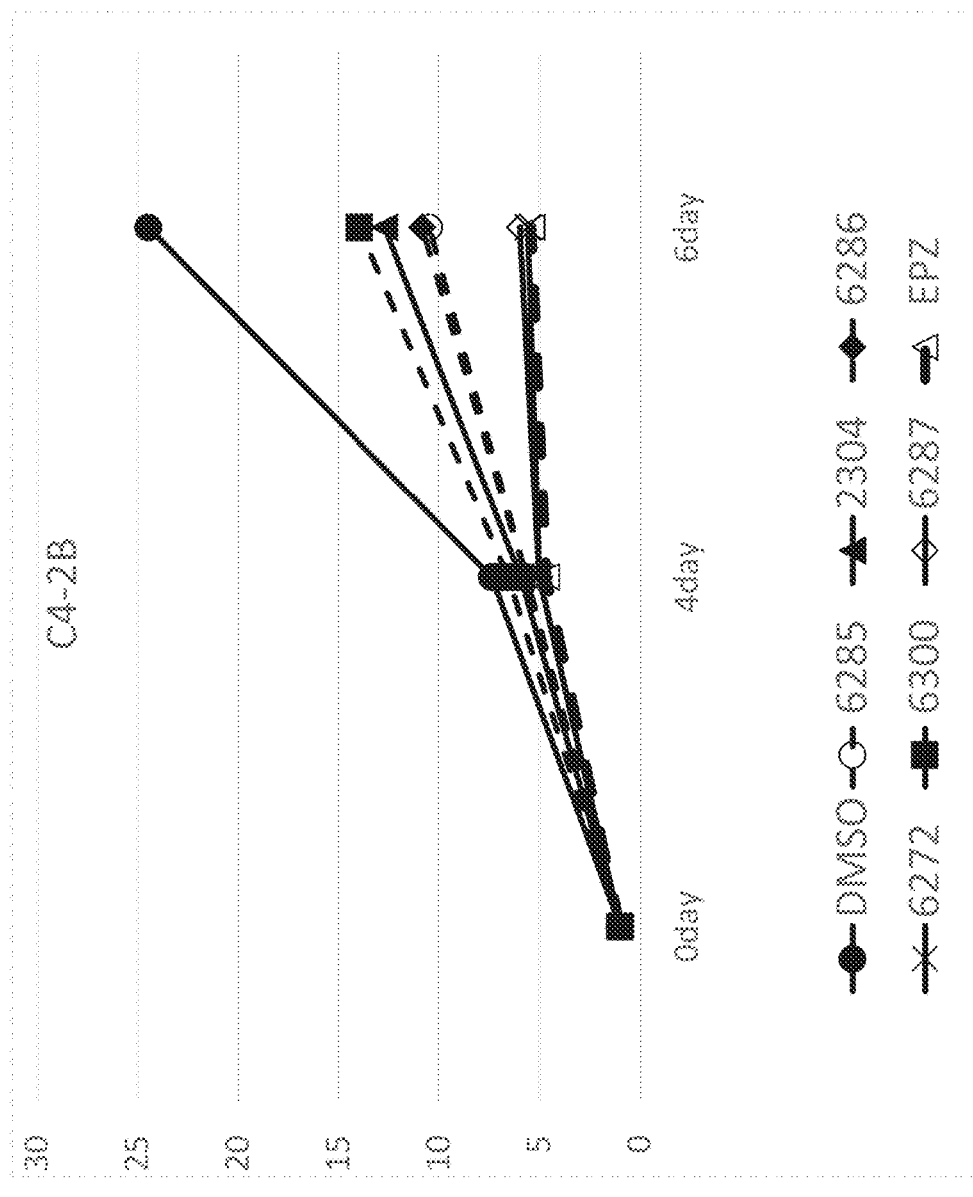
Figure 22B:
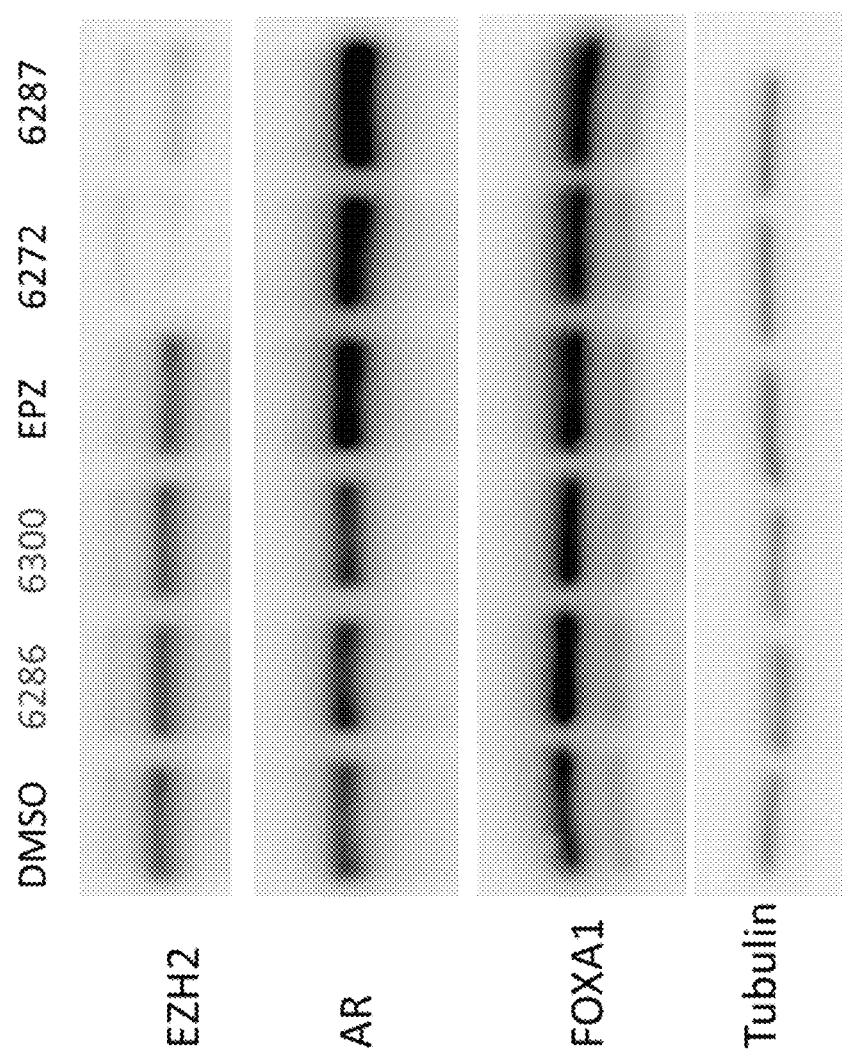

FIG. 22A-22B. WST cell proliferation assay of indicated compounds in C4-2B cells. Cells were treated for 6 days. EPZ-6438, 6287, and 6272 all had similarly potent effects on inhibiting the proliferation of C4-2B cells at 6 days. Other, less potent EZH2 degraders, had a weaker ability to inhibit proliferation. (FIG. 19B) Effects of indicated compounds on EZH2, AR, and FOXA1 by western blot at 1 µM in C4-2B cells.

Figure 23:
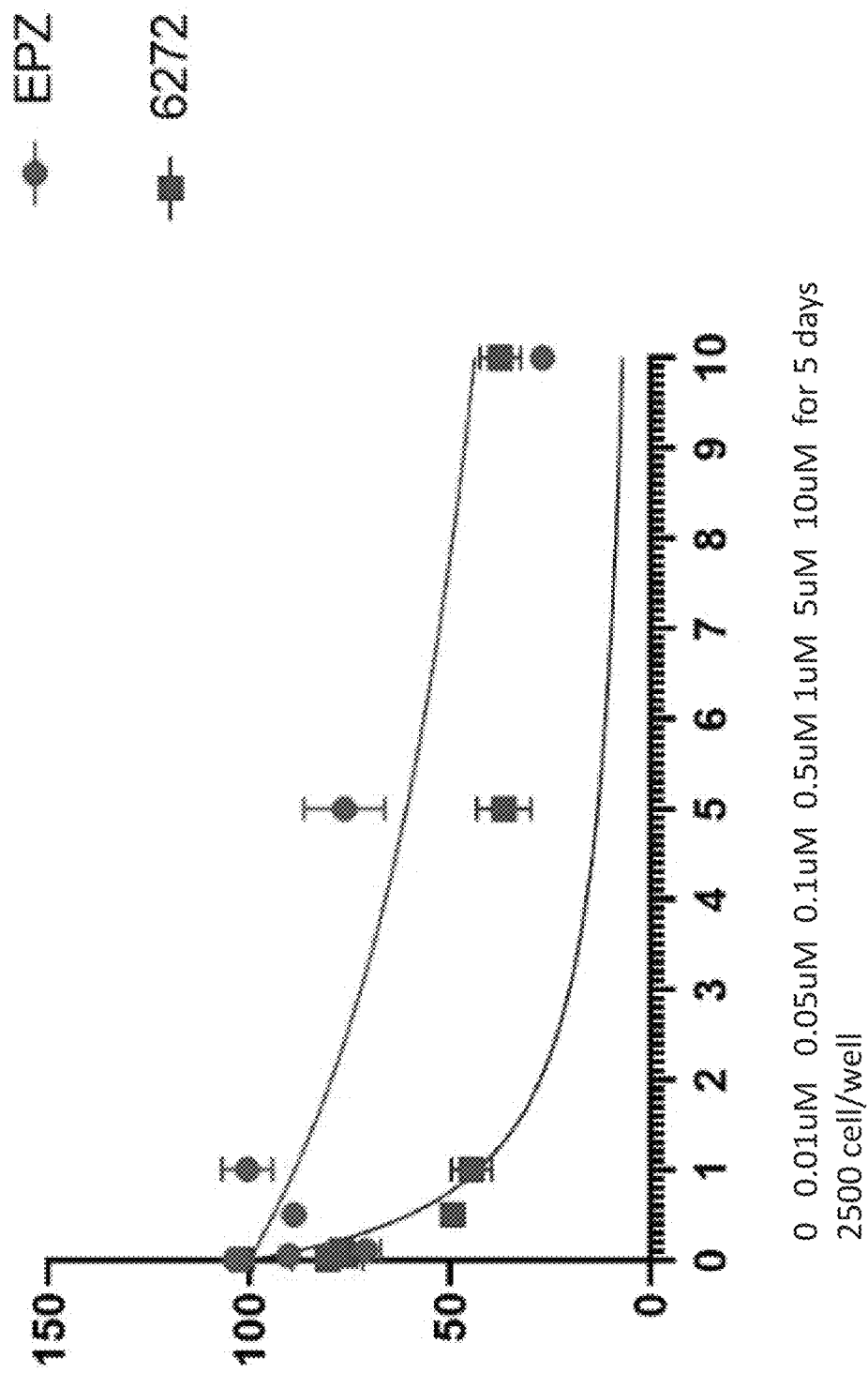

FIG. 23. WST cell viability assay of EPZ-6438 ("EPZ") and 6272 across a concentration range in LNCaP cells after 5 days' treatment. Degrader 6272 shows a greater anti-proliferative effect than EPZ-6438, especially at lower concentrations.

Figure 24:
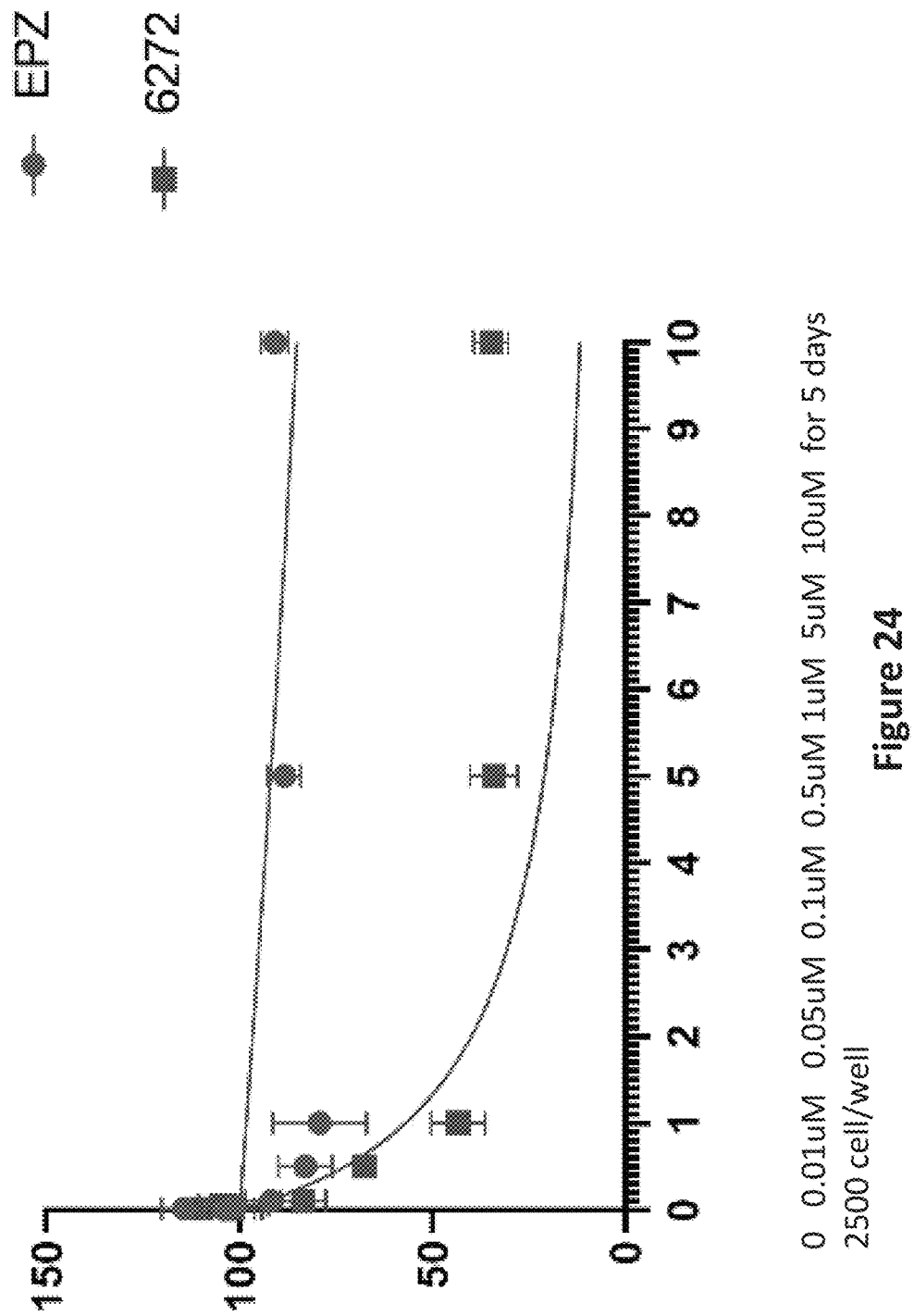

FIG. 24. WST cell viability assay of EPZ-6438 ("EPZ") and 6272 across a concentration range in 22Rv1 cells after 5 days' treatment. Degrader 6272 shows a greater anti-proliferative effect than EPZ-6438.

Figure 25:
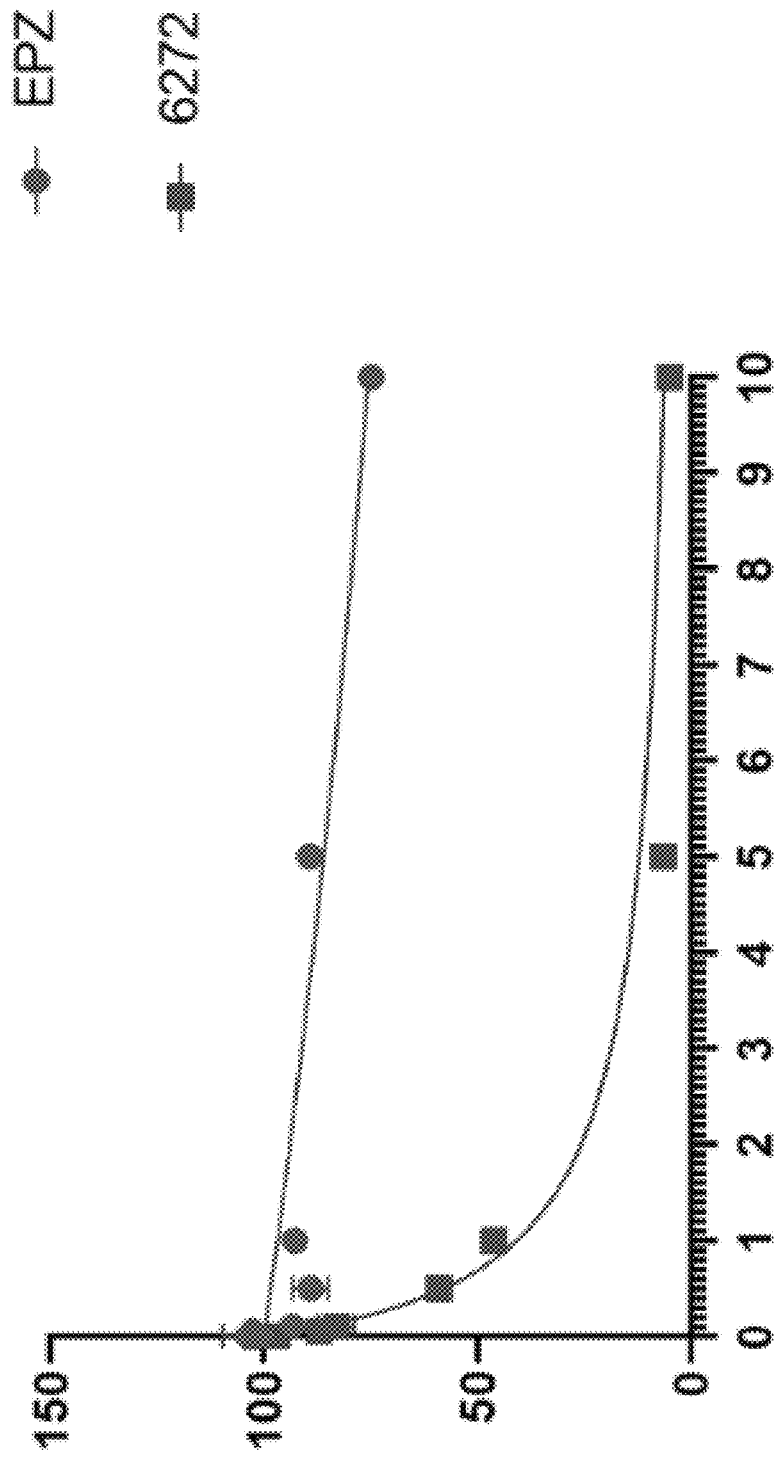

FIG. 25. Cell titer glo cell viability assay of EPZ-6438 ("EPZ") and 6272 across a concentration range in 22Rv1 cells after 5 days' treatment. Degrader 6272 shows a greater anti-proliferative effect than EPZ-6438.

Figure 26:
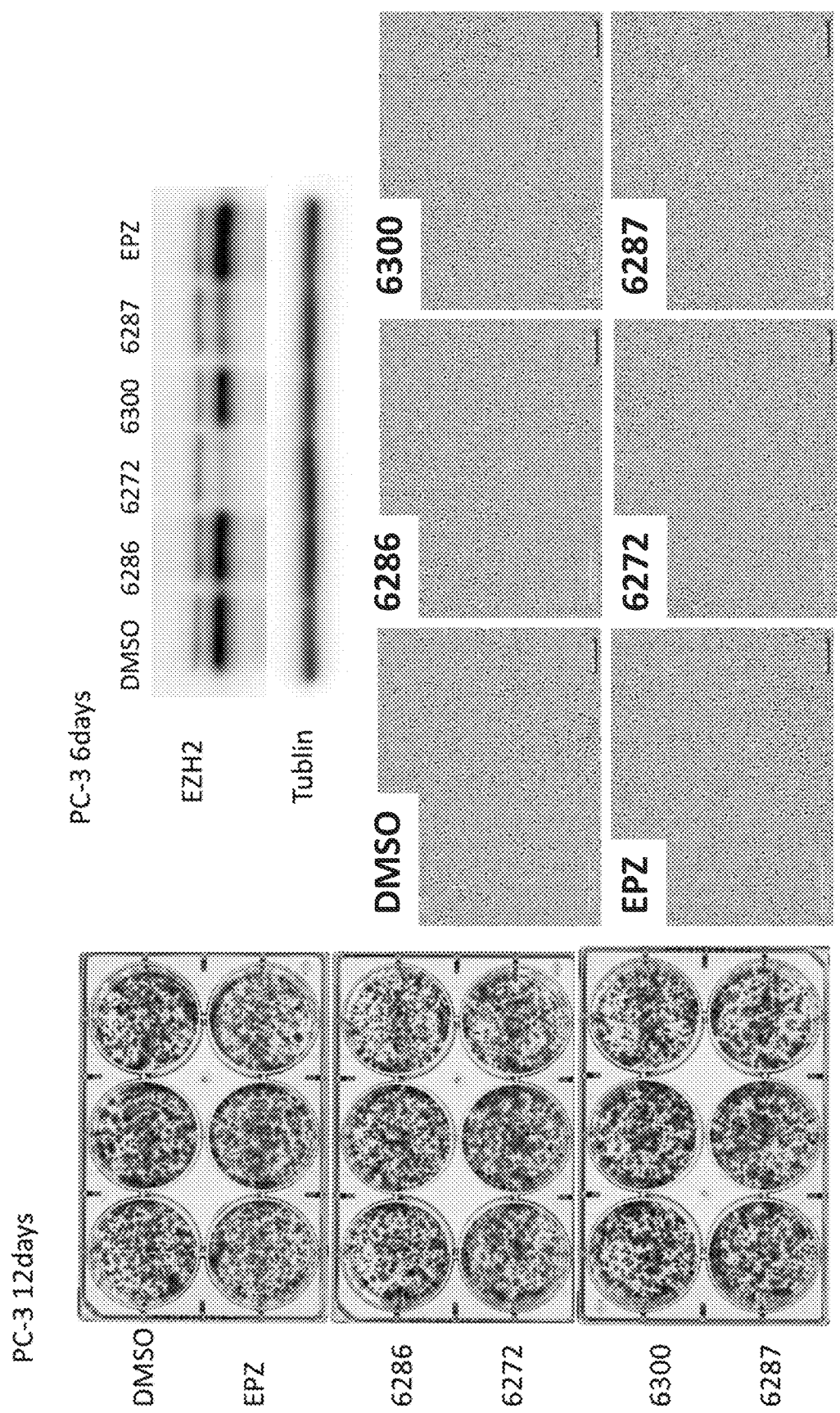

FIG. 26. (Left panel) Colony assay of PC3 cell colonies after 12 days' treatment with indicated compounds. (Upper right western blot) Western blot analysis of EZH2 protein in PC3 cells after 6 days treatment. Compounds 6272 and 6287 show significant reduction in EZH2, while inactive controls 6286 and 6300, along with EPZ-6438, show no changes. (Bottom right data) Cell imagining of PC3 cells after 12 days' treatment with indicated compounds.

Figure 27:
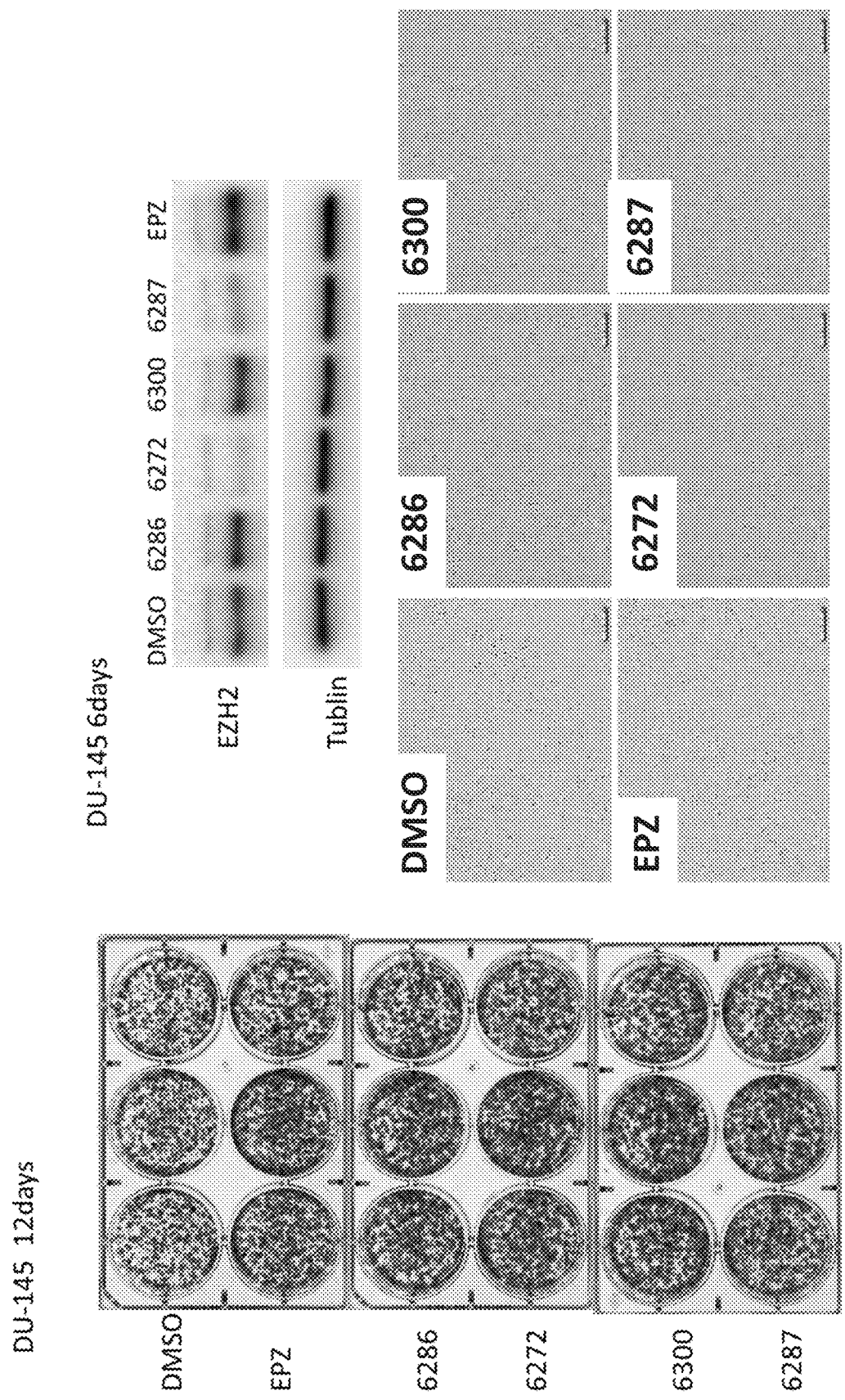

FIG. 27. (Left panel) Colony assay of DU-145 cell colonies after 12 days' treatment with indicated compounds. (Upper right western blot) Western blot analysis of EZH2 protein in DU-145 cells after 6 days treatment. Compounds 6272 and 6287 show significant reduction in EZH2, while inactive controls 6286 and 6300, along with EPZ-6438, show no changes. (Bottom right data) Cell imagining of DU-145 cells after 12 days' treatment with indicated compounds.

Figure 28:
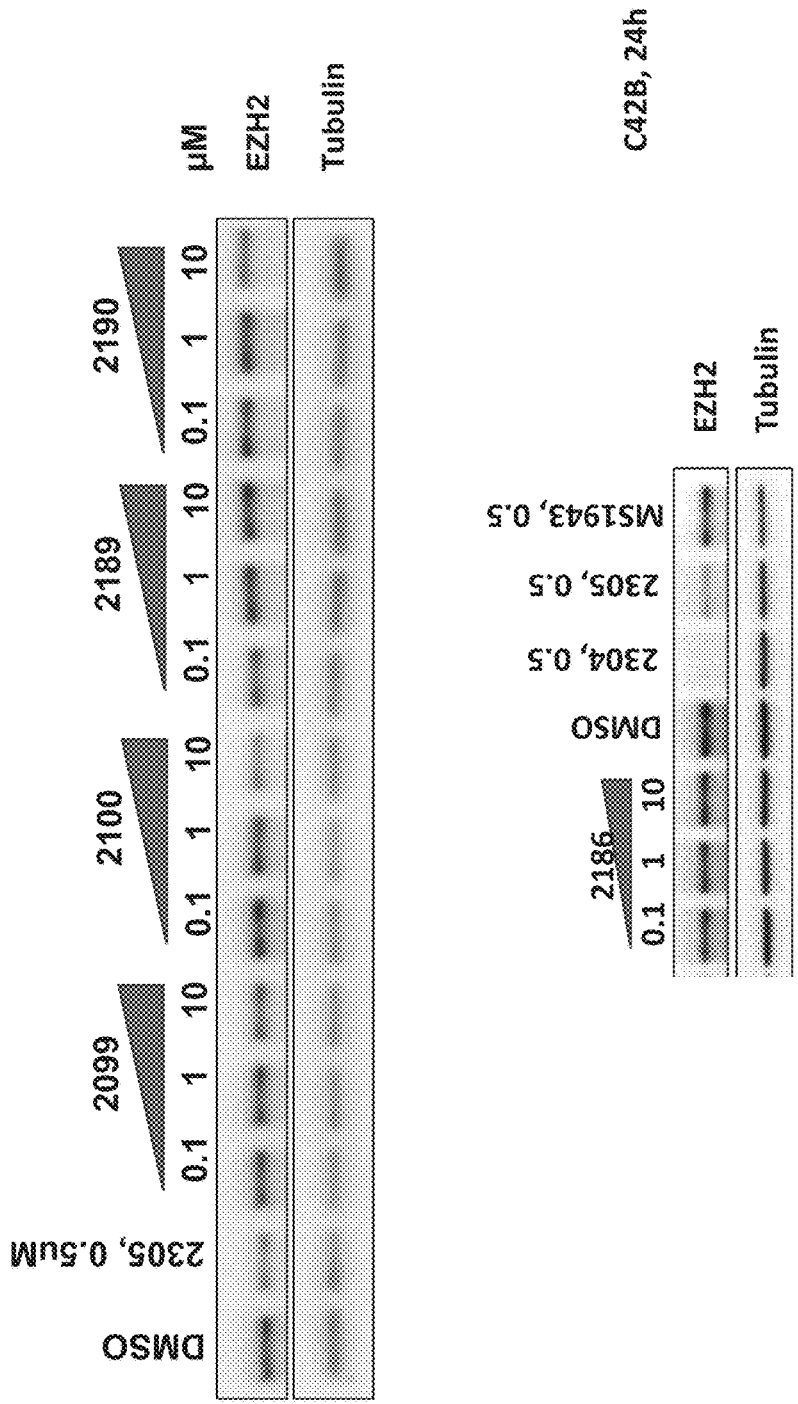

FIG. 28. (Upper) Western blot analysis of the indicated compounds at the concentrations shown, in C4-2B cells for 24 hours, showing 2099, 2100, and 2190 reduce EZH2 protein levels. (Lower) Western blot analysis of indicated compounds at the concentrations shown, in C4-2B cells at 24 hours. Data shows 2186 is inactive at degrading EZH2, while 2304 and 2305 show significant reduction in EZH2. Reported compound MS1943 (Ma, A. et al. Nat. Chem. Biol. (2020) 16(2):214-222) was used as a control and shows no ability to degrade EZH2 at 0.5 µM in C4-2B cells.

Figure 29:
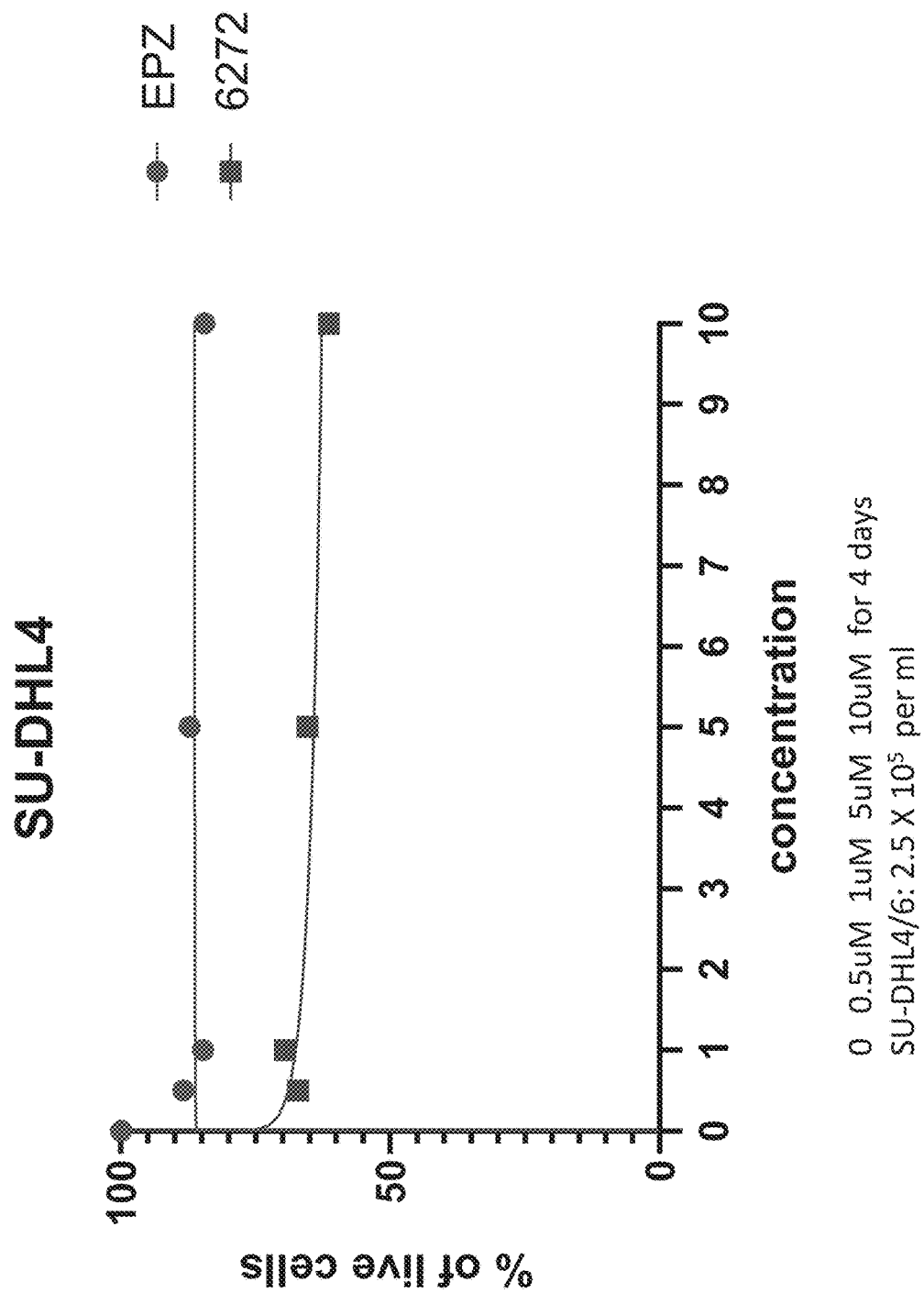

FIG. 29. WST cell viability assay of EPZ-6438 ("EPZ") and 6272 across a concentration range in SU-DHL4 cells after 4 days' treatment. Degrader 6272 shows a greater anti-proliferative effect than EPZ-6438.

Figure 30:
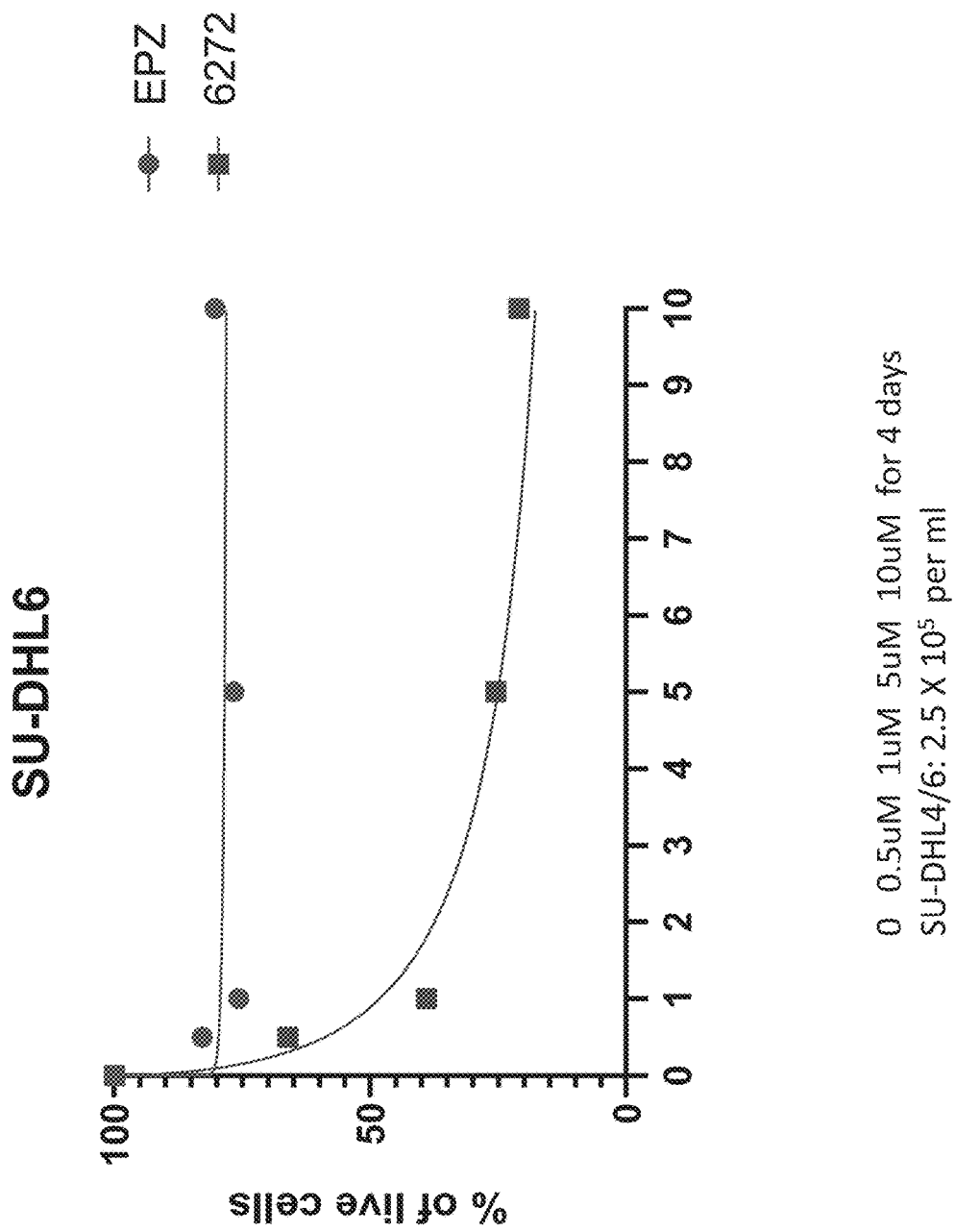

FIG. 30. WST cell viability assay of EPZ-6438 ("EPZ") and 6272 across a concentration range in SU-DHL6 cells after 4 days' treatment. Degrader 6272 shows a greater anti-proliferative effect than EPZ-6438.

Figure 31:
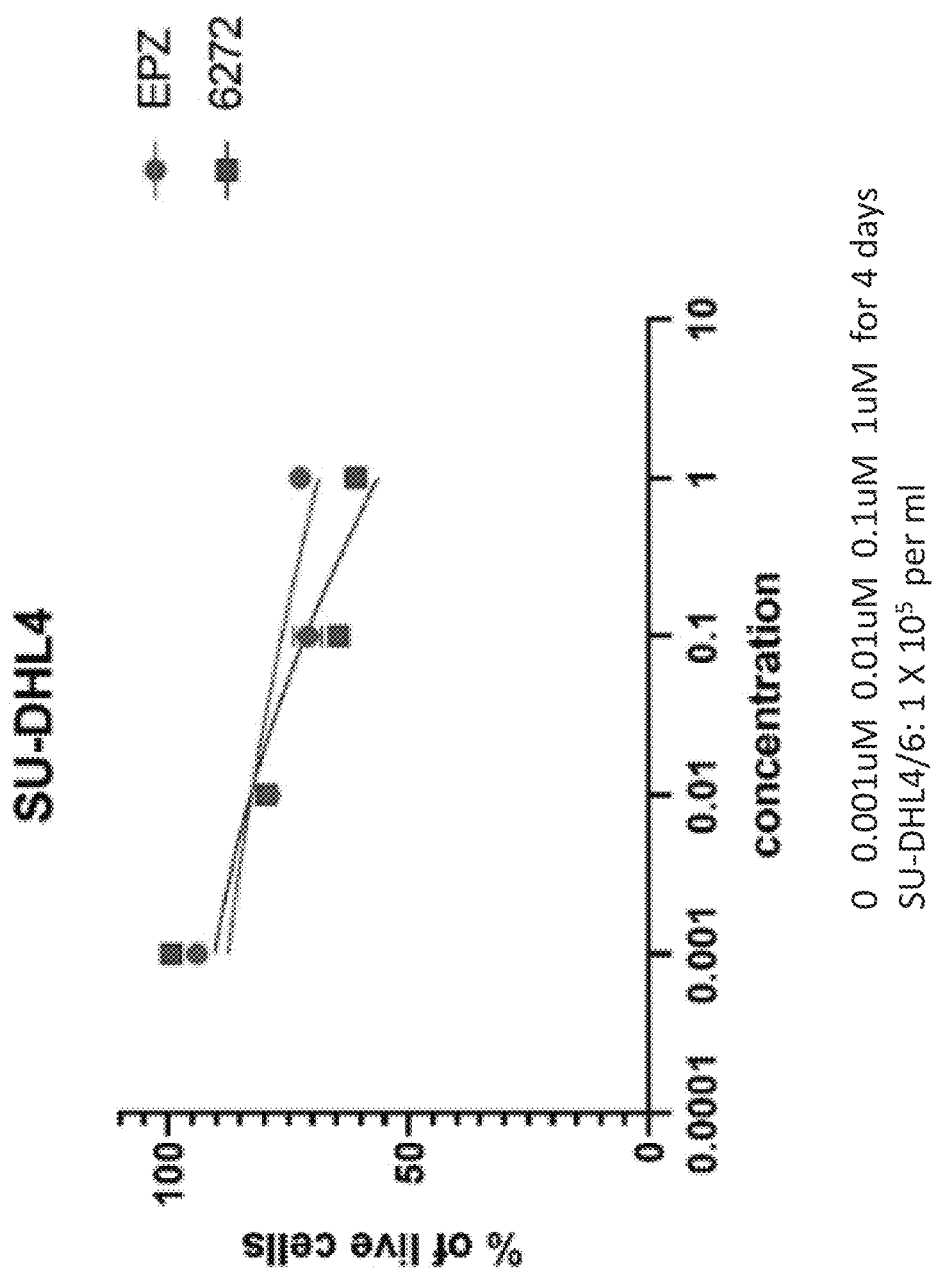

FIG. 31. WST cell viability assay of EPZ-6438 ("EPZ") and 6272 across a concentration range in SU-DHL4 cells after 4 days' treatment. Degrader 6272 and EPZ-6438 show similar anti-proliferative effects at these concentrations.

Figure 32:
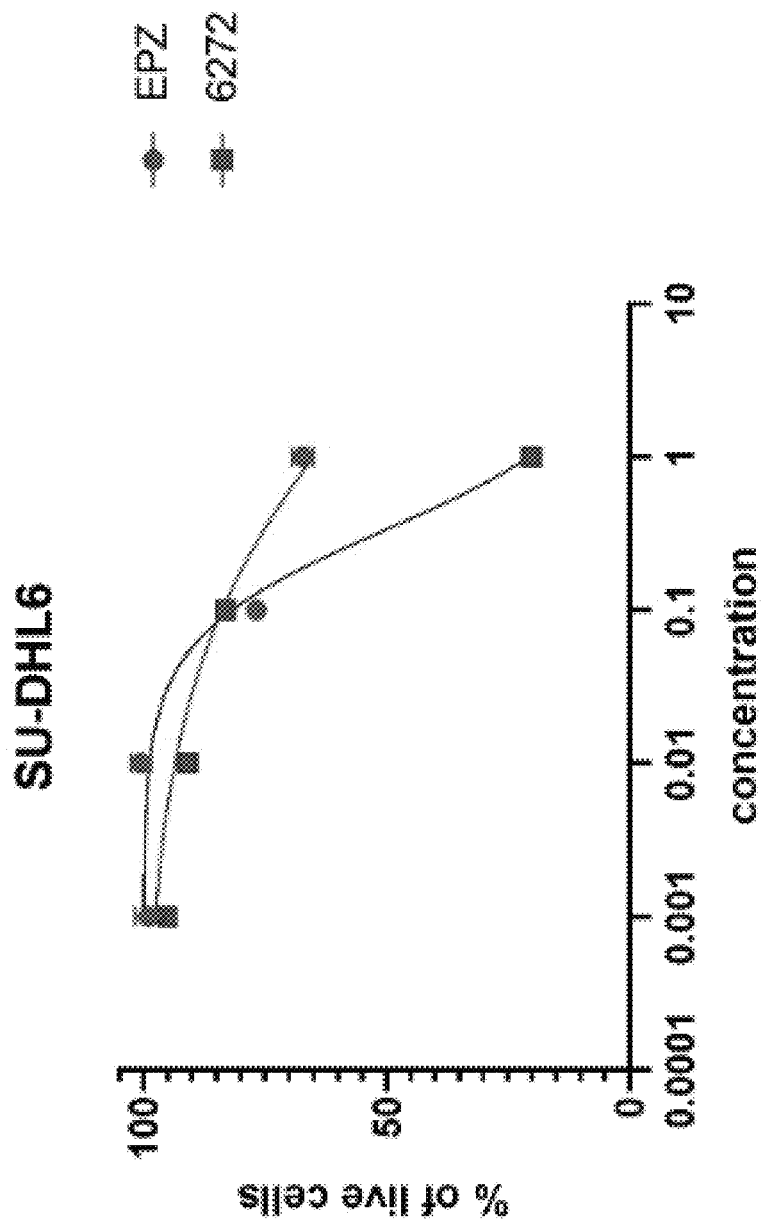

FIG. 32. WST cell viability assay of EPZ-6438 ("EPZ") and 6272 across a concentration range in SU-DHL6 cells after 4 days' treatment. Degrader 6272 shows a greater anti-proliferative effect than EPZ-6438 at 1 µM.

Figure 33:
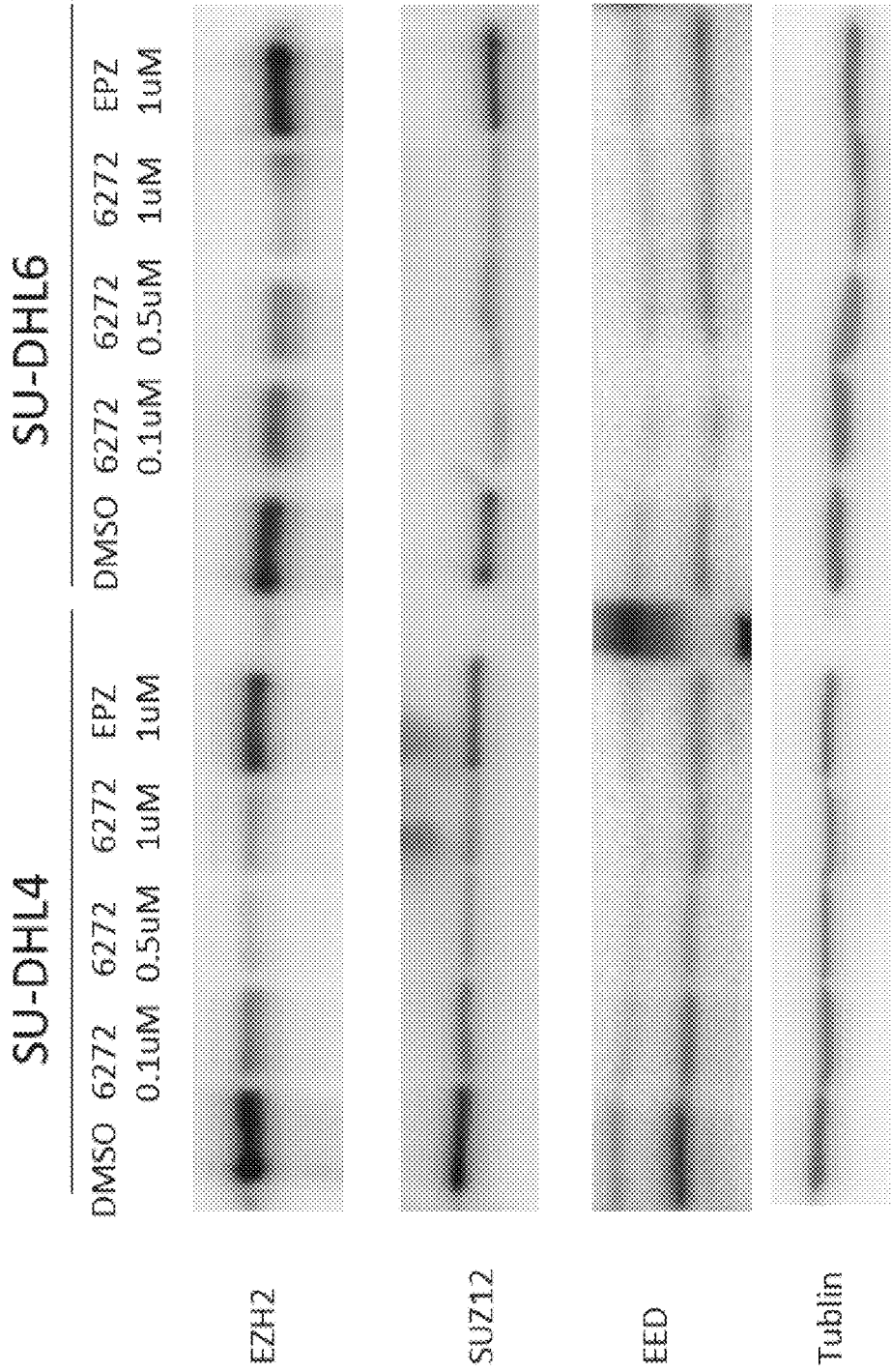

FIG. 33. Western blot analysis of 6272 and EPZ-6438 and their effects on EZH2, SUZ12, and EED proteins in SU-DHL4 (left) and SU-DHL6 (right) cells. Cell were treated for 48 hours with the indicated concentrations of compounds. Compound 6272 shows significant degradation of EZH2, SUZ1, and EED in both cell lines, while EPZ-6438 has little or no effect.

Figure 34:
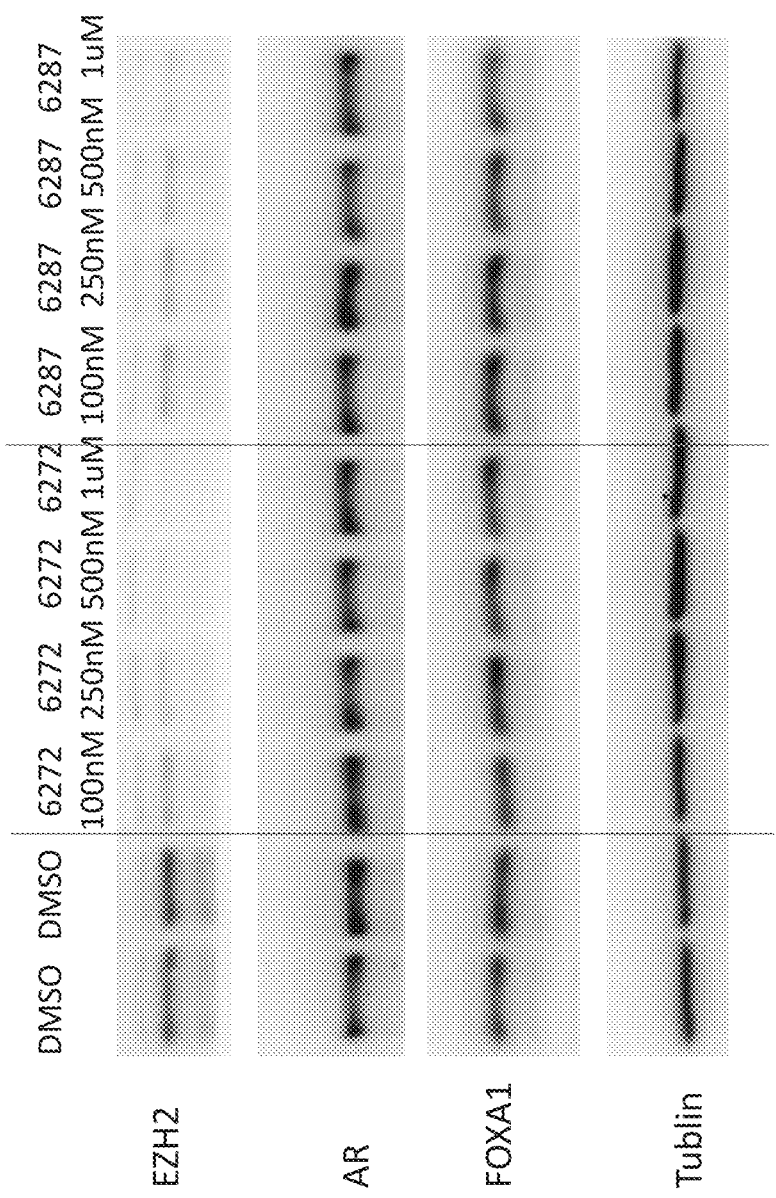

FIG. 34. Western blot analysis of 6272 and 6287 and their effects on EZH2, AR, and FOXA1 proteins in C4-2B cells. Cell were treated for 24 hours with the indicated concentrations of compounds.

FIG. 35. Pharmacokinetics of indicated compounds. Compounds were administered to C57Bl/6 mouse mice at 4 mg/kg using intraperitoneal (IP) injection in cassette format. Plasma was collected at the indicated time points and analyzed by LC/MS/MS using standard methods.

DETAILED DESCRIPTION OF THE INVENTION

The present invention is described herein using several definitions, as set forth below and throughout the application.

Unless otherwise specified or indicated by context, the terms "a", "an", and "the" mean "one or more." For example, "a compound" and "a substituent" and a "moiety" and a "PROTAC" should be interpreted to mean "one or more compounds" and "one or more substituents" and "one or more moieties" and "one or more PROTACs", respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, a "subject" may be interchangeable with "patient" or "individual" and means an animal, which may be a human or non-human animal, in need of treatment.

A "subject in need of treatment" may include a subject having a disease, disorder, or condition that is responsive to therapy with a compound that inhibits the biological activity of EZH2. Biological activities of EZH2 which are inhibited by the disclosed compounds may include methyltransferase activity of EZH2 (e.g., using a histone substrate for methylation).

A "subject in need of treatment" may include a subject having a disease, disorder, or condition that is responsive to therapy with a proteolysis-targeted chimeric molecule (PROTAC) that targets EZH2 and induces degradation of EZH2, for example via ubiquitinization.

A "subject in need of treatment" may include a subject having a cell proliferative disease, disorder, or condition such as cancer (e.g., cancers such as multiple myeloma, leukemia, non-small cell lung cancer, colon cancer, cancer of the central nervous system, melanoma, ovarian cancer, renal cancer, prostate cancer, lymphoma, and breast cancer). A "subject in need of treatment" may include a subject having a cell proliferative disease, disorder, or condition such as cancer that is associated with EZH2 activity and/or that may be treated by administering an effective amount of an agent that modulates EZH2 activity.

As used herein, the phrase "effective amount" shall mean that drug dosage that provides the specific pharmacological response for which the drug is administered in a significant number of subject in need of such treatment. An effective amount of a drug that is administered to a particular subject in a particular instance will not always be effective in treating the conditions/diseases described herein, even though such dosage is deemed to be a therapeutically effective amount by those of skill in the art.

As used herein, the term "modulate" means decreasing or inhibiting activity and/or increasing or augmenting activity. For example, modulating EZH2 activity may mean increasing or augmenting EZH2 activity and/or decreasing or inhibiting EZH2 activity. The disclosed compounds and PROTACs may be administered to modulate EZH2 activity (e.g., in a cell).

Chemical Entities

New chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of straight-chain or branched alkyl group (i.e., a diradical of straight-chain or branched C1-C6 alkyl group). Exemplary alkylene groups include, but are not limited to —CH$_2$—, —CH$_2$CH$_2$—, —CH$_2$CH$_2$CH$_2$—, —CH(CH$_3$)CH$_2$—, —CH$_2$CH(CH$_3$)CH$_2$—, —CH(CH$_2$CH$_3$)CH$_2$—, and the like.

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido or carboxyamido (or amidocarboxyl), amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloheteroalkyl" refers to a monovalent saturated cyclic, bicyclic, or bridged cyclic hydrocarbon group of 3-12, 3-8, 4-8, or 4-6 carbons in which at least one carbon of the cycloalkane is replaced with a heteroatom such as, for example, N, O, and/or S.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido or carboxyamido (or amidocarboxyl), amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido or carboxyamido (or amidocarboxyl), carboxylic acid, —C(O) alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently hydrogen, alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —R$^1$C(O)N(R$^2$)—, —R$^1$C(O)N(R$^2$)R$^3$—, —C(O)NR$^2$R$^3$, or —C(O)NH$_2$, wherein R$^1$, R$^2$ and R$^3$, for example, are each independently hydrogen, alkyl, alkoxy, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds and molecules (e.g., PROTACs) of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds and molecules may be designated by the symbols "R" or "S," or "+" or "–" depending on the configuration of substituents around the stereogenic carbon atom and or the optical rotation observed. The present invention encompasses various stereo isomers of these compounds and molecules and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds and molecules, unless indicated otherwise.

Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

The formulae of the compounds and molecules disclosed herein should be interpreted as encompassing all possible stereoisomers, enantiomers, or epimers of the compounds and molecules unless the formulae indicates a specific stereoisomer, enantiomer, or epimer. The formulae of the compounds and molecules disclosed herein should be interpreted as encompassing salts, esters, amides, or solvates thereof of the compounds and molecules.

Substituted 3-Amino-5-Phenylbenzamide Compounds as Covalent Inhibitor of Enhancer Zeste Homolog 2 Protein (EZH2) and Proteolysis-Targeting Chimeric Derivatives Thereof (PROTACs) that Induce Degradation of EZH2

Disclosed are covalent inhibitors of enhancer zeste homolog 2 (EZH2) which may be utilized as EZH2 targeting agents. The disclosed compounds may be characterized as substituted 3-amino-5-phenylbenzamide compounds. The disclosed compounds may be utilized as covalent inhibitors of EZH2 and further may be derivatized to form proteolysis-targeting chimeric molecules (PROTACs) that target EZH2 for degradation. The disclosed compounds and PROTACs may be used in pharmaceutical compositions and methods for treating cell proliferative disorders associated with EZH2 activity, such as cancer.

In some embodiments, the disclosed compounds may have a Formula I or a salt, hydrate, or solvate thereof:

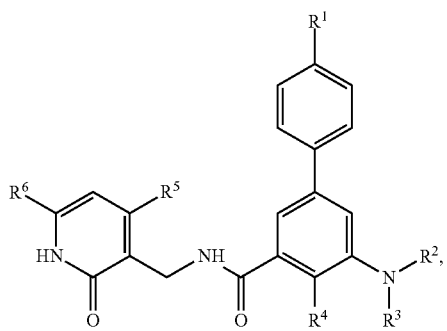

wherein

R$^1$ is hydrogen, alkyl, or —CH$_2$—X, wherein X is selected from hydrogen, alkyl, amino, piperazinyl (e.g. piperazin-1-yl or N-piperazinyl), morpholinyl (e.g., morpholin-4-yl or N-morpholinyl), piperidinyl (e.g., piperidin-4-yl or N-piperidinyl), and maleimidyl (e.g., N-maleimidyl), and X optionally is substituted with a substituent selected from alkyl, alkoxy, —C(O)—H, —C(O)—(CH$_2$)$_m$—CH$_3$ where m is 0-20, —(CH$_2$CH$_2$O)$_n$—H or —(CH$_2$CH$_2$O)$_n$—CH$_3$ where n is 0-20, —C(O)—(CH$_2$CH$_2$O)$_n$—H or —C(O)—(CH$_2$CH$_2$O)$_n$—CH$_3$ where n is 0-20, —C(O)—CH$_2$OCH$_3$, —C(O)—CH$_2$—CH(CH$_2$CH$_2$CH$_3$)$_2$, —C(O)—CH=CH-phenyl, —C(O)—CH$_3$, —C(O)—CH$_2$Cl, —C(O)—CH=C(CH$_3$)$_2$, —C(O)—

CH=CH₂, —C(O)-ethynyl, —C(O)-adamantyl, —S(O)(O)—H, —S(O)(O)—CH₃, —S(O)(O)-phenyl, —C(O)—CH₂—CH₃, —CH₂—S(O)(O)—H, —CH₂—CH₂—S(O)(O)—H, —CH₂—CH₂—S(O)(O)—CH₃, —CH₂—CH₂—S(O)(O)-phenyl, —CH=CH—S(O)(O)—H, —CH=CH—S(O)(O)—CH₃, and —CH=CH—S(O)(O)-phenyl;

$R^2$ is selected from hydrogen, alkyl, piperidinyl (e.g., piperidin-4-yl) and oxane (e.g., oxan-4-yl), wherein $R^3$ optionally is substituted with a substituent selected from alkyl, alkoxy, —C(O)—H, —C(O)—(CH₂)ₘ—CH₃ where m is 0-20, —(CH₂CH₂O)ₙ—H or —(CH₂CH₂O)ₙ—CH₃ where n is 0-20, —C(O)—(CH₂CH₂O)ₙ—H or —C(O)—(CH₂CH₂O)ₙ—CH₃ where n is 0-20, —C(O)—CH₂OCH₃, —C(O)—CH₂—CH(CH₂CH₂CH₃)₂, —C(O)—CH=CH-phenyl, —C(O)—CH₃, —C(O)—CH₂Cl, —C(O)—CH=C(CH₃)₂, —C(O)—CH=CH₂, —C(O)-ethynyl, —C(O)-adamantyl, —S(O)(O)—H, —S(O)(O)—CH₃, —S(O)(O)-phenyl, —C(O)—CH₂—CH₃, —CH₂—S(O)(O)—H, —CH₂—CH₂—S(O)(O)—H, —CH₂—CH₂—S(O)(O)—CH₃, —CH₂—CH₂—S(O)(O)-phenyl, —CH=CH—S(O)(O)—H, —CH=CH—S(O)(O)—CH₃, and —CH=CH—S(O)(O)-phenyl;

$R^3$ is hydrogen or alkyl;

$R^4$ is hydrogen or alkyl;

$R^5$ is hydrogen or alkyl; and $R^6$ is hydrogen or alkyl.

In some embodiments, $R^1$ is an electrophile and $R^1$ optionally is —CH₂—X. In further embodiments, $R^1$ is —CH₂—X and X is optionally substituted piperazinyl (e.g., optionally substituted piperazin-1-yl or N-piperazinyl).

In some embodiments, $R^1$ is an electrophile and $R^1$ optionally is selected from:

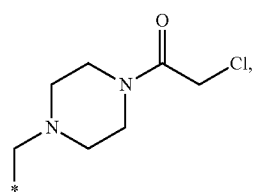

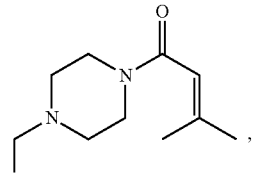

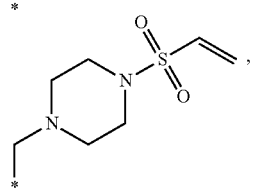

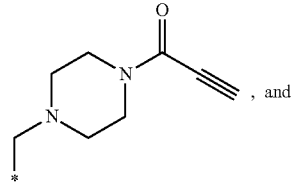

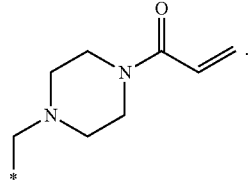

In some embodiments, $R^1$ is an electrophile and $R^1$ optionally is —CH₂—X and X is morpholinyl. In particular embodiments, $R^1$ may be —CH₂—X and X is morpholin-4-yl or N-morpholinyl.

In some embodiments, $R^2$ is optionally substituted piperidinyl. In particular embodiments, $R^2$ is optionally substituted piperidin-4-yl.

In some embodiments, $R^2$ is selected from

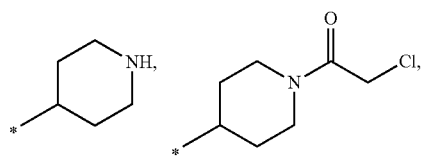

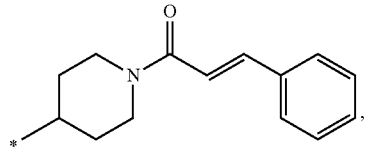

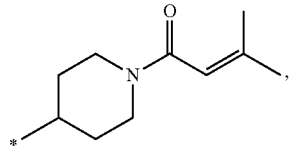

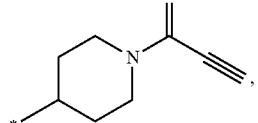

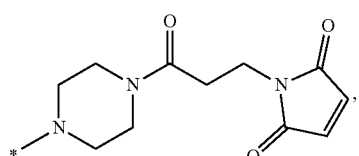

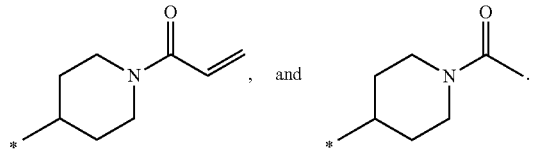

In some embodiments, $R^2$ is oxane. In particular embodiments, $R^2$ is oxan-4-yl.

In some embodiments, $R^3$ is alkyl. In particular embodiments, $R^3$ is ethyl.

In some embodiments, $R^4$ is alkyl. In particular embodiments, $R^4$ is methyl.

In some embodiments, one or both of $R^5$ and $R^6$ are alkyl. In particular embodiments, both of $R^5$ and $R^6$ are methyl.

Also disclosed herein are proteolysis-targeted chimeric molecules (PROTACs) that induce degradation of EZH2 protein. In some embodiments, the disclosed molecules may be described as having a having a formula: $M_{EZH2}$-L-$M_{E3}$ or alternatively $M_{E3}$-L-$M_{EZH2}$, wherein $M_{EZH2}$ is a moiety that binds to EZH2 such as the compounds disclosed herein, L is a bond or a linker covalently attaching $M_{EZH2}$ and $M_{E3}$, and $M_{E3}$ is a moiety that binds to an E3 ubiquitin ligase.

In some embodiments of the disclosed PROTACS, $M_{EZH2}$ has a formula derived from a compound having a Formula I as per the disclosed compounds above or a radicalized or functionalized form thereof,

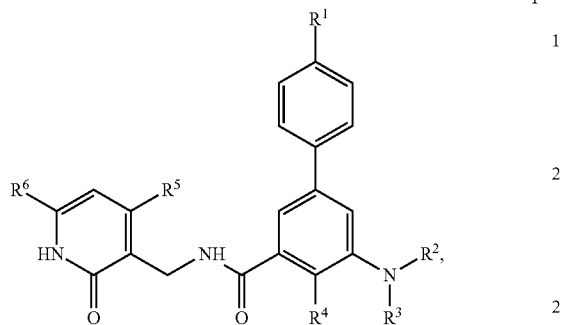

I wherein:
$R^1$ is an electrophile or $R^1$ is hydrogen, alkyl, or —$CH_2$—X, wherein X is selected from hydrogen, alkyl, amino, piperazinyl (e.g. piperazin-1-yl or N-piperazinyl), morpholinyl (e.g., morpholin-4-yl or N-morpholinyl), piperidinyl (e.g., piperidin-4-yl or N-piperidinyl), and maleimidyl (e.g., N-maleimidyl), and X optionally is substituted with a substituent selected from alkyl, alkoxy, —C(O)—H, —C(O)—$(CH_2)_m$—$CH_3$ where m is 0-20, —$(CH_2CH_2O)_n$—H or —$(CH_2CH_2O)_n$—$CH_3$ where n is 0-20, —C(O)—$(CH_2CH_2O)_n$—H or —C(O)—$(CH_2CH_2O)_n$—$CH_3$ where n is 0-20, —C(O)—$CH_2OCH_3$, —C(O)—$CH_2$—CH$(CH_2CH_2CH_3)_2$, —C(O)—$CH_2$—CH=CH-phenyl, —C(O)—$CH_3$, —C(O)—$CH_2Cl$, —C(O)—CH=C$(CH_3)_2$, —C(O)—CH=$CH_2$, —C(O)-ethynyl, —C(O)-adamantyl, —S(O)(O)—H, —S(O)(O)—$CH_3$, —S(O)(O)-phenyl, —C(O)—$CH_2$—$CH_3$, —$CH_2$—S(O)(O)—H, —$CH_2$—$CH_2$—S(O)(O)—H, —$CH_2$—$CH_2$—S(O)(O)—$CH_3$, —$CH_2$—$CH_2$—S(O)(O)-phenyl, —CH=CH—S(O)(O)—H, —CH=CH—S(O)(O)—$CH_3$, and —CH=CH—S(O)(O)-phenyl; or $R^2$ is selected from hydrogen, alkyl, piperidinyl (e.g., piperidin-4-yl) and oxane (e.g., oxan-4-yl), wherein $R^3$ optionally is substituted with a substituent selected from alkyl, alkoxy, —C(O)—H, —C(O)—$(CH_2)_m$—$CH_3$ where m is 0-20, —$(CH_2CH_2O)_n$—H or —$(CH_2CH_2O)_n$—$CH_3$ where m is 0-20, —C(O)—$(CH_2CH_2O)_n$—H or —C(O)—$(CH_2CH_2O)_n$—$CH_3$ where n is 0-20, —C(O)—$CH_2OCH_3$, —C(O)—$CH_2$—CH$(CH_2CH_2CH_3)_2$, —C(O)—CH=CH-phenyl, —C(O)—$CH_3$, —C(O)—$CH_2Cl$, —C(O)—CH=C$(CH_3)_2$, —C(O)—CH=$CH_2$, —C(O)-ethynyl, —C(O)-adamantyl, —S(O)(O)—H, —S(O)(O)—$CH_3$, —S(O)(O)-phenyl, —C(O)—$CH_2$—$CH_3$, —$CH_2$—S(O)(O)—H, —$CH_2$—$CH_2$—S(O)(O)—$CH_3$, —$CH_2$—$CH_2$—S(O)(O)-phenyl, —CH=CH—S(O)(O)—H, —CH=CH—S(O)(O)—$CH_3$, and —CH=CH—S(O)(O)-phenyl;

$R^3$ is hydrogen or alkyl;
$R^4$ is hydrogen or alkyl;
$R^5$ is hydrogen or alkyl; and
$R^6$ is hydrogen or alkyl.

In some embodiments of the disclosed PROTACS, $M_{EZH2}$ has a formula:

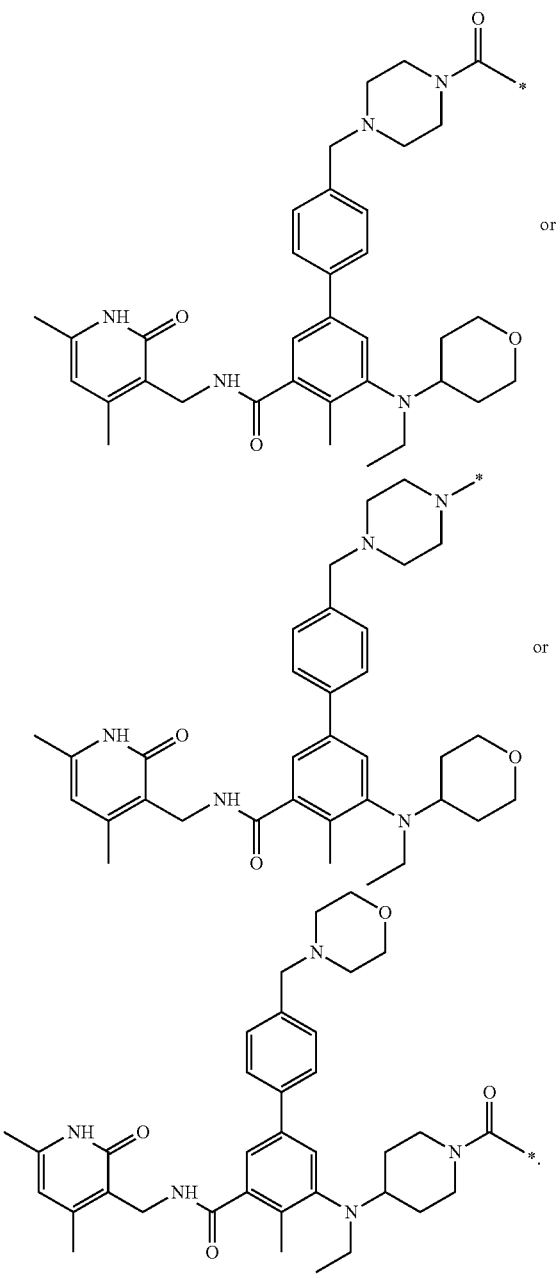

The disclosed PROTACs may include a bond or a linker (L) that conjugates the EZH2 binding moiety ($M_{EZH2}$) and the E3 ubiquitin ligase binding moiety ($M_{E3}$). The PROTAC linker connects the functional moieties of a PROTAC, a target protein binder and an E3 ligase recruiter. Linkers used in the development of PROTACs include polyethylene glycol (PEG) linkers, Alkyl-Chain linkers, and Alkyl/ether linkers. Other PROTAC linkers may include those linkers described in one or more of U.S. Publication Nos. 2020/0140456; 2020/0102298; 2020/0085817; 2020/0022966;

2019/0275161; 2019/0263798; 2019/0262502; 2019/0194190; 2019/0151457; 2019/0151295; 2019/0106417; 2019/0076542; 2019/0076541; 2019/0076540; 2019/0076539; 2019/0071415; 2019/0016703; 2018/0327419; 2018/0186785; 2018/0134684; and 2018/0085465; the contents of which are incorporated herein by reference in their entireties.

In some embodiments, of the disclosed PROTACS, L comprises a polyethylene glycol moiety, an alkylalkyne moiety, and/or an aminoalkyl alkyne moiety.

In some embodiments of the disclosed PROTACs, L has a formula selected from: —$(CH_2)_m$—, —$(CH_2)_mCH_2CH_2C(O)NHCH_2CH_2$—, —$(CH_2)_mCH_2CH_2C(O)NHCH_2CH_2CH_2$—, —$(CH_2CH_2O)_nCH_2CH_2C(O)NHCH_2CH_2$—, —$(CH_2CH_2O)_nCH_2CH_2C(O)NHCH_2CH_2CH_2$—, —$(CH_2CH_2O)_nCH_2CH_2$—, —$(CH_2CH_2O)_nCH_2$—, —$(CH_2)_mC(O)NHCH_2CH_2$—, —$(CH_2CH_2O)_nCH_2CH_2C(O)NHCH_2CH_2$—, —$CH_2CH_2C(O)NHCH_2CH_2CH_2$—, —$CH_2CH_2C(O)NHCH_2CH_2CH_2C(O)NHCH_2CH_2$—, —$CH_2CH_2C(O)NHCH_2CH_2CH_2C(O)NHCH_2CH_2CH_2C(O)NHCH_2CH_2$—, —$CH_2CH_2C(O)NHCH_2CH_2CH_2C(O)NHCH_2CH_2CH_2C(O)NHCH_2CH_2CH_2$—, —$(CH_2CH_2O)_nCH_2CH_2$—, —$CH_2OCH_2$—, —$CH_2OCH_2C(O)NHCH_2CH_2$—, —$CH_2OCH_2C(O)NHCH_2CH_2$—, —$CH_2OCH_2C(O)NHCH_2CH_2CH_2C(O)NHCH_2CH_2$—, and —$CH_2OCH_2C(O)NHCH_2CH_2CH_2C(O)NHCH_2CH_2CH_2$—, wherein m and n are 0-20.

The disclosed PROTACs typically include a moiety that binds to an E3 ubiquitin ligase ($M_{E3}$), for example, as a ligand for the E3 ubiquitin ligase ($M_{E3}$). Ligands for E3 ubiquitin ligases for use in preparing PROTACs are known in the art. (See, e.g., An et al., "Small-molecule PROTACs: An emerging and promising approach for the development of targeted therapy drugs," EBioMedicine. 2018 October; 36: 553-562; and Gu et al., "PROTACs: An Emerging Targeting Technique for Protein Degradation in Drug Discovery," Bioessays. 2018 April; 40(4):e1700247, the contents of which are incorporated herein by reference in their entireties).

In some embodiments of the disclosed PROTACs, $M_{E3}$ is a moiety that binds to an E3 ubiquitin ligase selected from Von Hippel-Lindau (VHL) E3 ubiquitin ligase, cereblon (CRBN) E3 ubiquitin ligase, inhibitor of apoptosis protein (IAP) E3 ubiquitin ligase, and mouse double minute 2 homolog (MDM2) E3 ubiquitin ligase.

In other embodiments of the disclosed PROTACs, $M_{E3}$ is a moiety derived from thalidomide, pomalidomide, lenalidomide, iberdomide, (S,R,S)-AHPC-Me hydrochloride, (S,R,S)-AHPC-Me dihydrochloride, cereblon modulator 1, thalidomide-propargyl, (S,R,S)-AHPC-propargyl, (S,R,S)-AHPC hydrochloride, CC-885, thalidomide-O—COOH, lenalidomide hemihydrate, thalidomide fluoride, thalidomide-OH, lenalidomide-Br, thalidomide D4, lenalidomide hydrochloride, (S,R,S)-AHPC-Me, cIAP1 ligand 1, TD-106, E3 ligase Ligand 8, E3 ligase Ligand 9, E3 ligase Ligand 10, E3 ligase Ligand 13, E3 ligase Ligand 14, E3 ligase Ligand 18, BC-1215, VHL ligand 1 (VHL-1), VHL ligand 2 (VHL-2), VHL Ligand 8 (VHL-8), VH032, VH032-cyclopropane-F, VH032 thiol, VH-298, VL-269, VL-285, LCL161, hydroxyproline-based ligands, HIF-1α-derived (R)-hydroxyproline, Nutlin carboxylic acid, (4R,5S)-Nutlin carboxylic acid, (S,R,S)-AHPC-Boc, AR antagonist 1, NV03, (S,R,S)-AHPC TFA, (S,R,S)-AHPC, β-Naphthoflavone-CH2-Br, β-Naphthoflavone-CH2-OH, Bestatin-amido-Me, MV-1-NH-Me, (S,S,S)-AHPC hydrochloride, and cIAP1 ligand 2.

In some embodiments of the disclosed PROTACs, $M_{E3}$ has a formula selected from:

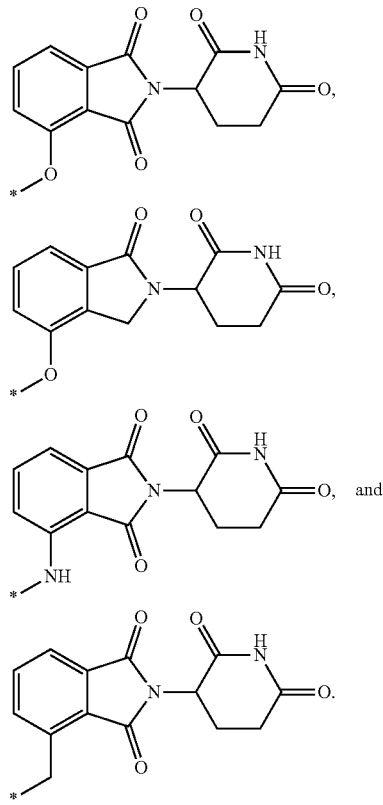

In some embodiments of the disclosed PROTACs, $M_{E3}$ has a formula:

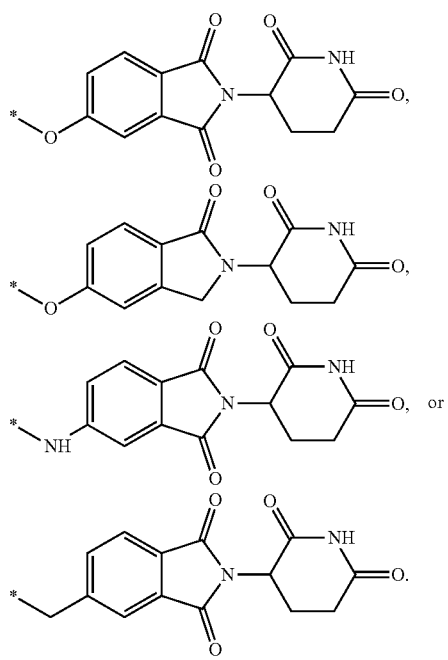

In some embodiments of the disclosed PROTACs, $M_{E3}$ has a formula:

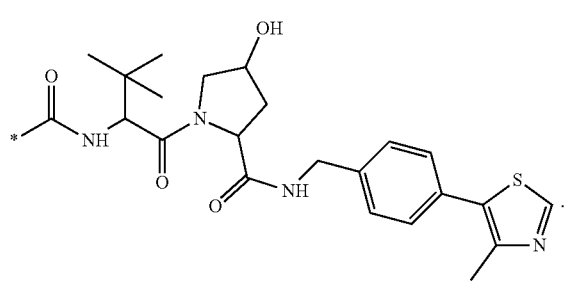 [SMILES: *C(=O)NC(C(=O)N1CC(O)CC1C(=O)NCc1ccc(-c2scnc2C)cc1)C(C)(C)C]

In some embodiments, the disclosed PROTACs have a formula:

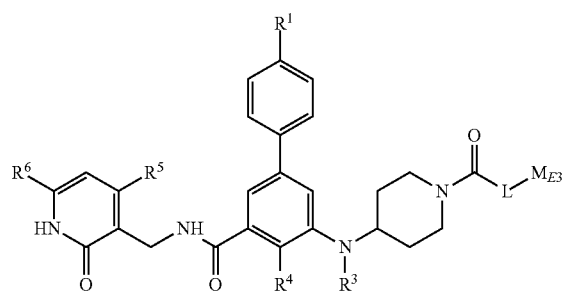

wherein
$R^1$ is an electrophile or $R^1$ is hydrogen, alkyl, or —CH$_2$—X, wherein X is selected from hydrogen, alkyl, amino, piperazinyl (e.g. piperazin-1-yl or N-piperazinyl), morpholinyl (e.g., morpholin-4-yl or N-morpholinyl), piperidinyl (e.g., piperidin-4-yl or N-piperidinyl), and maleimidyl (e.g., N-maleimidyl);
$R^3$ is hydrogen or alkyl;
$R^4$ is hydrogen or alkyl;
$R^5$ is hydrogen or alkyl;
$R^6$ is hydrogen or alkyl;
L is selected from:
(CH$_2$)$_m$—, —(CH$_2$)$_m$CH$_2$CH$_2$C(O)NHCH$_2$CH$_2$—,
(CH$_2$)$_m$CH$_2$CH$_2$C(O)NHCH$_2$CH$_2$CH$_2$—,
(CH$_2$CH$_2$O)$_n$CH$_2$CH$_2$C(O)NHCH$_2$CH$_2$—,
(CH$_2$CH$_2$O)$_n$CH$_2$CH$_2$C(O)NHCH$_2$CH$_2$CH$_2$—,
(CH$_2$CH$_2$O)$_n$CH$_2$CH$_2$—, —(CH$_2$CH$_2$O)$_n$CH$_2$—,
—(CH$_2$)$_m$C(O)NHCH$_2$CH$_2$—,
(CH$_2$CH$_2$O)$_n$CH$_2$CH$_2$C(O)NHCH$_2$CH$_2$—,
—CH$_2$CH$_2$C(O)NHCH$_2$CH$_2$CH$_2$—,
CH$_2$CH$_2$C(O)NHCH$_2$CH$_2$CH$_2$C(O)NHCH$_2$CH$_2$—,
CH$_2$CH$_2$C(O)NHCH$_2$CH$_2$CH$_2$C(O)NHCH$_2$CH$_2$CH$_2$C(O)NHCH$_2$CH$_2$—,
CH$_2$CH$_2$C(O)NHCH$_2$CH$_2$CH$_2$C(O)NHCH$_2$CH$_2$CH$_2$C(O)NHCH$_2$CH$_2$CH$_2$—,
(CH$_2$CH$_2$O)$_n$CH$_2$CH$_2$—, —CH$_2$OCH$_2$—,
—CH$_2$OCH$_2$C(O)NHCH$_2$CH$_2$—,
CH$_2$OCH$_2$C(O)NHCH$_2$CH$_2$CH$_2$—,
CH$_2$OCH$_2$C(O)NHCH$_2$CH$_2$CH$_2$C(O)NHCH$_2$CH$_2$—, and
CH$_2$OCH$_2$C(O)NHCH$_2$CH$_2$CH$_2$C(O)NHCH$_2$CH$_2$CH$_2$—, wherein m and n are 0-20 and $M_{E3}$ is selected from:

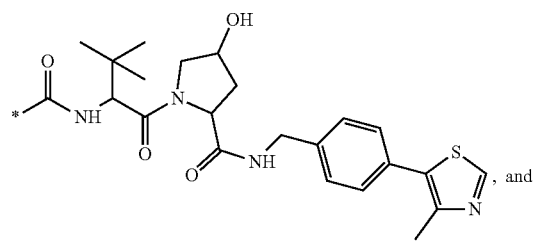

, and

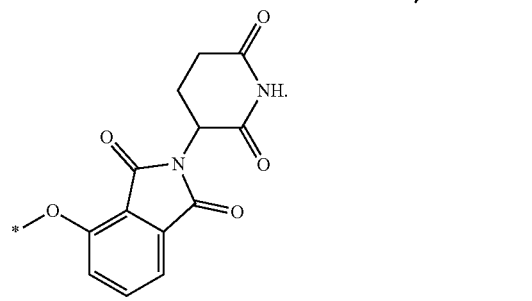

In some embodiments, the disclosed PROTACs have a formula:

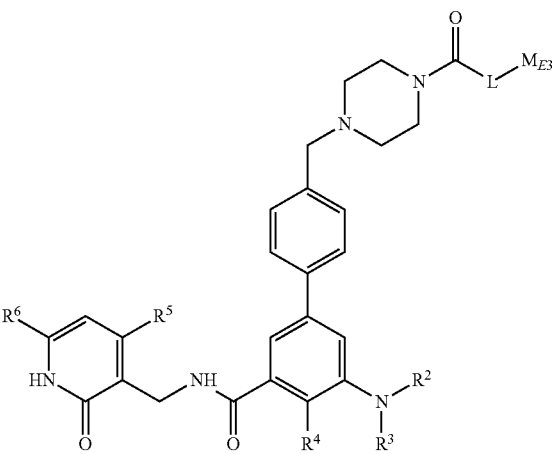

wherein
$R^2$ is selected from hydrogen, alkyl, piperidinyl (e.g., piperidin-4-yl) and oxane (e.g., oxan-4-yl);
$R^3$ is hydrogen or alkyl;
$R^4$ is hydrogen or alkyl;
$R^5$ is hydrogen or alkyl;
$R^6$ is hydrogen or alkyl;
L is selected from:
(CH$_2$)$_m$—, —(CH$_2$)$_m$CH$_2$CH$_2$C(O)NHCH$_2$CH$_2$—,
(CH$_2$)$_m$CH$_2$CH$_2$C(O)NHCH$_2$CH$_2$CH$_2$—,
(CH$_2$CH$_2$O)$_n$CH$_2$CH$_2$C(O)NHCH$_2$CH$_2$—,
(CH$_2$CH$_2$O)$_n$CH$_2$CH$_2$C(O)NHCH$_2$CH$_2$CH$_2$—,
(CH$_2$CH$_2$O)$_n$CH$_2$CH$_2$—, —(CH$_2$CH$_2$O)$_n$CH$_2$—,
—(CH$_2$)$_m$C(O)NHCH$_2$CH$_2$—,
(CH$_2$CH$_2$O)$_n$CH$_2$CH$_2$C(O)NHCH$_2$CH$_2$—,
—CH$_2$CH$_2$C(O)NHCH$_2$CH$_2$CH$_2$—,
CH$_2$CH$_2$C(O)NHCH$_2$CH$_2$CH$_2$C(O)NHCH$_2$CH$_2$—,
CH$_2$CH$_2$C(O)NHCH$_2$CH$_2$CH$_2$C(O)NHCH$_2$CH$_2$CH$_2$C(O)NHCH$_2$CH$_2$—,
CH$_2$CH$_2$C(O)NHCH$_2$CH$_2$CH$_2$C(O)NHCH$_2$CH$_2$CH$_2$C(O)NHCH$_2$CH$_2$CH$_2$—, (CH$_2$CH$_2$O)$_n$CH$_2$CH$_2$—, —CH$_2$OCH$_2$—,
—CH$_2$OCH$_2$C(O)NHCH$_2$CH$_2$—,
CH$_2$OCH$_2$C(O)NHCH$_2$CH$_2$CH$_2$—,
CH$_2$OCH$_2$C(O)NHCH$_2$CH$_2$CH$_2$C(O)NHCH$_2$CH$_2$—, and
CH$_2$OCH$_2$C(O)NHCH$_2$CH$_2$CH$_2$C(O) NHCH$_2$CH$_2$CH$_2$—, wherein m and n are 0-20; and $M_{E3}$ is selected from:

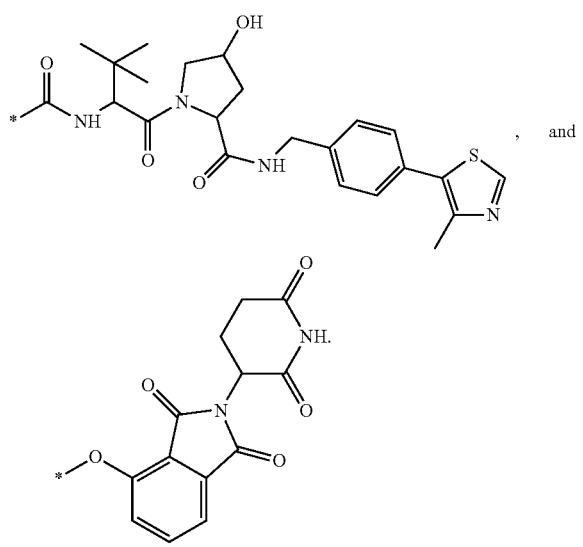

The disclosed compounds and PROTAC derived therefrom may be formulated as pharmaceutical compositions. In some embodiments, pharmaceutical compositions as contemplated herein include a compound or PROTAC as disclosed herein, for example, in an effective amount for treating a disease or disorder associated with EZH2, and a suitable pharmaceutical carrier, excipient, or diluent.

The disclosed compounds, PROTACs, and/or pharmaceutical compositions comprising the disclosed compounds or PROTACs may be administered to subjects in need thereof, for example, to treat and/or prevent a disease or disorder associated with expression of EZH2. Suitable diseases or disorders associated with expression of EZH2 may include cell proliferative diseases or disorders such as cancer. Suitable cancers treated and/or prevented in the disclosed methods may include, but are not limited to, multiple myeloma, leukemia, non-small cell lung cancer, colon cancer, cancer of the central nervous system, melanoma, ovarian cancer, renal cancer, prostate cancer, lymphoma, and breast cancer.

Use of the Disclosed Compounds and Proteolysis-Targeted Chimeric Molecules (PROTACs) for Inhibiting EZH2 Activity The disclosed compounds and proteolysis-targeted chimeric molecules (PROTACs) may exhibit one or more biological activities. The disclosed compound and PROTACs may inhibit the growth of cells that express EZH2 (preferably by at least 50%, 60%, 70%, 80%, 90%, 95%, 96%, 97%, 98%, or 99% at a concentration of less than about 100 μM, 50 μM, 10 μM, 1 μM, 0.1 μM, 0.05 μM, 0.01 μM, 0.005 μM, 0.001 μM, or less). The disclosed compound and PROTACs may not inhibit the growth of cells that do not express EZH2 (preferably by not more than 50%, 40%, 30%, 20%, 10%, 5%, 4%, 3%, 2% or less at a concentration of greater than about 0.001 μM, 0.005 μM, 0.01 μM, 0.5 μM, 0.1 μM, 1.0 μM, 10 μM, and 100 μM or higher). Concentration ranges also are contemplated herein, for example, a concentration range bounded by end-point concentrations selected from 0.001 μM, 0.005 μM, 0.01 μM, 0.5 μM, 0.1 μM, 1.0 μM, 10 μM, and 100 μM.

The disclosed compounds and PROTACs may be effective in inhibiting cell proliferation of cancer cells, including cancer cells that express EZH2 and whose proliferation is inhibiting by inhibiting the biological activity of EZH2. The disclosed compounds and PROTACs may be effective in inhibiting cell proliferation of one or more types of cancer cells including: multiple myeloma cells, such as MM.1S cells; leukemia cells, such as CCRF-CEM, HL-60(TB), MOLT-4, RPMI-8226 and SR; non-small lung cancer cells, such as A549/ATCC, EKVX, HOP-62, HOP-92, NCI-H226, NCI-H23, NCI-H322M, NCI-H460 and NCI-H522; colon cancer cells, such as COLO 205, HCC-2998, HCT-116, HCT-15, HT29, KM12 and SW-620; CNS: SF-268, SF-295, SF-539, SNB-19, SNB-75 and U251; melanoma cancer cells, such as LOX IMVI, MALME-3M, M14, MDA-MB-435, SK-MEL-2, SK-MEL-28, SK-MEL-5, UACC-257 and UACC-62; ovarian cancer cells, such as IGR-OV1, OVCAR-3, OVCAR-4, OVCAR-5, OVCAR-8, NCI/ADR-RES and SK-OV-3; renal cancer cells, such as 786-0, A498, ACHN, CAKI-1, RXF 393, SN12C, TK-10 and UO-31; prostate cancer cells, such as C4-2B, LNCaP, 22Rv1, DU-145 and PC-3; lymphoma cells, such as SU-DHL4 and SU-DHL6; and breast cancer cells, such as MCF7, MDA-MB-231/ATCC, MDA-MB-468, HS 578T, BT-549 and T-47D.

Cell proliferation and inhibition thereof by the presently disclosed compound and PROTACs may be assessed by cell viability methods disclosed in the art including colorimetric assays that utilize dyes such as MTT, XTT, and MTS to assess cell viability. Preferably, the disclosed compound and PROTACs have an IC$_{50}$ of less than about 10 μM, 5 μM, 1 μM, 0.5 μM, 0.01 μM, 0.005 μM, 0.001 μM or lower in the selected assay.

The disclosed compounds and PROTACs may be formulated as anti-cancer therapeutics, including hematologic malignancies (e.g., lymphoma), breast, lung, pancreas and prostate malignancies. The disclosed compounds and molecules also may be formulated as anti-inflammation therapeutics.

The disclosed compounds and PROTACs may be utilized in the methods disclosed herein may be formulated as pharmaceutical compositions that include: (a) a therapeutically effective amount of one or more compounds and molecules as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to about 1000 mg/kg body weight (preferably about 0.5 to about 500 mg/kg body weight, more preferably about 50 to about 100 mg/kg body weight). In some embodiments, after the pharmaceutical composition is administered to a subject (e.g., after about 1, 2, 3, 4, 5, or 6 hours post-administration), the concentration of the compound at the site of action may be within a concentration range bounded by end-points selected from 0.001 μM, 0.005 μM, 0.01 μM, 0.5 μM, 0.1 μM, 1.0 μM, 10 μM, and 100 μM (e.g., 0.1 μM-1.0 μM).

The disclosed compounds and molecules and pharmaceutical compositions comprising the disclosed compounds and molecules may be administered in methods of treating a subject in need thereof. For example, in the methods of treatment a subject in need thereof may include a subject having a cell proliferative disease, disorder, or condition such as cancer (e.g., cancers such as multiple myeloma, leukemia, non-small cell lung cancer, colon cancer, cancer of the central nervous system, melanoma, ovarian cancer, renal cancer, prostate cancer, and breast cancer).

In some embodiments of the disclosed treatment methods, the subject may be administered a dose of a compound as low as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg once daily, twice daily, three times daily, four times daily, once weekly, twice weekly, or three times per week in order to treat the disease or disorder in the subject. In some embodiments, the subject may be administered a dose of a compound as high as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg, once daily, twice daily, three times daily, four times daily, once weekly, twice weekly, or three times per week in order to treat the disease or disorder in the subject. Minimal and/or maximal doses of the compounds and molecules may include doses falling within dose ranges having as end-points any of these disclosed doses (e.g., 2.5 mg-200 mg).

In some embodiments, a minimal dose level of a compound for achieving therapy in the disclosed methods of treatment may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. In some embodiments, a maximal dose level of a compound for achieving therapy in the disclosed methods of treatment may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. Minimal and/or maximal dose levels of the compounds and molecules for achieving therapy in the disclosed methods of treatment may include dose levels falling within ranges having as end-points any of these disclosed dose levels (e.g., 500-2000 ng/kg body weight of the subject).

The compounds and molecules utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds and molecules utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds and molecules utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds and molecules such as phenol, or quaternary compounds and molecules such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds and molecules utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules. In some embodiments, the compounds and molecules are formulated as a composition for administration orally (e.g., in a solvent such as 5% DMSO in oil such as vegetable oil).

The compounds and molecules utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds and molecules may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

Combination Therapies and Pharmaceutical Compositions

The disclosed compounds and PROTACS or pharmaceutical compositions comprising the disclosed compounds and PROTACS may be administered in methods of treatment. For example, the disclosed compounds and PROTACS or pharmaceutical compositions comprising the disclosed compounds and PROTACS may be administered in methods of treating cell proliferative diseases and disorders. Cell proliferative diseases and disorders treated by the disclosed methods may include, but are not limited to, cancers selected from the group consisting of multiple myeloma, leukemia, non-small cell lung cancer, colon cancer, cancer of the central nervous system, melanoma, ovarian cancer, renal cancer, prostate cancer, lymphoma, and breast cancer.

Optionally, the disclosed compounds and PROTACS or pharmaceutical compositions comprising the disclosed compounds and PROTACS may be administered with additional therapeutic agents, optionally in combination, in order to treat cell proliferative diseases and disorders. In some embodiments of the disclosed methods, one or more additional therapeutic agents are administered with the disclosed compounds and PROTACS s or with pharmaceutical compositions comprising the disclosed compounds and molecules, where the additional therapeutic agent is administered prior to, concurrently with, or after administering the disclosed compounds and PROTACS or the pharmaceutical compositions comprising the disclosed compounds and PROTACS. In some embodiments, the disclosed pharmaceutical composition are formulated to comprise the disclosed compounds and PROTACS and further to comprise one or more additional therapeutic agents, for example, one or more additional therapeutic agents for treating cell proliferative diseases and disorders.

ILLUSTRATIVE EMBODIMENTS

Embodiment 1. A compound of a Formula I or a salt, hydrate, or solvate thereof:

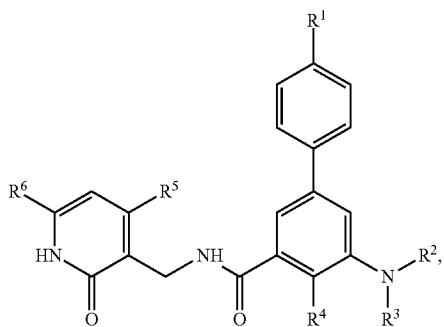

wherein
- $R^1$ is and electrophile or $R^1$ is hydrogen, alkyl, or —$CH_2$—X, wherein X is selected from hydrogen, alkyl, amino, piperazinyl (e.g. piperazin-1-yl or N-piperazinyl), morpholinyl (e.g., morpholin-4-yl or N-morpholinyl), piperidinyl (e.g., piperidin-4-yl or N-piperidinyl), and maleimidyl (e.g., N-maleimidyl), and X optionally is substituted with a substituent selected from alkyl, alkoxy, —C(O)—H, —C(O)—$(CH_2)_m$—$CH_3$ where m is 0-20, —$(CH_2CH_2O)_n$—H or —$(CH_2CH_2O)_n$—$CH_3$ where m is 0-20, —C(O)—$(CH_2CH_2O)_n$—H or —C(O)—$(CH_2CH_2O)_n$—$CH_3$ where n is 0-20, —C(O)—$CH_2OCH_3$, —C(O)—$CH_2$—CH($CH_2CH_2CH_3$)$_2$, —C(O)—CH=CH-phenyl, —C(O)—$CH_3$, —C(O)—$CH_2Cl$, —C(O)—CH=C($CH_3$)$_2$, —C(O)—CH=$CH_2$, —C(O)-ethynyl, —C(O)-adamantyl, —S(O)(O)—H, —S(O)(O)—$CH_3$, —S(O)(O)-phenyl, —C(O)—$CH_2$—$CH_3$, —$CH_2$—S(O)(O)—H, —$CH_2$—$CH_2$—S(O)(O)—H, —$CH_2$—$CH_2$—S(O)(O)—$CH_3$, —$CH_2$—$CH_2$—S(O)(O)-phenyl, —CH=CH—S(O)(O)—H, —CH=CH—S(O)(O)—$CH_3$, and —CH=CH—S(O)(O)-phenyl;
- $R^2$ is selected from hydrogen, alkyl, piperidinyl (e.g., piperidin-4-yl) and oxane (e.g., oxan-4-yl), wherein $R^3$ optionally is substituted with a substituent selected from alkyl, alkoxy, —C(O)—H, —C(O)—$(CH_2)_m$—$CH_3$ where m is 0-20, —$(CH_2CH_2O)_n$—H or —$(CH_2CH_2O)_n$—$CH_3$ where m is 0-20, —C(O)—$(CH_2CH_2O)_n$—H or —C(O)—$(CH_2CH_2O)_n$—$CH_3$ where n is 0-20, —C(O)—$CH_2OCH_3$, —C(O)—$CH_2$—CH($CH_2CH_2CH_3$)$_2$, —C(O)—CH=CH-phenyl, —C(O)—$CH_3$, —C(O)—$CH_2Cl$, —C(O)—CH=C($CH_3$)$_2$, —C(O)—CH=$CH_2$, —C(O)-ethynyl, —C(O)-adamantyl, —S(O)(O)—H, —S(O)(O)—$CH_3$, —S(O)(O)-phenyl, —C(O)—$CH_2$—$CH_3$, —$CH_2$—S(O)(O)—H, —$CH_2$—$CH_2$—S(O)(O)—H, —$CH_2$—$CH_2$—S(O)(O)—$CH_3$, —$CH_2$—$CH_2$—S(O)(O)-phenyl, —CH=CH—S(O)(O)—H, —CH=CH—S(O)(O)—$CH_3$, and —CH=CH—S(O)(O)-phenyl;
- $R^3$ is hydrogen or alkyl;
- $R^4$ is hydrogen or alkyl;
- $R^5$ is hydrogen or alkyl; and
- $R^6$ is hydrogen or alkyl.

Embodiment 2. The compound of embodiment 1, wherein $R^1$ is —$CH_2$—X.

Embodiment 3. The compound of any of the foregoing embodiments, wherein $R^1$ is optionally substituted methyl-piperazinyl (e.g., optionally substituted methyl-piperazin-1-yl or methyl-N-piperazinyl)

Embodiment 4. The compound of any of the foregoing embodiments, wherein $R^1$ is selected from

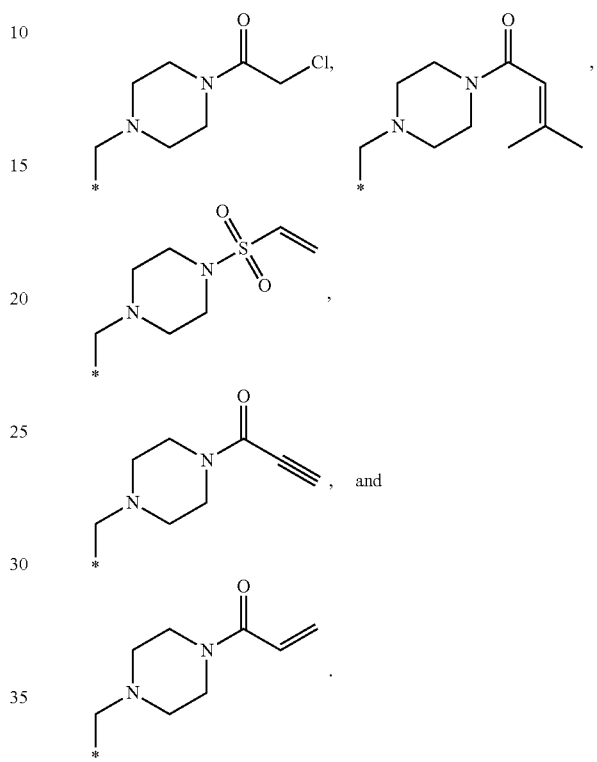

Embodiment 5. The compound of any of embodiments 1-4, wherein $R^1$ is methyl-morpholinyl (e.g., methyl-morpholin-4-yl or methyl-N-morpholinyl).

Embodiment 6. The compound of any of the foregoing embodiments, wherein $R^2$ is optionally substituted piperidinyl (e.g., piperidin-4-yl).

Embodiment 7. The compound of any of the foregoing embodiments, wherein $R^2$ is selected from:

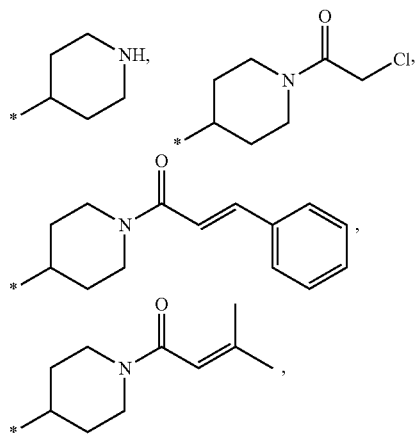

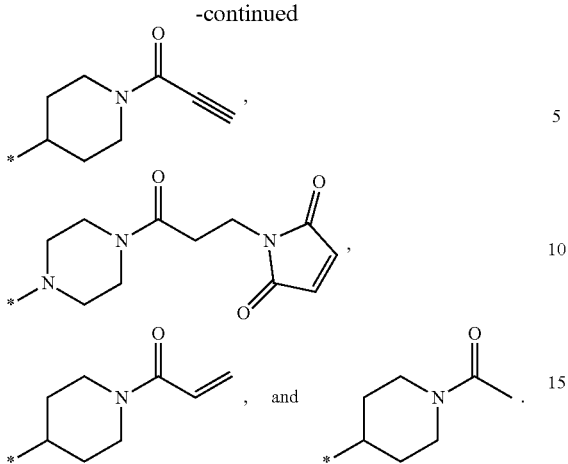

Embodiment 8. The compound of any of embodiments 1-5, wherein $R^2$ is oxane (e.g., oxan-4-yl).

Embodiment 9. The compound of any of the foregoing embodiments, wherein $R^3$ is alkyl.

Embodiment 10. The compound of any of the foregoing embodiments, wherein $R^3$ is ethyl.

Embodiment 11. The compound of any of the foregoing embodiments, wherein $R^4$ is methyl.

Embodiment 12. The compound of any of the foregoing embodiments, wherein one or both of $R^5$ and $R^6$ are methyl.

Embodiment 13. A molecule having a formula: $M_{EZH2}$-L-$M_{E3}$ or a salt, hydrate, or solvate thereof, wherein $M_{EZH2}$ is a moiety that binds to EZH2, L is a bond or a linker covalently attaching $M_{EZH2}$ and $M_{E3}$, and $M_{E3}$ is a moiety that binds to an E3 ubiquitin ligase.

Embodiment 14. The molecule of embodiment 13, wherein $M_{EZH2}$ has a formula derived from a compound having a Formula I

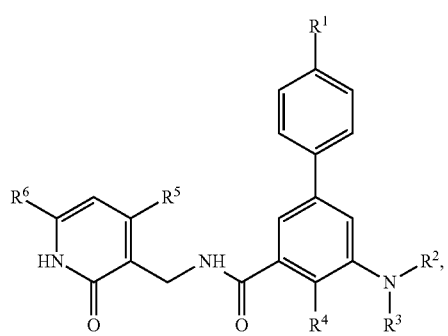

wherein
$R^1$ is an electrophile or $R^1$ is hydrogen, alkyl, or —CH$_2$—X, wherein X is selected from hydrogen, alkyl, amino, piperazinyl (e.g. piperazin-1-yl or N-piperazinyl), morpholinyl (e.g., morpholin-4-yl or N-morpholinyl), piperidinyl (e.g., piperidin-4-yl or N-piperidinyl), and maleimidyl (e.g., N-maleimidyl), and X optionally is substituted with a substituent selected from alkyl, alkoxy, —C(O)—H, —C(O)—(CH$_2$)$_m$—CH$_3$ where m is 0-20, —(CH$_2$CH$_2$O)$_n$—H or —(CH$_2$CH$_2$O)$_n$—CH$_3$ where n is 0-20, —C(O)—(CH$_2$CH$_2$O)$_n$—H or —C(O)—(CH$_2$CH$_2$O)$_n$—CH$_3$ where n is 0-20, —C(O)—CH$_2$OCH$_3$, —C(O)—CH$_2$—CH(CH$_2$CH$_2$CH$_3$)$_2$, —C(O)—CH=CH-phenyl, —C(O)—CH$_3$, —C(O)—CH$_2$Cl, —C(O)—CH=C(CH$_3$)$_2$, —C(O)—CH=CH$_2$, —C(O)-ethynyl, —C(O)-adamantyl, —S(O)(O)—H, —S(O)(O)—CH$_3$, —S(O)(O)-phenyl, —C(O)—CH$_2$—CH$_3$, —CH$_2$—S(O)(O)—H, —CH$_2$—CH$_2$—S(O)(O)—H, —CH$_2$—CH$_2$—S(O)(O)—CH$_3$, —CH$_2$—CH$_2$—S(O)(O)-phenyl, —CH=CH—S(O)(O)—H, —CH=CH—S(O)(O)—CH$_3$, and —CH=CH—S(O)(O)-phenyl;

$R^2$ is hydrogen or alkyl;

$R^3$ is selected from hydrogen, alkyl, piperidinyl (e.g., piperidin-4-yl) and oxane (e.g., oxan-4-yl), wherein $R^3$ optionally is substituted with a substituent selected from alkyl, alkoxy, —C(O)—H, —C(O)—(CH$_2$)$_m$—CH$_3$ where m is 0-20, —(CH$_2$CH$_2$O)$_n$—H or —(CH$_2$CH$_2$O)$_n$—CH$_3$ where n is 0-20, —C(O)—(CH$_2$CH$_2$O)$_n$—H or —C(O)—(CH$_2$CH$_2$O)$_n$—CH$_3$ where n is 0-20, —C(O)—CH$_2$OCH$_3$, —C(O)—CH$_2$—CH(CH$_2$CH$_2$CH$_3$)$_2$, —C(O)—CH=CH-phenyl, —C(O)—CH$_3$, —C(O)—CH$_2$Cl, —C(O)—CH=C(CH$_3$)$_2$, —C(O)—CH=CH$_2$, —C(O)-ethynyl, —C(O)-adamantyl, —S(O)(O)—H, —S(O)(O)—CH$_3$, —S(O)(O)-phenyl, —C(O)—CH$_2$—CH$_3$, —CH$_2$—S(O)(O)—H, —CH$_2$—CH$_2$—S(O)(O)—H, —CH$_2$—CH$_2$—S(O)(O)—CH$_3$, —CH$_2$—CH$_2$—S(O)(O)-phenyl, —CH=CH—S(O)(O)—H, —CH=CH—S(O)(O)—CH$_3$, and —CH=CH—S(O)(O)-phenyl;

$R^4$ is hydrogen or alkyl;

$R^5$ is hydrogen or alkyl; and $R^6$ is hydrogen or alkyl.

Embodiment 15. The molecule of embodiment 14, wherein $R^1$ is —CH$_2$—X.

Embodiment 16. The molecule of embodiments 14 or 15, wherein $R^1$ is methyl-piperazinyl (e.g. methyl-piperazin-1-yl or methyl-N-piperazinyl.

Embodiment 17. The molecule of any of embodiments 14-16, wherein $R^1$ is an electrophile, and $R^1$ optionally is selected from

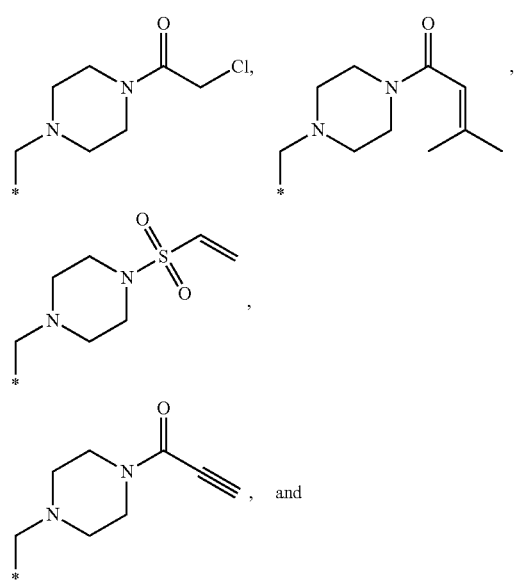

-continued

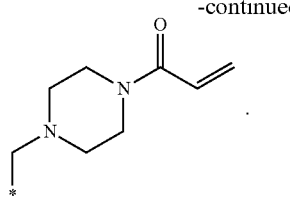

Embodiment 18. The molecule of embodiments 14 or 15, wherein $R^1$ is methyl-morpholinyl (e.g., methyl-morpholin-4-yl or methyl-N-morpholinyl).

Embodiment 19. The molecule of any of embodiments 14-18, wherein $R^2$ optionally substituted piperidinyl (e.g., piperidin-4-yl).

Embodiment 20. The molecule of any of embodiments 14-19, wherein $R^2$ is selected from:

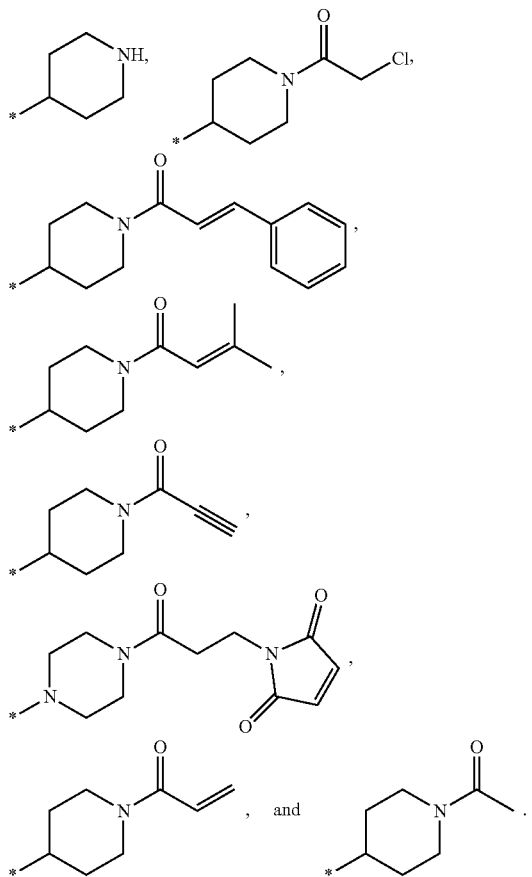

Embodiment 21. The molecule of any of embodiments 14-18, wherein $R^2$ is oxane (e.g., oxan-4-yl).

Embodiment 22. The molecule of any of embodiments 14-21, wherein $R^3$ is alkyl.

Embodiment 23. The molecule of any of embodiments 14-22, wherein $R^3$ is ethyl.

Embodiment 24. The molecule of any of embodiments 14-23, wherein $R^4$ is methyl.

Embodiment 25. The molecule of any of embodiments 14-24, wherein one or both of $R^5$ and $R^6$ are methyl.

Embodiment 26. The molecule of any of embodiments 13-25, wherein $M_{EZH2}$ has a formula:

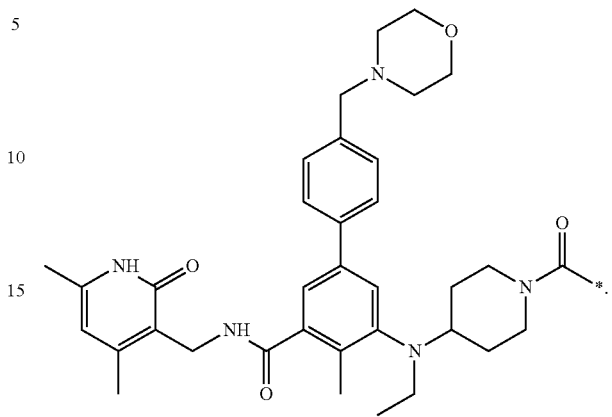

Embodiment 27. The molecule of any of embodiments 13-25, wherein $M_{EZH2}$ has a formula:

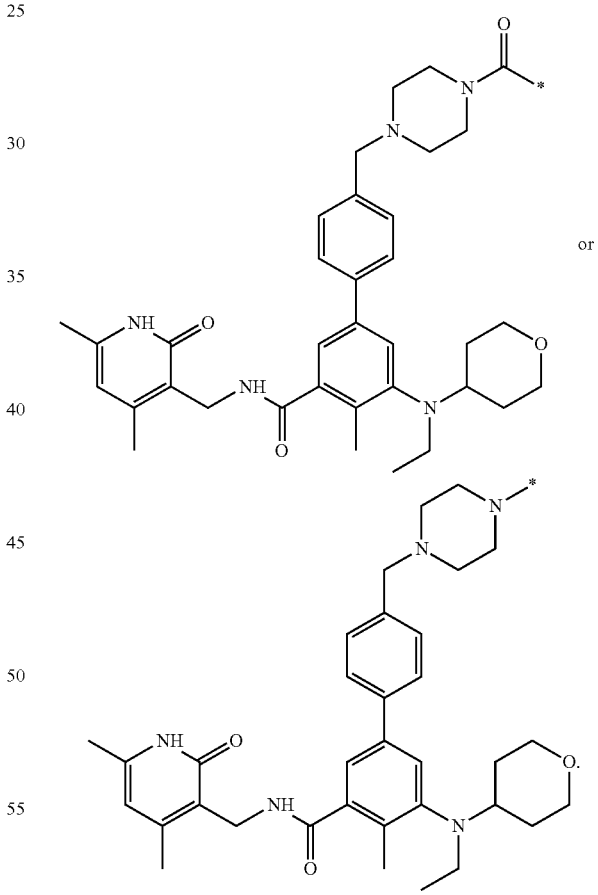

or,

Embodiment 28. The molecule of any of embodiments 13-27, wherein L comprises a polyethylene glycol moiety, an alkylalkyne moiety, and/or an aminoalkyl alkyne moiety, or, wherein L has a formula selected from: —$(CH_2)_m$—, —$(CH_2)_m CH_2 CH_2 C(O)NHCH_2 CH_2$—, —$(CH_2)_m CH_2 CH_2 C(O)NHCH_2 CH_2 CH_2$—, —$(CH_2 CH_2 O)_n CH_2 CH_2 C(O)NHCH_2 CH_2$—, —$(CH_2 CH_2 O)_n CH_2 CH_2 C(O)NHCH_2 CH_2 CH_2$—, —(CH₂CH₂O)$_n$CH₂CH₂—, —(CH₂CH₂O)$_n$CH₂—, —(CH₂CH₂O)$_n$CH₂CH₂—, —(CH₂)$_m$C(O)NHCH₂CH₂—, —(CH₂CH₂O)$_n$CH₂CH₂C(O)NHCH₂CH₂—, —CH₂CH₂C(O)NHCH₂CH₂CH₂—, —CH₂CH₂C(O)NHCH₂CH₂CH₂C(O)NHCH₂CH₂, —CH₂CH₂C(O)NHCH₂CH₂CH₂C(O)NHCH₂CH₂CH₂C(O)NHCH₂CH₂, —CH₂CH₂C(O)NHCH₂CH₂CH₂C(O)NHCH₂CH₂CH₂C(O)NHCH₂CH₂CH₂—(CH₂CH₂O)$_n$CH₂CH₂—, —CH₂OCH₂—, —CH₂OCH₂C(O)NHCH₂CH₂—, —CH₂OCH₂C(O)NHCH₂CH₂CH₂—, and —CH₂OCH₂C(O)NHCH₂CH₂CH₂C(O)NHCH₂CH₂—CH₂OCH₂C(O)NHCH₂CH₂CH₂C(O)NHCH₂CH₂CH₂—, wherein m and n are 1-20.

Embodiment 29. The molecule of any of embodiments 13-28, wherein $M_{E3}$ is a moiety that binds to an E3 ubiquitin ligase selected from Von Hippel-Lindau (VHL) E3 ubiquitin ligase, cereblon (CRBN) E3 ubiquitin ligase, inhibitor of apoptosis protein (IAP) E3 ubiquitin ligase, and mouse double minute 2 homolog (MDM2) E3 ubiquitin ligase.

Embodiment 30. The molecule of any of embodiments 13-28, wherein $M_{E3}$ is a moiety derived from thalidomide, pomalidomide, lenalidomide, VHL ligand 1 (VHL-1), VHL ligand 2 (VHL-2), VH032, VL-269, LCL161, hydroxyproline-based ligands, or HIF-1α-derived (R)-hydroxyproline.

Embodiment 31. The molecule of any of embodiments 13-30, wherein $M_{E3}$ has a formula selected from:

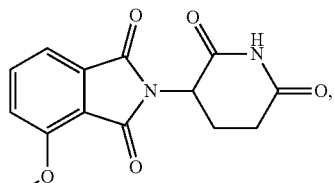

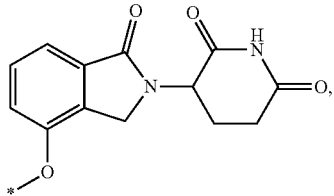

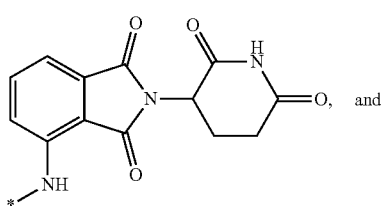

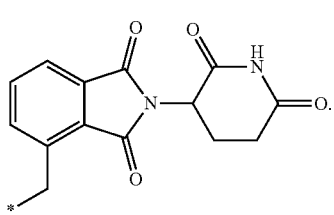

Embodiment 32. The molecule of any of embodiments 13-29, wherein $M_{E3}$ has a formula:

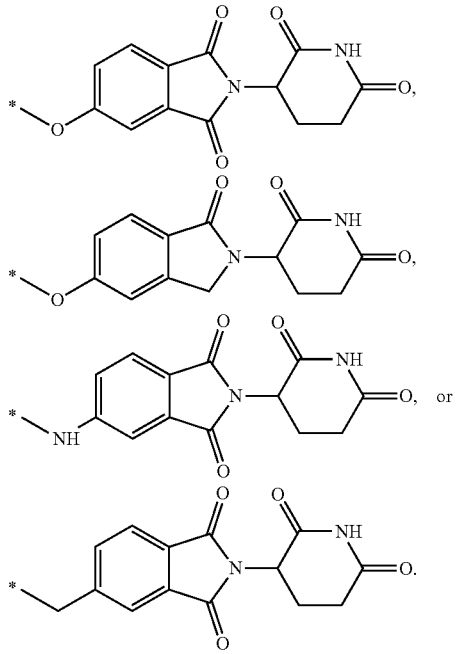

Embodiment 33. The molecule of any of embodiments 13-29, wherein $M_{E3}$ has a formula:

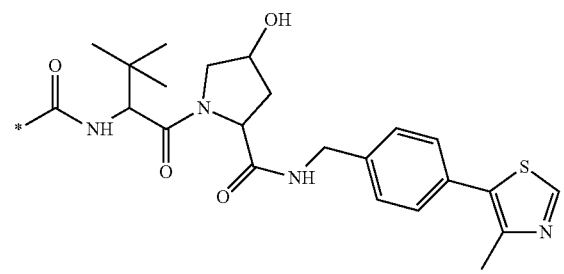

Embodiment 34. The molecule of embodiment 13 having a formula:

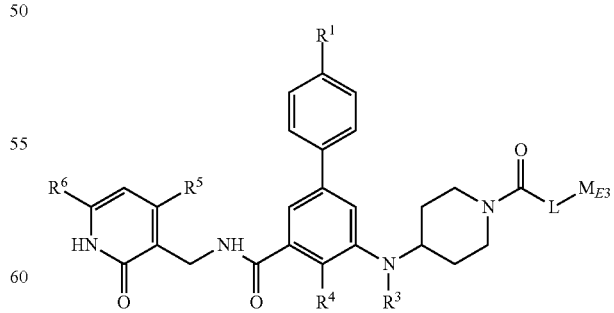

wherein $R^1$ is hydrogen, alkyl, or —CH₂—X, wherein X is selected from hydrogen, alkyl, amino, piperazinyl (e.g. piperazin-1-yl or N-piperazinyl), morpholinyl (e.g., morpholin-4-yl or N-morpholinyl), piperidinyl (e.g., piperidin-4-yl or N-piperidinyl), and maleimidyl (e.g., N-maleimidyl);

$R^3$ is hydrogen or alkyl;
$R^4$ is hydrogen or alkyl;
$R^5$ is hydrogen or alkyl;
$R^6$ is hydrogen or alkyl;
L is selected from —$(CH_2)_m$—, —$(CH_2)_mCH_2CH_2C(O)NHCH_2CH_2$—, —$(CH_2)_mCH_2CH_2C(O)NHCH_2CH_2CH_2$—, —$(CH_2CH_2O)_nCH_2CH_2C(O)NHCH_2CH_2$—, —$(CH_2CH_2O)_nCH_2CH_2C(O)NHCH_2CH_2CH_2$—, —$(CH_2CH_2O)_nCH_2CH_2$—, —$(CH_2CH_2O)_nCH_2$—, $(CH_2)_mC(O)NHCH_2CH_2$—, —$(CH_2CH_2O)_nCH_2CH_2C(O)NHCH_2CH_2$—, —$CH_2CH_2C(O)NHCH_2CH_2CH_2$—, —$CH_2CH_2C(O)NHCH_2CH_2CH_2C(O)NHCH_2CH_2$, —$CH_2CH_2C(O)NHCH_2CH_2CH_2C(O)NHCH_2CH_2CH_2C(O)NHCH_2CH_2$, —$CH_2CH_2C(O)NHCH_2CH_2CH_2C(O)NHCH_2CH_2CH_2C(O)NHCH_2CH_2CH_2$—$(CH_2CH_2O)_nCH_2CH_2$—, —$CH_2OCH_2$—, —$CH_2OCH_2C(O)NHCH_2CH_2$—, —$CH_2OCH_2C(O)NHCH_2CH_2CH_2$—, and —$CH_2OCH_2C(O)NHCH_2CH_2CH_2C(O)NHCH_2CH_2$—$CH_2OCH_2C(O)NHCH_2CH_2CH_2C(O)NHCH_2CH_2CH_2$—, wherein m and n are 1-20; and $M_{E3}$ is selected from:

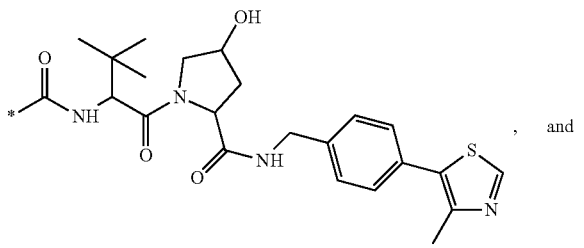
, and

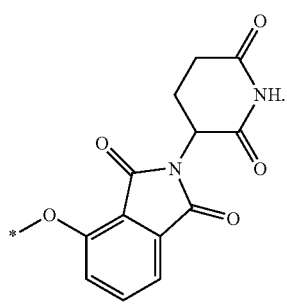

Embodiment 35. The molecule of embodiment 13 having a formula:

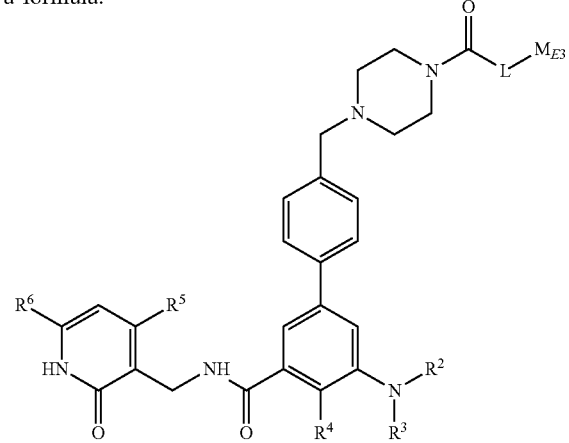

wherein
$R^2$ is selected from hydrogen, alkyl, piperidinyl (e.g., piperidin-4-yl) and oxane (e.g., oxan-4-yl);
$R^3$ is hydrogen or alkyl;
$R^4$ is hydrogen or alkyl;
$R^5$ is hydrogen or alkyl;
$R^6$ is hydrogen or alkyl;
L is selected from —$(CH_2)_m$—, —$(CH_2)_mCH_2CH_2C(O)NHCH_2CH_2$—, —$(CH_2)_mCH_2CH_2C(O)NHCH_2CH_2CH_2$—, —$(CH_2CH_2O)_nCH_2CH_2C(O)NHCH_2CH_2$—, —$(CH_2CH_2O)_nCH_2CH_2C(O)NHCH_2CH_2CH_2$—, —$(CH_2CH_2O)_nCH_2CH_2$—, —$(CH_2CH_2O)_nCH_2$—, —$(CH_2)_mC(O)NHCH_2CH_2$—, —$(CH_2CH_2O)_nCH_2CH_2C(O)NHCH_2CH_2$—, —$CH_2CH_2C(O)NHCH_2CH_2CH_2$—, —$CH_2CH_2C(O)NHCH_2CH_2CH_2C(O)NHCH_2CH_2$, —$CH_2CH_2C(O)NHCH_2CH_2CH_2C(O)NHCH_2CH_2CH_2C(O)NHCH_2CH_2$, —$CH_2CH_2C(O)NHCH_2CH_2CH_2C(O)NHCH_2CH_2CH_2C(O)NHCH_2CH_2CH_2$—$(CH_2CH_2O)_nCH_2CH_2$—, —$CH_2OCH_2$—, —$CH_2OCH_2C(O)NHCH_2CH_2$—, —$CH_2OCH_2C(O)NHCH_2CH_2CH_2$—, and —$CH_2OCH_2C(O)NHCH_2CH_2CH_2C(O)NHCH_2CH_2$—, —$CH_2OCH_2C(O)NHCH_2CH_2CH_2C(O)NHCH_2CH_2CH_2$—, wherein m and n are 1-20; and $M_{E3}$ is selected from:

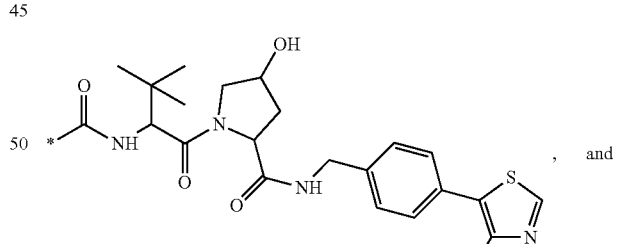
, and

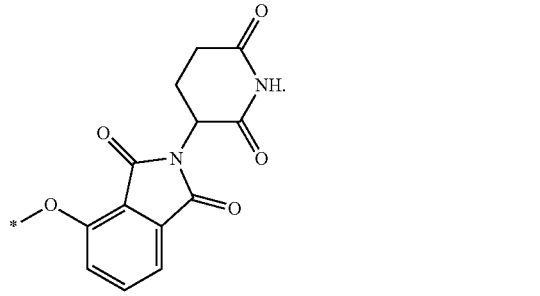

Embodiment 36. A compound or a salt, hydrate, or solvate thereof selected from Table 1.

Embodiment 37. A molecule or a salt, hydrate, or solvate thereof selected from Table 2.

Embodiment 38. A pharmaceutical composition comprising a compound of any of embodiments 1-12 or 36 or the molecule of any of embodiments 13-35 or 38 and a suitable pharmaceutical carrier, excipient, or diluent.

Embodiment 39. A method of treating cancer, the method comprising administering the composition of embodiment 38 to a subject having the cancer.

Embodiment 40. The method of embodiment 39, wherein the cancer is associated with aberrant EZH2 activity.

Embodiment 41. The method of any of embodiments 39-40, wherein the cancer is selected from multiple myeloma, leukemia, non-small cell lung cancer, colon cancer, cancer of the central nervous system, melanoma, ovarian cancer, renal cancer, prostate cancer, lymphoma, and breast cancer.

Embodiment 42. The method of any of embodiments 39-41, wherein the subject is in need of a degrader or inhibitor of EZH2.

EXAMPLES

The following examples are illustrative and should not be interpreted to limit the scope of the claimed subject matter.

Example 1—Covalent Inhibitors of Enhance Zeste Homolog 2 (EZH2)

Synthesis of methyl 5-bromo-2-methyl-3-((tetrahydro-2H-pyran-4-yl)amino)benzoate

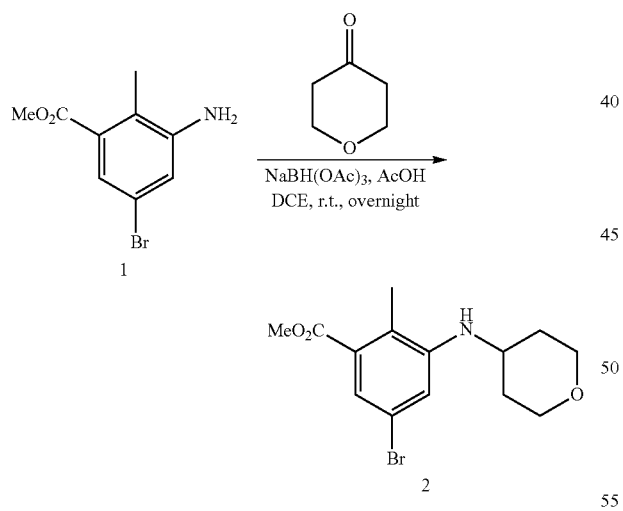

Ref: Bioorganic & Medicinal Chemistry Letters, 30(5), 126957; 2020

To a 50 mL flask was added methyl 3-amino-5-bromo-2-methylbenzoate (1.5 g, 6.1 mmol), tetrahydro-4H-pyran-4-one (0.92 g, 0.85 mL, 1.5 Eq, 9.2 mmol) and acetic acid (2.2 g, 2.1 mL, 6.0 Eq, 37 mmol) in 1,2-Dichloroethane (5 mL) and allowed to stir for 1 h at room temperature. Then sodium triacetoxyborohydride (5.2 g, 4.0 Eq, 25 mmol) was added to the reaction at room temperature and allowed to stir at room temperature overnight. LCMS showed complete conversion. A saturated solution of NaHCO₃ was added to the reaction mixture and extracted with DCM. The organic layers were dried by Na2SO4 and concentrated to dryness and purified via flash column chromatography with EtOAc/Hex (25 g Biotage column, 1/3) to give the title compound (1.99 g, 6.06 mmol, 99%) as an off-white solid.

Synthesis of methyl 5-bromo-3-(ethyl(tetrahydro-2H-pyran-4-yl)amino)-2-methylbenzoate

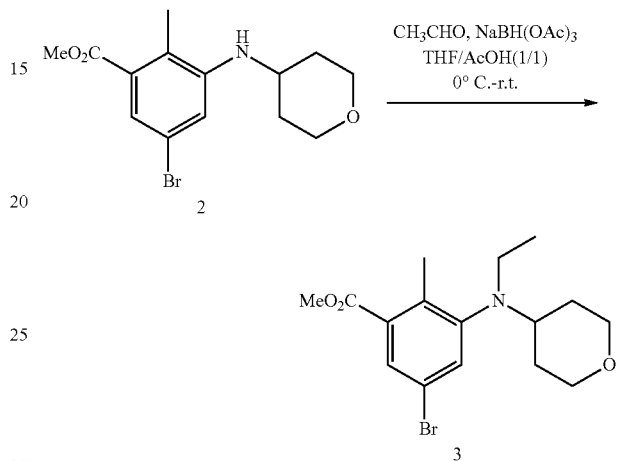

Ref: Bioorganic & Medicinal Chemistry Letters, 30(5), 126957; 2020

To a 100 ml flask was added methyl 5-bromo-2-methyl-3-((tetrahydro-2H-pyran-4-yl)amino)benzoate (7.7 g, 23 mmol) and CH₃CHO (35 mmol) in TFA/AcOH (1:1, 134 mL). Then sodium triacetoxyborohydride (9.9 g, 2.0 eq, 46 mmol) was added to the reaction at 0° C. and allowed to stir at room temperature overnight. LCMS showed complete conversion (if not, added proper eq of CH3CHO and NaBH(OAc)3). Remove most of THF and AcOH by rotavap, then adjust the pH to 5-6 by saturated solution of NaHCO3, extracted with DCM. The organic layers were dried by Na2SO4 and concentrated to dryness and purified via flash column chromatography with EtOAc/Hex(dry loading, 100 g Biotage Column, 3-8%) to give the title compound (7.35 g, 88%) as a light yellow oil.

Synthesis of 5-bromo-N-((4,6-dimethyl-2-oxo-1,2-dihydropyridin-3-yl)methyl)-3-(ethyl(tetrahydro-2H-pyran-4-yl)amino)-2-methylbenzamide

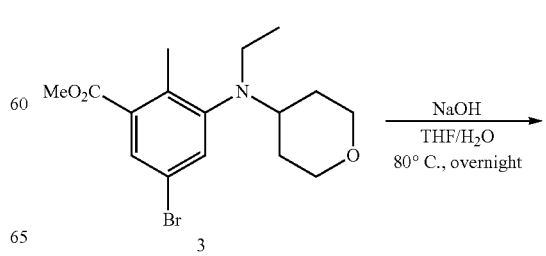

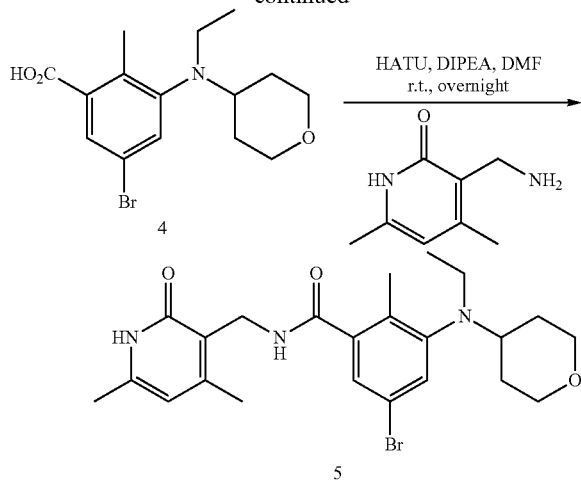

Ref: Bioorganic & Medicinal Chemistry Letters, 30(5), 126957; 2020

To a 250 mL flask was added methyl 5-bromo-3-(ethyl(tetrahydro-2H-pyran-4-yl)amino)-2-methylbenzoate (8. g, 22 mmol) in THF/H2O (5/3, 160 mL) followed by addition of NaOH (9 g, 10 eq, 220 mmol) and allowed to stir at 80° C. overnight. LCMS showed complete conversion. The reaction mixture was allowed to cool to room temperature and removed most of solvent by rotavap, and addition of 2M HCl (110 ml) to reaction mixture until pH=2, extracted with EtOAc, dried by Na2SO4 and concentrated to dryness to give a white fluffy solid 4. The solid was used for the next step without additional purification.

Compound 4 was transferred to 250 ml flask by dissolving in 75 ml DMF, followed by addition of DIPEA (11.6 ml, 3 eq, 66 mmol) and HATU (12.7 g, 1.5 eq, 33 mmol), stirred at room temperature for 30 min, then added 3-(aminomethyl)-4,6-dimethylpyridin-2(1H)-one (5.07 g, 1.5 eq, 33 mmol), stirred at room temperature overnight. 50 ml CH3CN was added to dilute the mixture, filtered under vacuum, washed by 100-150 ml CH3CN, dispense the solid in 100 ml CH3CN, stirred for 10 min at room temperature, filter again, wash by 100 ml CH3CN, dried it under rotavap at 45° C. for 40 min, give gray solid 9.5 g (90% pure by HNMR, 81% yield) used for next step without further purification.

Synthesis of tert-butyl 4-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)methyl)piperazine-1-carboxylate

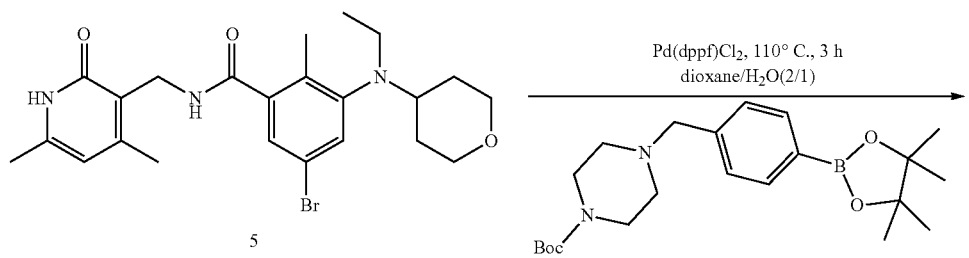

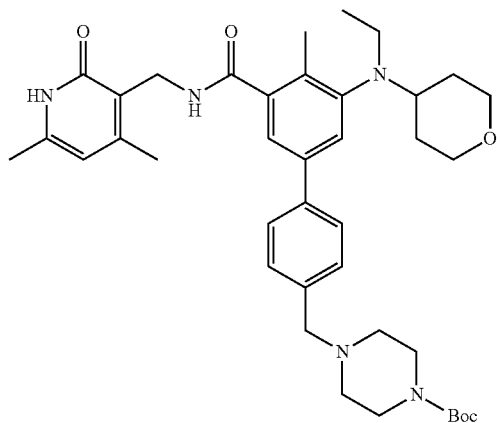

Ref: *Nat. Chem. Bio.* 2017, 13, 381-388 and *ACS Med. Chem. Lett.* 2019, 10, 334

To a 100 ml flask was added 5-bromo-N-((4,6-dimethyl-2-oxo-1,2-dihydropyridin-3-yl)methyl)-3-(ethyl(tetrahydro-2H-pyran-4-yl)amino)-2-methylbenzamide (7.42 g, 15.6 mmol), tert-butyl 4-(4-(4,4,5,5-tetramethyl-1,3,2-dioxaborolan-2-yl)benzyl)piperazine-1-carboxylate (7.52 g, 1.2 eq, 18.7 mmol), Pd(dppf)Cl2 (1.27 g, 0.10 eq, 1.56 mmol) and sodium bicarbonate (3.27 g, 2.5 eq, 38.9 mmol) in 1,4-Dioxane (100 mL) and Water (50 mL), bubbled by N2 for 10 min and allowed to stir at 110° C. for 3 h. LCMS shows complete conversion. Dioxane was removed by rotavap, H2O (100 ml) was added to the reaction mixture and extracted with EtOAc (100 ml), solid was filtered under vacuum, washed by H2O (40 ml) and EtOAc (100 ml). The liquid part was separated and extracted by DCM and concentrated. The solid part was dissolved in DCM (50 ml), dried by Na2SO4 and filter through short SiO2 pad, washed by DCM/MeOH (10/1, 200 ml), concentrated and recrystallized by Hex/EtOAc (3/1, 100 ml), filtered at normal pressure, washed by Hex/EtOAc (3/1), the solid part (compound 6, 7.1 g, 90% HNMR pure) is dried on rotavap and was pure enough for next step. The mother liquid was combined with the extracted part and purified by via flash column chromatography with MeOH/DCM (dry loading, 100 g Biotage Column, 0-3%, then 3-5%) and recrystallized by Hex/EtOAc (3/1, 40 ml) to give another fraction of the title compound (3.5 g) as yellow solid.

General Scheme for the Preparation of Compounds.

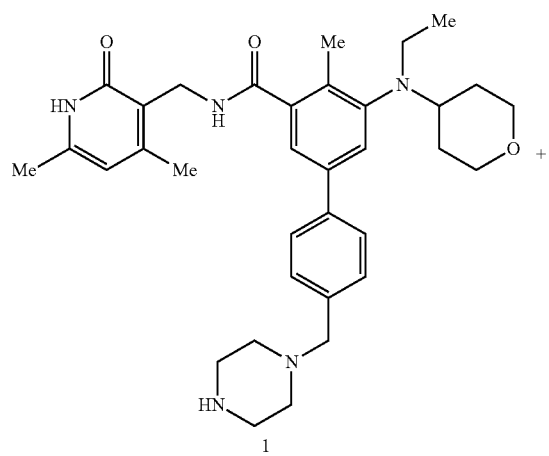

1

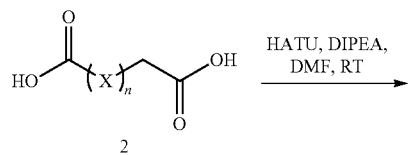

2

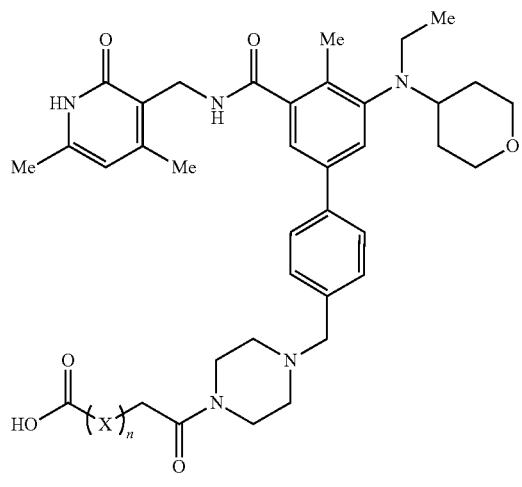

3

-continued
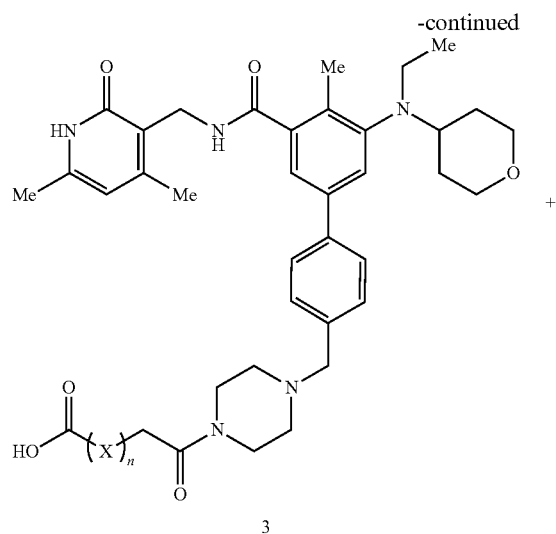
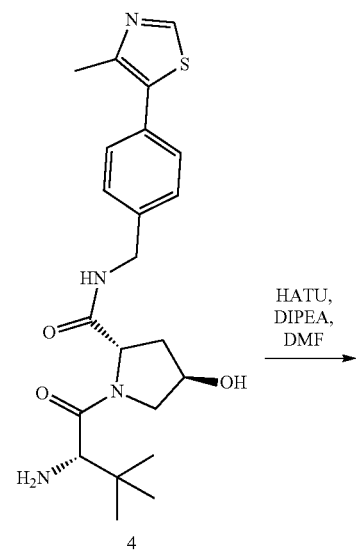

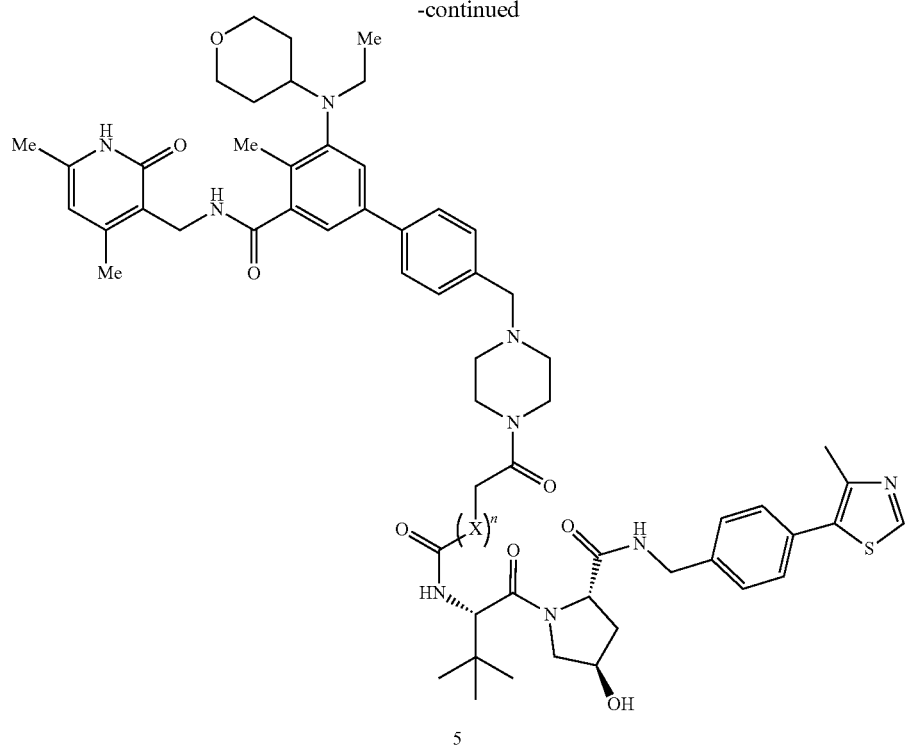
5
Synthesis of tert-butyl 11-(4-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)methyl)piperazin-1-yl)-11-oxoundecanoate (NUCC-0226272)
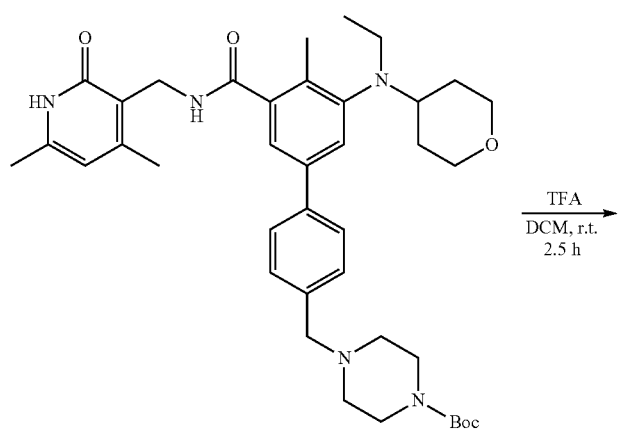
6

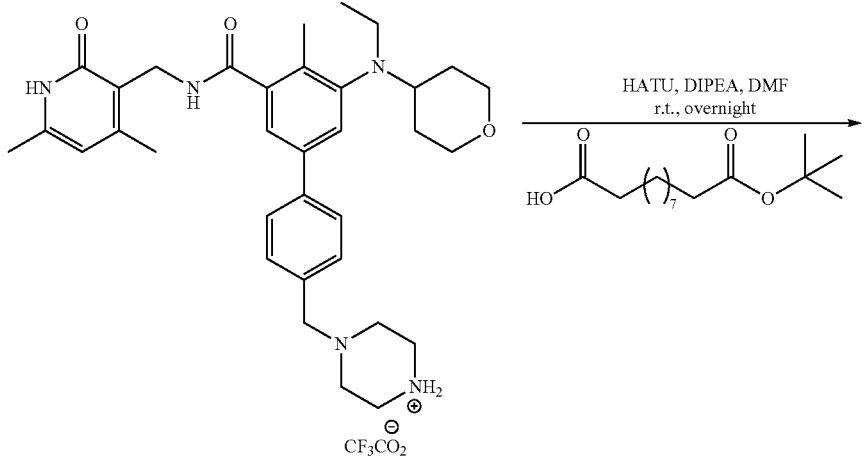

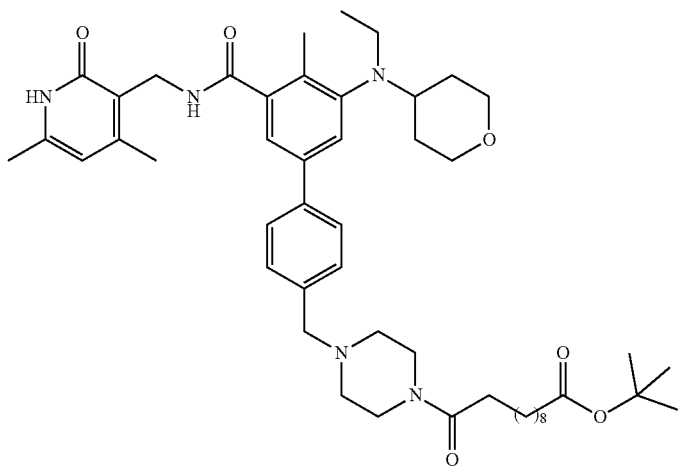

Step 1 Ref: *ACS Med. Chem. Lett.* 2019, 10, 334

To a 100 ml flask was added tert-butyl 4-((3'-(ethyl (tetrahydro-2H-pyran-4-yl)amino)-4'-methyl-5'-(((6-methyl-2-oxo-1,2-dihydropyridin-3-yl)methyl)carbamoyl)-[1,1'-biphenyl]-4-yl)methyl)piperazine-1-carboxylate (4.1 g, 5.42 mmol) in DCM (100 ml) was added TFA (10.8 ml, 26 eq, 141 mmol) at 0° C. for 10 min and room temperature for 2.5 hour, LCMS shows complete conversion. The solvent and excess TFA were removed by rotavap, added DCM to redissolve the mixture to help remove the TFA under rotavap, put it under N2 steam for 2 hours and used directly in next step.

To a 100 ml flask was added 11-(tert-butoxy)-11-oxoundecanoic acid (1.55 g. 1.05 eq) in DMF (30 ml), followed by DIPEA (3.78 ml, 4 eq, 21.7 mmol) and HATU (2.16 g, 1.05 eq, 5.69 mmol) and stirred at room temperature for 30 min, then the whole mixture was added to compound 7 (1.0 eq, 5.42 mmol) (caution the pH, if excess TFA remained in G, adjust the pH to 8 by DIPEA before mixed with the mixture) and stirred at room temperature overnight, LCMS shows complete conversion. Most of DMF was removed by N2 steam overnight, then added saturated NaHCO₃ solution (40 mL), extracted by EtOAc (2*70 ml), (sodium salt of HOAt precipitate from solution which can be removed by filter), then extracted by DCM (2*40 ml), combined the organic phase of EtOAc and DCM separately, washed by saturated NaCl (2*20 ml) separately, combined the organic phase, dried by Na2SO4 and concentrated to dryness, purified via flash column chromatography with MeOH/DCM (dry loading, 100 g Biotage Column, 0-3%, 3-5%) to give the title compound (7.1 g, 66% pure by HNMR, about 100% yield) as an brown oil (contains a small amount of DCM, DMF, TMU, DIPEA.TFA salt and 11-(tert-butoxy)-11-oxoundecanoic acid) which was used as-is in the next step.

Synthesis of (2S,4S)-1-((S)-2-(11-(4-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)methyl)piperazin-1-yl)-11-oxoundecanamido)-3,3-dimethylbutanoyl)-4-hydroxy-N-(4-(4-methylthiazol-5-yl)benzyl)pyrrolidine-2-carboxamide
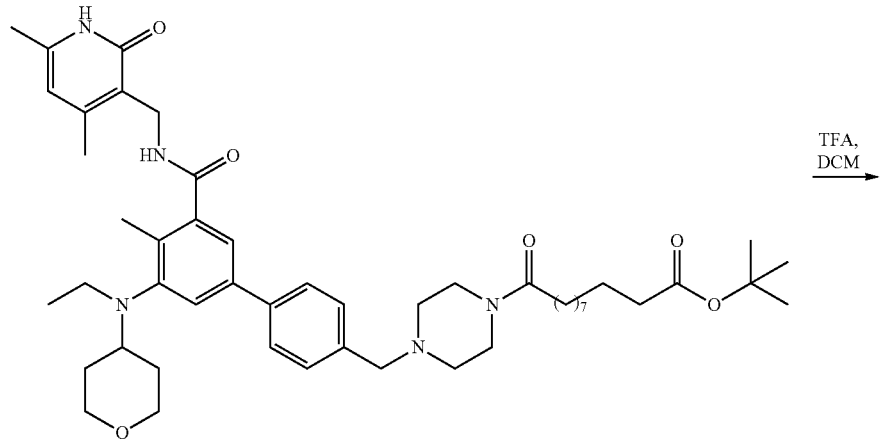
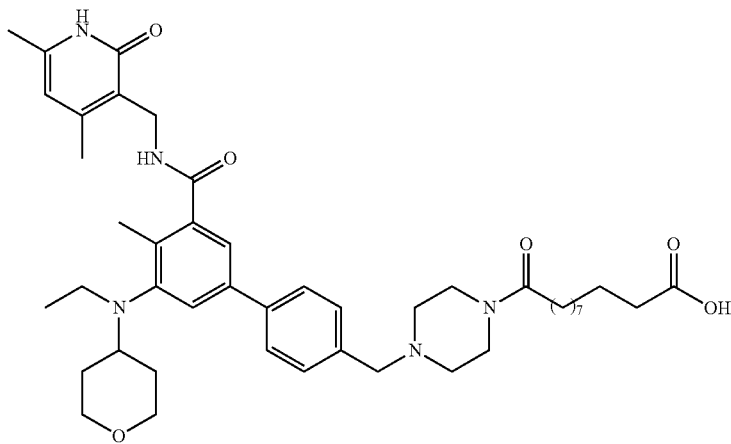
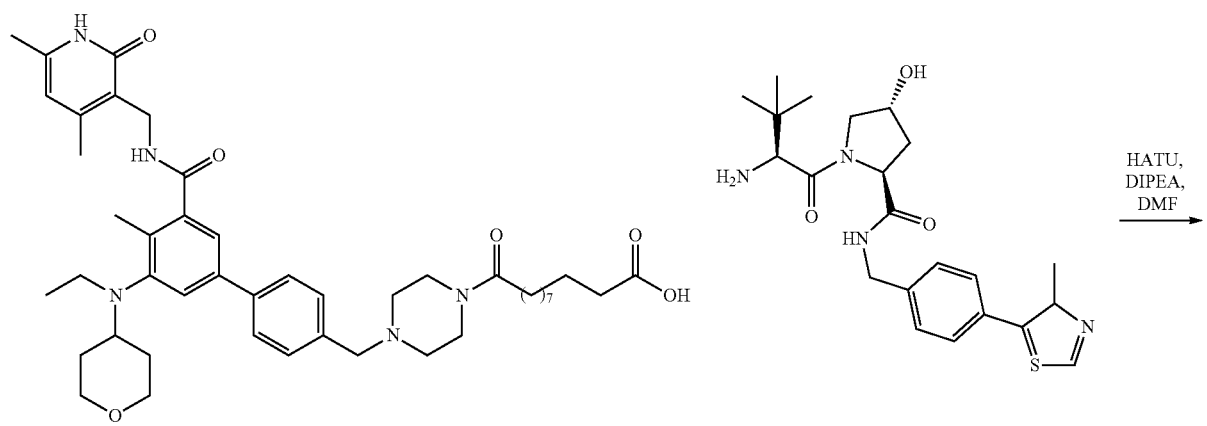

-continued

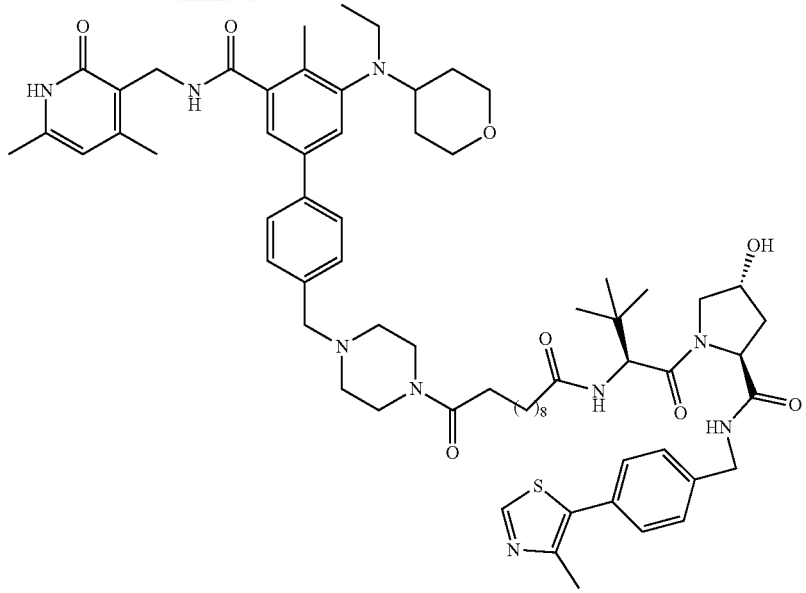

NUCC-0226272

To a 100 ml flask was added compound 8 (4.5 g, about 66% pure, 3.51 mmol) in DCM (36 ml), TFA (8.4 ml, 30 eq) was added at room temperature and stirred at room temperature overnight, LCMS showed complete conversion, removed the solvent and excess TFA by rotavap, added DCM to redissolve the mixture to help remove the TFA under rotavap, put it under N2 steam for 3 hours to give dark red oil used directly in next step. The red oil was dissolved in DMF (30 ml), adjusted the pH to 8 by DIPEA (9.2 ml, 15 eq, 52.8 mmol), followed by addition of HATU (1.34 g, 1.0 eq, 3.6 mmol), stirred at room temperature for 30 min, then added VHL1 ligand (free base or HCl salt), stirred at room temperature overnight. LCMS showed completed conversion of acid (if not, added another 0.2 eq of HATU for 10 min, then 0.2 eq VHL1 ligand, check LCMS after 2 hours until acid was fully consumed), removed most of DMF by N2 steam overnight, then added saturated NaHCO$_3$ solution 60 ml, extracted by DCM (3*90 ml), combined the organic phase, washed by saturated NaCl (3*30 ml), combined the organic phase, dried by Na2SO4 and concentrated to dryness, purified via flash column chromatography with MeOH/DCM (wet loading, 100 g Biotage Column, 3-5%, hold 5%, 5-7%, then 10%) to give the title compound (3.6 g) as yellow solid. 1H NMR (500 MHz, CD3OD) δ 8.88 (s, 1H), 7.57 (d, J=8.2 Hz, 2H), 7.48 (d, J=8.2 Hz, 3H), 7.45-7.37 (m, 4H), 7.34 (d, J=1.6 Hz, 1H), 6.13 (s, 1H), 4.66 (s, 1H), 4.62-4.53 (m, 2H), 4.51 (s, 3H), 4.37 (d, J=15.5 Hz, 1H), 3.93 (t, J=10.2 Hz, 3H), 3.82 (dd, J=10.9, 3.9 Hz, 1H), 3.58 (d, J=14.3 Hz, 6H), 3.42-3.35 (m, 2H), 3.17 (d, J=7.0 Hz, 3H), 2.49 (d, J=4.6 Hz, 5H), 2.47-2.43 (m, 2H), 2.41 (s, 3H), 2.40-2.36 (m, 2H), 2.35 (s, 3H), 2.33-2.19 (m, 6H), 2.10 (ddd, J=13.3, 9.1, 4.5 Hz, 1H), 1.77 (d, J=11.3 Hz, 2H), 1.63 (ddd, J=32.6, 13.3, 5.5 Hz, 6H), 1.33 (s, 12H), 1.05 (s, 9H), 0.92 (t, J=7.0 Hz, 3H). 13C NMR (126 MHz, CD3OD) δ 175.95, 174.38, 174.02, 172.88, 172.31, 165.57, 153.42, 152.77, 150.67, 148.98, 144.82, 140.73, 140.48, 140.26, 139.63, 137.78, 134.39, 133.34, 131.46, 131.08, 130.30, 128.96, 127.77, 125.19, 122.73, 122.14, 111.00, 71.04, 68.22, 63.28, 60.80, 59.73, 58.90, 58.02, 43.67, 43.10, 42.61, 38.92, 36.63, 36.58, 33.96, 31.85, 30.43, 30.39, 30.36, 30.33, 30.22, 27.08, 26.99, 26.55, 19.77, 18.65, 15.89, 15.16, 13.16. MS (ESI+): 592.83 (M/2+1).

Synthesis of (2S,4R)-1-[(2S)-2-(12-{4-[(3'-{[(4,6-dimethyl-2-oxo-1,2-dihydropyridin-3-yl)methyl]carbamoyl}-5'-[ethyl(oxan-4-yl)amino]-4'-methyl-[1,1'-biphenyl]-4-yl)methyl]piperazin-1-yl}dodecanamido)-3,3-dimethylbutanoyl]-4-hydroxy-N-{[4-(4-methyl-1,3-thiazol-5-yl)phenyl]methyl}pyrrolidine-2-carboxamide

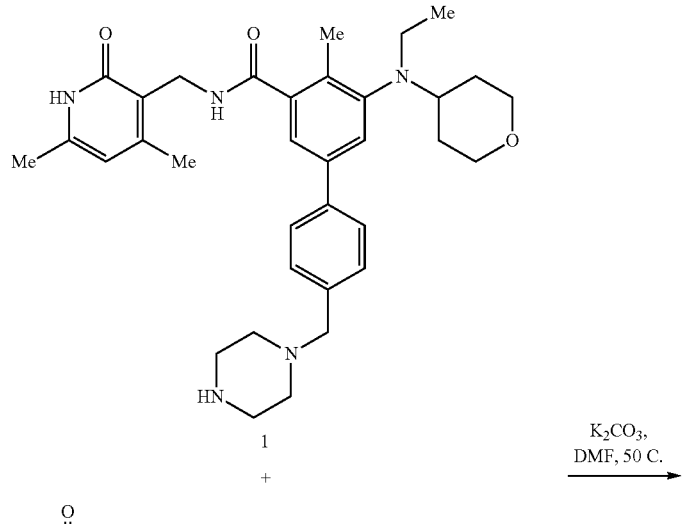

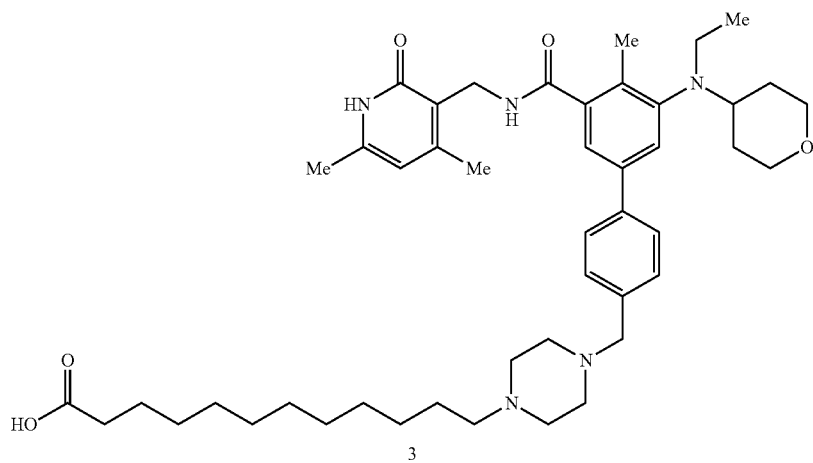

To a solution of N-((4,6-dimethyl-2-oxo-1,2-dihydropyridin-3-yl)methyl)-5-(ethyl(tetrahydro-2H-pyran-4-yl)amino)-4-methyl-4'-(piperazin-1-ylmethyl)-[1,1'-biphenyl]-3-carboxamide (450 mg, 1 Eq, 787 μmol) and potassium carbonate (163 mg, 1.5 Eq, 1.18 mmol) in N,N-Dimethylformamide (5 mL) was added 12-bromododecanoic acid (220 mg, 1.0 Eq, 787 μmol). The reaction mixture was allowed to stir at 50° C. overnight. 2 more equivalences of potassium carbonate was added followed by one additional equivalence of 12-bromododecanoic acid. The reaction was allowed to go for another 24 h. LCMS showed complete conversion. The reaction mixture was filtered and purified by Gilson prep HPLC using 10-90% gradient to obtain 12-(4-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)methyl)piperazin-1-yl)dodecanoic acid (118 mg, 153 μmol, 19.5%) as a brown solid. MS (ESI+)=770.5.

55
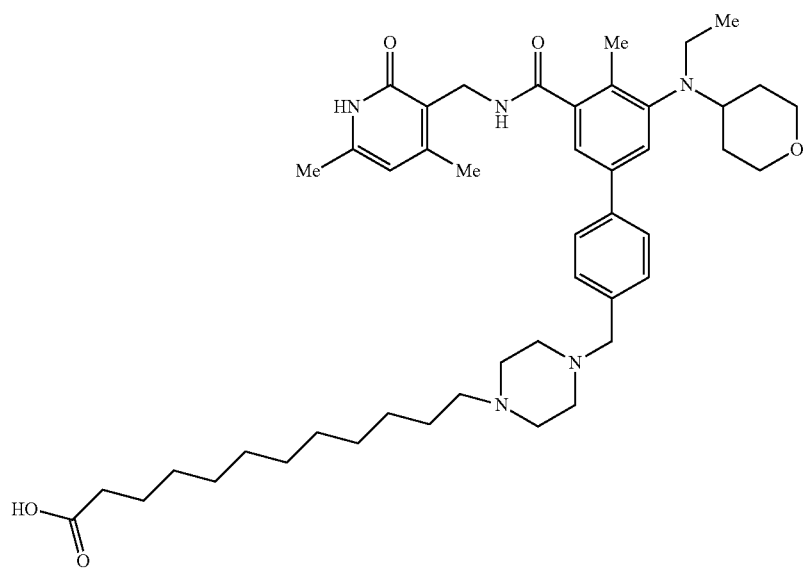
3
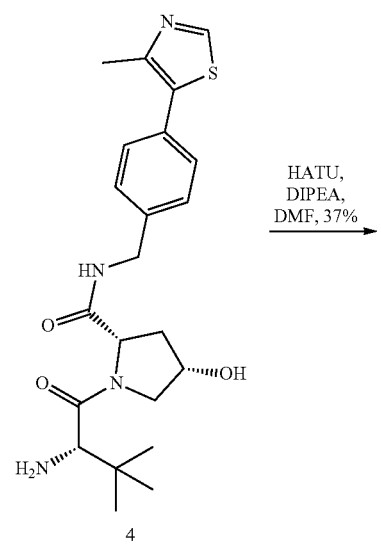
4
HATU, DIPEA, DMF, 37%
56
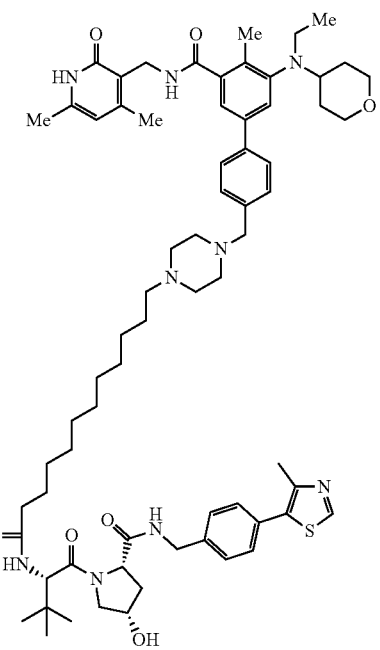
5
NUCC-0226287

Synthesis of (2R,4R)-1-[(2S)-2-(12-{4-[(3'-{[(4,6-dimethyl-2-oxo-1,2-dihydropyridin-3-yl)methyl]carbamoyl}-5'-[ethyl(oxan-4-yl)amino]-4'-methyl-[1,1'-biphenyl]-4-yl)methyl]piperazin-1-yl}-12-oxododecanamido)-3,3-dimethylbutanoyl]-4-hydroxy-N-{[4-(4-methyl-1,3-thiazol-5-yl)phenyl]methyl}pyrrolidine-2-carboxamide (NUCC-0202304)
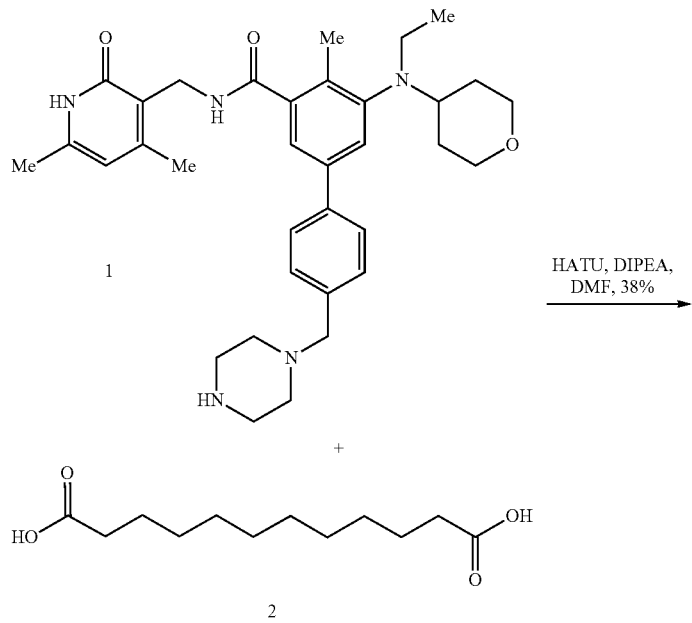
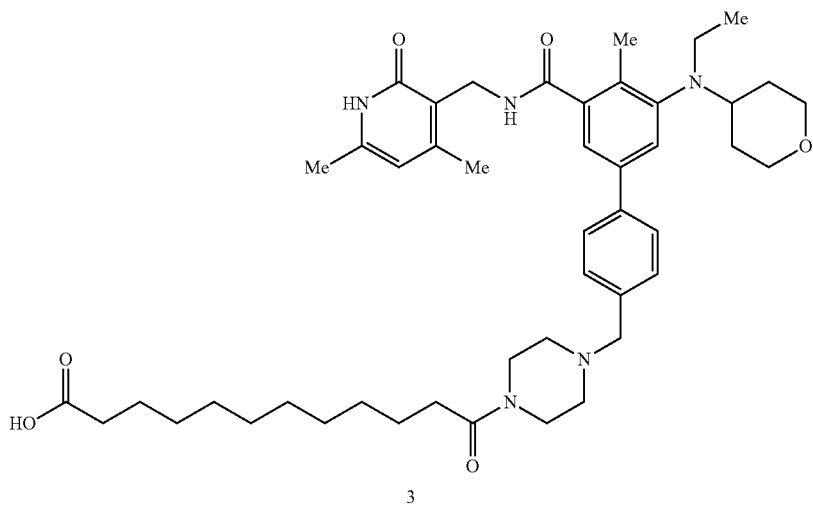

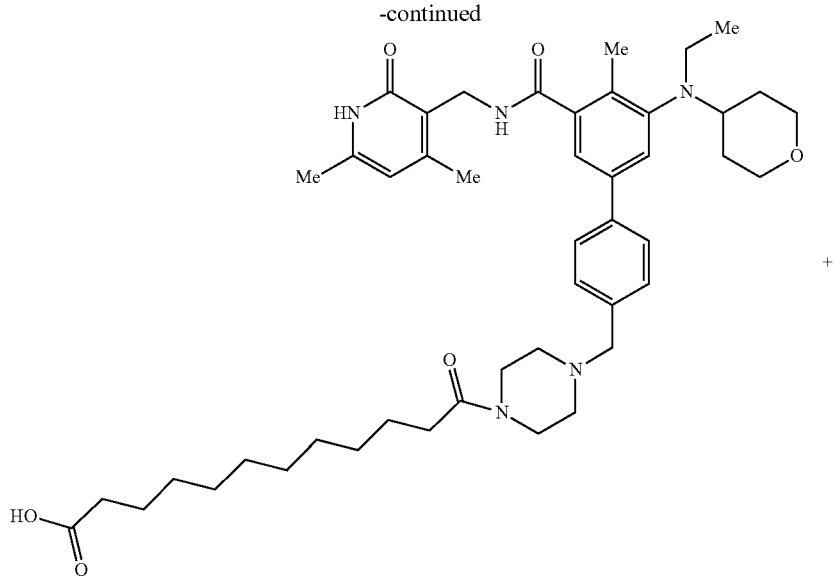

3

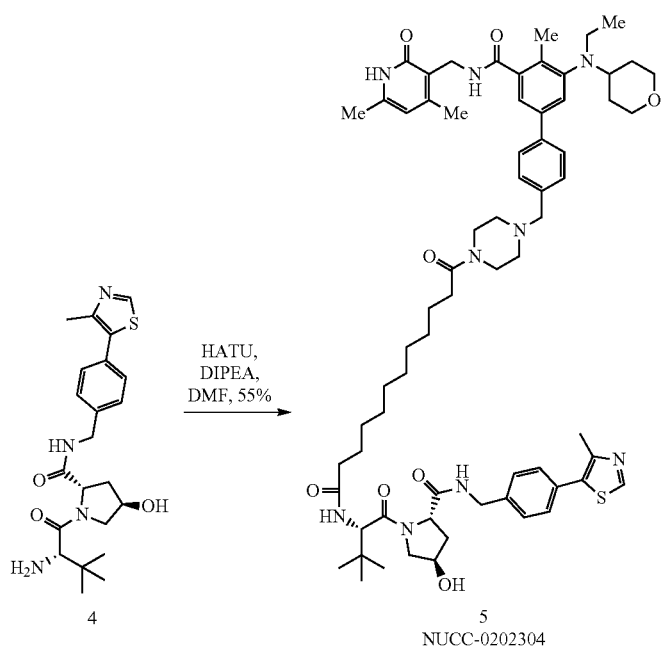

To a 4 mL vial was added 12-(4-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)methyl)piperazin-1-yl)-12-oxododecanoic acid (78 mg, 1 Eq, 99 μmol), DIEA (39 mg, 52 μL, 3.0 Eq, 0.30 mmol), HATU (57 mg, 1.5 Eq, 0.15 mmol) in N,N-Dimethylformamide (1 mL) and allowed to stir at room temperature for 5-10 min. (2S,4R)-1-((S)-2-amino-3,3-dimethylbutanoyl)-4-hydroxy-N-(4-(4-methylthiazol-5-yl)benzyl)pyrrolidine-2-carboxamide, HCl (46 mg, 1 Eq, 99 μmol) was then added to the reaction mixture and allowed to stir at 50° C. for 2 h. The reaction mixture was purified using GILSON prep HPLC using a 10-90% gradient and concentrated to afford (2S,4R)-1-((S)-2-(12-(4-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)methyl)piperazin-1-yl)-12-oxododecanamido)-3,3-dimethylbutanoyl)-4-hydroxy-N-(4-(4-methylthiazol-5-yl)benzyl)pyrrolidine-2-carboxamide (65 mg, 54 μmol, 55%). MS (ESI+)=599.2 (m/2).

Synthesis of (2S,4R)-1-[(2S)-2-(19-{4-[(3'-{[(4,6-dimethyl-2-oxo-1,2-dihydropyridin-3-yl)methyl]carbamoyl}-5'-[ethyl(oxan-4-yl)amino]-4'-methyl-[1,1'-biphenyl]-4-yl)methyl]piperazin-1-yl}-19-oxo-4,7,10,13,16-pentaoxanonadecanamido)-3,3-dimethylbutanoyl]-4-hydroxy-N-{[4-(4-methyl-1,3-thiazol-5-yl)phenyl]methyl}pyrrolidine-2-carboxamide (NUCC-0202298)
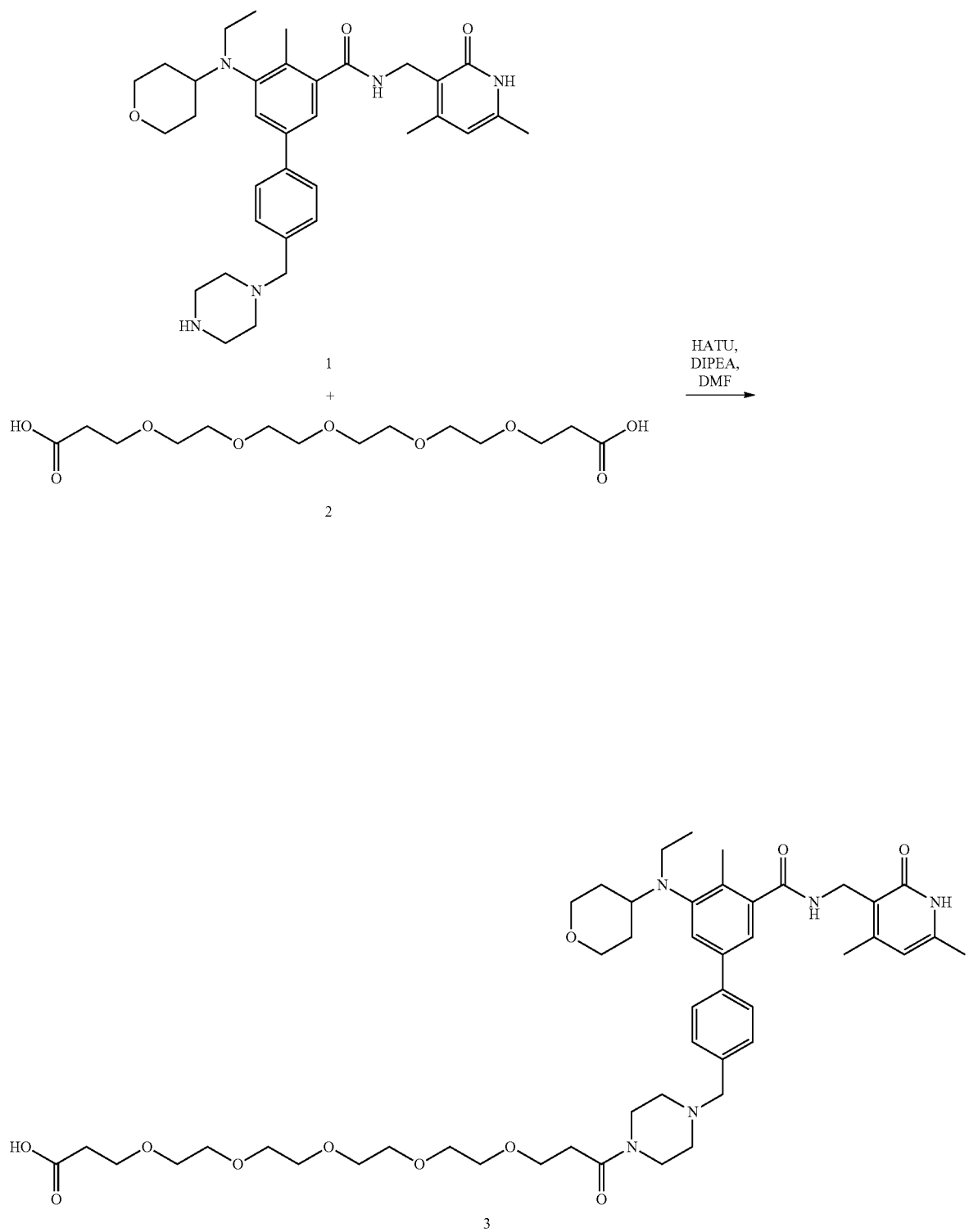

-continued
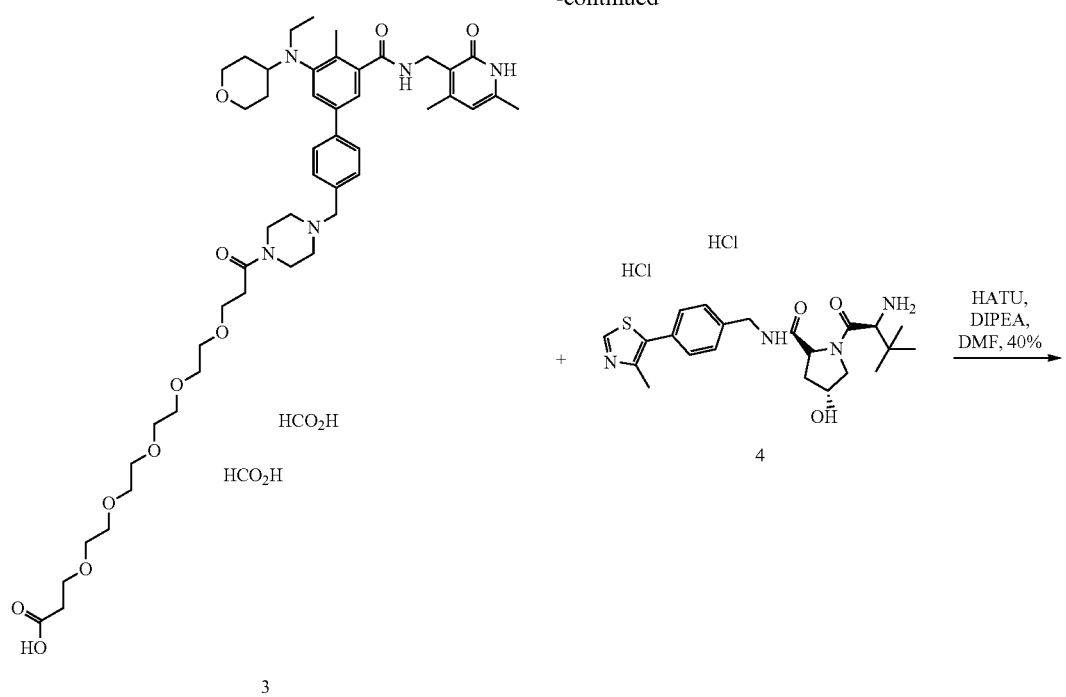
3
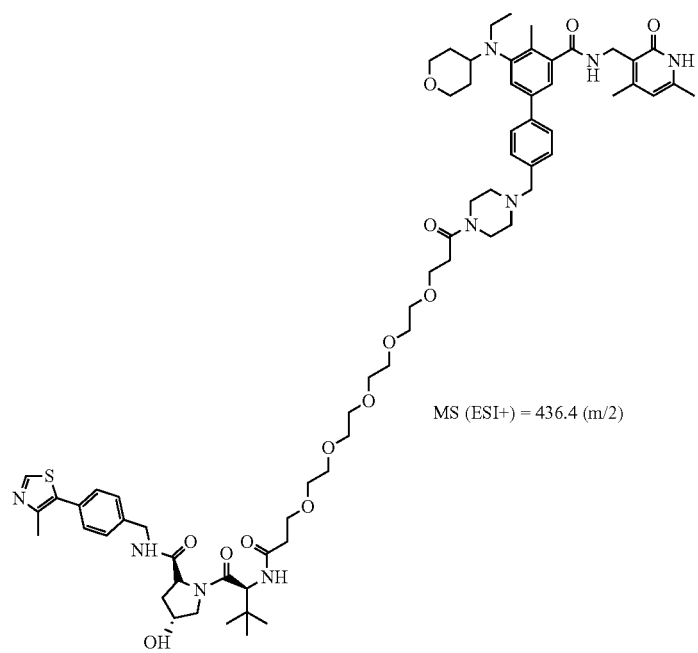
5
NUCC-0202298
MS (ESI+) = 436.4 (m/2)

Synthesis of N-[(4,6-dimethyl-2-oxo-1,2-dihydropyridin-3-yl)methyl]-5-[(1-{7-[(2-{[2-(2,6-dioxopiperidin-3-yl)-1,3-dioxo-2,3-dihydro-1H-isoindol-4-yl]oxy}ethyl)carbamoyl]heptanoyl}piperidin-4-yl)(ethyl)amino]-4-methyl-4'-[(morpholin-4-yl)methyl]-[1,1'-biphenyl]-3-carboxamide (NUCC-0202098)

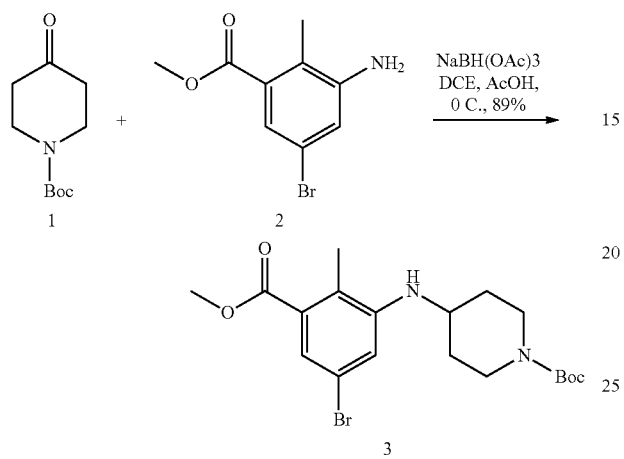

A solution containing tert-butyl 4-oxopiperidine-1-carboxylate (1.96 g, 1.2 Eq, 9.83 mmol) and methyl 3-amino-5-bromo-2-methylbenzoate (2.00 g, 1.0 Eq, 8.19 mmol) in AcOH (2.95 g, 2.81 mL, 6.0 Eq, 49.2 mmol) and 1,2-Dichloroethane (21 mL) was stirred for 15 min before being cooled to 0° C. To the cooled solution was added sodium triacetoxyborohydride (6.95 g, 4.0 Eq, 32.8 mmol) in parts. The reaction was allowed to warm to rt and stirred for 3 h before quenching with saturated sodium bicarbonate. The pH was raised to 7-8 and organic layer extracted. The aqueous layer was then washed with ethyl acetate, and the combined organics were dried over anhydrous sodium sulfate. The product was dry loaded onto Biotage KP-Sil 100 g column and eluted with 25% EA in Hx (10 CV) to give compound 3 in 89% yield.

A solution containing 3 (1.15 g, 2.69 mmol) and AcOH (0.97 g, 16.2 mmol), in acetaldehyde (0.30 mL) and 1,2-dichloroethane (9.5 mL) and was stirred for 15 min before being cooled to 0° C. To the cooled solution was added NaBH(OAc)$_3$ in parts. The reaction was allowed to warm to rt and stirred for 3 h before quenching with saturated sodium bicarbonate. The pH was raised to 7-8 and organic layer extracted. The aqueous layer was then washed with ethyl acetate, and the combined organics were dried over anhydrous sodium sulfate. The product was dry loaded onto Biotage KP-Sil 50 g column and eluted with 25% EA in Hx (10 CV).

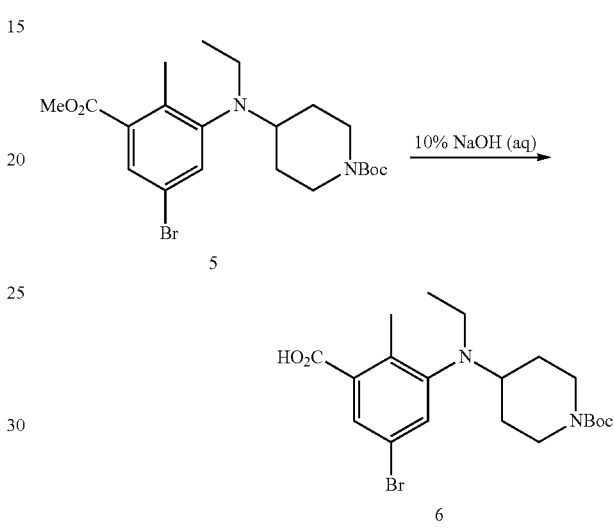

To a 20 mL vial was added tert-butyl 4-((5-bromo-3-(methoxycarbonyl)-2-methylphenyl)(ethyl)amino)piperidine-1-carboxylate (283 mg, 1 Eq, 621 µmol) in Ethanol (3 mL) followed by addition of NaOH (10% aqueous solution) (0.3 g, 3 mL, 2.5 molar) and allowed to stir at 50° C. for 3 h. LCMS showed complete conversion. The reaction mixture was allowed to cool to room temperature and addition of 1M HCl to reaction mixture until pH=2, extracted with EtOAc and concentrated to dryness to give a white fluffy solid. The solid was used for the next step without additional purification.

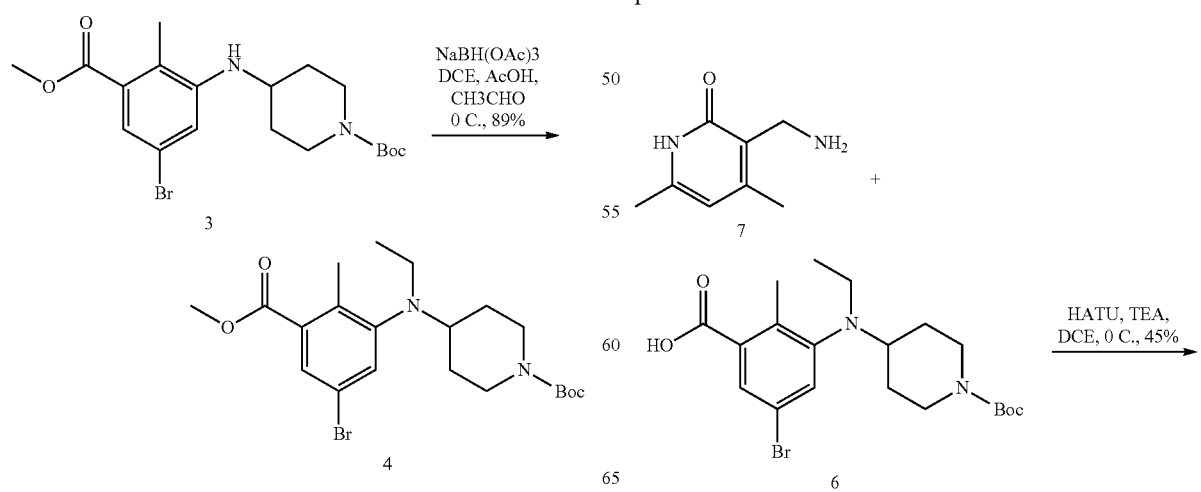

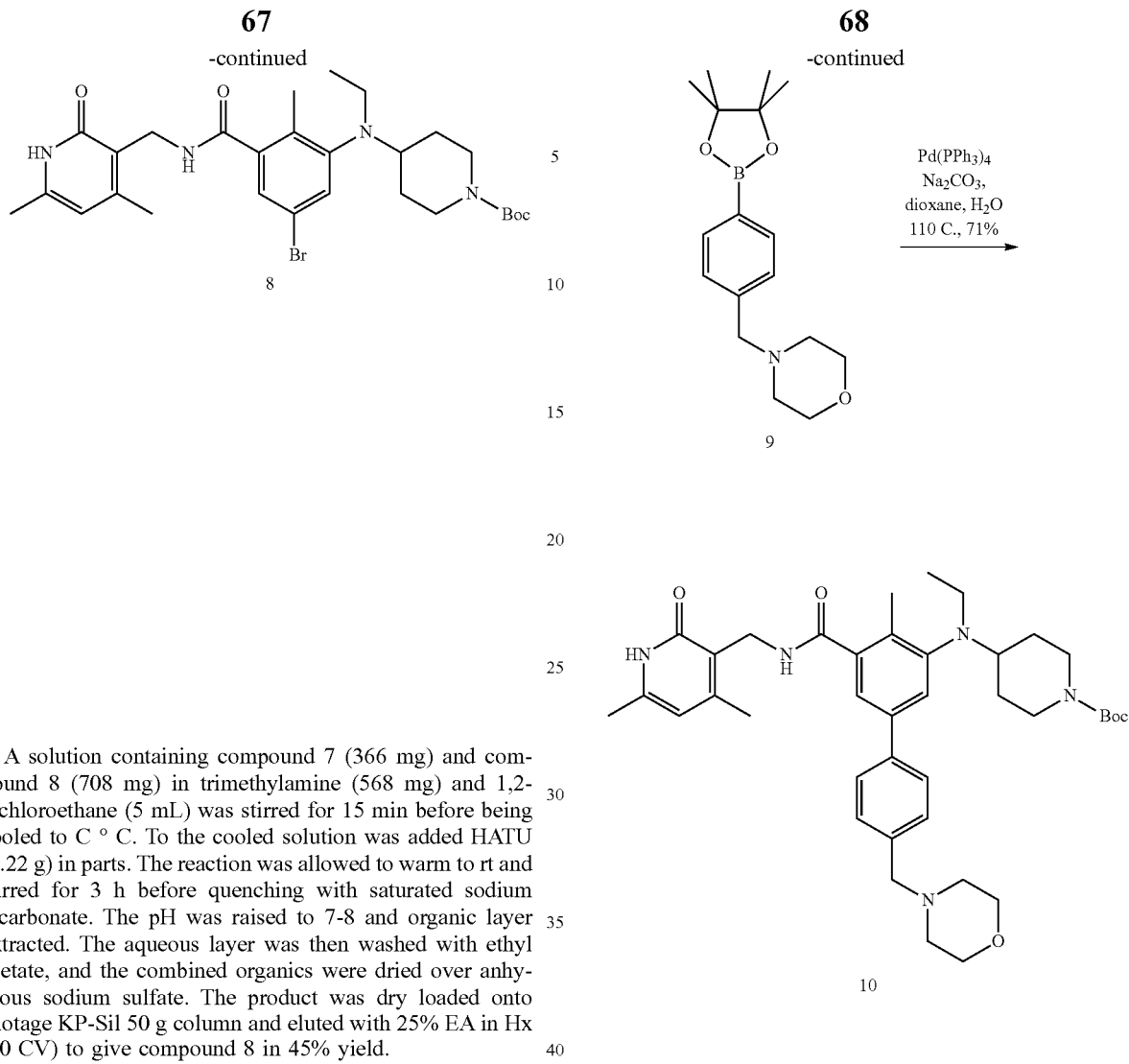

A solution containing compound 7 (366 mg) and compound 8 (708 mg) in trimethylamine (568 mg) and 1,2-dichloroethane (5 mL) was stirred for 15 min before being cooled to C ° C. To the cooled solution was added HATU (1.22 g) in parts. The reaction was allowed to warm to rt and stirred for 3 h before quenching with saturated sodium bicarbonate. The pH was raised to 7-8 and organic layer extracted. The aqueous layer was then washed with ethyl acetate, and the combined organics were dried over anhydrous sodium sulfate. The product was dry loaded onto Biotage KP-Sil 50 g column and eluted with 25% EA in Hx (10 CV) to give compound 8 in 45% yield.

A solution containing tert-butyl 4-((5-bromo-3-(((4,6-dimethyl-2-oxo-1,2-dihydropyridin-3-yl)methyl)carbamoyl)-2-methylphenyl)(ethyl)amino)piperidine-1-carboxylate (118.0 mg, 1 Eq, 205.0 mol), 4-(4-(4,4,5,5-tetramethyl-1,3,2-dioxaborolan-2-yl)benzyl)morpholine (93.25 mg, 1.5 Eq, 307.5 μmol), and Na2CO3 (78.23 mg, 3.6 Eq, 738.1 μmol) in 1,4-Dioxane (1.0 mL) and Water (0.20 mL) was purged with nitrogen for 30 min. To the solution was added Pd(Ph3p)4 (23.69 mg, 0.1 Eq, 20.50 μmol). The solution was purged with nitrogen for 10 min before heating at 110° C. for 4 h. The reaction was cooled to room temp, diluted with water, and extracted with 10% MeOH in DCM. The organic layer was dried over anhydrous sodium sulfate and concentrated in vacuo. The pure product was obtained via flash chromatography (10% MeOH in DCM) to yield tert-butyl 4-((5-(((4,6-dimethyl-2-oxo-1,2-dihydropyridin-3-yl) methyl)carbamoyl)-4-methyl-4'-(morpholinomethyl)-[1,1'-biphenyl]-3-yl)(ethyl)amino)piperidine-1-carboxylate (98 mg, 0.15 mmol, 71%).

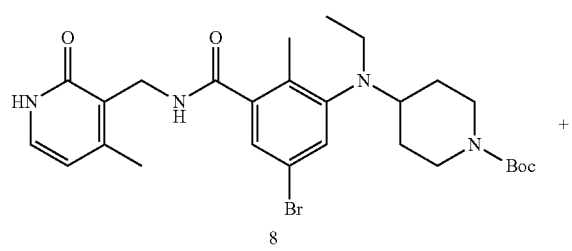

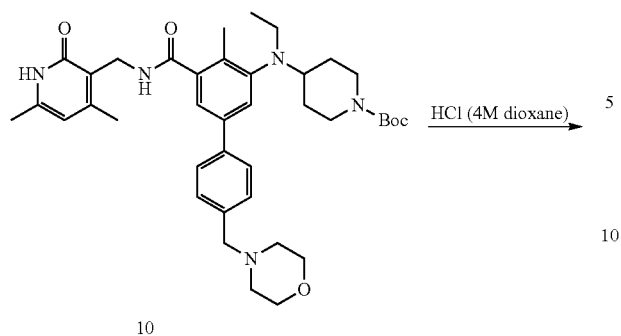
10
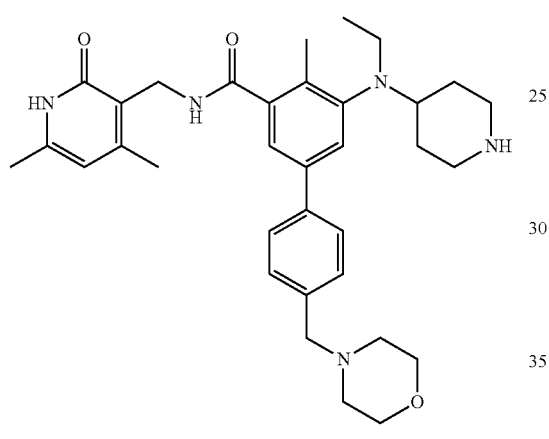
11
A solution containing compound 10 in 1,4-dioxane (5 mL) was cooled to 0° C. A solution of 4 N HCl in 1,4-dioxanes (5 mL) was added, and the reaction was monitored by LCMS. After 2 h, the reaction was completed and solvent removed in vacuo. The crude product was used without further purification.
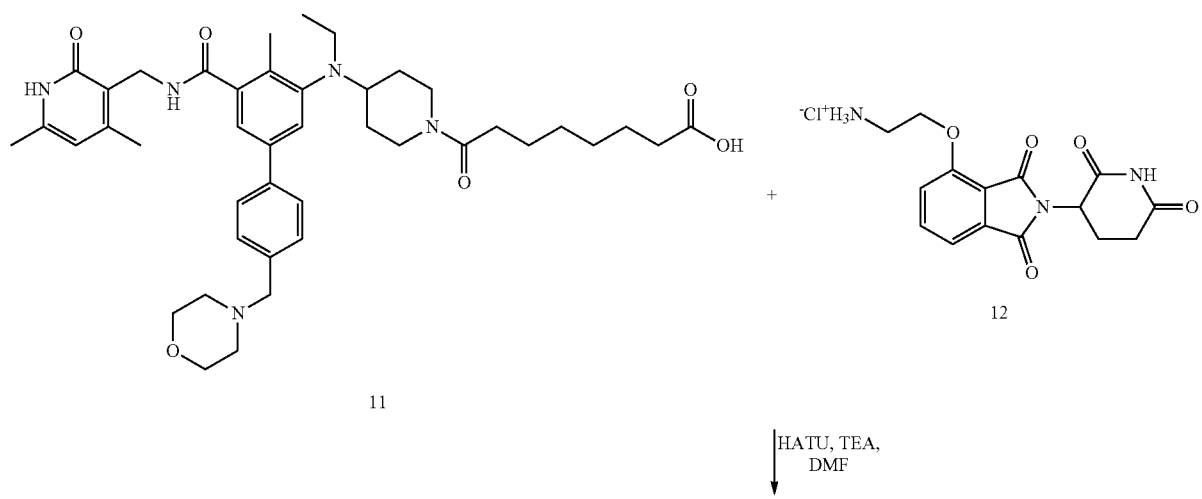
HATU, TEA, DMF

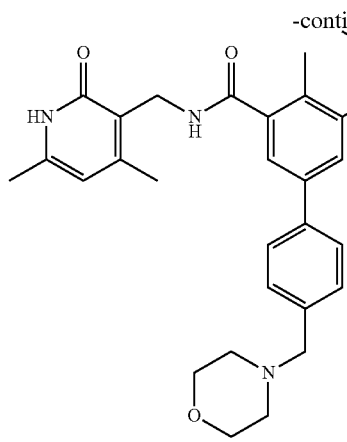
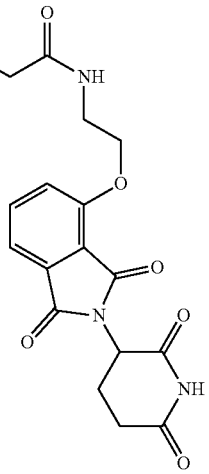

13
NUCC-0202098

Compound 11 (16.5 mg), compound 12 (7.6 mg), triethylamine (12 µL), and HATU (12.3 mg) were mixed in DMF. After purification, compound 13 (NUCC-0202098) was obtained. MS (ESI+)=515.24 (m/2).

Synthesis of 4'-({4-[(1E)-2-(benzenesulfonyl)ethenyl]piperidin-1-yl}methyl)-N-[(4,6-dimethyl-2-oxo-1,2-dihydropyridin-3-yl)methyl]-5-[ethyl(oxan-4-yl)amino]-4-methyl-[1,1'-biphenyl]-3-carboxamide (NUCC-0202059)

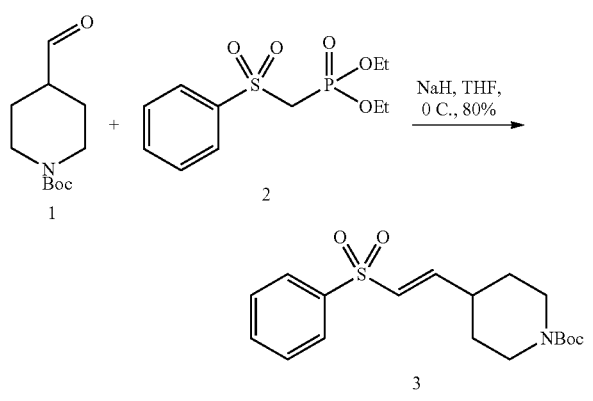

To a solution of diethyl ((phenylsulfonyl)methyl)phosphonate (2, 542 mg, 1.98 Eq, 1.85 mmol) in THF (4.0 mL) at 0° C. was added NaH (40.5 mg, 60% Wt, 1.1 Eq, 1.0 mmol) and the reaction stirred at 0° C. for 60 min. A solution of tert-butyl 4-formylpiperidine-1-carboxylate (1, 200 mg, 1 Eq, 938 µmol) in THF (2.0 mL) was added slowly, and the reaction was stirred for 18 hours at room temperature. The reaction was quenched by the addition of water and the aqueous phase was extracted with EtOAc. The combined organic phases were dried over Na2SO4, decanted into a round bottom flask and concentrated by rotary evaporation. The crude material was purified by flash column chromatography (20% EtOAc in hexanes as eluent) to obtain tert-butyl (E)-4-(2-(phenylsulfonyl)vinyl)piperidine-1-carboxylate (265 mg, 754 µmol, 80.4%) as a clear, colorless oil.

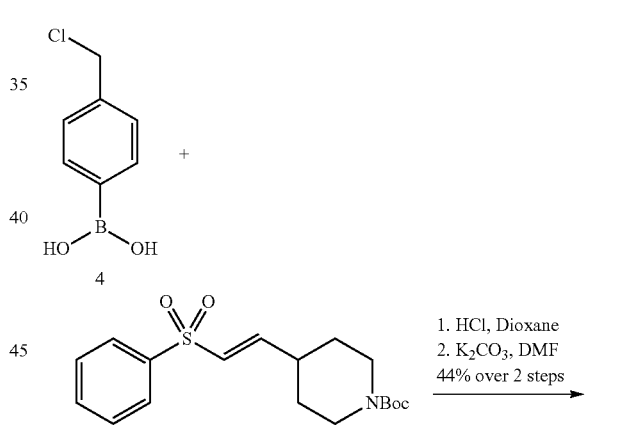

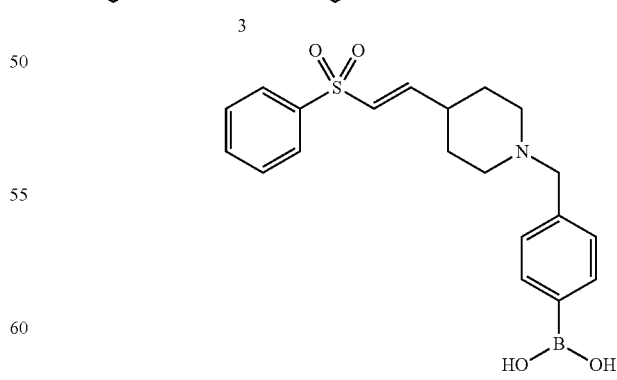

tert-butyl (E)-4-(2-(phenylsulfonyl)vinyl)piperidine-1-carboxylate (3, 261 mg, 1.0 Eq, 743 µmol) was dissolved in 1,4-Dioxane (1 mL) and HCl (108 mg, 0.74 mL, 4.0 molar, 4.0 Eq, 2.97 mmol) was added. The reaction stirred at room temperature until complete, approximately 20 hours. The solvent was removed under vacuum and the residue was dissolved in DMF (1 mL). To this solution was added K2CO3 (205 mg, 2.0 Eq, 1.49 mmol) and (4-(chloromethyl) phenyl)boronic acid (4, 190 mg, 1.5 Eq, 1.11 mmol) and the mixture was stirred for 1.5 hours at 45 C. The mixture was concentrated under a stream of nitrogen gas and methanol was added. The solids were removed by filtration and the crude material was purified by flash column chromatography to obtain (E)-(4-((4-(2-(phenylsulfonyl)vinyl)piperidin-1-yl)methyl)phenyl)boronic acid (127 mg, 330 μmol, 44.4%) as a white solid.

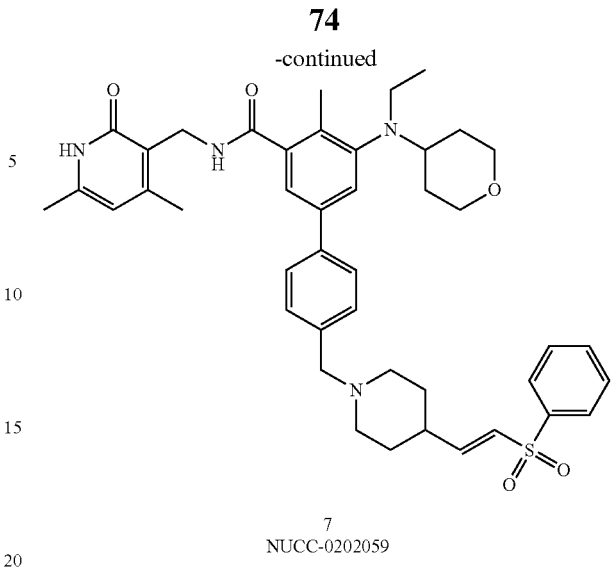

7
NUCC-0202059

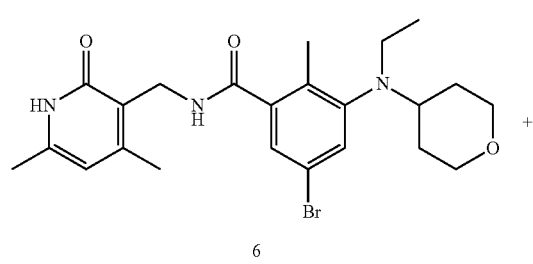

6

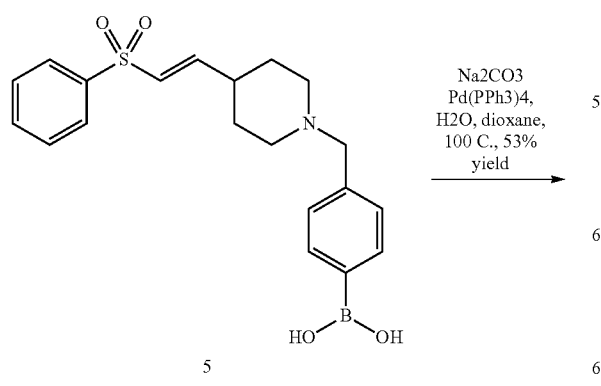

5

Na2CO3
Pd(PPh3)4,
H2O, dioxane,
100 C., 53% yield
→

A suspension of (E)-(4-((4-(2-(phenylsulfonyl)vinyl)piperidin-1-yl)methyl)phenyl)boronic acid (5, 121 mg, 1.5 Eq, 315 μmol), 5-bromo-N-((4,6-dimethyl-2-oxo-1,2-dihydropyridin-3-yl)methyl)-3-(ethyl(tetrahydro-2H-pyran-4-yl)amino)-2-methylbenzamide (6, 100 mg, 1.0 Eq, 210 μmol) and Na2CO3 (80.1 mg, 3.6 Eq, 756 μmol) in 1,4-Dioxane (2 mL)/Water (0.4 mL) was degassed with nitrogen for 20 min. Pd(Ph3p)4 (24.3 mg, 0.1 Eq, 21.0 μmol) was added, and the mixture was degassed another 10 min. The mixture was heated to 100° C. for 45 min., then concentrated under a stream of nitrogen. The reaction only progressed to about 50%, so the solids were redissolved in 1,4-Dioxane (2 mL)/Water (0.4 mL) and degassed for 20 min. Pd(Ph3p)4 (24.3 mg, 0.1 Eq, 21.0 μmol) was added, and the reaction was degassed for another 10 min. and heated to 100° C. for 1 hour. The solvents were removed under a stream of nitrogen and the residue was purified by flash column chromatography (1-5% MeOH in DCM as eluent) to obtain the compound contaminated with MW 385 (M+H). The material was concentrated and purified by reverse phase HPLC (10-90% ACN in water with 0.1% formic acid modifier) to obtain NUCC-0202059 in 53% yield.

1H NMR (500 MHz, Methanol-d4) δ 8.31 (d, J=1.9 Hz, 2H), 7.91-7.86 (m, 2H), 7.73-7.66 (m, 3H), 7.65-7.57 (m, 2H), 7.53 (dd, J=8.2, 2.0 Hz, 2H), 7.47 (s, 1H), 7.34 (s, 11H), 6.92 (ddd, J=15.3, 6.3, 1.9 Hz, 1H), 6.66 (d, J=15.2 Hz, 1H), 6.12 (s, 1H), 4.49 (d, J=1.9 Hz, 2H), 4.22 (s, 2H), 4.03-3.86 (m, 2H), 3.42 (d, J=12.4 Hz, 2H), 3.35 (t, J=11.7 Hz, 2H), 3.16 (dt, J=8.2, 5.9 Hz, 2H), 3.10 (t, J=11.3 Hz, 1H), 2.92 (t, J=12.4 Hz, 2H), 2.55 (td, J=11.7, 6.6 Hz, 1H), 2.42-2.38 (m, 3H), 2.33 (d, J=2.0 Hz, 3H), 2.24 (d, J=1.9 Hz, 3H), 2.02-1.94 (m, 2H), 1.75 (dd, J=13.3, 3.3 Hz, 2H), 1.72-1.57 (m, 4H), 0.89 (td, J=7.0, 1.9 Hz, 3H). MS (ESI+)=737.53.

TABLE 1
| Molecule Name | Structure |
| --- | --- |
| NUCC-0202367 | 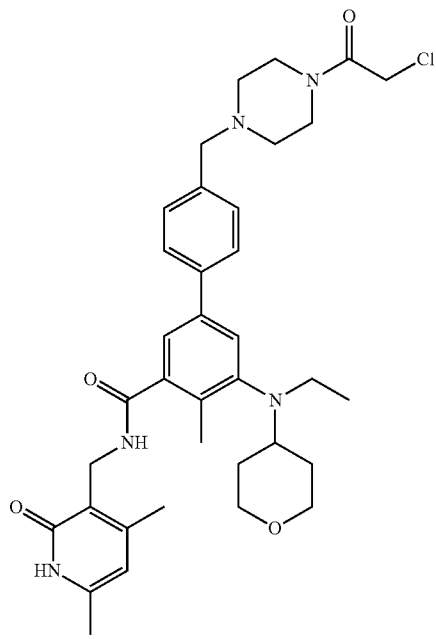 [SMILES: CCN(c1cc(-c2ccc(CN3CCN(C(=O)CCl)CC3)cc2)cc(C(=O)NCc2c(C)cc(C)[nH]c2=O)c1C)C1CCOCC1] |
| NUCC-0202366 | 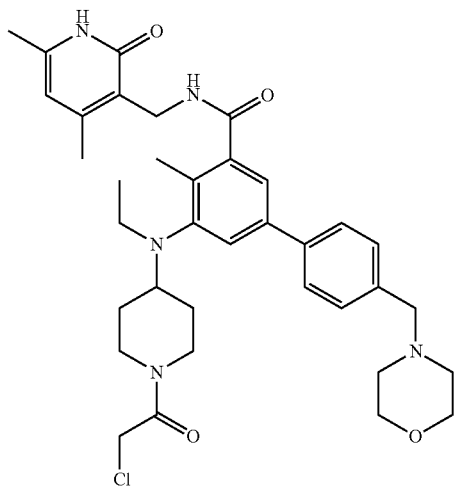 [SMILES: CCN(c1cc(-c2ccc(CN3CCOCC3)cc2)cc(C(=O)NCc2c(C)cc(C)[nH]c2=O)c1C)C1CCN(C(=O)CCl)CC1] |

TABLE 1-continued
| Molecule Name | Structure |
|---|---|
| NUCC-0202345 | 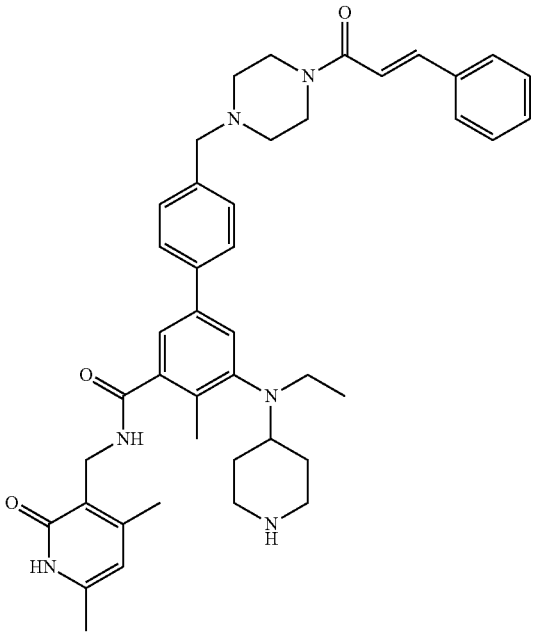 [SMILES: CCN(c1cc(-c2ccc(CN3CCN(C(=O)/C=C/c4ccccc4)CC3)cc2)cc(C(=O)NCc2c(C)cc(C)[nH]c2=O)c1C)C1CCNCC1] |
| NUCC-0202344 | 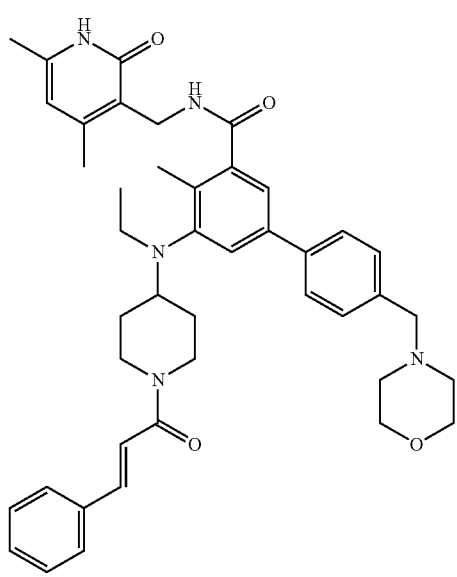 [SMILES: CCN(c1cc(-c2ccc(CN3CCOCC3)cc2)cc(C(=O)NCc2c(C)cc(C)[nH]c2=O)c1C)C1CCN(C(=O)/C=C/c2ccccc2)CC1] |

TABLE 1-continued
| Molecule Name | Structure |
| --- | --- |
| NUCC-0202343 | 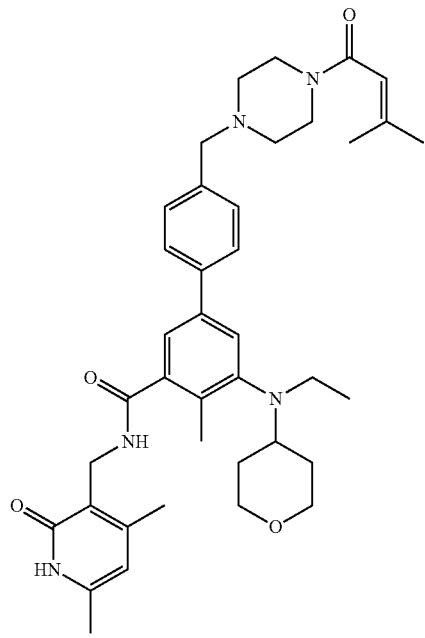 [SMILES: CCN(c1cc(-c2ccc(CN3CCN(C(=O)C=C(C)C)CC3)cc2)cc(C(=O)NCc2c(C)cc(C)[nH]c2=O)c1C)C1CCOCC1] |
| NUCC-0202342 | 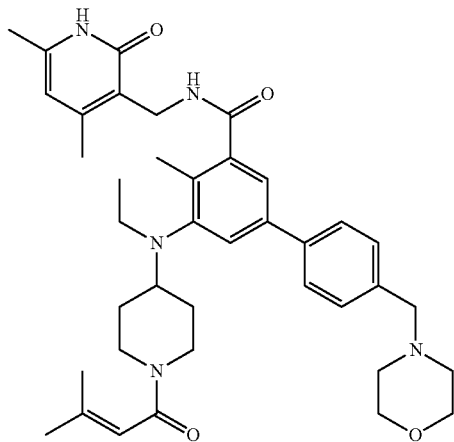 [SMILES: CCN(c1cc(-c2ccc(CN3CCOCC3)cc2)cc(C(=O)NCc2c(C)cc(C)[nH]c2=O)c1C)C1CCN(C(=O)C=C(C)C)CC1] |

TABLE 1-continued
| Molecule Name | Structure |
| --- | --- |
| NUCC-0202333 | 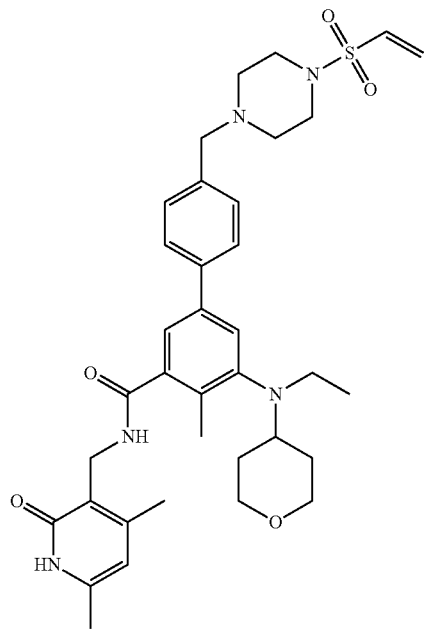 [SMILES: C=CS(=O)(=O)N1CCN(Cc2ccc(-c3cc(C(=O)NCc4c(C)cc(C)[nH]c4=O)c(C)c(N(CC)C4CCOCC4)c3)cc2)CC1] |
| NUCC-0202332 | 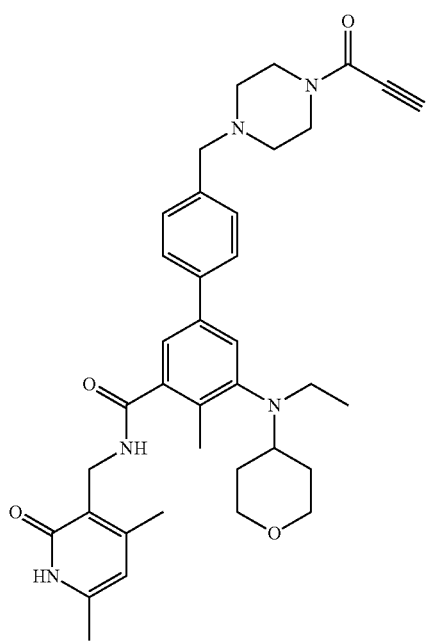 [SMILES: C#CC(=O)N1CCN(Cc2ccc(-c3cc(C(=O)NCc4c(C)cc(C)[nH]c4=O)c(C)c(N(CC)C4CCOCC4)c3)cc2)CC1] |

TABLE 1-continued

| Molecule Name | Structure |
| --- | --- |
| NUCC-0202306 | 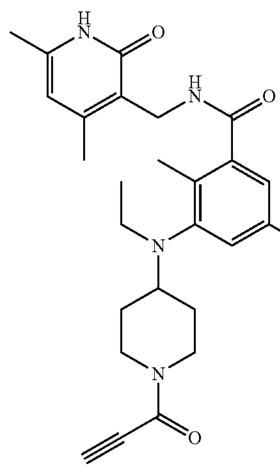 |
| NUCC-0202243 | 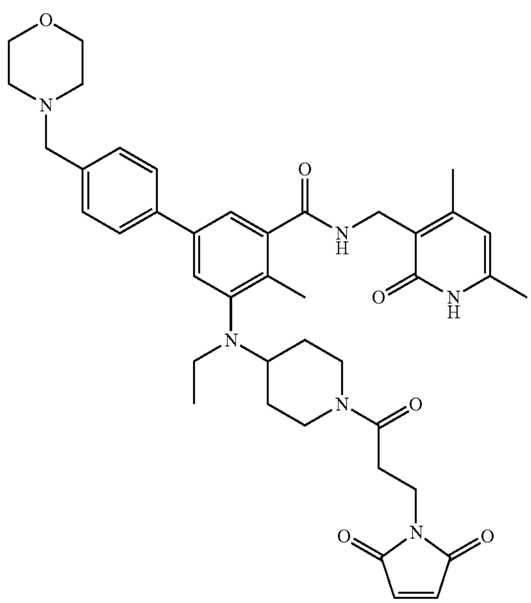 [SMILES: CCN(c1cc(-c2ccc(CN3CCOCC3)cc2)cc(C(=O)NCc2c(C)cc(C)[nH]c2=O)c1C)C1CCN(C(=O)CCN2C(=O)C=CC2=O)CC1] |
| NUCC-0202182 | 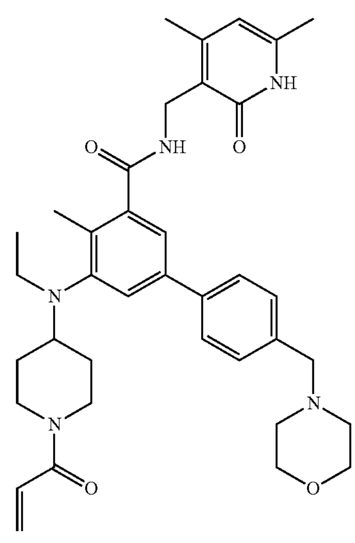 [SMILES: C=CC(=O)N1CCC(N(CC)c2cc(-c3ccc(CN4CCOCC4)cc3)cc(C(=O)NCc3c(C)cc(C)[nH]c3=O)c2C)CC1] |

TABLE 1-continued
| Molecule Name | Structure |
|---|---|
| NUCC-0202139 | 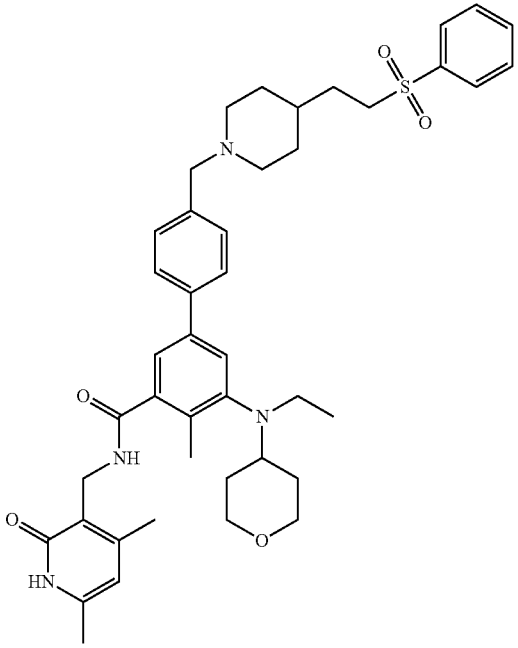 [SMILES: CCN(c1cc(-c2ccc(CN3CCC(CCS(=O)(=O)c4ccccc4)CC3)cc2)cc(C(=O)NCc2c(C)cc(C)[nH]c2=O)c1C)C1CCOCC1] |
| NUCC-0202059 | 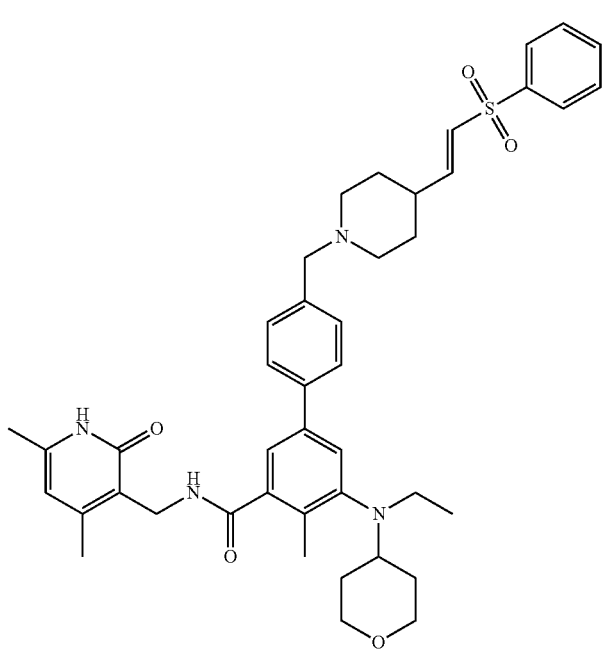 [SMILES: CCN(c1cc(-c2ccc(CN3CCC(/C=C/S(=O)(=O)c4ccccc4)CC3)cc2)cc(C(=O)NCc2c(C)cc(C)[nH]c2=O)c1C)C1CCOCC1] |

TABLE 1-continued
| Molecule Name | Structure |
|---|---|
| NUCC-0202045 | 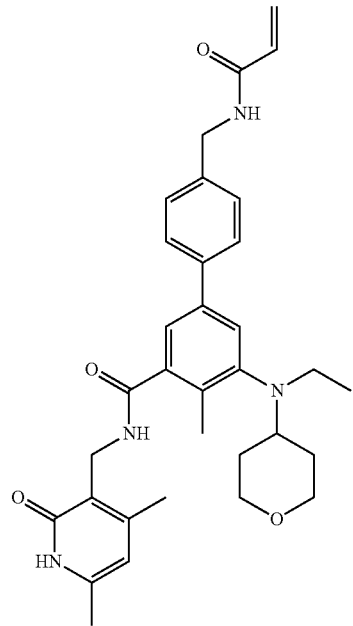 [SMILES: C=CC(=O)NCc1ccc(-c2cc(C(=O)NCc3c(C)cc(C)[nH]c3=O)c(C)c(N(CC)C3CCOCC3)c2)cc1] |
| NUCC-0202044 | 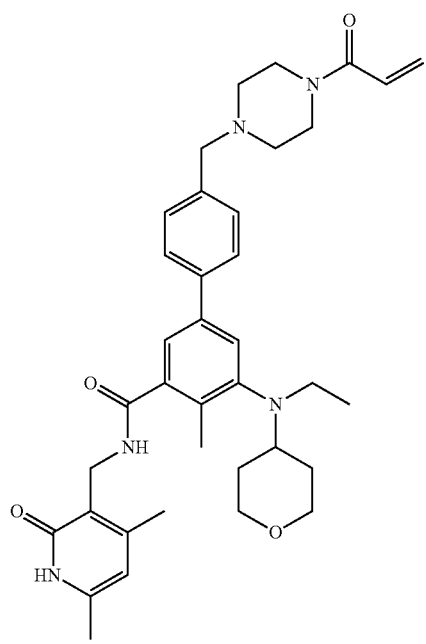 [SMILES: C=CC(=O)N1CCN(Cc2ccc(-c3cc(C(=O)NCc4c(C)cc(C)[nH]c4=O)c(C)c(N(CC)C4CCOCC4)c3)cc2)CC1] |

TABLE 1-continued

| Molecule Name | Structure |
| --- | --- |
| NUCC-0202043 | 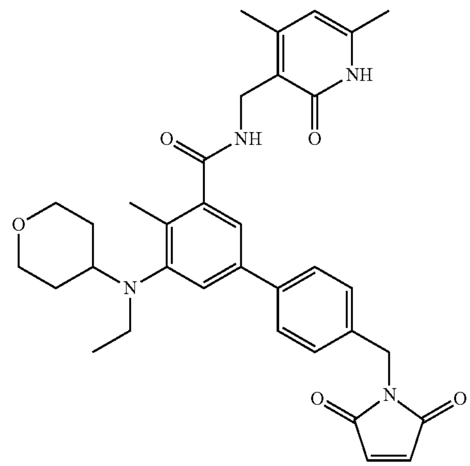 [SMILES: CCN(c1cc(-c2ccc(CN3C(=O)C=CC3=O)cc2)cc(C(=O)NCc2c(C)cc(C)[nH]c2=O)c1C)C1CCOCC1] |
| NUCC-0202036 | 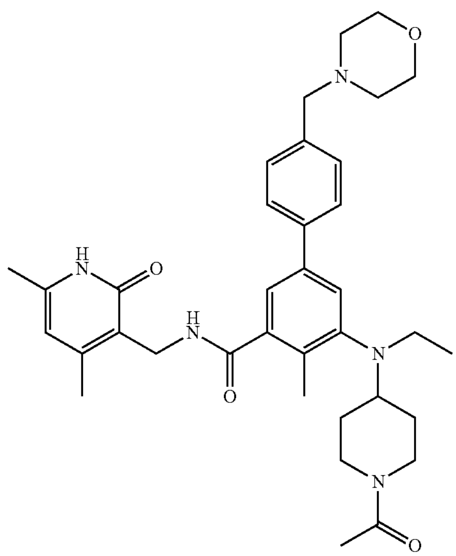 [SMILES: CCN(c1cc(-c2ccc(CN3CCOCC3)cc2)cc(C(=O)NCc2c(C)cc(C)[nH]c2=O)c1C)C1CCN(C(C)=O)CC1] |
| NUCC-0202035 | 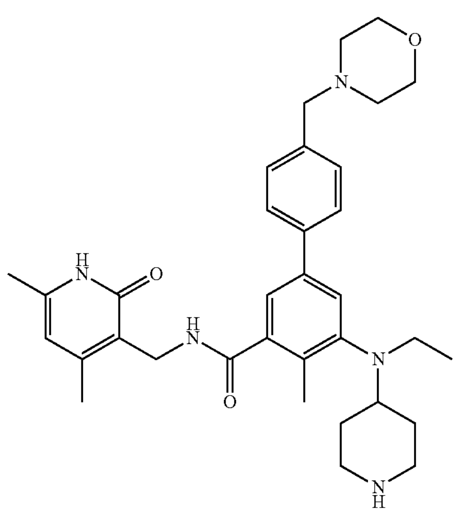 [SMILES: CCN(c1cc(-c2ccc(CN3CCOCC3)cc2)cc(C(=O)NCc2c(C)cc(C)[nH]c2=O)c1C)C1CCNCC1] |

TABLE 1-continued
| Molecule Name | Structure |
|---|---|
| NUCC-0199298 | 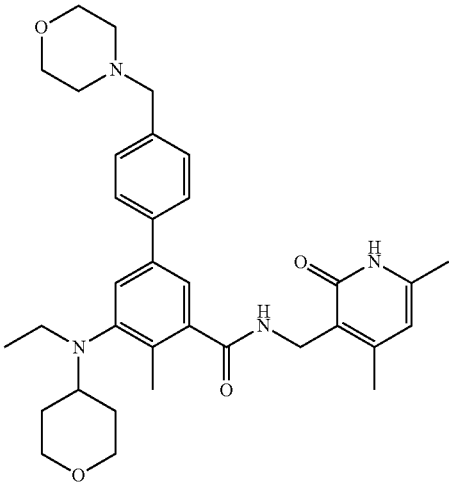 [SMILES: CCN(c1cc(-c2ccc(CN3CCOCC3)cc2)cc(C(=O)NCc2c(C)cc(C)[nH]c2=O)c1C)C1CCOCC1] |
Example 2—Proteolysis Targeting Chimeric Molecules (PROTACS) Comprising a Enhancer Zeste Homolog 2 Protein (EZH2) Binding Moiety TABLE 2
| Molecule Name | Structure |
|---|---|
| NUCC-0202037 | 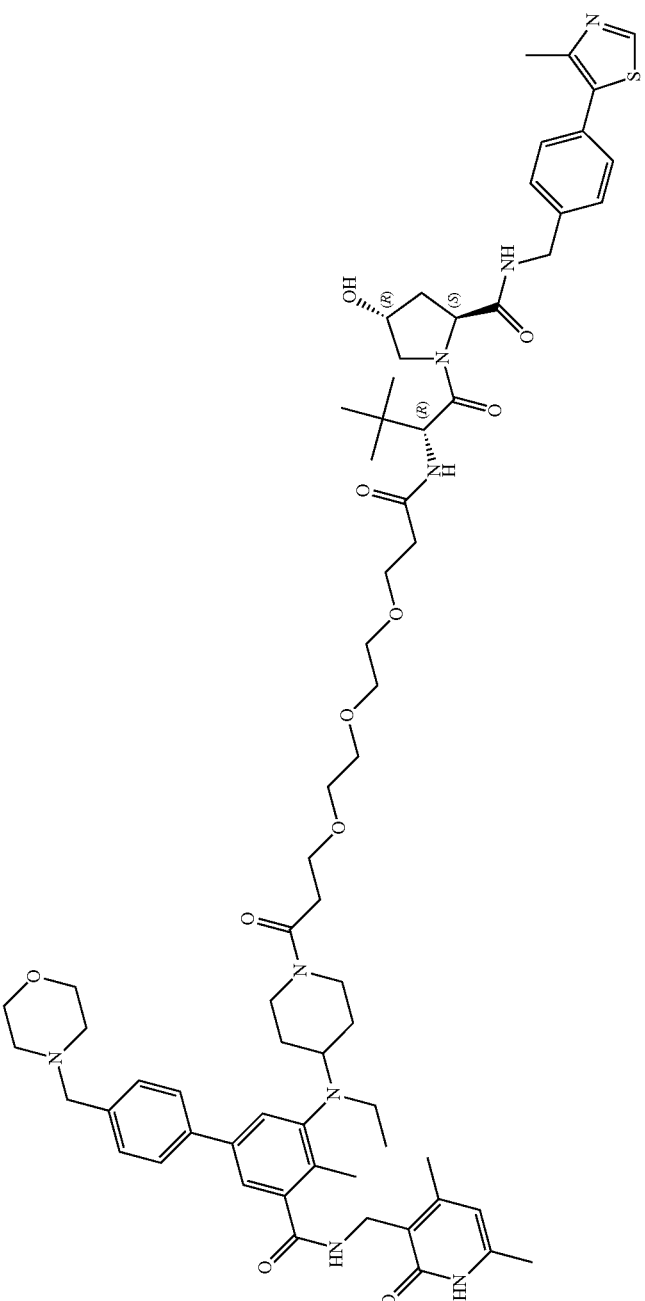 |

TABLE 2-continued
| Molecule Name | Structure |
|---|---|
| NUCC-0202038 | 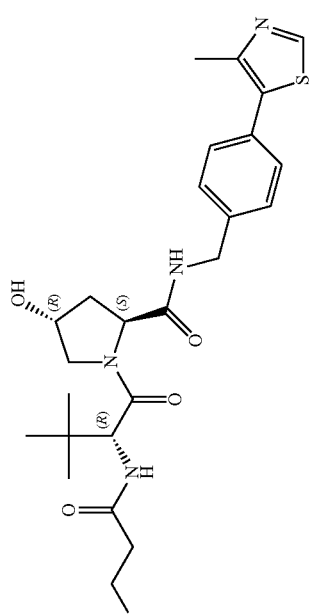 |

TABLE 2-continued
| Molecule Name | Structure |
|---|---|
| NUCC-0202039 | 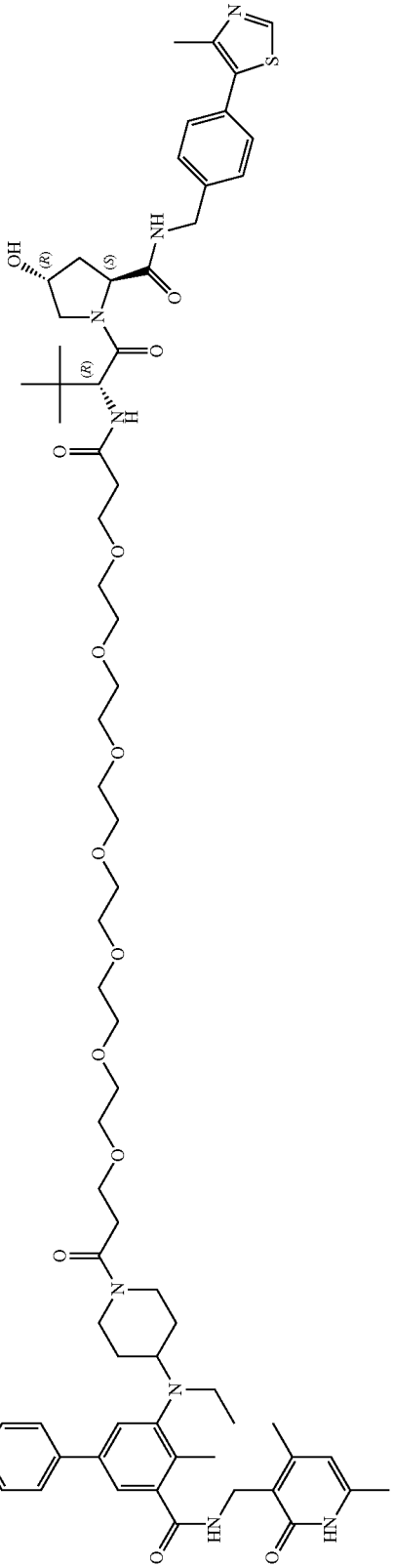 |
| NUCC-0202042 | 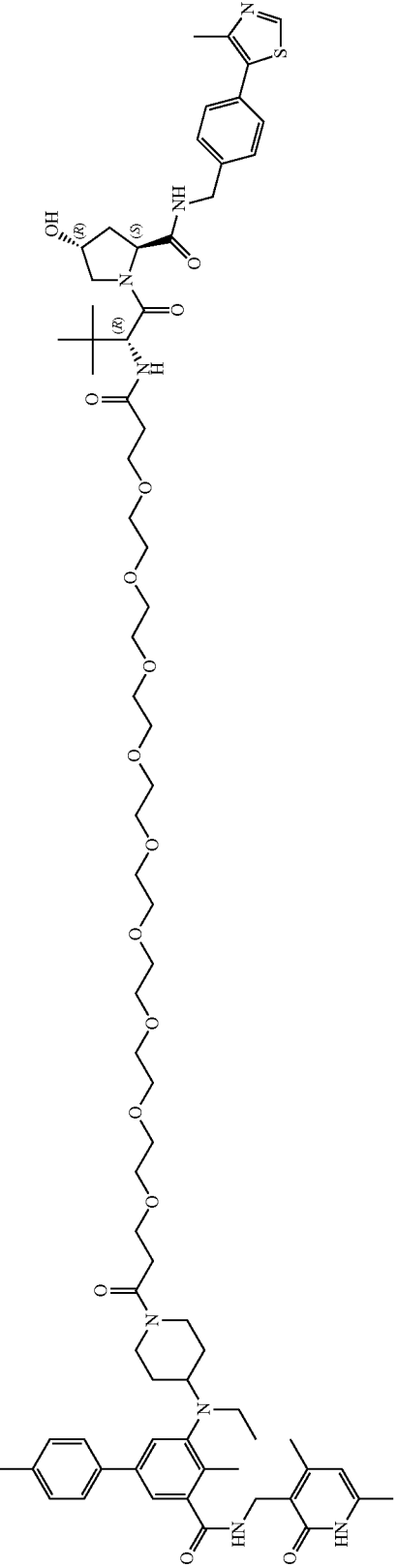 |

TABLE 2-continued
| Molecule Name | Structure |
|---|---|
| NUCC-0202060 | 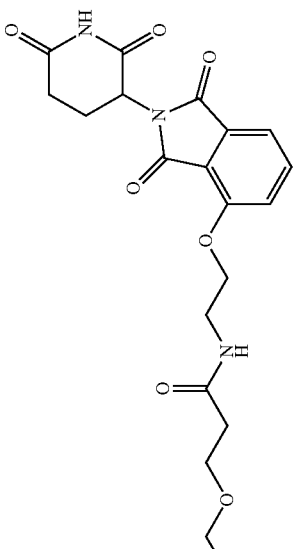 |

TABLE 2-continued
| Molecule Name | Structure |
|---|---|
| NUCC-0202061 | 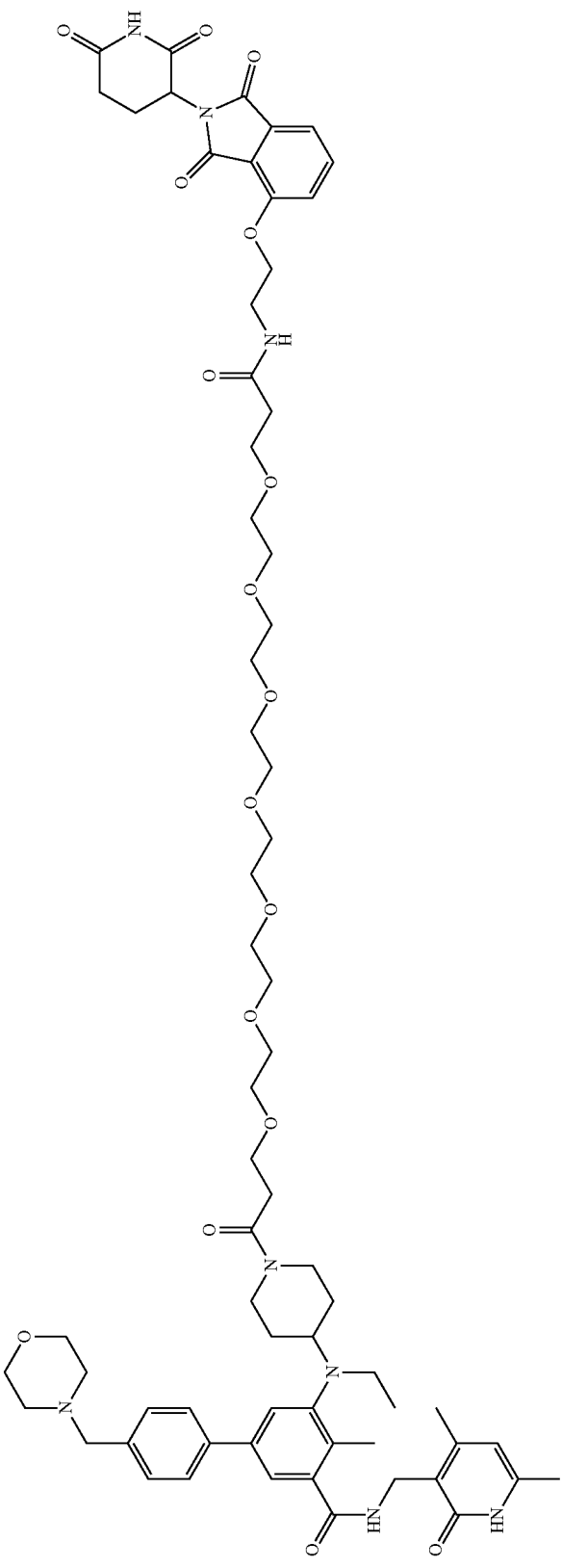 |

TABLE 2-continued
| Molecule Name | Structure |
|---|---|
| NUCC-0202062 | 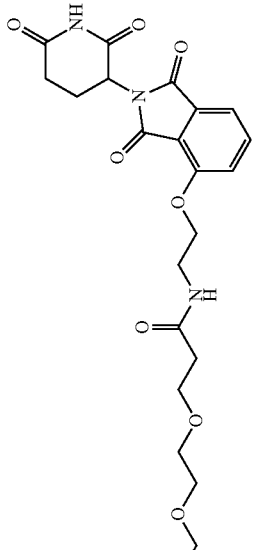 |

TABLE 2-continued
| Molecule Name | Structure |
|---|---|
| NUCC-0202093 | 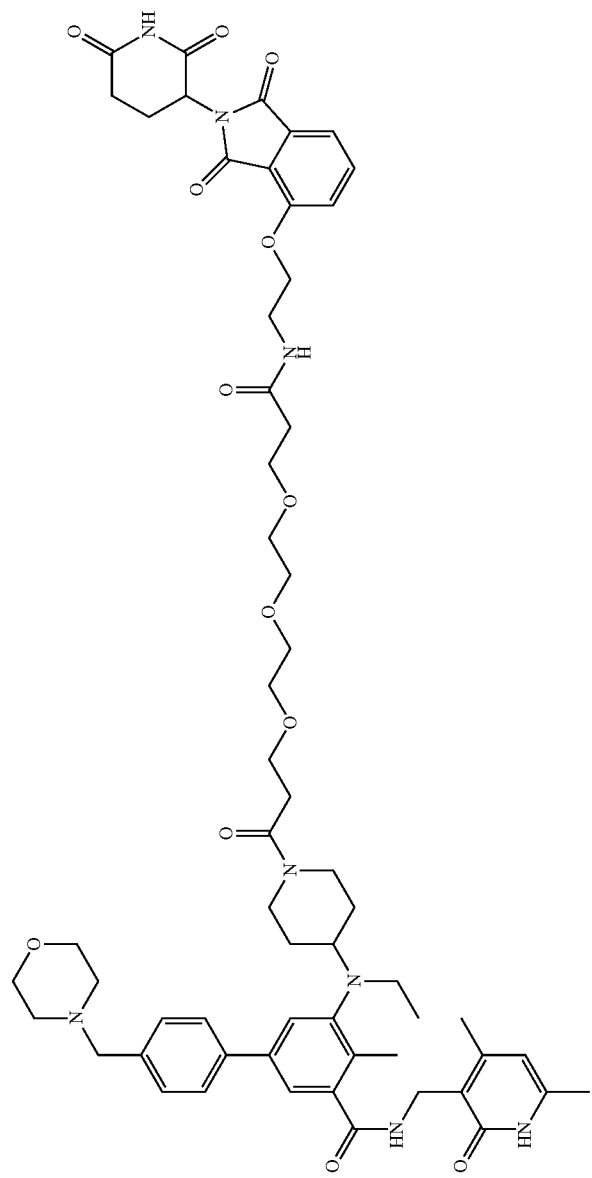 |

TABLE 2-continued
| Molecule Name | Structure |
|---|---|
| NUCC-0202094 | 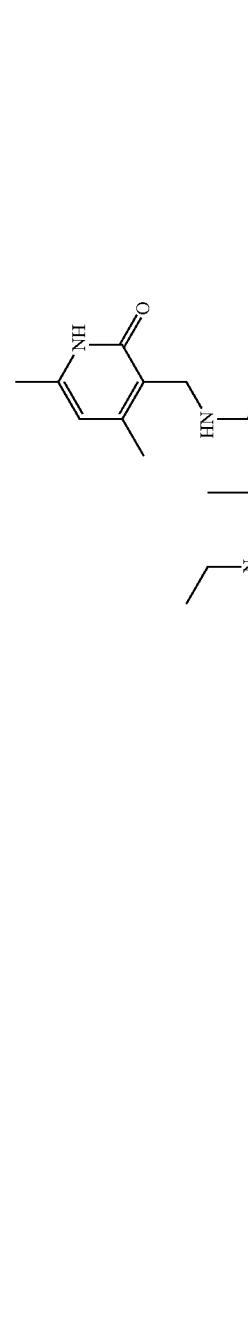 |

TABLE 2-continued
| Molecule Name | Structure |
|---|---|
| NUCC-0202095 | 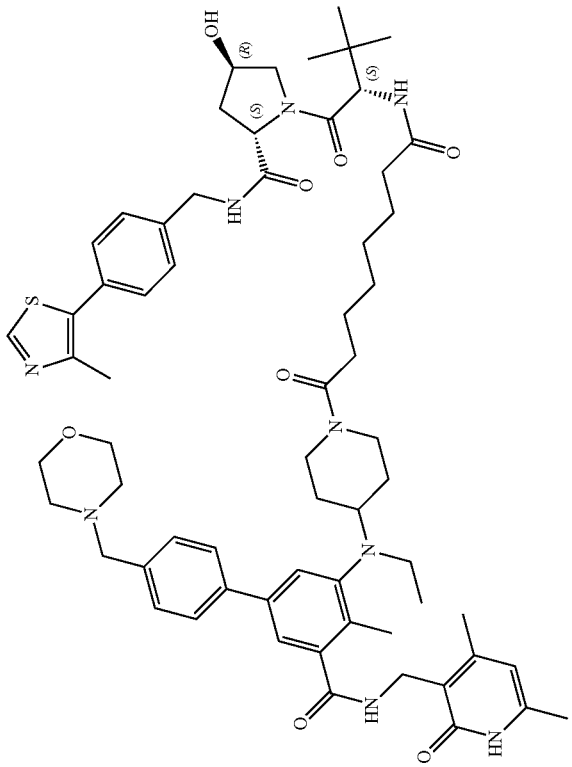 |

TABLE 2-continued
| Molecule Name | Structure |
|---|---|
| NUCC-0202096 | 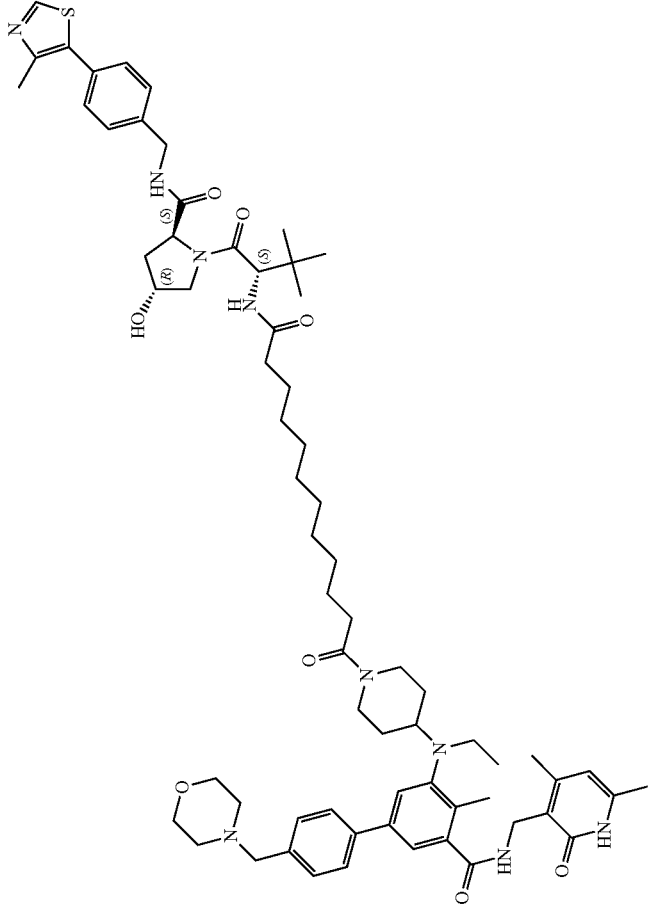 |

TABLE 2-continued
| Molecule Name | Structure |
|---|---|
| NUCC-0202097 | 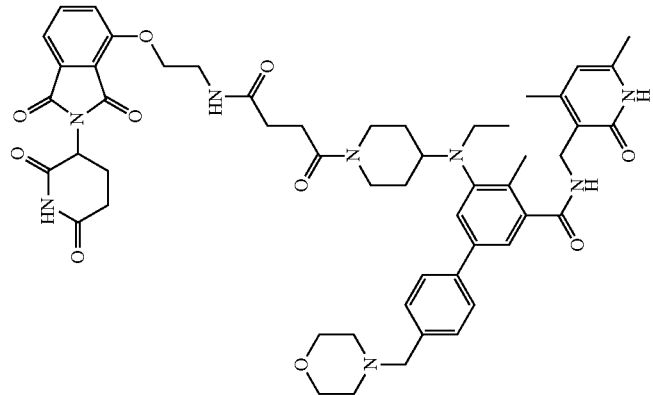 |

TABLE 2-continued
| Molecule Name | Structure |
|---|---|
| NUCC-0202098 | 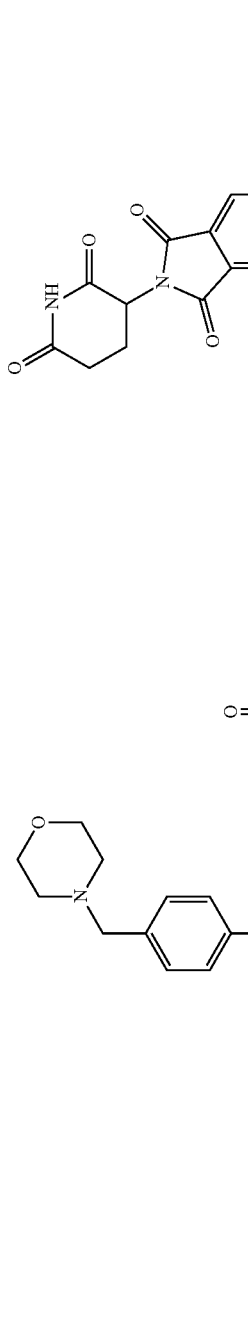 |

TABLE 2-continued
| Molecule Name | Structure |
|---|---|
| NUCC-0202099 | 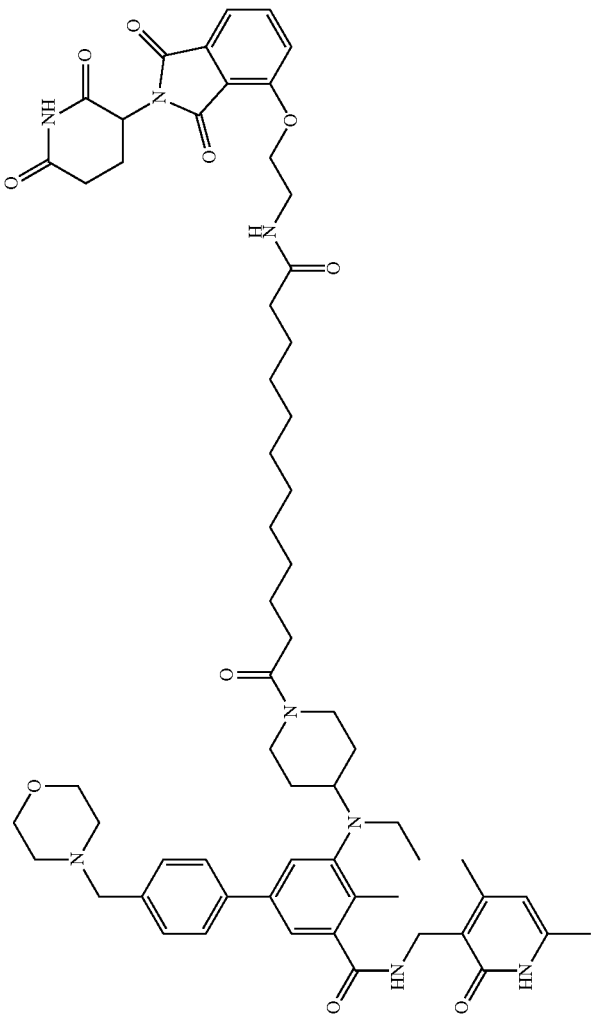 |

TABLE 2-continued

| Molecule Name | Structure |
|---|---|
| NUCC-0202100 | 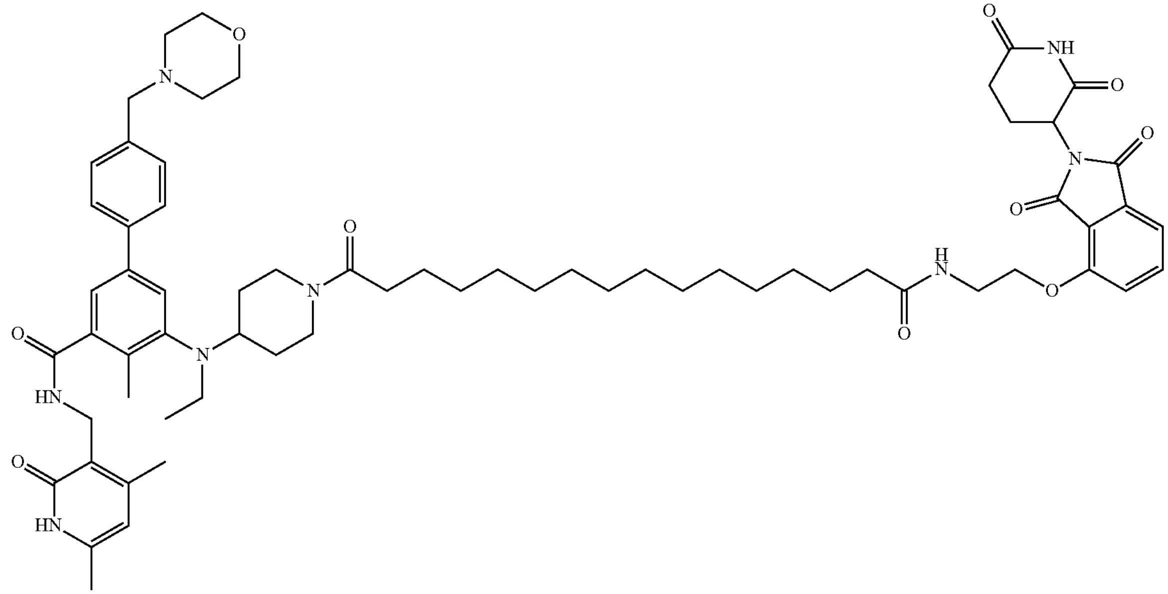 [SMILES: CCN(c1cc(-c2ccc(CN3CCOCC3)cc2)cc(C(=O)NCc2c(C)cc(C)[nH]c2=O)c1C)C1CCN(C(=O)CCCCCCCCCCCCCCC(=O)NCCOc2cccc3c2C(=O)N(C2CCC(=O)NC2=O)C3=O)CC1] |

TABLE 2-continued
| Molecule Name | Structure |
|---|---|
| NUCC-0202127 | 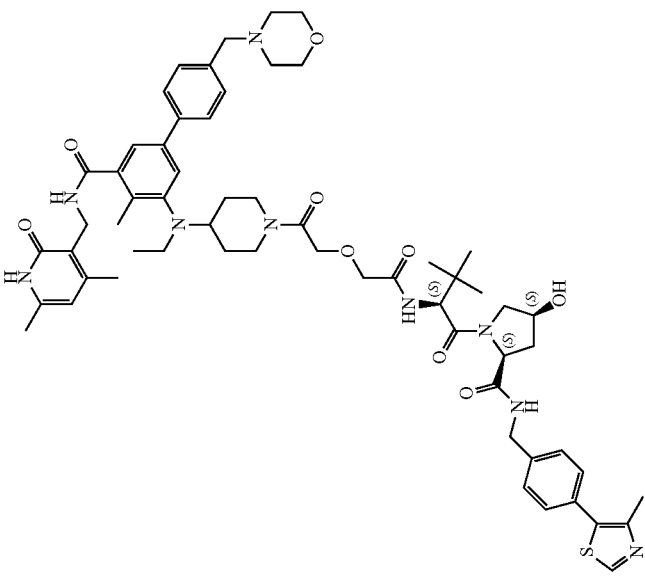 |

TABLE 2-continued
| Molecule Name | Structure |
|---|---|
| NUCC-0202177 | 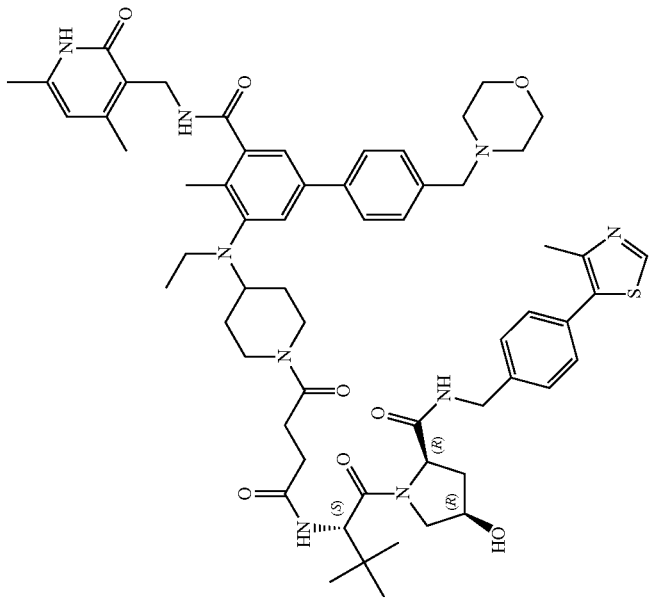 |

TABLE 2-continued
| Molecule Name | Structure |
|---|---|
| NUCC-0202178 | 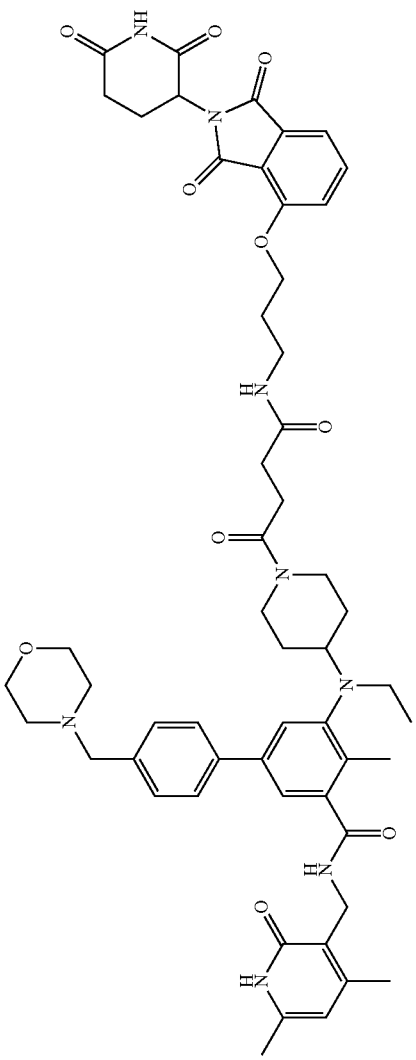 |
| NUCC-0202179 | 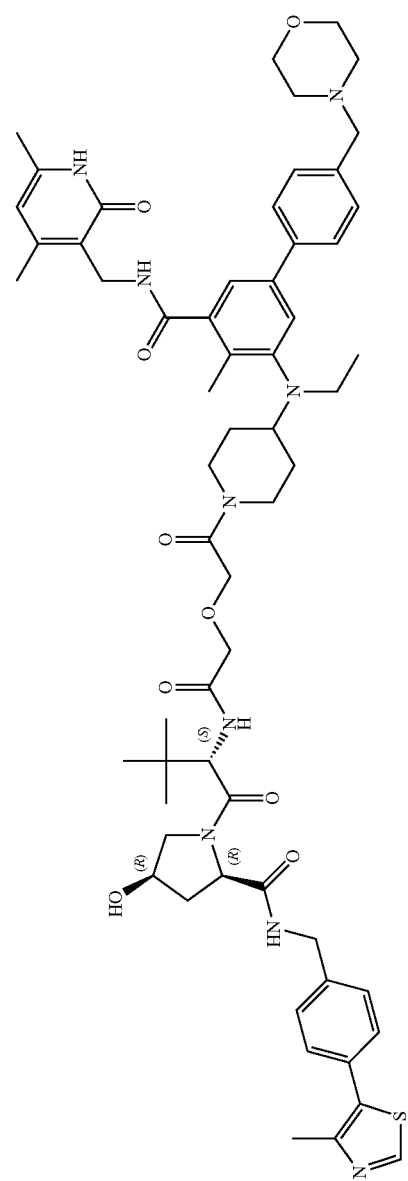 |

TABLE 2-continued
| Molecule Name | Structure |
|---|---|
| NUCC-0202180 | 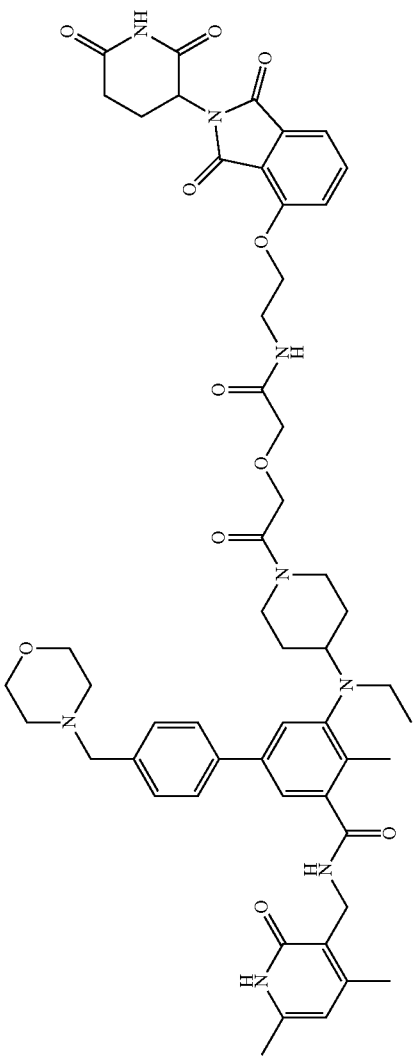 |
| NUCC-0202181 | 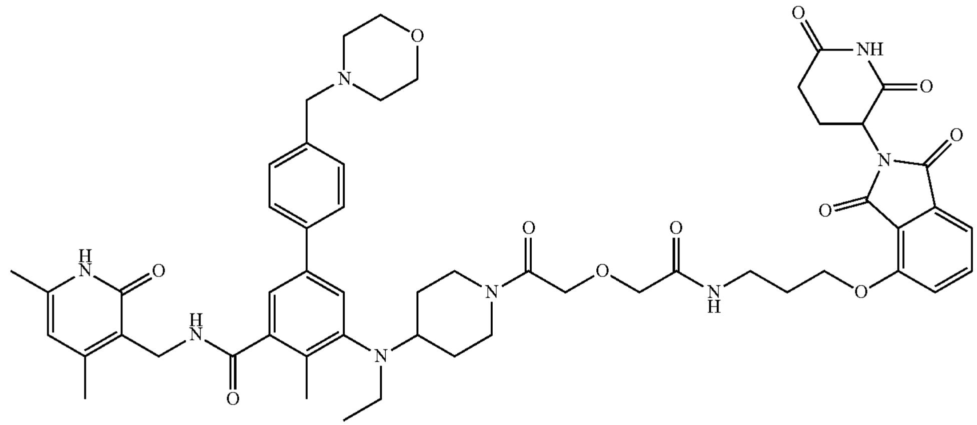 [SMILES: CCN(c1cc(-c2ccc(CN3CCOCC3)cc2)cc(C(=O)NCc2c(C)cc(C)[nH]c2=O)c1C)C1CCN(C(=O)COCC(=O)NCCCOc2cccc3c2C(=O)N(C2CCC(=O)NC2=O)C3=O)CC1] |

TABLE 2-continued
Molecule Name: NUCC-0202183
Structure:
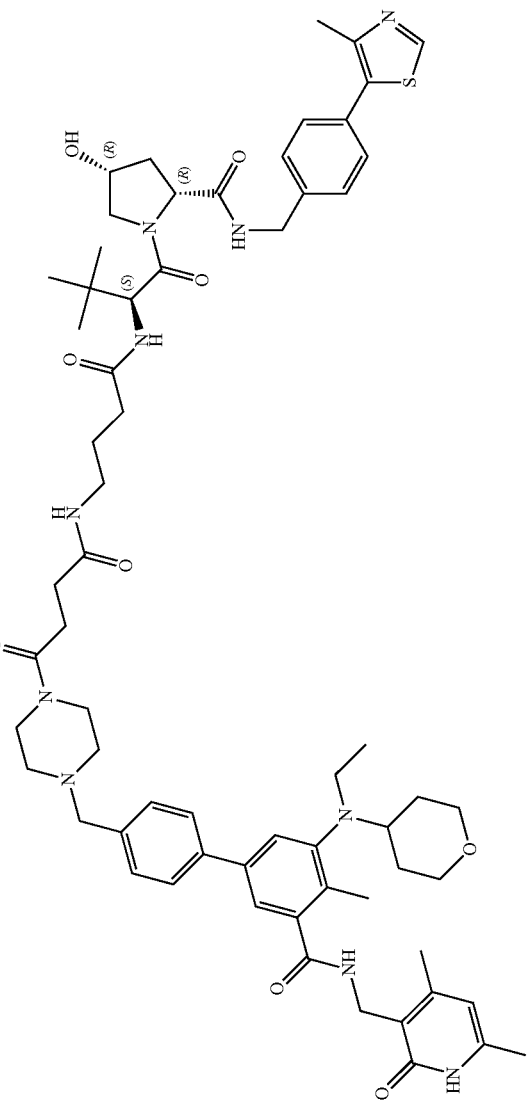

TABLE 2-continued
| Molecule Name | Structure |
|---|---|
| NUCC-0202184 | 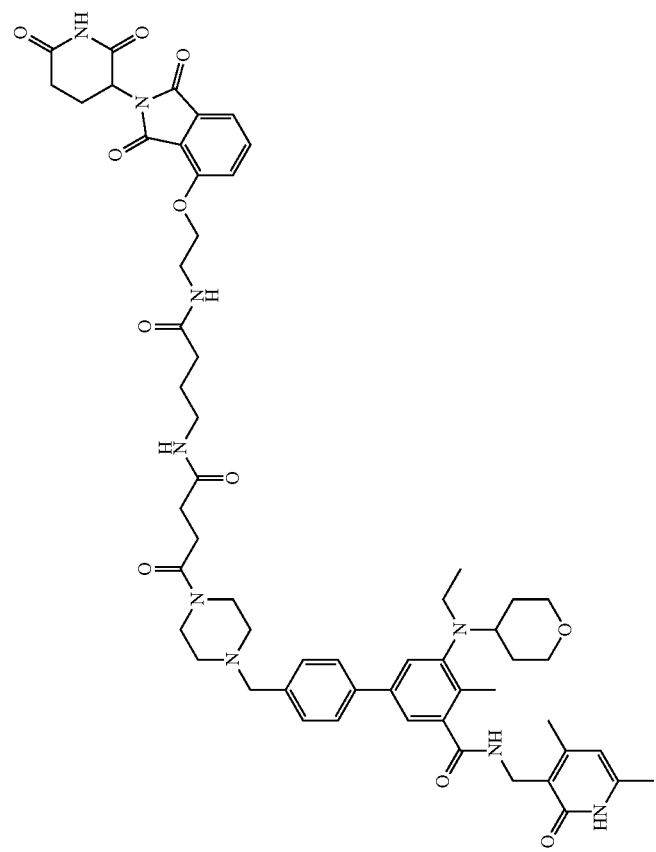 |

TABLE 2-continued
| Molecule Name | Structure |
|---|---|
| NUCC-0202185 | 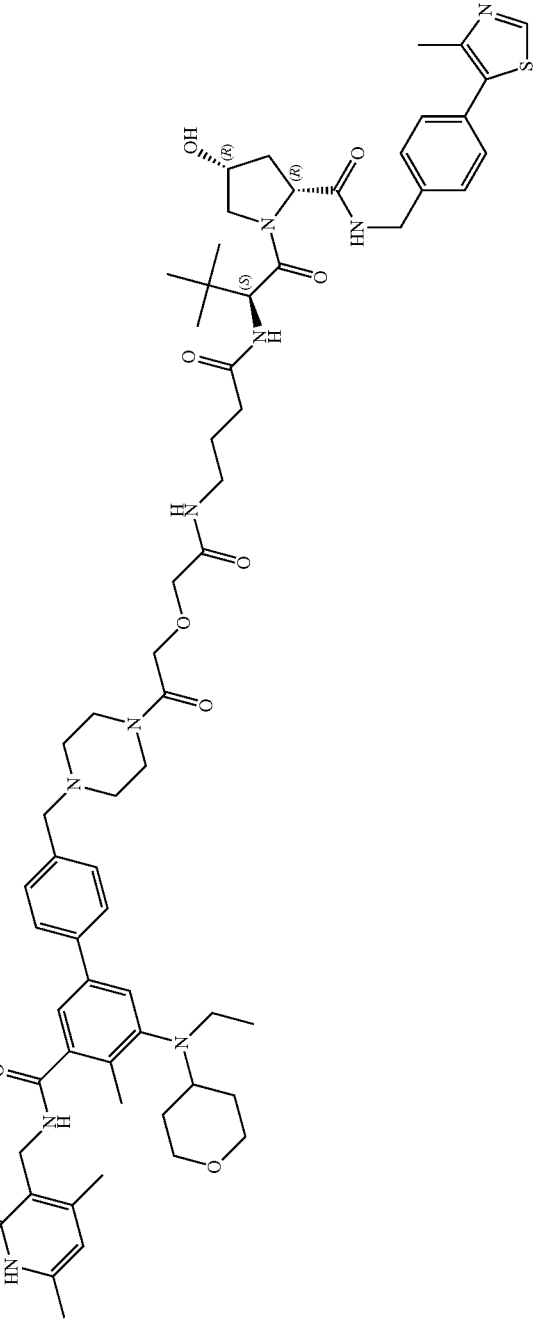 |
| NUCC-0202186 | 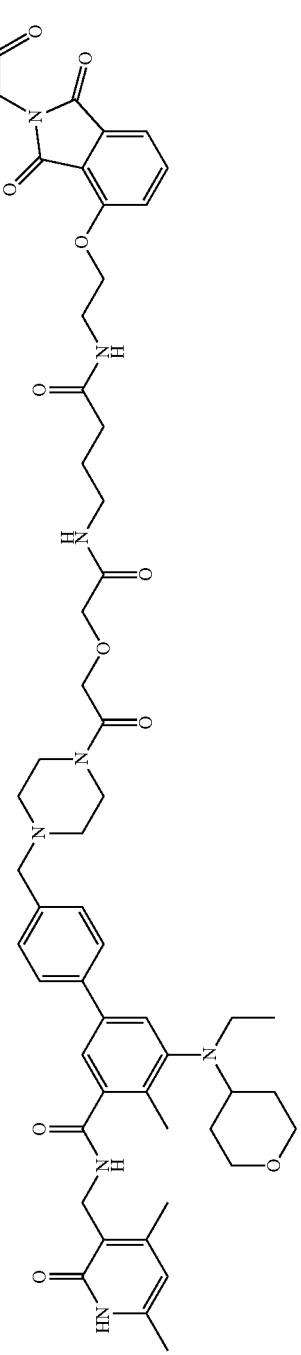 |

TABLE 2-continued
| Molecule Name | Structure |
|---|---|
| NUCC-0202187 | 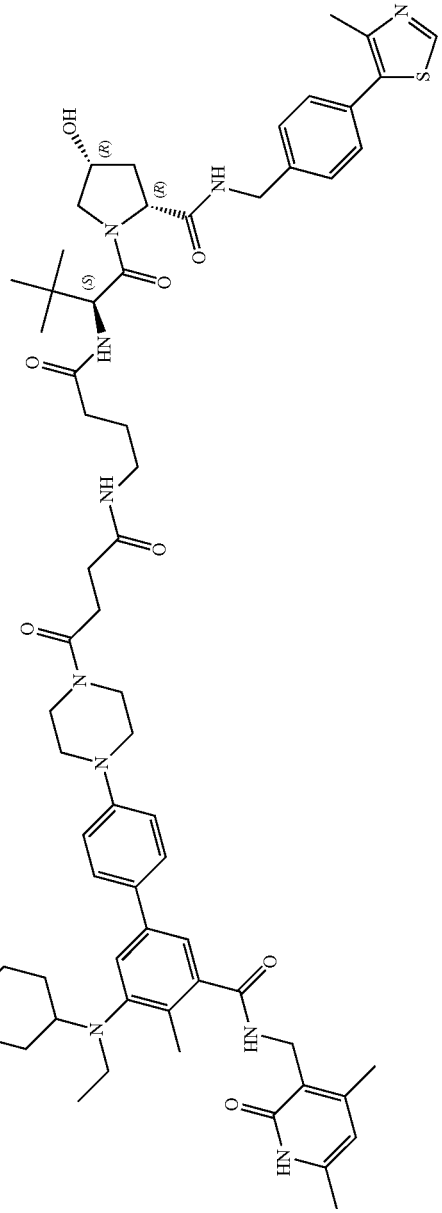 |

TABLE 2-continued
| Molecule Name | Structure |
|---|---|
| NUCC-0202188 | 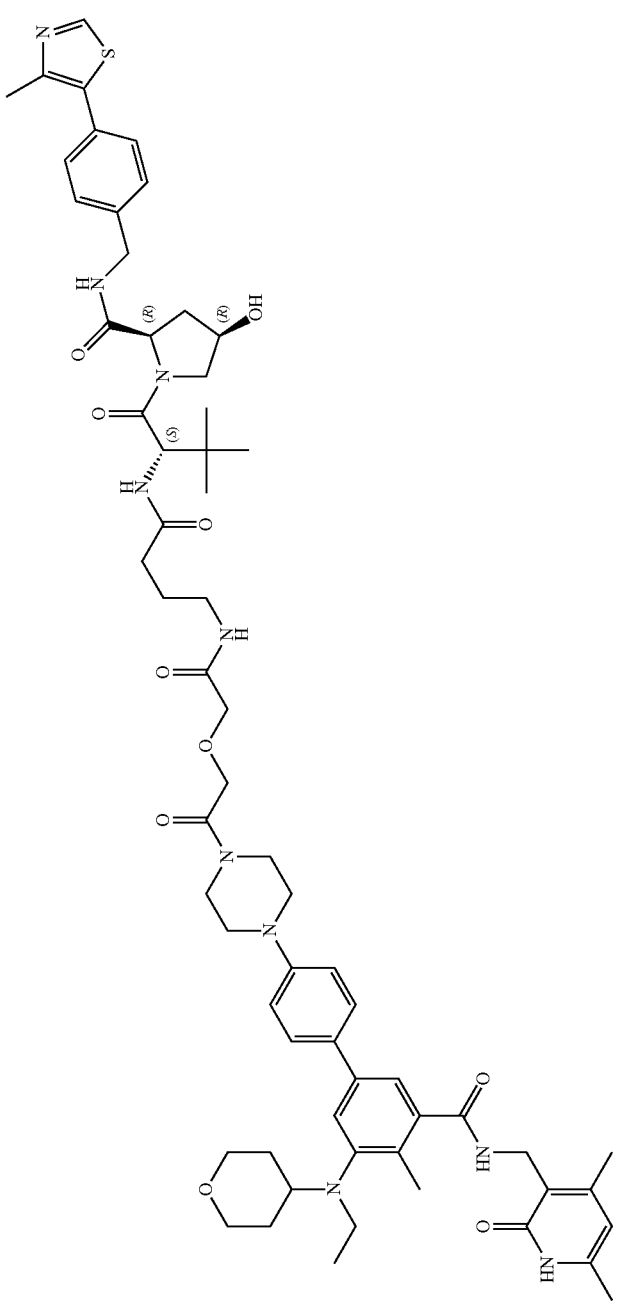 |

TABLE 2-continued
| Molecule Name | Structure |
|---|---|
| NUCC-0202189 | 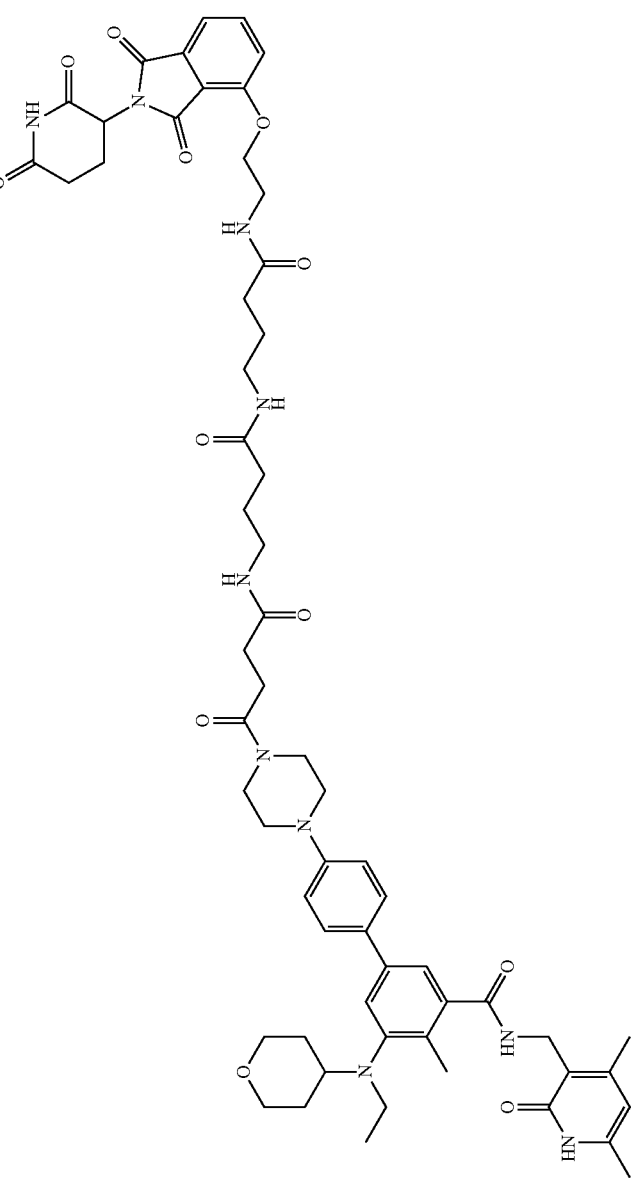 |

TABLE 2-continued
| Molecule Name | Structure |
|---|---|
| NUCC-0202190 | 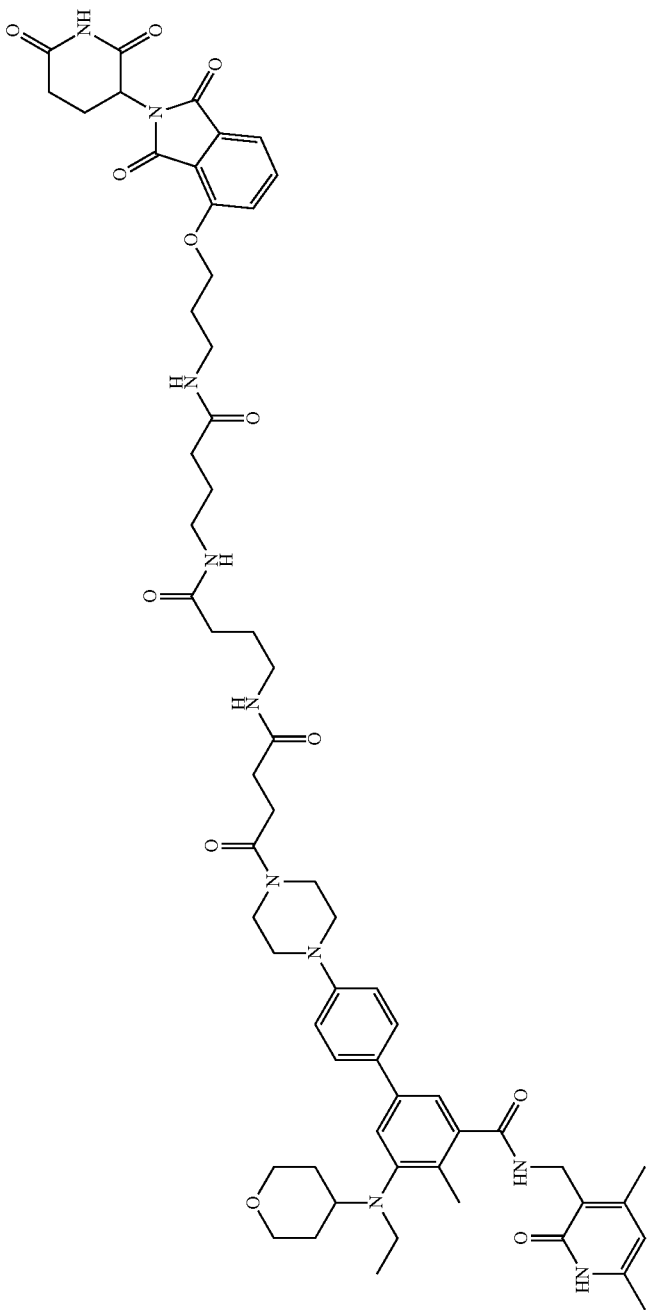 |

TABLE 2-continued

| Molecule Name | Structure |
|---|---|
| NUCC-0202191 | (chemical structure) |

TABLE 2-continued
| Molecule Name | Structure |
|---|---|
| NUCC-0202192 | 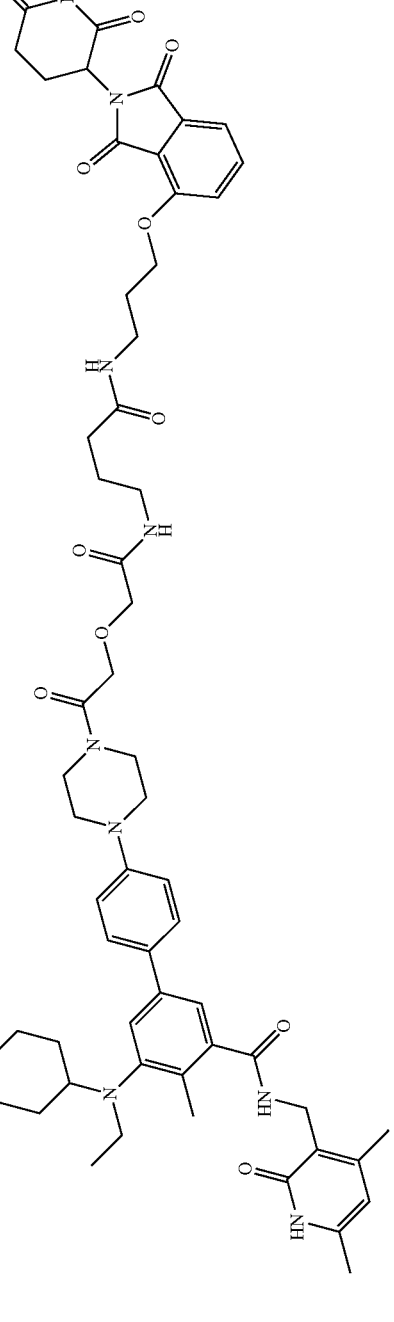 |
| NUCC-0202298 | 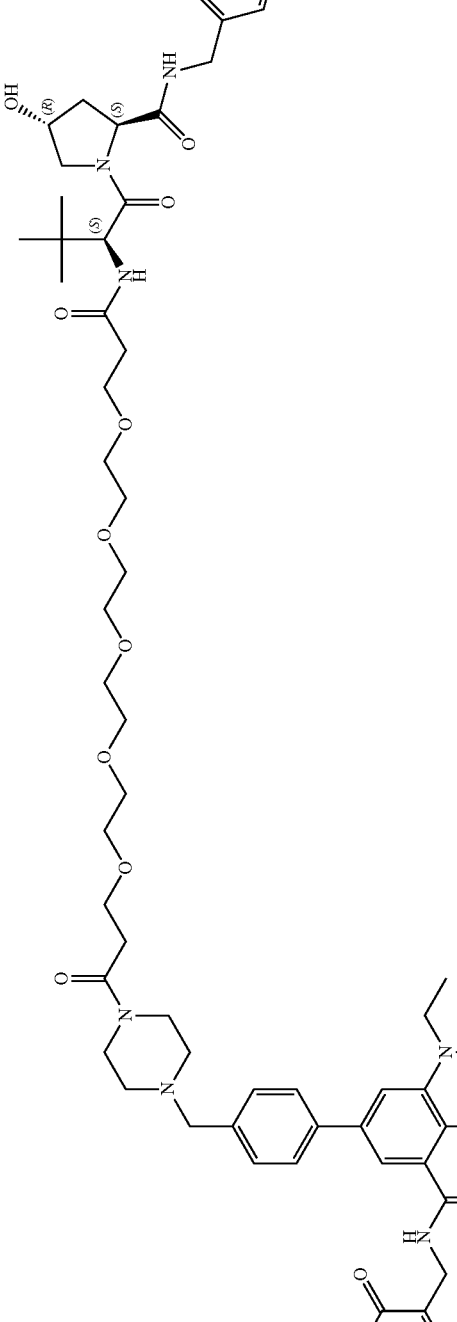 |

TABLE 2-continued
| Molecule Name | Structure |
|---|---|
| NUCC-0202299 | 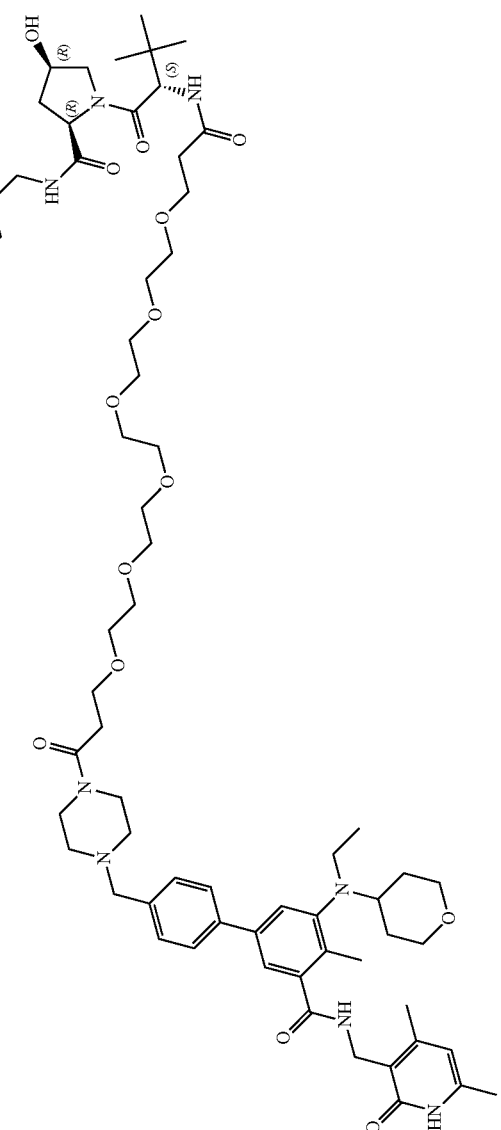 |

TABLE 2-continued
| Molecule Name | Structure |
|---|---|
| NUCC-0202300 | 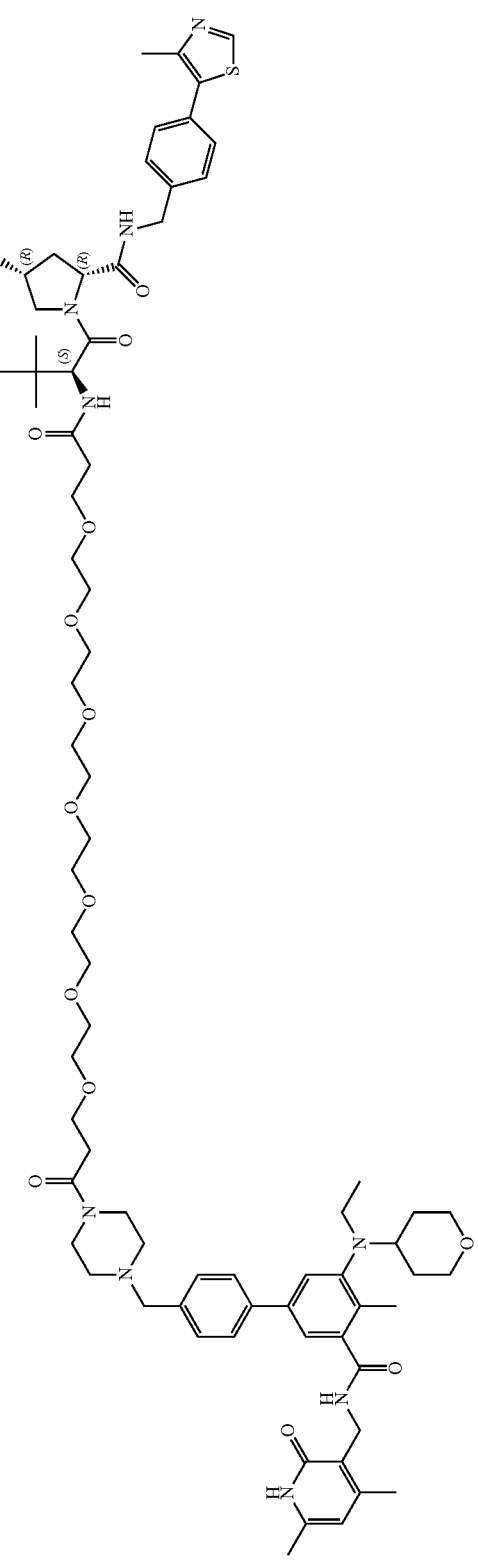 |
| NUCC-0202301 | 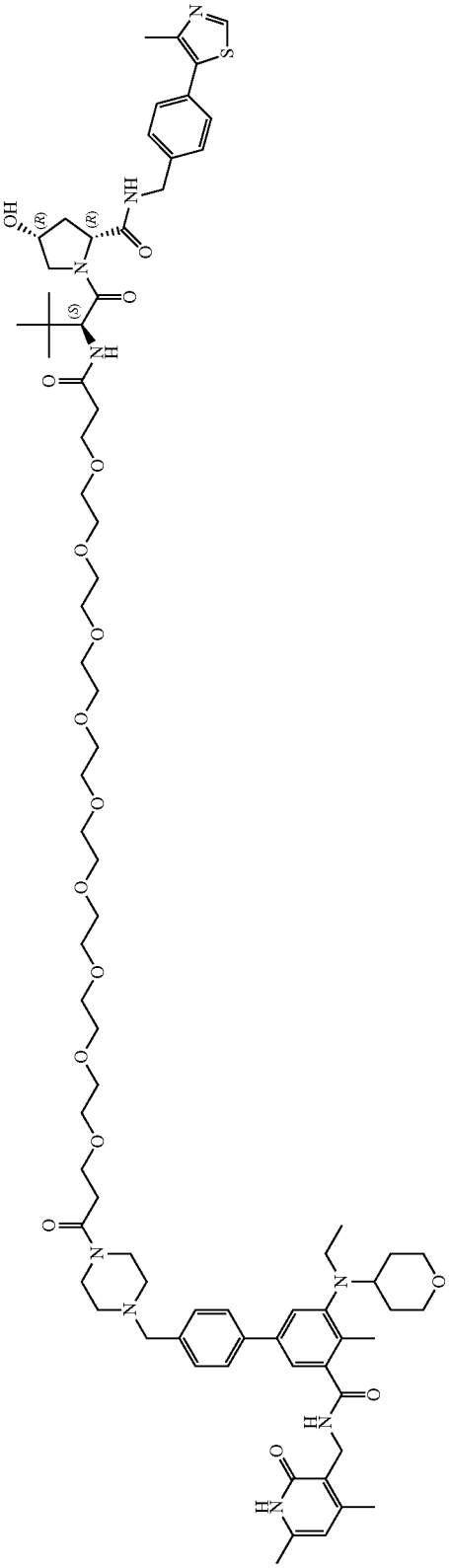 |

TABLE 2-continued
| Molecule Name | Structure |
|---|---|
| NUCC-0202302 | 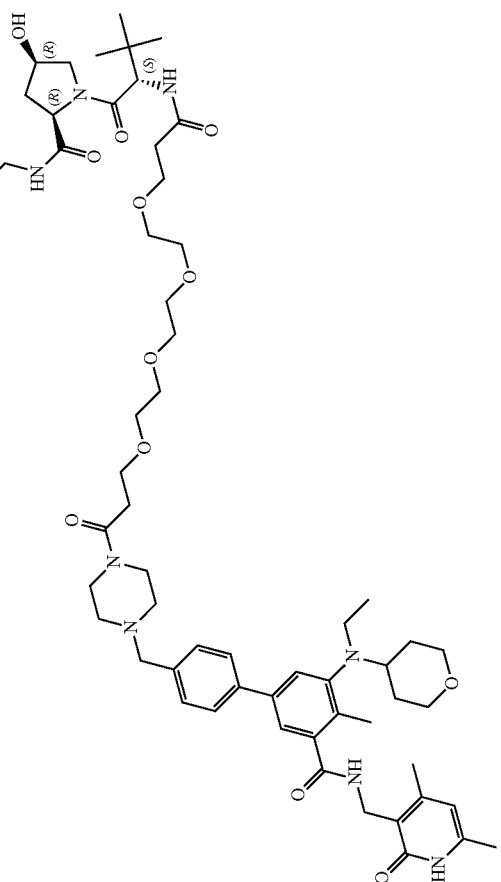 |

TABLE 2-continued
| Molecule Name | Structure |
|---|---|
| NUCC-0202303 | 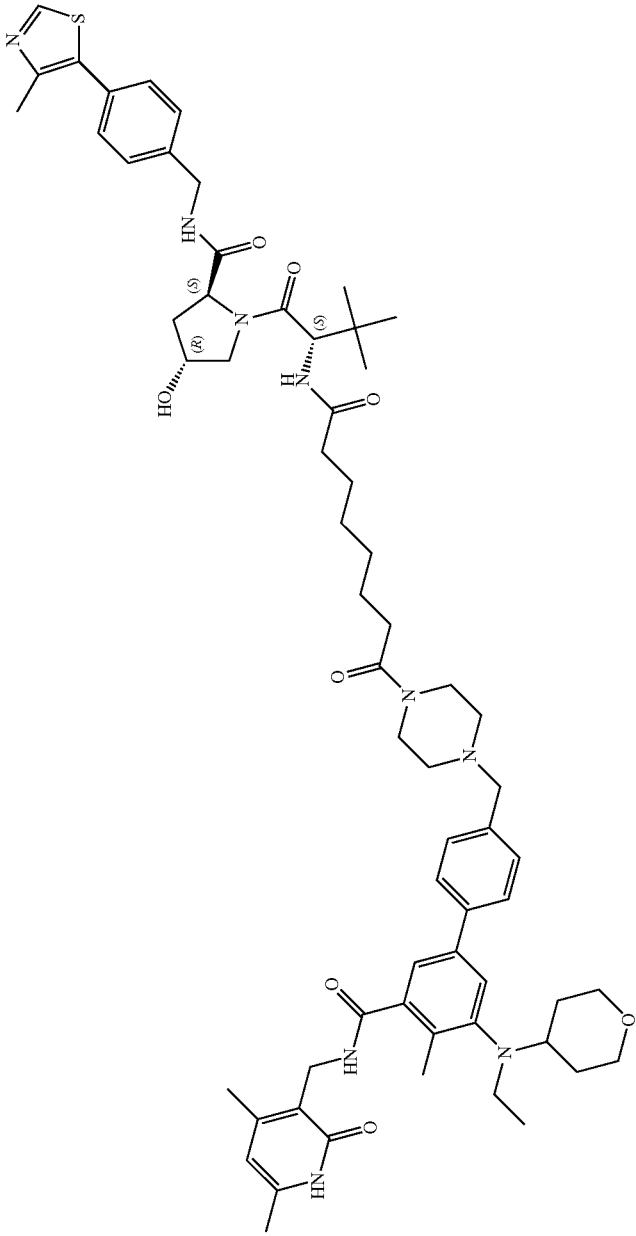 |

TABLE 2-continued
| Molecule Name | Structure |
|---|---|
| NUCC-0202304 | 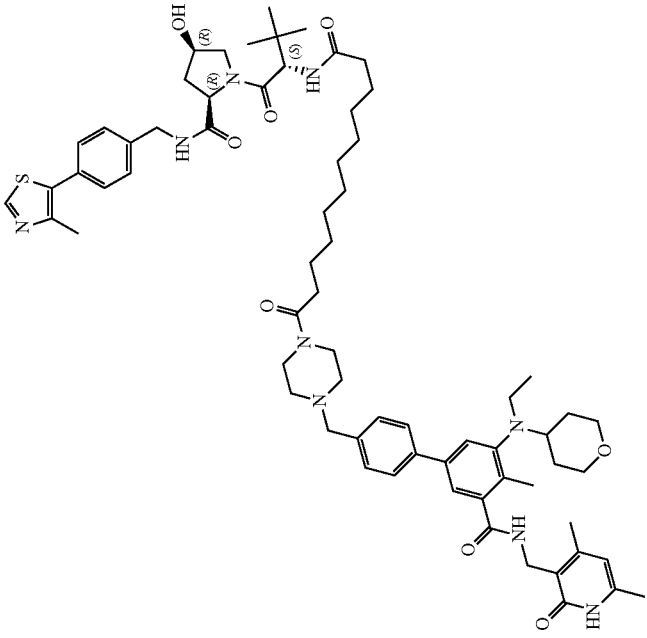 |

TABLE 2-continued
| Molecule Name | Structure |
|---|---|
| NUCC-0202305 | 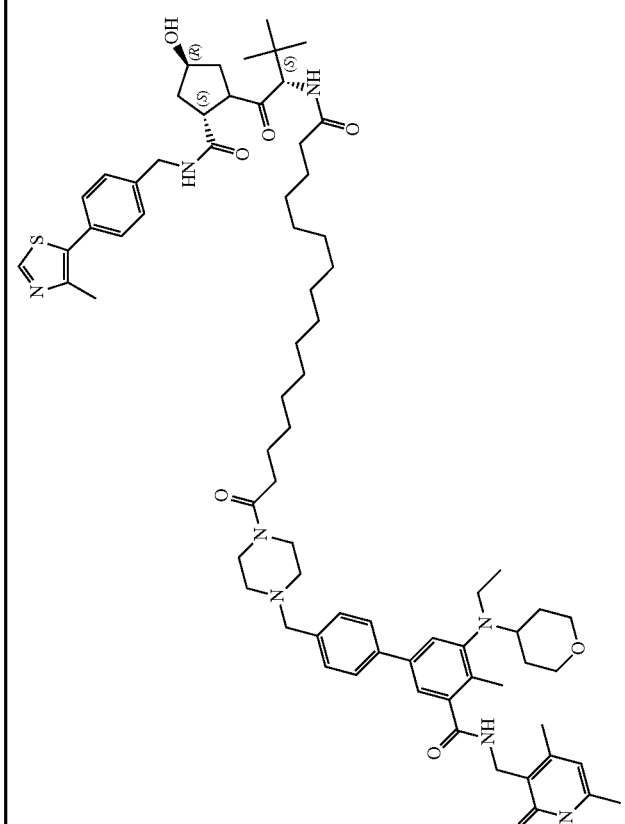 |

| Molecule Name | Structure |
|---|---|
| NUCC-0202346 | 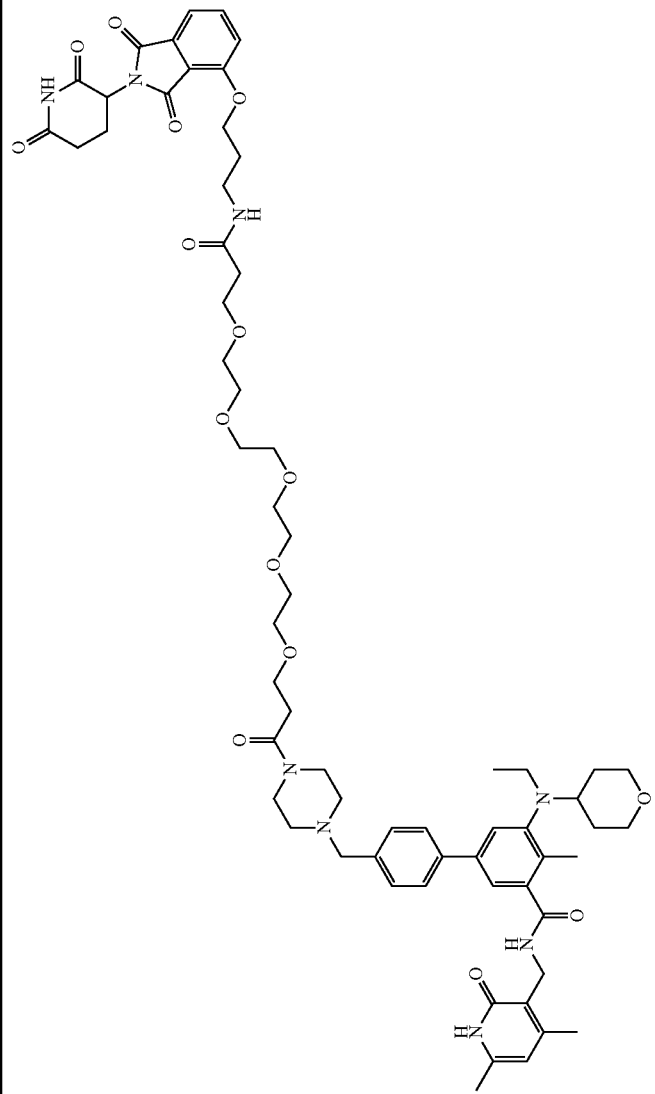 |

TABLE 2-continued
| Molecule Name | Structure |
|---|---|
| NUCC-0202347 | 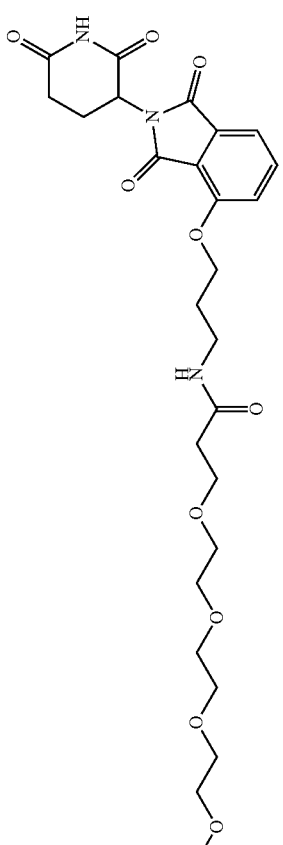 |

TABLE 2-continued
| Molecule Name | Structure |
|---|---|
| NUCC-0202348 | 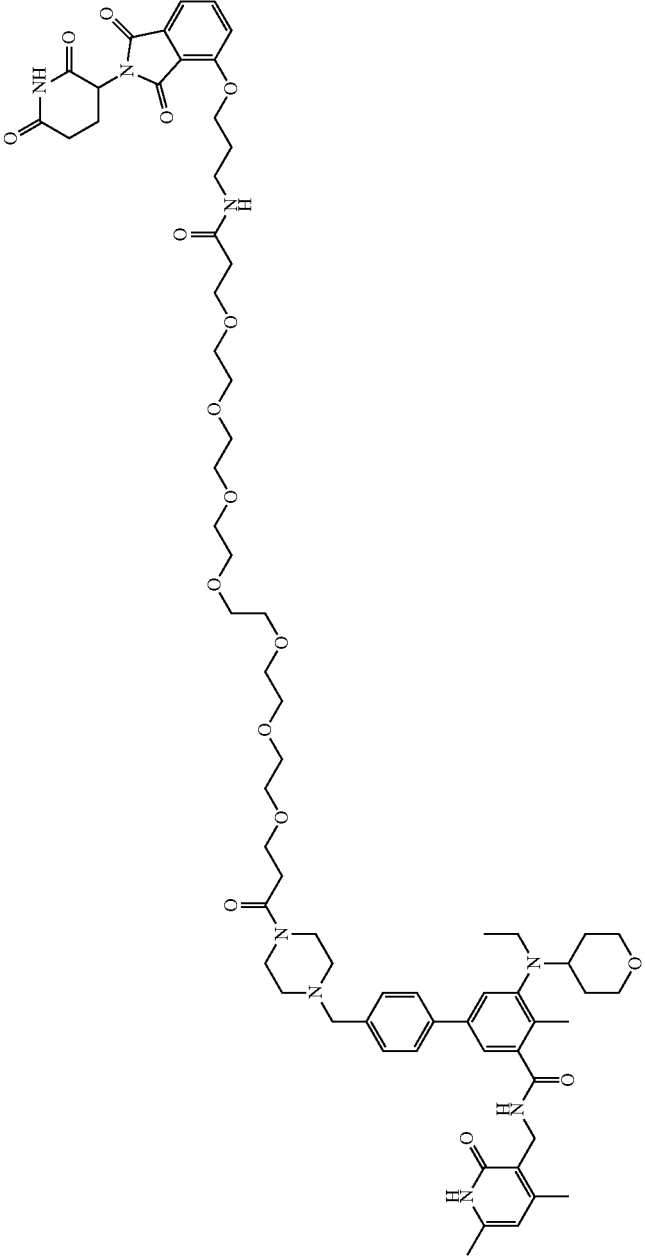 |

| Molecule Name | Structure |
|---|---|
| NUCC-0202349 | 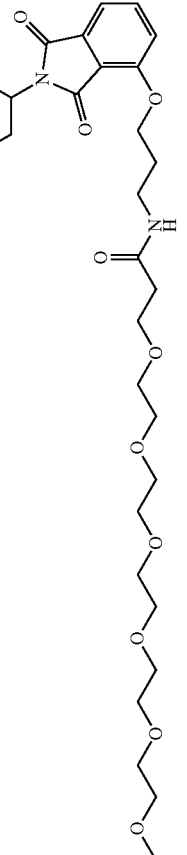 |
TABLE 2-continued TABLE 2-continued
| Molecule Name | Structure |
|---|---|
| NUCC-0202350 | 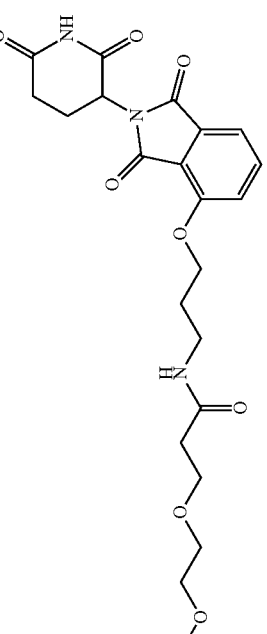 |

TABLE 2-continued
| Molecule Name | Structure |
|---|---|
| NUCC-0202351 | 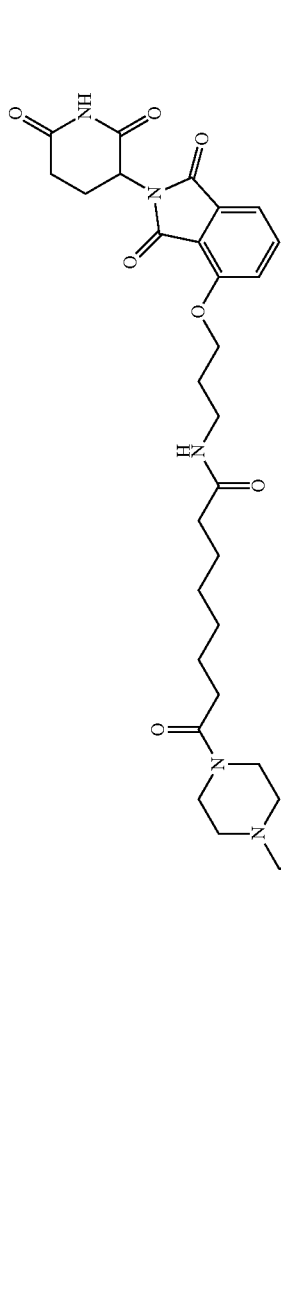 |

TABLE 2-continued
| Molecule Name | Structure |
|---|---|
| NUCC-0202352 | 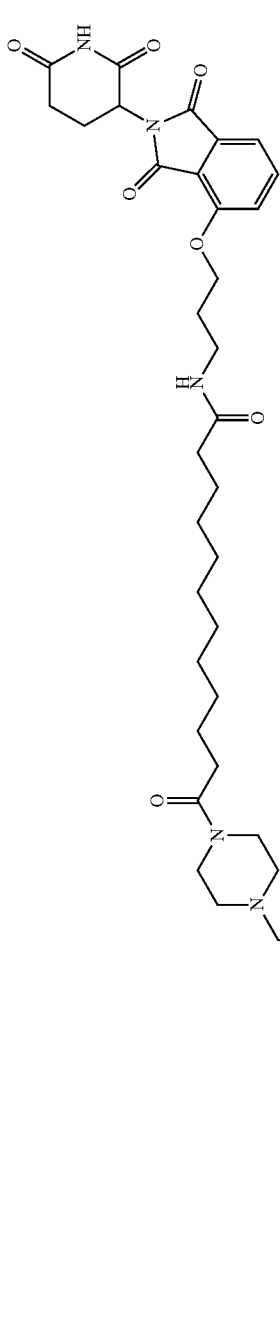 |

TABLE 2-continued
| Molecule Name | Structure |
|---|---|
| NUCC-0202353 | 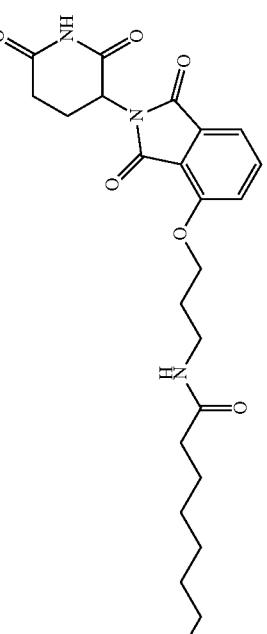 |

TABLE 2-continued

| Molecule Name | Structure |
|---|---|
| NUCC-0202551 | 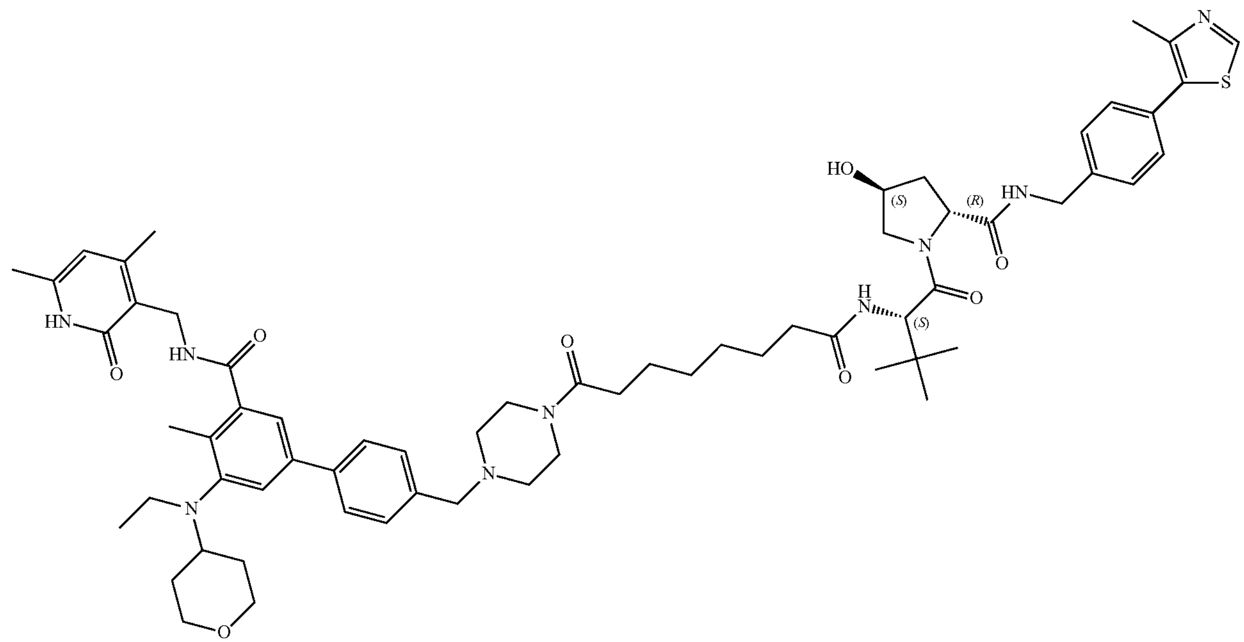 |
| NUCC-0202589 | 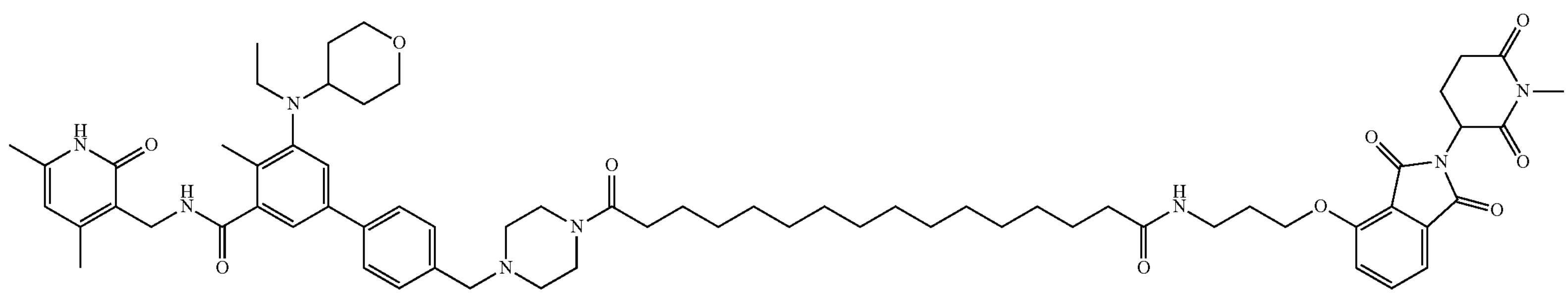 |

| Molecule Name | Structure |
|---|---|
| NUCC-0203195 | 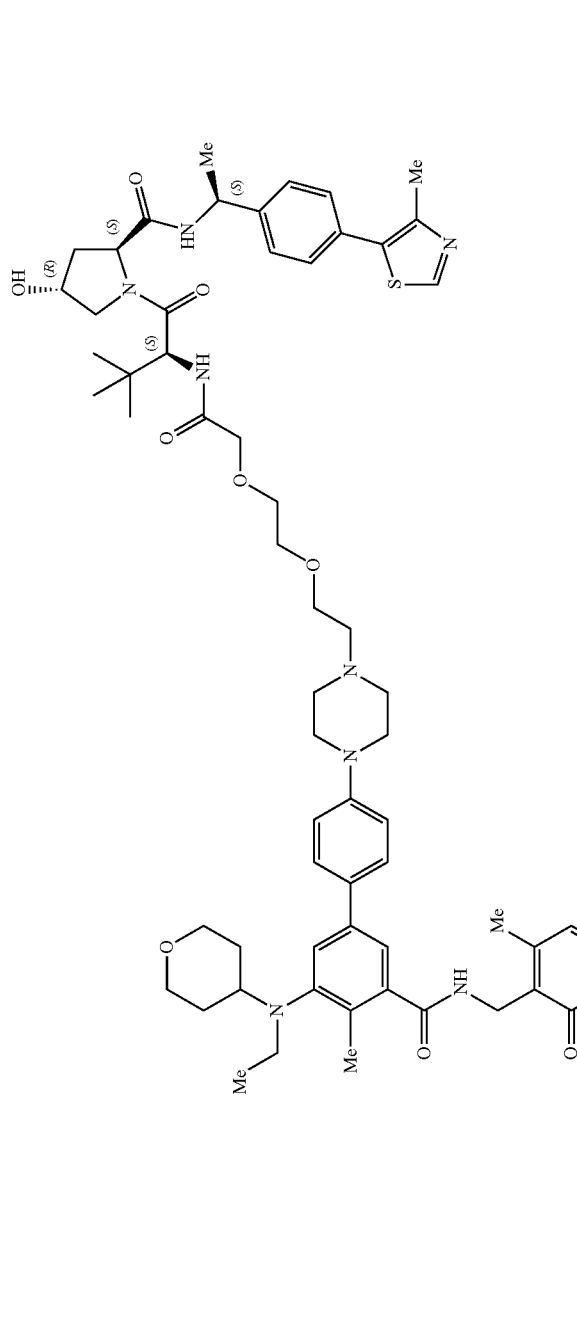 |

TABLE 2-continued
| Molecule Name | Structure |
|---|---|
| NUCC-0203196 | 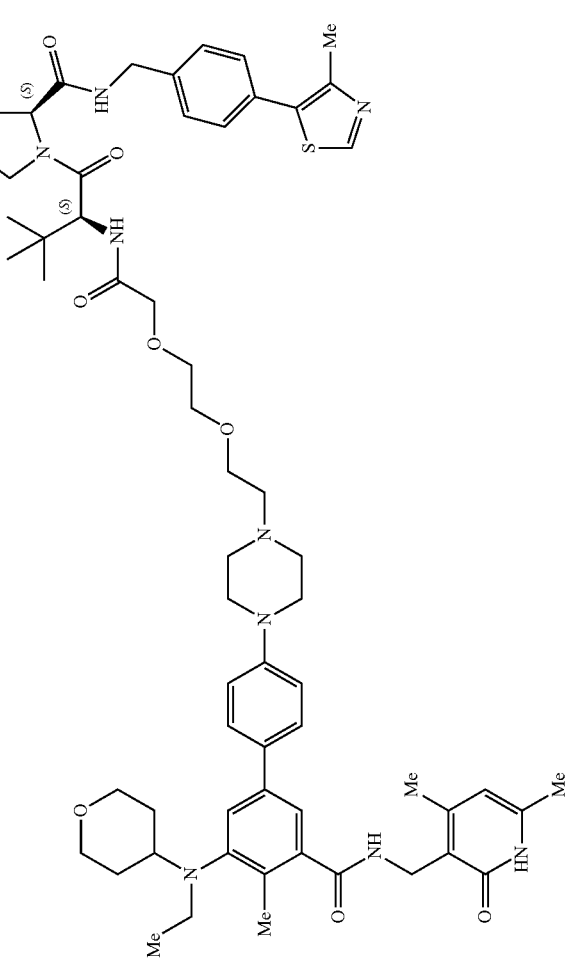 |

TABLE 2-continued
| Molecule Name | Structure |
|---|---|
| NUCC-0203197 | 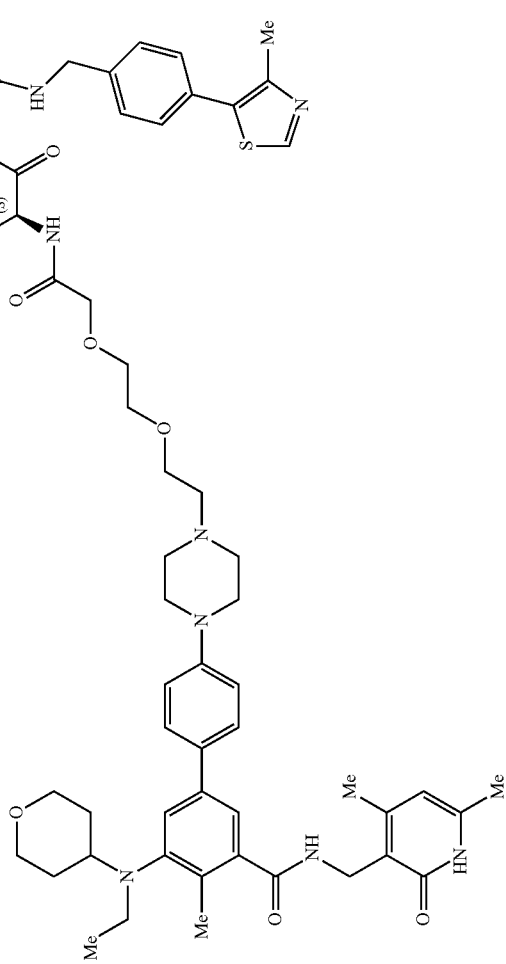 |

TABLE 2-continued
| Molecule Name | Structure |
|---|---|
| NUCC-0203223 | 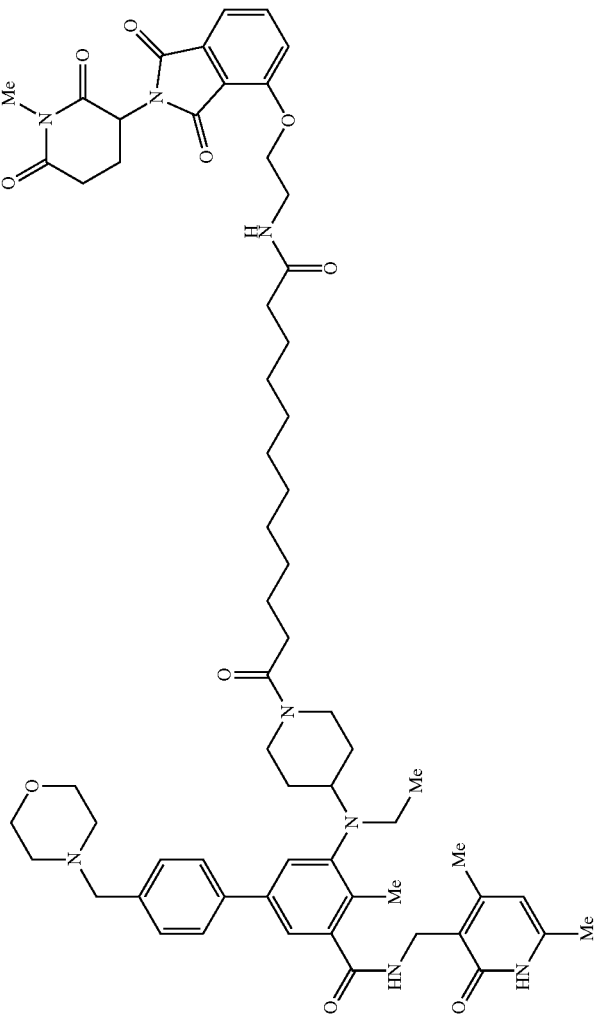 |

TABLE 2-continued
| Molecule Name | Structure |
|---|---|
| NUCC-0223571 | 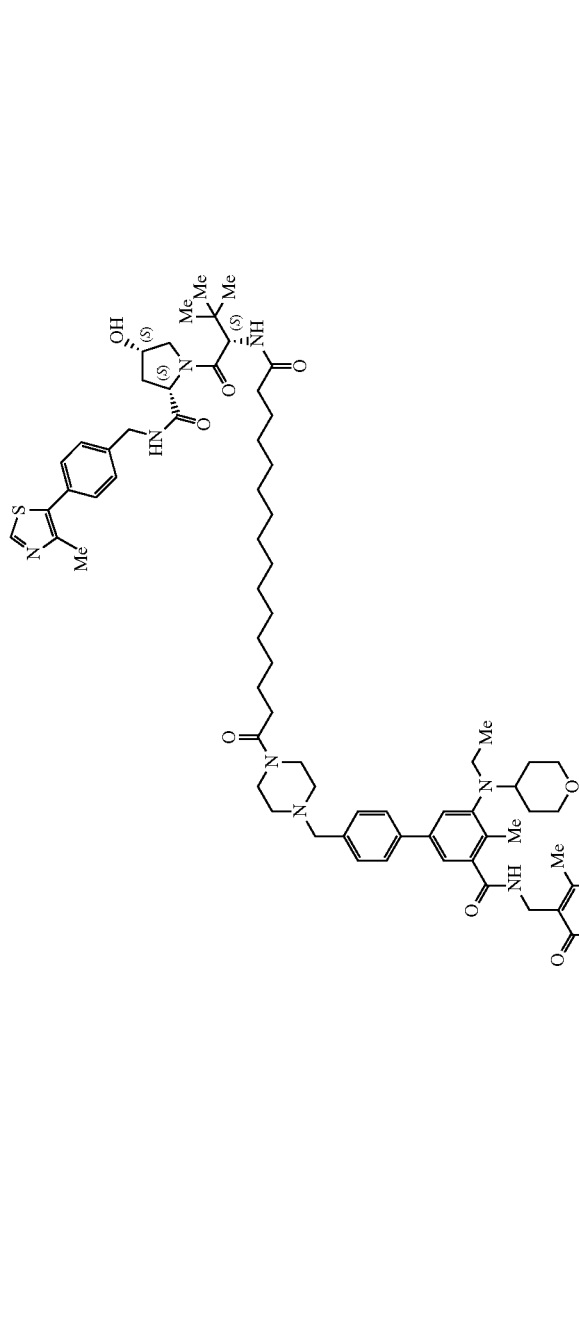 |

TABLE 2-continued
| Molecule Name | Structure |
|---|---|
| NUCC-0226269 | 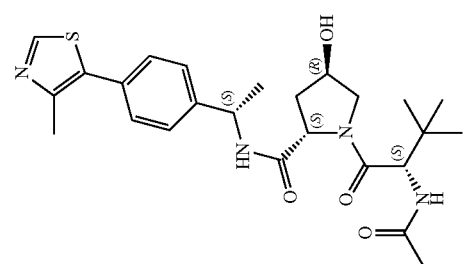 |

TABLE 2-continued
| Molecule Name | Structure |
|---|---|
| NUCC-0226270 | 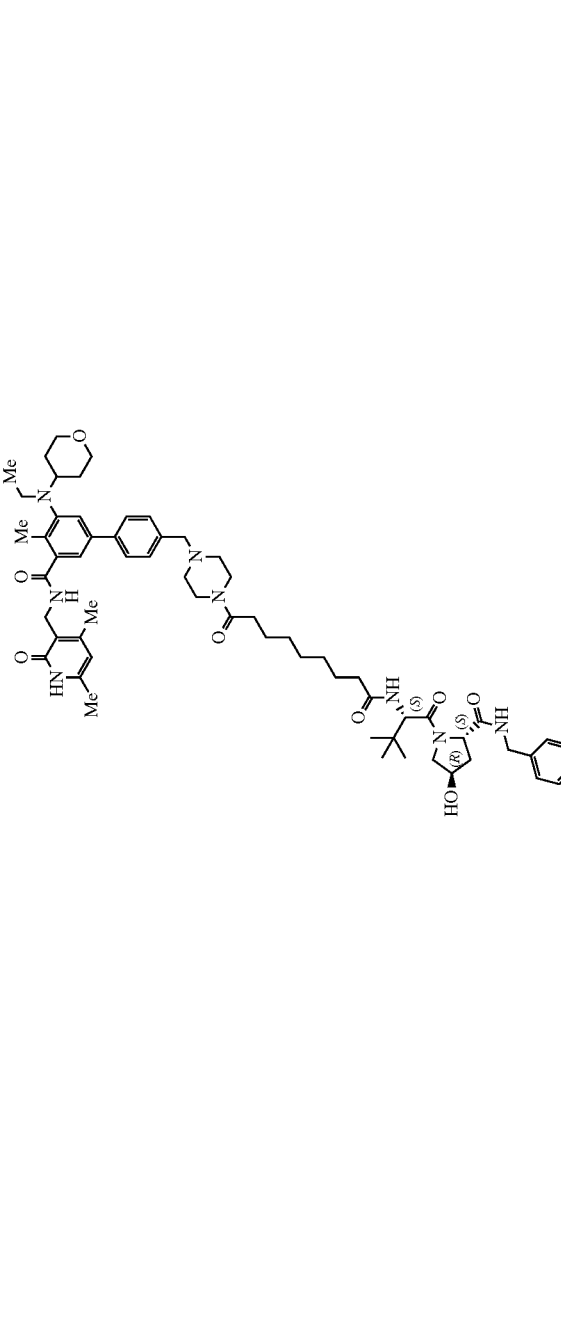 |

TABLE 2-continued
| Molecule Name | Structure |
|---|---|
| NUCC-0226271 | 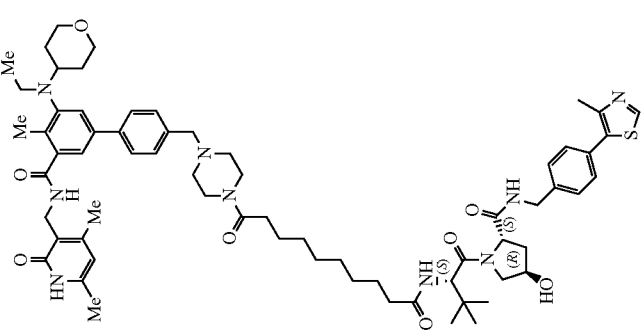 |

TABLE 2-continued
| Molecule Name | Structure |
|---|---|
| NUCC-0226272 | 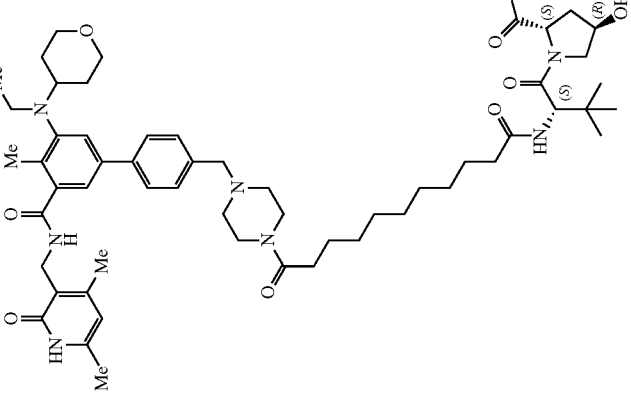 |

TABLE 2-continued
| Molecule Name | Structure |
|---|---|
| NUCC-0226273 | 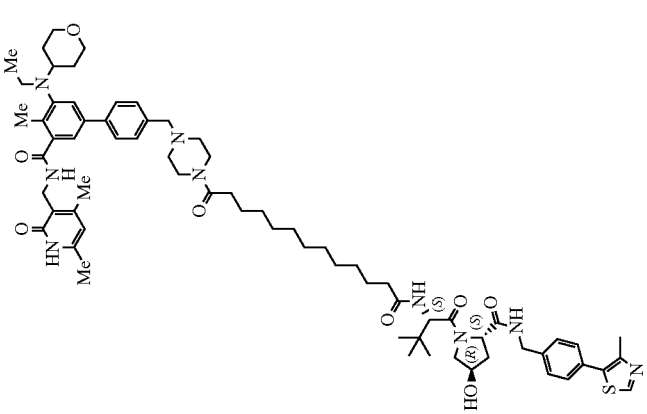 |

TABLE 2-continued
| Molecule Name | Structure |
|---|---|
| NUCC-0226274 | 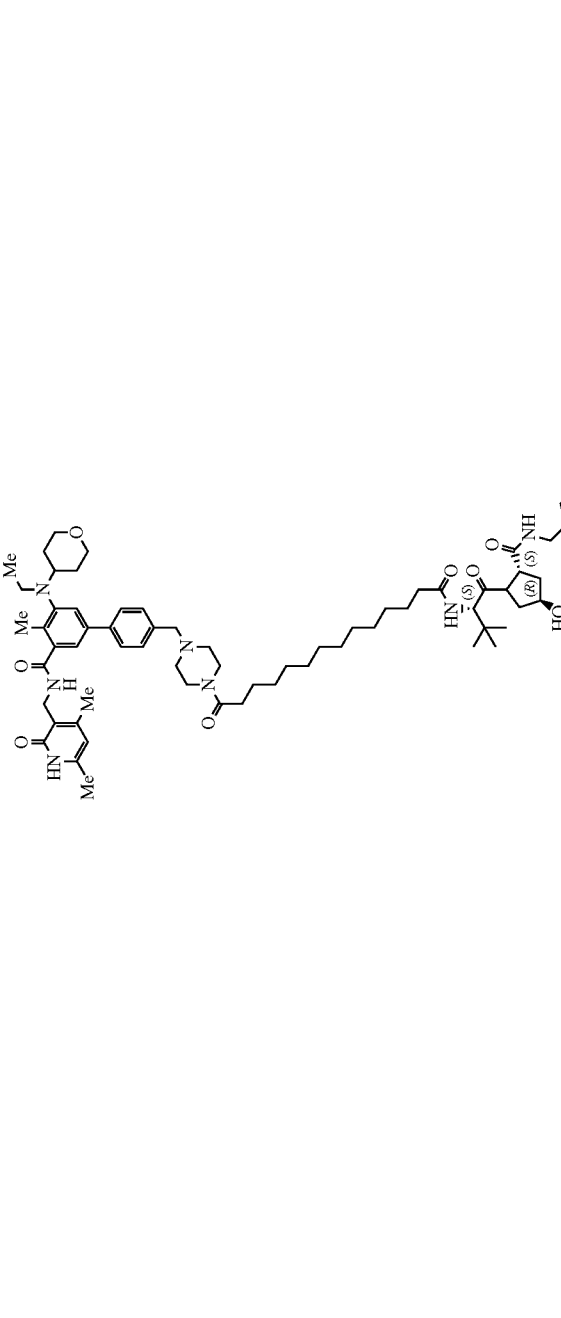 |

TABLE 2-continued
| Molecule Name | Structure |
|---|---|
| NUCC-0226275 | 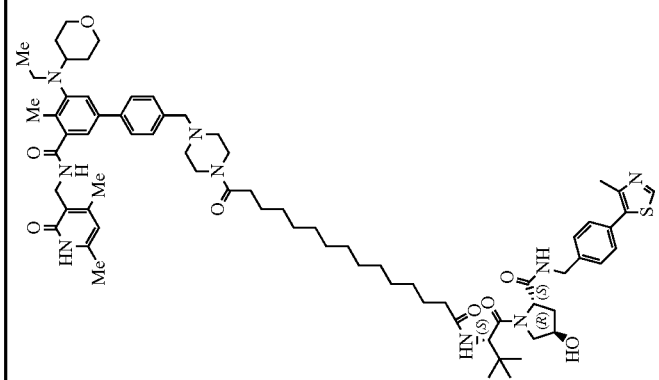 |

TABLE 2-continued
| Molecule Name | Structure |
|---|---|
| NUCC-0226281 | 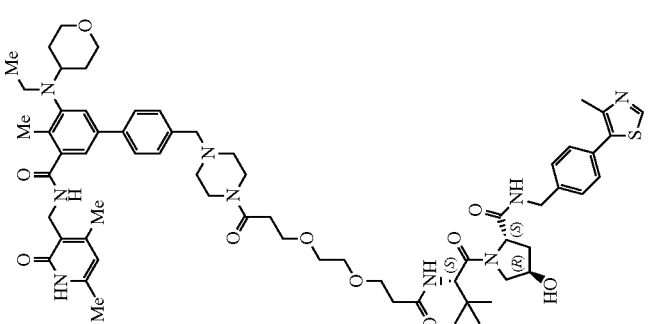 |

TABLE 2-continued
| Molecule Name | Structure |
|---|---|
| NUCC-026282 | 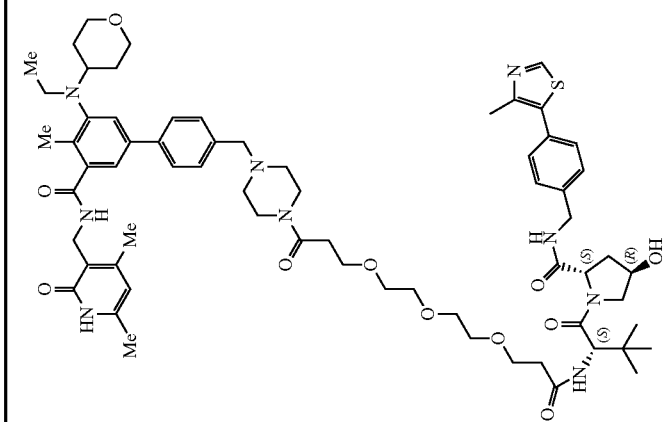 |

TABLE 2-continued
| Molecule Name | Structure |
|---|---|
| NUCC-0226283 | 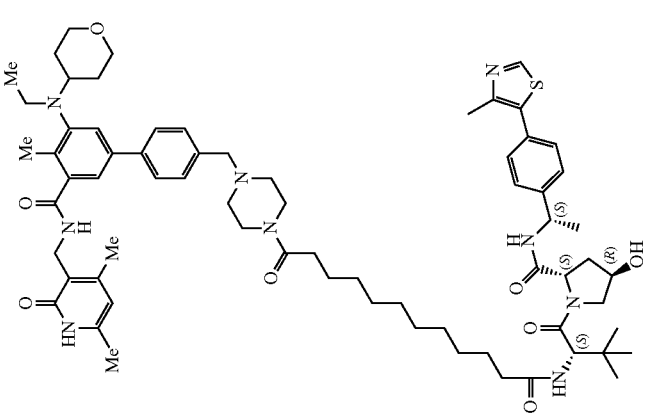 |

TABLE 2-continued
| Molecule Name | Structure |
|---|---|
| NUCC-0226284 | 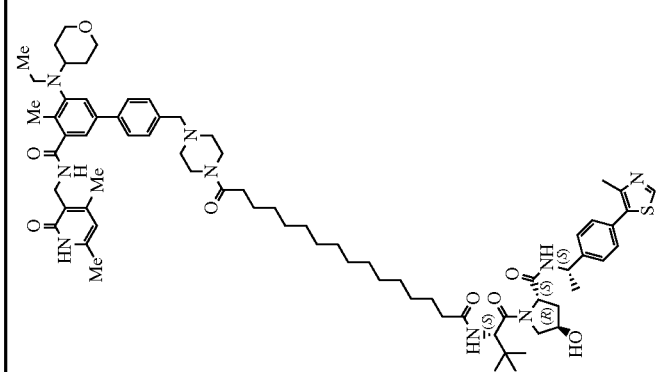 |

TABLE 2-continued
| Molecule Name | Structure |
|---|---|
| NUCC-0226285 | 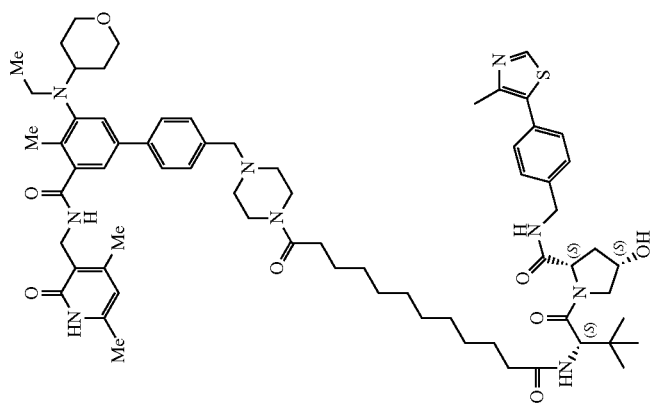 |

TABLE 2-continued
| Molecule Name | Structure |
|---|---|
| NUCC-0226286 | 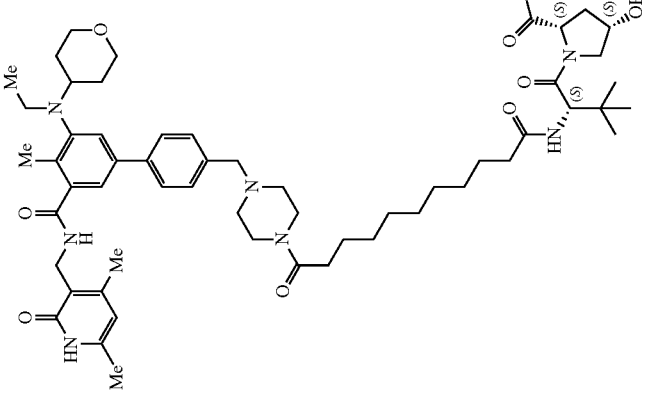 |

TABLE 2-continued
| Molecule Name | Structure |
|---|---|
| NUCC-0226287 | 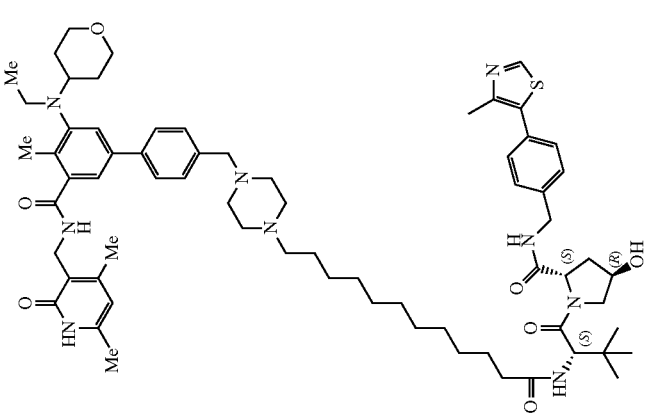 |

TABLE 2-continued
| Molecule Name | Structure |
|---|---|
| NUCC-0223630 | 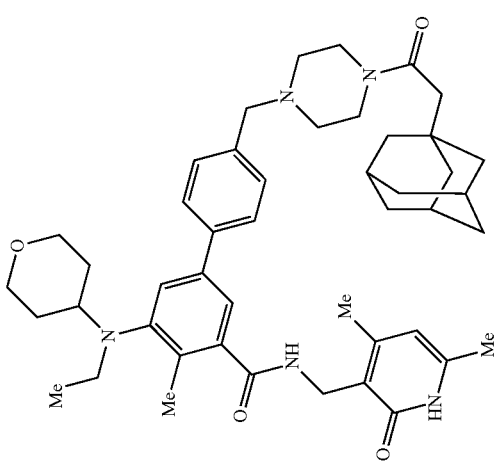 |
| NUCC-0223631 | 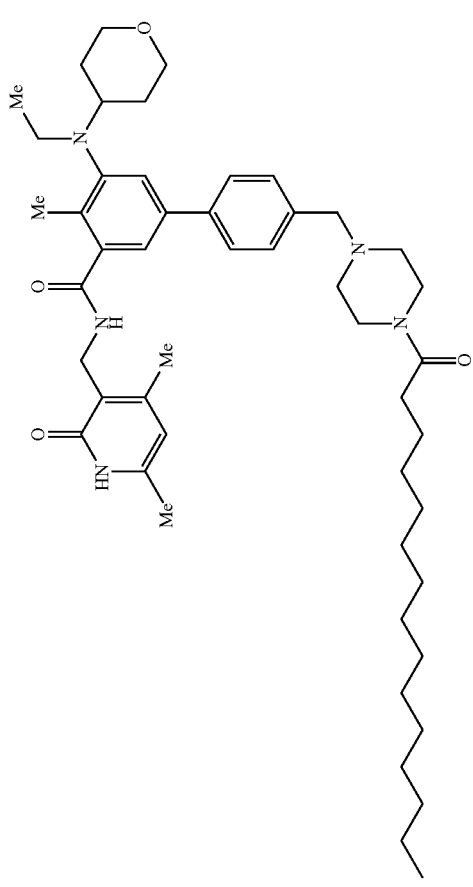 |

TABLE 2-continued
| Molecule Name | Structure |
|---|---|
| NUCC-0223832 | 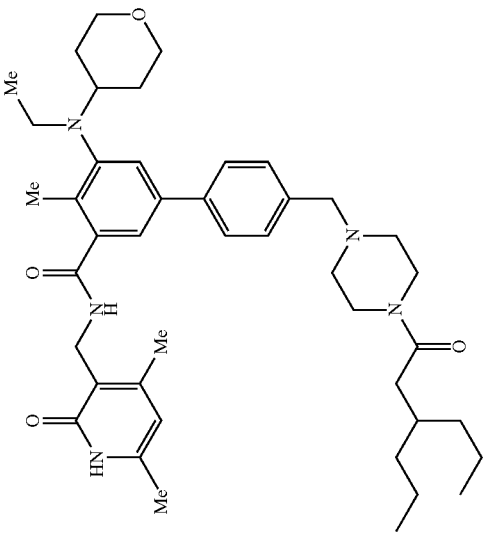 |
| NUCC-0223833 | 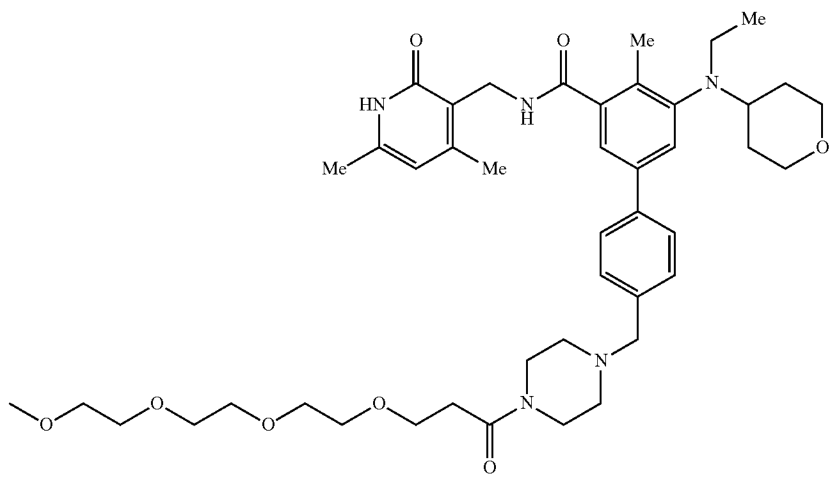 [SMILES: CCN(c1cc(-c2ccc(CN3CCN(C(=O)CCOCCOCCOCCOC)CC3)cc2)cc(C(=O)NCc2c(C)cc(C)[nH]c2=O)c1C)C1CCOCC1] |

TABLE 2-continued
| Molecule Name | Structure |
|---|---|
| NUCC-0223834 | 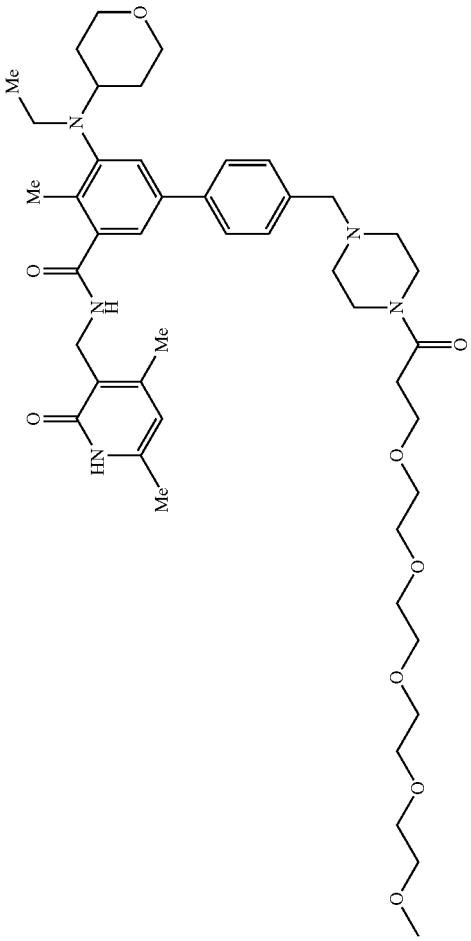 |
| NUCC-0223835 | 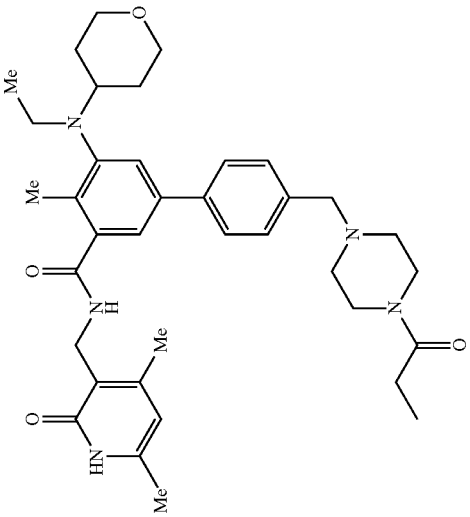 |

TABLE 2-continued
| Molecule Name | Structure |
|---|---|
| NUCC-0223836 | 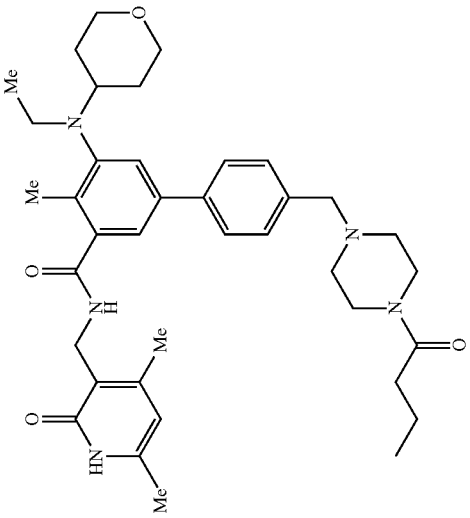 |
| NUCC-0223837 | 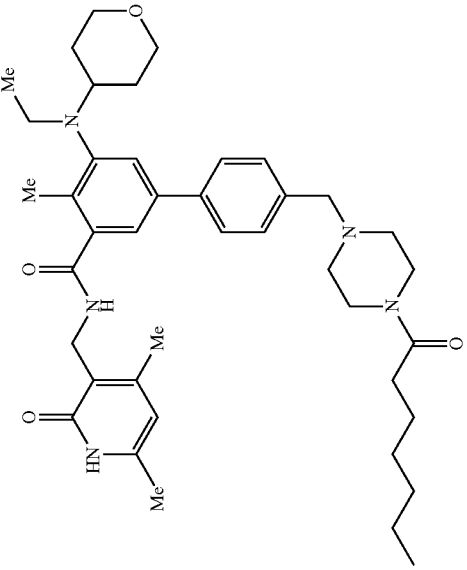 |

TABLE 2-continued
| Molecule Name | Structure |
|---|---|
| NUCC-0223838 | 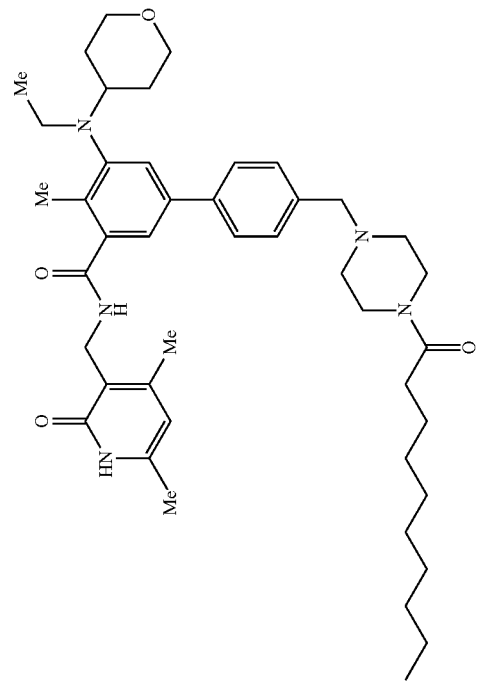 |
| NUCC-0223839 | 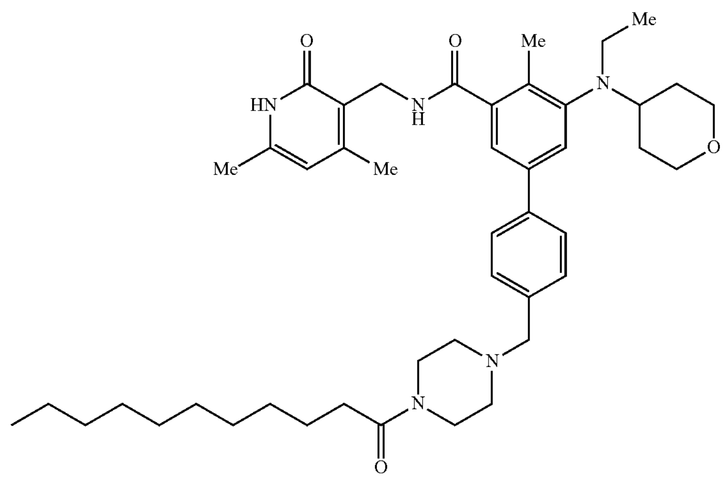 [SMILES: CCCCCCCCCCC(=O)N1CCN(Cc2ccc(-c3cc(C(=O)NCc4c(C)cc(C)[nH]c4=O)c(C)c(N(CC)C4CCOCC4)c3)cc2)CC1] |

TABLE 2-continued
| Molecule Name | Structure |
|---|---|
| NUCC-0223840 | 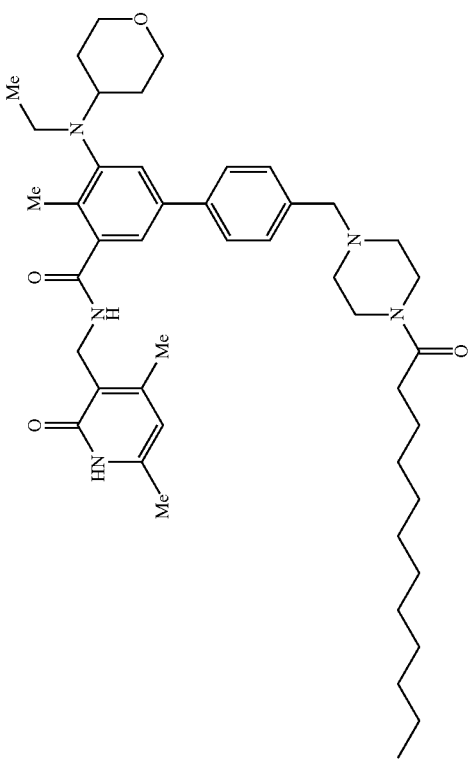 |
| NUCC-0223841 | 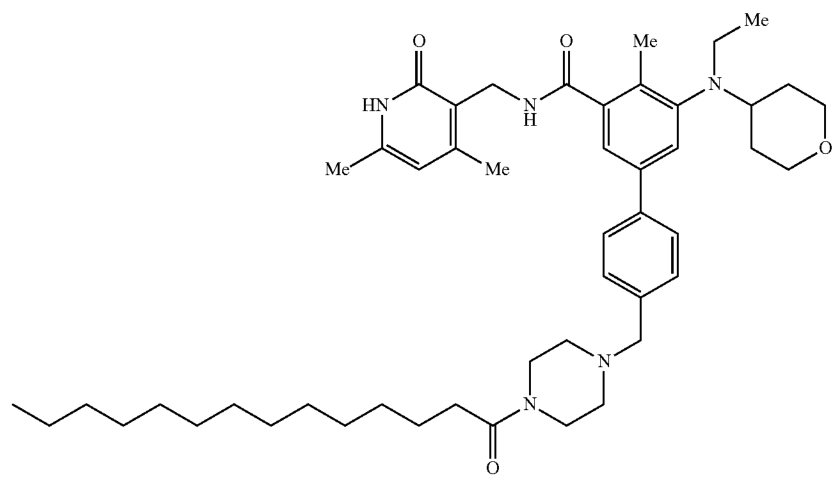 [SMILES: CCCCCCCCCCCCCC(=O)N1CCN(Cc2ccc(-c3cc(C(=O)NCc4c(C)cc(C)[nH]c4=O)c(C)c(N(CC)C4CCOCC4)c3)cc2)CC1] |

TABLE 2-continued
| Molecule Name | Structure |
|---|---|
| NUCC-0223842 | 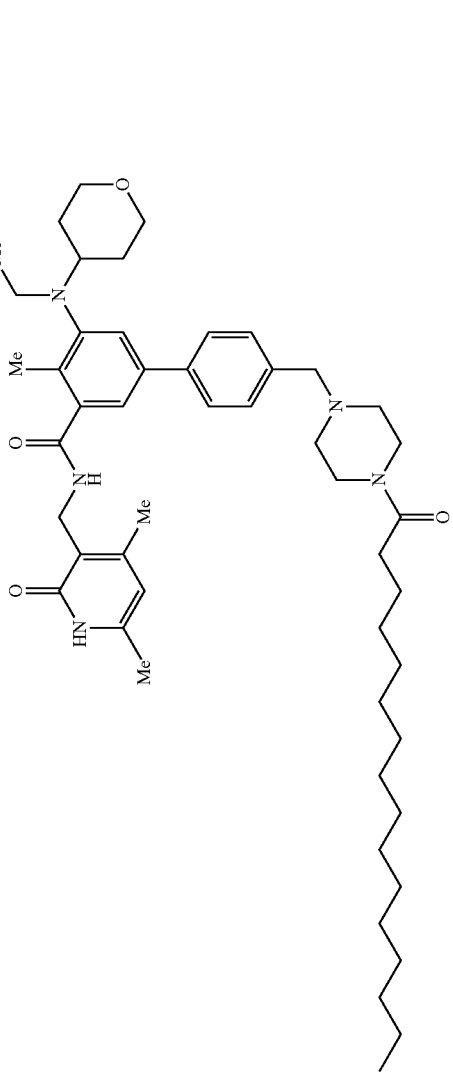 |
| NUCC-0223843 | 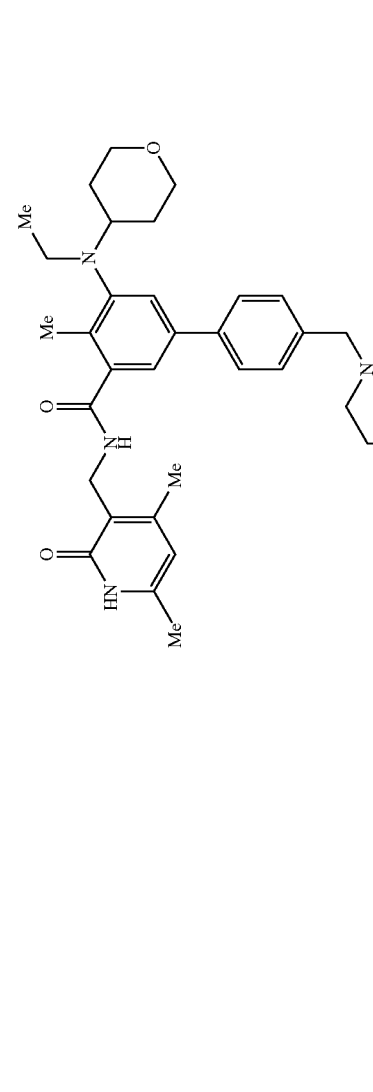 |

TABLE 2-continued
| Molecule Name | Structure |
|---|---|
| NUCC-0223844 | 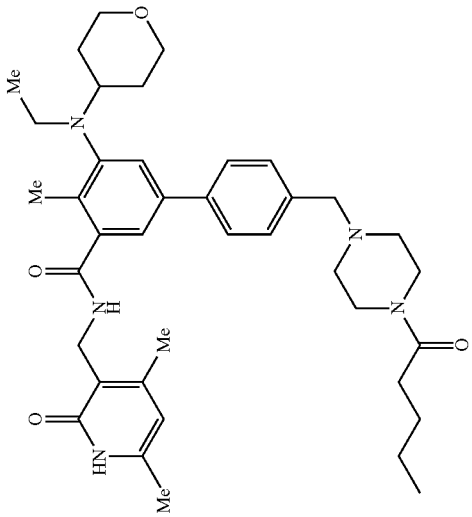 |
| NUCC-0223845 | 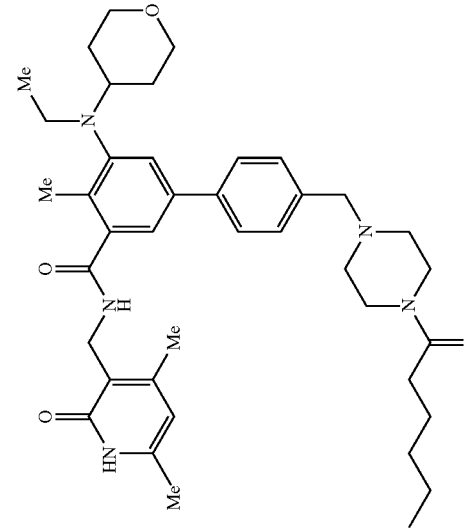 |

TABLE 2-continued
| Molecule Name | Structure |
|---|---|
| NUCC-0223846 | 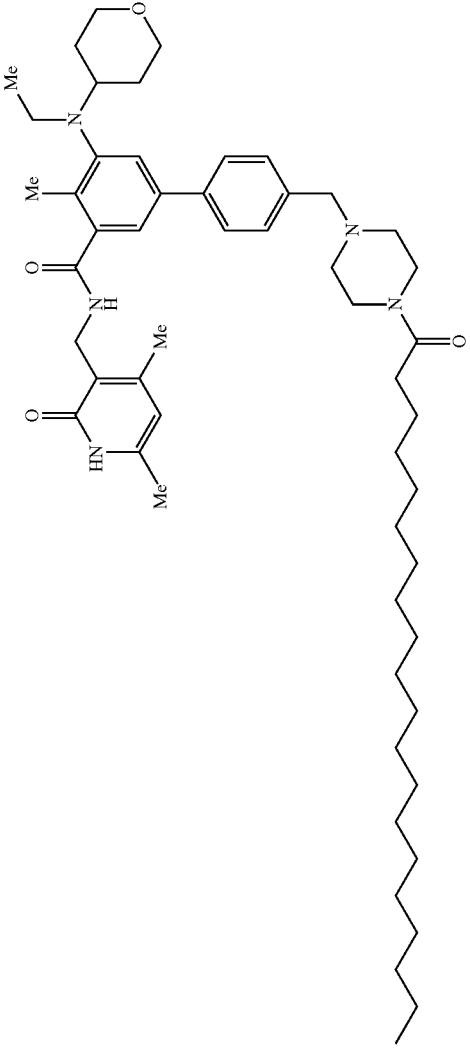 |
| NUCC-0223847 | 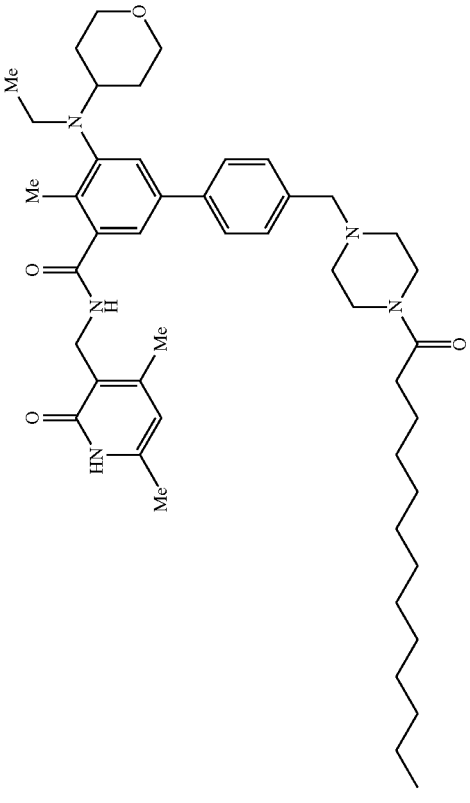 |

TABLE 2-continued
| Molecule Name | Structure |
|---|---|
| NUCC-0223848 | 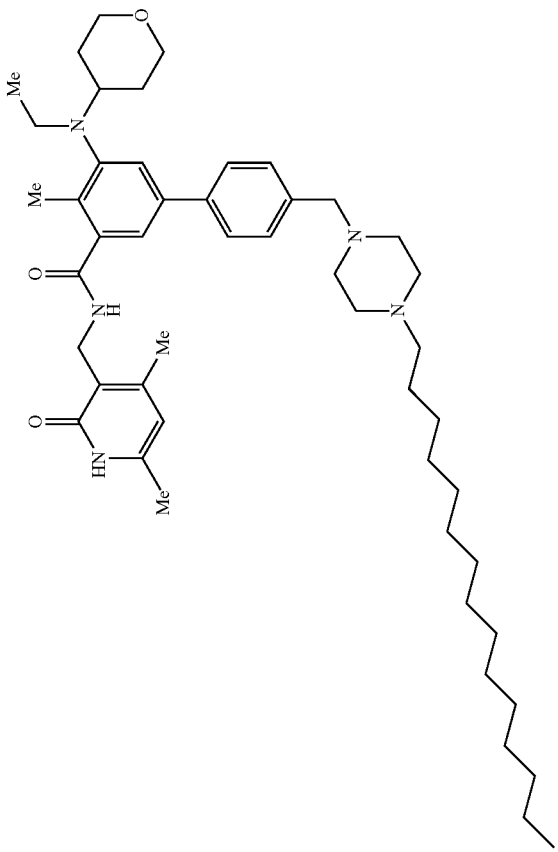 |

TABLE 2-continued
Molecule Name: NUCC-0226300
Structure:
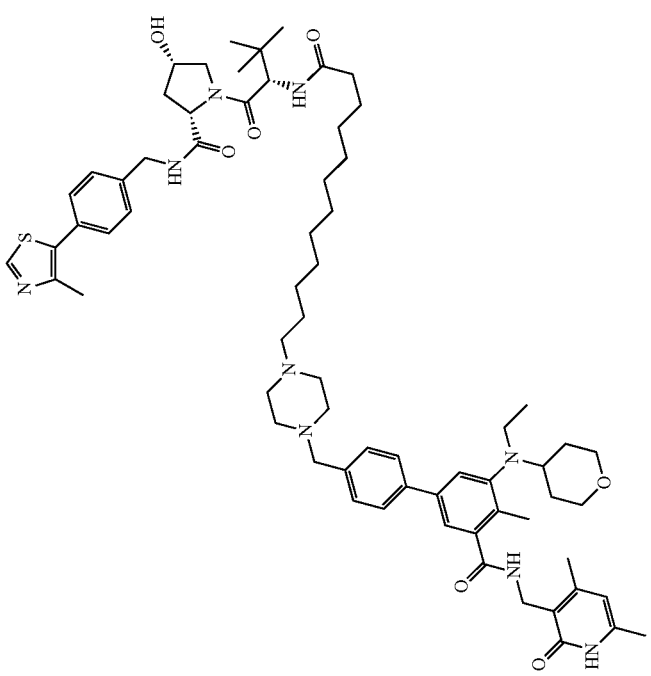

Example 3—Activity in Prostate Cancer (PCa) Cells

FIGS. 1-28 and Tables 3-5 show the activity of the described compounds in prostate cancer (PCa) cells.

Cell proliferation was measured using WST-1 Kit (Clontech) according to manufacturer's protocol. Data show that degrader 6272 is more potent and effective at inhibiting cell proliferation than the catalytic EZH2 inhibitor EPZ-6438 in multiple prostate cancer cell lines, indicating that the degradation of EZH2, separate from its inhibition, produces additional anti-proliferative benefit.

TABLE 3

WST1 test cell viability on LNCaP

| | EPZ | 6272 |
|---|---|---|
| [Inhibitor] vs. normalized response Best-fit values | | |
| IC50 | 7.798 | 0.7585 |
| logIC50 | 0.8920 | −0.1200 |
| 95% CI (profile likelihood) | | |
| IC50 | 4.957 to 12.59 | 0.3657 to 1.647 |
| logIC50 | 0.6952 to 1.100 | −0.4369 to 0.2168 |
| Goodness of Fit | | |
| Degrees of Freedom | 23 | 23 |
| R squared | 0.6394 | 0.4012 |
| Sum of Squares | 5011 | 7515 |
| Sy · x | 14.76 | 18.08 |
| Constraints | | |
| IC50 | IC50 > 0 | IC50 > 0 |
| Number of points | | |
| # of X values | 24 | 24 |
| # Y values analyzed | 24 | 24 |

TABLE 4

WST1 cell viability with different doses on 22Rv1

| | EPZ | 6272 |
|---|---|---|
| [Inhibitor] vs. normalized response Best-fit values | | |
| IC50 | 57.51 | 1.335 |
| logIC50 | 1.760 | 0.1256 |
| 95% CI (profile likelihood) | | |
| IC50 | 25.48 to 1024 | 0.8228 to 2.249 |
| logIC50 | 1.406 to 3.010 | −0.08472 to 0.3520 |
| Goodness of Fit | | |
| Degrees of Freedom | 23 | 23 |
| R squared | 0.003543 | 0.8145 |
| Sum of Squares | 3778 | 4106 |
| Sy · x | 12.82 | 13.36 |
| Constraints | | |
| IC50 | IC50 > 0 | IC50 > 0 |
| Number of points | | |
| # of X values | 24 | 24 |
| # Y values analyzed | 24 | 24 |

TABLE 5

Cell titer glo test cell viability with different doses on 22Rv1

| | EPZ | 6272 |
|---|---|---|
| [Inhibitor] vs. normalized response Best-fit values | | |
| IC50 | 30.94 | 0.6924 |
| logIC50 | 1.491 | −0.1597 |
| 95% CI (profile likelihood) | | |
| IC50 | 23.88 to 41.97 | 0.5926 to 0.8084 |
| logIC50 | 1.378 to 1.623 | −0.2273 to −0.09239 |
| Goodness of Fit | | |
| Degrees of Freedom | 23 | 23 |
| R squared | 0.6829 | 0.9821 |
| Sum of Squares | 614.0 | 564.5 |
| Sy · x | 5.167 | 4.954 |
| Constraints | | |
| IC50 | IC50 > 0 | IC50 > 0 |
| Number of points | | |
| # of X values | 24 | 24 |
| # Y values analyzed | 24 | 24 |

Example 4—Activity in Lymphoma Cancer Cells

FIGS. 29-34 and Tables 6-9 show the activity of the described compounds in lymphoma cancer cells.

Cell proliferation was measured using WST-1 Kit (Clontech) according to manufacturer's protocol. Data show that degrader 6272 is more potent and effective at inhibiting cell proliferation than the catalytic EZH2 inhibitor EPZ-6438 in multiple lymphoma cell lines, indicating that the degradation of EZH2, separate from its inhibition, produces additional anti-proliferative benefit.

TABLE 6

WST1 test cell viability with higher dose on SU-DHL4

| | EPZ | 6272 |
|---|---|---|
| [Inhibitor] vs. normalized response -- Variable slope Best-fit values | Interrupted | |
| IC50 | 2.533e−137 | 2784 |
| HillSlope | 0.005835 | −0.09300 |
| logIC50 | −136.6 | 3.445 |
| 95% CI (profile likelihood) | | |
| IC50 | | 279.3 to 1568244 |
| HillSlope | | −0.1370 to −0.04923 |
| logIC50 | | 2.446 to 6.195 |
| Goodness of Fit | | |
| Degrees of Freedom | | 28 |
| R squared | | 0.9630 |
| Sum of Squares | | 219.6 |
| Sy · x | | 2.801 |
| Constraints | | |
| IC50 | IC50 > 0 | IC50 > 0 |
| Number of points | | |
| # of X values | 30 | 30 |
| # Y values analyzed | 30 | 30 |

TABLE 7

WST1 test cell viability with higher dose on SU-DHL6

| | EPZ | 6272 |
|---|---|---|
| [Inhibitor] vs. normalized response -- Variable slope Best-fit values | | |
| IC50 | Unstable | 0.8923 |
| HillSlope | −0.03015 | −0.6321 |
| logIC50 | Unstable | −0.04950 |
| 95% CI (profile likelihood) | | |
| IC50 | (Very wide) | 0.7242 to 1.074 |
| HillSlope | −0.09779 to ??? | −0.7443 to −0.5289 |
| logIC50 | (Very wide) | −0.1401 to 0.03090 |
| Goodness of Fit | | |
| Degrees of Freedom | 28 | 28 |
| R squared | 0.8735 | 0.9645 |
| Sum of Squares | 309.3 | 921.8 |
| Sy · x | 3.323 | 5.738 |
| Constraints | | |
| IC50 | IC50 > 0 | IC50 > 0 |
| Number of points | | |
| # of X values | 30 | 30 |
| # Y values analyzed | 30 | 30 |

TABLE 8

WST1 test cell viability within 1 μM on SU-DHL4

| | EPZ | 6272 |
|---|---|---|
| [Inhibitor] vs. normalized response -- Variable slope Best-fit values | | |
| IC50 | 103.9 | 2.497 |
| HillSlope | −0.1692 | −0.2858 |
| logIC50 | 2.016 | 0.3975 |
| 95% CI (profile likelihood) | | |
| IC50 | 14.55 to 5358 | 1.214 to 7.075 |
| HillSlope | −0.2316 to −0.1112 | −0.3541 to −0.2239 |
| logIC50 | 1.163 to 3.729 | 0.08425 to 0.8497 |
| Goodness of Fit | | |
| Degrees of Freedom | 28 | 28 |
| R squared | 0.7738 | 0.8606 |
| Sum of Squares | 1018 | 1177 |
| Sy · x | 6.029 | 6.484 |
| Constraints | | |
| IC50 | IC50 > 0 | IC50 > 0 |
| Number of points | | |
| # of X values | 30 | 30 |
| # Y values analyzed | 30 | 30 |

TABLE 9

WST1 test cell viability within 1 μM on SU-DHL4

| | EPZ | 6272 |
|---|---|---|
| [Inhibitor] vs. normalized response -- Variable slope Best-fit values | | |
| IC50 | 4.076 | 0.3371 |
| HillSlope | −0.4432 | −1.235 |
| logIC50 | 0.6103 | −0.4722 |
| 95% CI (profile likelihood) | | |
| IC50 | 2.134 to 11.35 | 0.2847 to 0.3992 |
| HillSlope | −0.5831 to −0.3316 | −1.448 to −1.049 |
| logIC50 | 0.3292 to 1.055 | −0.5456 to −0.3988 |
| Goodness of Fit | | |
| Degrees of Freedom | 28 | 28 |
| R squared | 0.8105 | 0.9668 |
| Sum of Squares | 1218 | 874.0 |
| Sy · x | 6.595 | 5.587 |
| Constraints | | |
| IC50 | IC50 > 0 | IC50 > 0 |
| Number of points | | |
| # of X values | 30 | 30 |
| # Y values analyzed | 30 | 30 |

Example 5—Pharmacokinetics

FIG. 35 shows the pharmacokinetics of the described compounds in mice.

For assessing pharmacokinetics, compounds were administered to C57Bl/6 mouse mice at 4 mg/kg using intraperitoneal (IP) injection in cassette format. Plasma was collected at the indicated time points and analyzed by LC/MS/MS using standard methods. Compounds 2305, 6272, and 2304 each reached plasma concentrations of >1 μM and had half-lives of between 3.5-6 hours. Compound 6287 had a half-life of 6.5 hours and had a Cmax in plasma of 487 nM. These data indicate that the compounds are capable of being administered to an animal and achieving sufficient drug exposure to potentially produce a therapeutic benefit.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. A molecule having a formula: $M_{EZH2}$-L-$M_{E3}$ or a salt, hydrate, or solvate thereof, wherein $M_{EZH2}$ is a moiety that binds to EZH2, L is a bond or a linker covalently attaching $M_{EZH2}$ and $M_{E3}$, and $M_{E3}$ is a moiety that binds to an E3 ubiquitin ligase, wherein $M_{EZH2}$ has a formula:

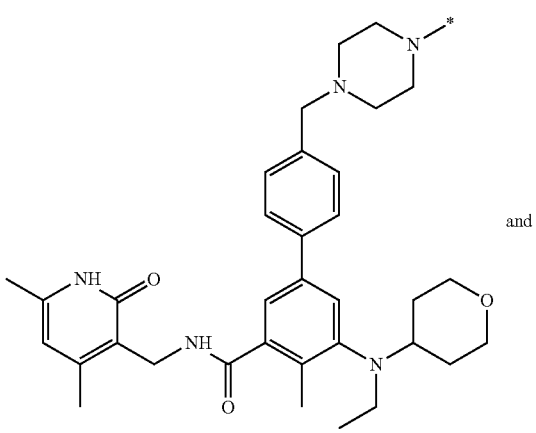 [SMILES: *N1CCN(Cc2ccc(-c3cc(C(=O)NCc4c(C)cc(C)[nH]c4=O)c(C)c(N(CC)C4CCOCC4)c3)cc2)CC1]

and wherein $M_{E3}$ has a formula selected from:

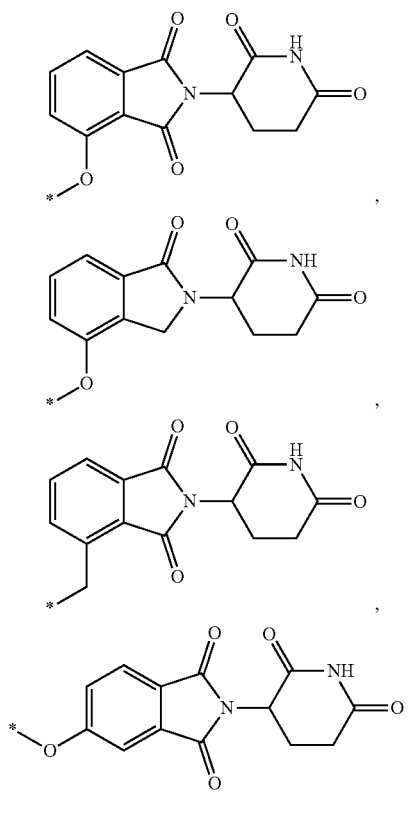

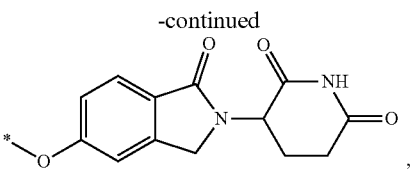

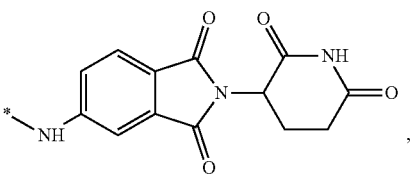

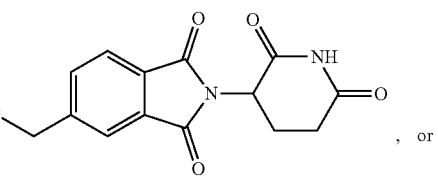

, or

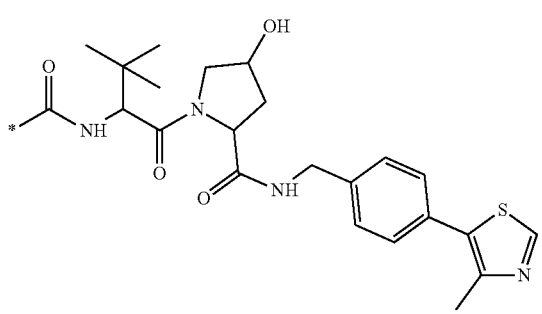

.

2. The molecule of claim 1, wherein L comprises a polyethylene glycol moiety, an alkylalkyne moiety, and/or an aminoalkyl alkyne moiety, or, wherein L has a formula selected from: —(CH$_2$)$_m$—, —(CH$_2$)$_m$CH$_2$CH$_2$C(O)NHCH$_2$CH$_2$—, —(CH$_2$)$_m$CH$_2$CH$_2$C(O)NHCH$_2$CH$_2$CH$_2$—, —(CH$_2$CH$_2$O)$_n$CH$_2$CH$_2$C(O)NHCH$_2$CH$_2$—, —(CH$_2$CH$_2$O)$_n$CH$_2$CH$_2$C(O)NHCH$_2$CH$_2$CH$_2$—, —(CH$_2$CH$_2$O)$_n$CH$_2$CH$_2$—, —(CH$_2$CH$_2$O)$_n$CH$_2$—, —(CH$_2$)$_m$C(O)NHCH$_2$CH$_2$—, —(CH$_2$CH$_2$O)$_n$CH$_2$CH$_2$C(O)NHCH$_2$CH$_2$—, —CH$_2$CH$_2$C(O)NHCH$_2$CH$_2$CH$_2$—, —CH$_2$CH$_2$C(O)NHCH$_2$CH$_2$CH$_2$C(O)NHCH$_2$CH$_2$—, —CH$_2$CH$_2$C(O)NHCH$_2$CH$_2$CH$_2$C(O)NHCH$_2$CH$_2$CH$_2$C(O)NHCH$_2$CH$_2$—, —CH$_2$CH$_2$C(O)NHCH$_2$CH$_2$CH$_2$C(O)NHCH$_2$CH$_2$CH$_2$C(O)NHCH$_2$CH$_2$CH$_2$—, —(CH$_2$CH$_2$O)$_n$CH$_2$CH$_2$—, —CH$_2$OCH$_2$—, —CH$_2$OCH$_2$C(O)NHCH$_2$CH$_2$—, —CH$_2$OCH$_2$C(O)NHCH$_2$CH$_2$CH$_2$—, —CH$_2$OCH$_2$C(O)NHCH$_2$CH$_2$CH$_2$C(O)NHCH$_2$CH$_2$—, and —CH$_2$OCH$_2$C(O)NHCH$_2$CH$_2$CH$_2$C(O)NHCH$_2$CH$_2$CH$_2$—, wherein m and n are 0-20.

3. A molecule having a formula: $M_{EZH2}$-L-$M_{E3}$ or a salt, hydrate, or solvate thereof, wherein $M_{EZH2}$ is a moiety that binds to EZH2, L is a bond or a linker covalently attaching $M_{EZH2}$ and $M_{E3}$, and $M_{E3}$ is a moiety that binds to an E3 ubiquitin ligase, wherein $M_{EZH2}$ has a formula:

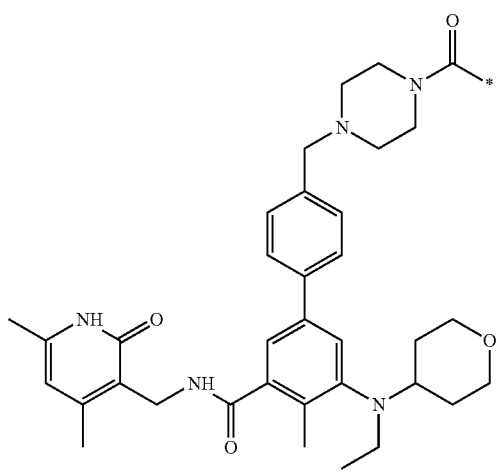

wherein $M_{E3}$ has a formula selected from:

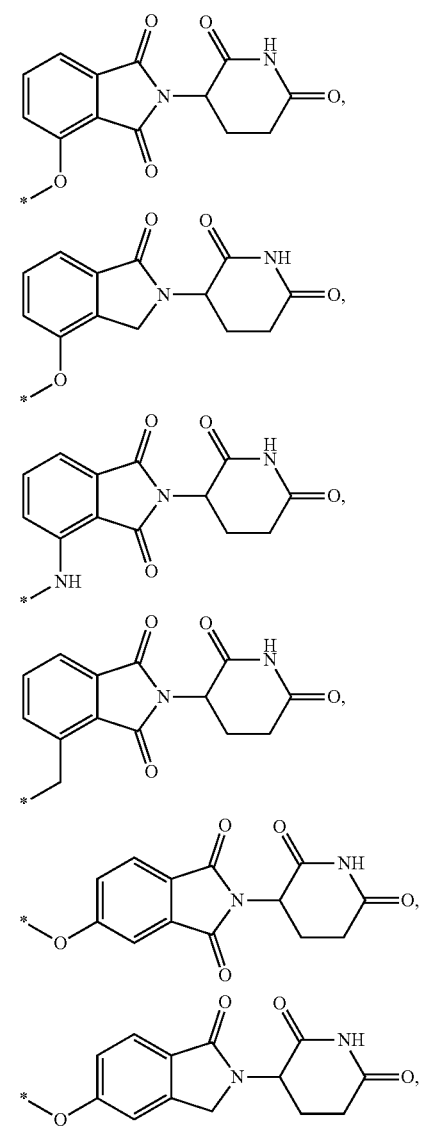

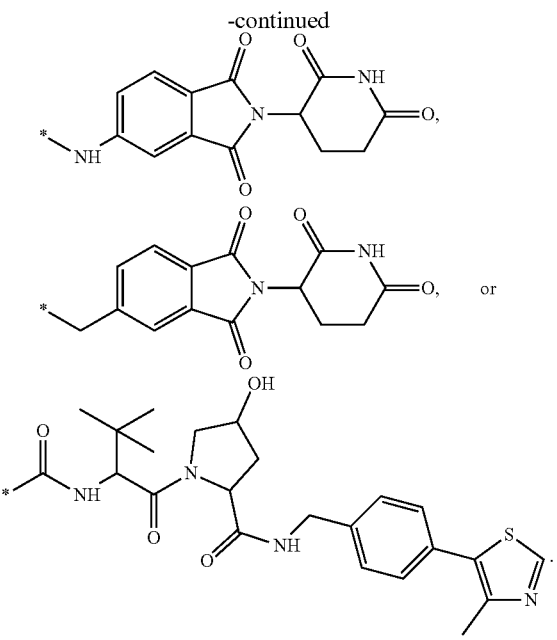

and

4. The molecule of claim 3, wherein L comprises a polyethylene glycol moiety, an alkylalkyne moiety, and/or an aminoalkyl alkyne moiety, or, wherein L has a formula selected from: —$(CH_2)_m$—, —$(CH_2)_mCH_2CH_2C(O)NHCH_2CH_2$—, —$(CH_2)_mCH_2CH_2C(O)NHCH_2CH_2CH_2$—, —$(CH_2CH_2O)_nCH_2CH_2C(O)NHCH_2CH_2$—, —$(CH_2CH_2O)_nCH_2CH_2C(O)NHCH_2CH_2CH_2$—, —$(CH_2CH_2O)_nCH_2CH_2$—, —$(CH_2CH_2O)_nCH_2$—, —$(CH_2)_mC(O)NHCH_2CH_2$—, —$(CH_2CH_2O)_nCH_2CH_2C(O)NHCH_2CH_2$—, —$CH_2CH_2C(O)NHCH_2CH_2CH_2$—, —$CH_2CH_2C(O)NHCH_2CH_2CH_2C(O)NHCH_2CH_2$—, —$CH_2CH_2C(O)NHCH_2CH_2CH_2C(O)NHCH_2CH_2CH_2C(O)NHCH_2CH_2$—, —$CH_2CH_2C(O)NHCH_2CH_2CH_2C(O)NHCH_2CH_2CH_2C(O)NHCH_2CH_2CH_2$—, —$(CH_2CH_2O)_nCH_2CH_2$—, —$CH_2OCH_2$—, —$CH_2OCH_2C(O)NHCH_2CH_2$—, —$CH_2OCH_2C(O)NHCH_2CH_2CH_2$—, —$CH_2OCH_2C(O)NHCH_2CH_2CH_2C(O)NHCH_2CH_2$—, and —$CH_2OCH_2C(O)NHCH_2CH_2CH_2C(O)NHCH_2CH_2CH_2$—, wherein m and n are 0-20.

5. The molecule of claim 3, wherein $M_{E3}$ has a formula selected from:

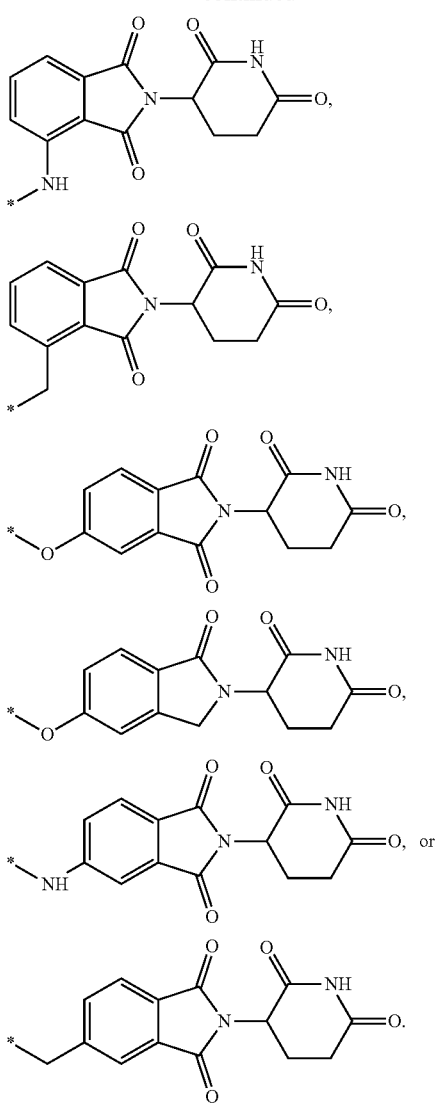
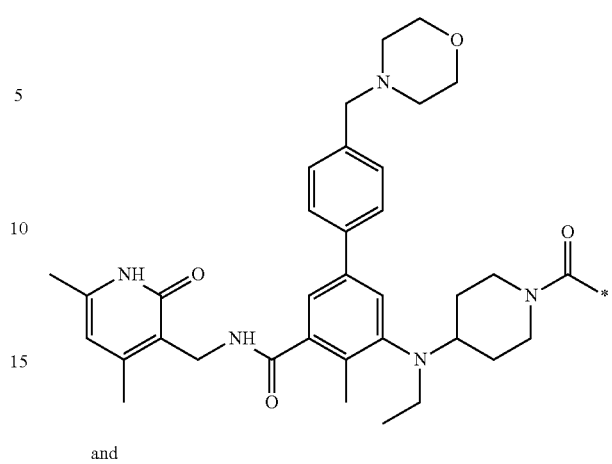
and
wherein $M_{E3}$ has a formula selected from:
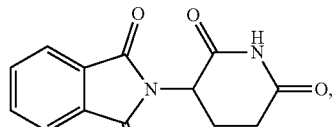
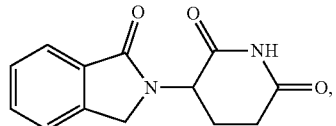
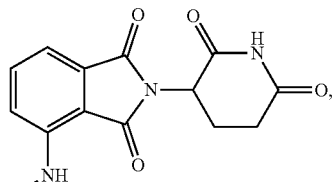
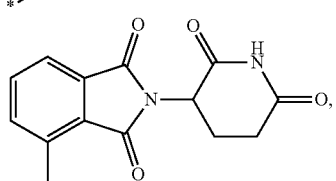
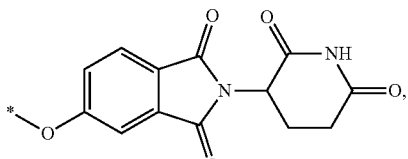
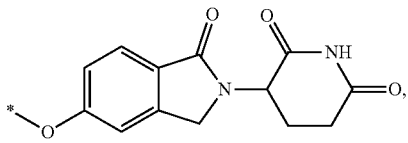
6. The molecule of claim 3, wherein $M_{E3}$ has a formula:
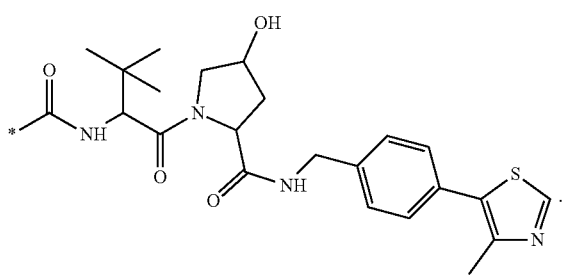 [SMILES: *C(=O)NC(C(=O)N1CC(O)CC1C(=O)NCc1ccc(-c2scnc2C)cc1)C(C)(C)C]
7. A molecule having a formula: $M_{EZH2}$-L-$M_{E3}$ or a salt, hydrate, or solvate thereof, wherein $M_{EZH2}$ is a moiety that binds to EZH2, L is a bond or a linker covalently attaching $M_{EZH2}$ and $M_{E3}$, and $M_{E3}$ is a moiety that binds to an E3 ubiquitin ligase, wherein $M_{EZH2}$ has a formula:

-continued

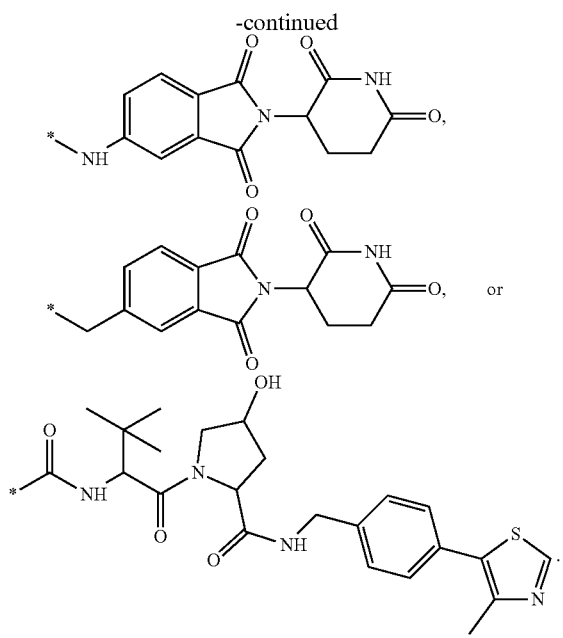

8. The molecule of claim 7, wherein L comprises a polyethylene glycol moiety, an alkylalkyne moiety, and/or an aminoalkyl alkyne moiety, or, wherein L has a formula selected from: —$(CH_2)_m$—, —$(CH_2)_mCH_2CH_2C(O)NHCH_2CH_2$—, —$(CH_2)_mCH_2CH_2C(O)NHCH_2CH_2CH_2$—, —$(CH_2CH_2O)_nCH_2CH_2C(O)NHCH_2CH_2$—, —$(CH_2CH_2O)_nCH_2CH_2C(O)NHCH_2CH_2CH_2$—, —$(CH_2CH_2O)_nCH_2CH_2$—, —$(CH_2CH_2O)_nCH_2$—, —$(CH_2)_mC(O)NHCH_2CH_2$—, —$(CH_2CH_2O)_nCH_2CH_2C(O)NHCH_2CH_2$—, —$CH_2CH_2C(O)NHCH_2CH_2CH_2$—, —$CH_2CH_2C(O)NHCH_2CH_2CH_2C(O)NHCH_2CH_2$—, —$CH_2CH_2C(O)NHCH_2CH_2CH_2C(O)NHCH_2CH_2CH_2C(O)NHCH_2CH_2$—, —$CH_2CH_2C(O)NHCH_2CH_2CH_2C(O)NHCH_2CH_2CH_2C(O)NHCH_2CH_2CH_2$—, —$(CH_2CH_2O)_nCH_2CH_2$—, —$CH_2OCH_2$—, —$CH_2OCH_2C(O)NHCH_2CH_2$—, —$CH_2OCH_2C(O)NHCH_2CH_2CH_2$—, —$CH_2OCH_2C(O)NHCH_2CH_2CH_2C(O)NHCH_2CH_2$—, and —$CH_2OCH_2C(O)NHCH_2CH_2CH_2C(O)NHCH_2CH_2CH_2$—, wherein m and n are 0-20.

9. The molecule of claim 7, wherein $M_{E3}$ has a formula selected from:

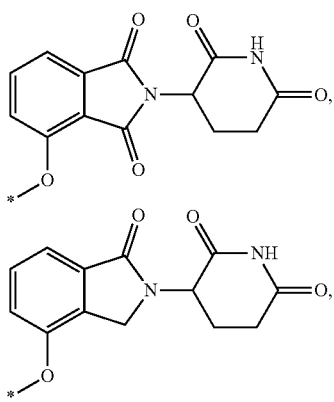

-continued

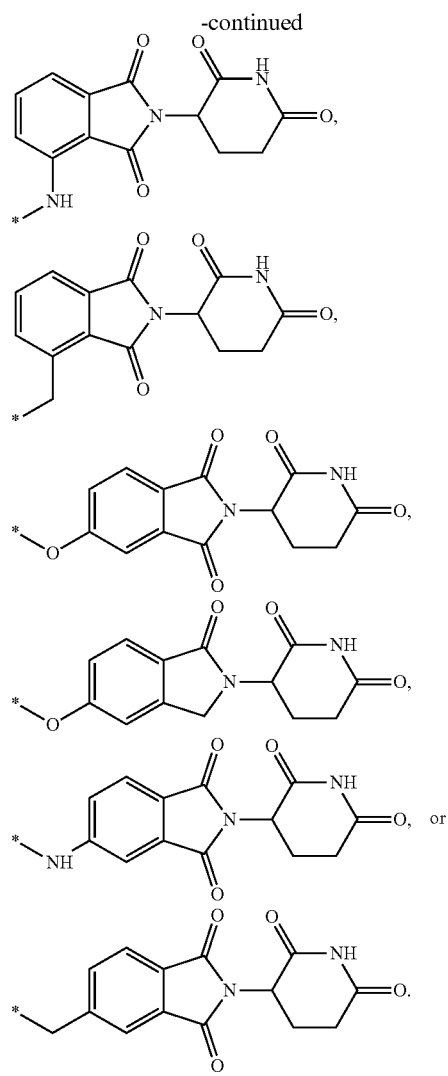

10. The molecule of claim 7, wherein $M_{E3}$ has a formula:

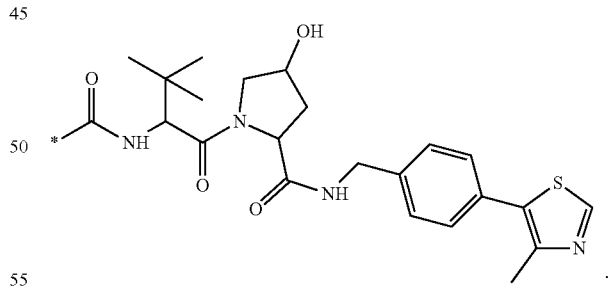

11. A pharmaceutical composition comprising the molecule of claim 1 and a suitable pharmaceutical carrier, excipient, or diluent.

12. A pharmaceutical composition comprising the molecule of claim 3 and a suitable pharmaceutical carrier, excipient, or diluent.

13. A pharmaceutical composition comprising the molecule of claim 7 and a suitable pharmaceutical carrier, excipient, or diluent.

* * * * *